(12) United States Patent
Gocal

(10) Patent No.: US 11,359,208 B2
(45) Date of Patent: Jun. 14, 2022

(54) SHATTERPROOF GENES AND MUTATIONS

(71) Applicants: CIBUS US LLC, San Diego, CA (US); CIBUS EUROPE, B.V., Breda (NL)

(72) Inventor: Gregory F. W. Gocal, San Diego, CA (US)

(73) Assignees: CIBUS US LLC, San Diego, CA (US); CIBUS EUROPE, B.V.

( * ) Notice: Subject to any disclaimer, the term of this patent is extended or adjusted under 35 U.S.C. 154(b) by 0 days.

(21) Appl. No.: 16/959,331

(22) PCT Filed: Jan. 9, 2019

(86) PCT No.: PCT/US2019/012938
§ 371 (c)(1),
(2) Date: Jun. 30, 2020

(87) PCT Pub. No.: WO2019/140009
PCT Pub. Date: Jul. 18, 2019

(65) Prior Publication Data
US 2021/0024947 A1    Jan. 28, 2021

Related U.S. Application Data

(60) Provisional application No. 62/615,409, filed on Jan. 9, 2018, provisional application No. 62/732,397, filed on Sep. 17, 2018.

(51) Int. Cl.
*C12N 15/82* (2006.01)
*A01H 6/20* (2018.01)

(52) U.S. Cl.
CPC ................................ *C12N 15/8266* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,873,191 A | 10/1989 | Wagner et al. | |
| 4,945,050 A | 7/1990 | Sanford et al. | |
| 4,959,317 A | 9/1990 | Sauer | |
| 4,987,071 A | 1/1991 | Cech et al. | |
| 5,008,200 A | 4/1991 | Ranch et al. | |
| 5,024,944 A | 6/1991 | Collins et al. | |
| 5,100,792 A | 3/1992 | Sanford et al. | |
| 5,204,253 A | 4/1993 | Sanford et al. | |
| 5,219,746 A | 6/1993 | Brinegar et al. | |
| 5,268,463 A | 12/1993 | Jefferson | |
| 5,302,523 A | 4/1994 | Coffee et al. | |
| 5,334,711 A | 8/1994 | Sproat et al. | |
| 5,380,831 A | 1/1995 | Adang et al. | |
| 5,399,680 A | 3/1995 | Zhu et al. | |
| 5,424,412 A | 6/1995 | Brown et al. | |
| 5,436,391 A | 7/1995 | Fujimoto et al. | |
| 5,466,785 A | 11/1995 | de Framon | |
| 5,484,956 A | 1/1996 | Lundquist et al. | |
| 5,489,520 A | 2/1996 | Adams et al. | |
| 5,543,508 A | 8/1996 | Haseloff et al. | |
| 5,569,597 A | 10/1996 | Grimsley et al. | |
| 5,593,874 A | 1/1997 | Brown et al. | |
| 5,604,121 A | 2/1997 | Hilder et al. | |
| 5,608,142 A | 3/1997 | Barton et al. | |
| 5,608,144 A | 3/1997 | Baden et al. | |
| 5,608,149 A | 3/1997 | Barry et al. | |
| 5,659,026 A | 8/1997 | Baszczynski et al. | |
| 5,756,325 A | 5/1998 | Kmiec | |
| 5,760,012 A | 6/1998 | Kmiec et al. | |
| 5,780,296 A | 7/1998 | Holloman et al. | |
| 5,792,633 A | 8/1998 | Schiestl et al. | |
| 5,795,972 A | 8/1998 | Kmiec | |
| 5,871,984 A | 2/1999 | Kmiec | |
| 5,888,983 A | 3/1999 | Kmiec et al. | |
| 5,945,339 A | 8/1999 | Holloman et al. | |
| 5,962,426 A | 10/1999 | Glazer | |
| 5,986,053 A | 11/1999 | Ecker et al. | |
| 6,004,804 A | 12/1999 | Kumar et al. | |
| 6,010,907 A | 1/2000 | Kmiec et al. | |
| 6,072,050 A | 6/2000 | Bowen et al. | |
| 6,177,611 B1 | 1/2001 | Rice | |
| 6,207,384 B1 | 3/2001 | Mekalanos et al. | |
| 6,271,360 B1 | 8/2001 | Metz et al. | |
| 6,479,292 B1 | 11/2002 | Metz et al. | |
| 6,489,127 B1 | 12/2002 | Duyk et al. | |
| 6,506,559 B1 | 1/2003 | Fire et al. | |
| 6,511,824 B1 | 1/2003 | Buchman et al. | |

(Continued)

FOREIGN PATENT DOCUMENTS

| | | |
|---|---|---|
| EP | 626387 B1 | 3/1999 |
| EP | 679657 B1 | 7/2003 |

(Continued)

OTHER PUBLICATIONS

Ferrandiz et al, 2000, Science, 289:436-438.*
Cheng et al, 2020, Frontiers in Plant Science, 10:1-13.*
Sauer et al, 2016, Plant Physiology, 170:1917-1928.*
Liljegren et al, 2000, Nature, 404:766-770.*
Raman et al, 2014, PLOS One, 9:1-13.*
Kord et al, 2015, 3 Biotech, 5:271-277.*
Tan et al, 2009, Botanical Studies, 50:403-412.*
Liu et al, 2020, Journal of Experimental Botany, 71:5402-5413.*
Altschul et al., (1990). "Basic local alignment search tool," J. Mol. Biol., 215:403-410.
Altschul et al., (1997). "Gapped BLAST and PSI-BLAST: a new generation of protein database search programs," Nucleic acids research, 25(17):3389-3402.
An et al., (1986). "Transformation of Tobacco, Tomato, Potato, and *Arabidopsis thaliana* Using a Binary Ti Vector System," Plant Physiol., 81:301-305.

(Continued)

*Primary Examiner* — Jason Deveau Rosen
(74) *Attorney, Agent, or Firm* — Morrison & Foerster LLP

(57) ABSTRACT

The present disclosure provides shatterproof (SHP) genes and plants and/or plant cells bearing one or more mutations in a shatterproof gene; as well as methods of making and using such plants. In some embodiments the plant or plant cell is resistant to preharvest dehiscence.

19 Claims, 9 Drawing Sheets

Specification includes a Sequence Listing.

(56) References Cited

U.S. PATENT DOCUMENTS

| | | |
|---|---|---|
| 6,573,099 B2 | 6/2003 | Graham |
| 6,753,458 B1 | 6/2004 | Filho et al. |
| 6,824,978 B1 | 11/2004 | Cox et al. |
| 6,870,075 B1 | 3/2005 | Beetham et al. |
| 6,924,146 B1 | 8/2005 | Wattler et al. |
| 6,933,113 B2 | 8/2005 | Case et al. |
| 6,979,539 B2 | 12/2005 | Cox et al. |
| 7,013,219 B2 | 3/2006 | Case et al. |
| 7,060,500 B2 | 6/2006 | Metz et al. |
| 7,070,934 B2 | 7/2006 | Cox et al. |
| 7,220,719 B2 | 5/2007 | Case et al. |
| 7,262,054 B2 | 8/2007 | Jamieson et al. |
| 7,273,923 B2 | 9/2007 | Jamieson et al. |
| 7,285,416 B2 | 10/2007 | Choo et al. |
| 7,361,635 B2 | 4/2008 | Miller et al. |
| 7,501,275 B2 | 3/2009 | Laplaza et al. |
| 7,521,241 B2 | 4/2009 | Choo et al. |
| 8,278,036 B2 | 10/2012 | Kariko et al. |
| 8,338,157 B2 | 12/2012 | Jantz et al. |
| 8,445,251 B2 | 5/2013 | Smith et al. |
| 2003/0084473 A1 | 5/2003 | Gocal et al. |
| 2003/0115641 A1 | 6/2003 | Dobres et al. |
| 2003/0221211 A1 | 11/2003 | Rottmann et al. |
| 2004/0029283 A1 | 2/2004 | Fillatti |

FOREIGN PATENT DOCUMENTS

| | | |
|---|---|---|
| WO | WO-1998049350 B1 | 1/1999 |
| WO | WO-1999007865 A1 | 2/1999 |
| WO | WO-1999040789 A1 | 8/1999 |
| WO | WO-1999043838 A1 | 9/1999 |
| WO | WO-1999058702 A1 | 11/1999 |
| WO | WO-1999058723 A1 | 11/1999 |
| WO | WO-2007073149 A1 | 6/2007 |
| WO | WO-2008148223 A1 | 12/2008 |
| WO | WO-2013176772 A1 | 11/2013 |
| WO | WO-2014093661 A2 | 6/2014 |

OTHER PUBLICATIONS

Archer et al., (1990). "Current views on chloroplast protein import and hypotheses on the origin of the transport mechanism," J. Bioenerg. Biomemb., 22(6):789-810.

Arimondo et al., (2000). "Recognition and cleavage of DNA by rebeccamycin- or benzopyridoquinoxaline conjugated of triple helix-forming oligonucleotides," Bioorganic and Medicinal Chem., 8:777-784.

Asano et al., (1994). "Transgenic plants of Agrostis alba obtained by electroporation-mediated direct gene transfer into protoplasts," Plant cell reports, 13(5):243-246.

Ayres et al., (1994). "Genetic Transformation of Rice," Crit. Rev. Plant. Sci., 13:219-239.

Ballas et al., (1989). "Efficient functioning of plant promoter and poly(A) sites in Xenopus oocytes," Nucleic Acids Res., 17:7891-7903.

Barcelo et al., (1994). "Transgenic cereal (tritordeum) plants obtained at high efficiency by microprojectile bombardment of inflorescence tissue," Plant. J., 5:583-592.

Barsby et al., (1996). "A Rapid and Efficient Alternative Procedure for the Regeneration of Plants from Hypocotyl Protoplasts of *Brassica napus*," Plant Cell Reports, 5:101-103.

Becker et al., (1994). "Fertile transgenic wheat from microprojectile bombardment of scutellar tissue," Plant. J., 5:299-307.

Belousov et al., (1997). "Sequence-specific targeting and covalent modification of human genomic DNA," Nucleic Acids Res, 25:3440-3444.

Bendinskas et al., (1998). "Sequence-Specific Photomodification of DNA by an Oligonucleotide-Phenanthrodihydrodioxin Conjugate," Bioconjugate Chem., 9:555-563.

Borkowska et al., (1994). "Transformation of diploid potato with an Agrobacterium tumefaciens binary vector system: I. Methodological approach," Acta Physiol. Plant., 16(3):225-230.

Brummelkamp et al., (2002). "A System for Stable Expression of Short Interfering RNAs in Mammalian Cells," Science, 296:550-553.

Burgess-Brown et al., (2008). "Codon optimization can improve expression of human genes in *Escherichia coli*: A multi-gene study," Protein Expr. Purif, 59:94-102.

Callis et al., (1987). "Introns increase gene expression in cultured maize cells," Genes and Development, 1:1183-1200.

Campbell et al., (1990). "Codon usage in higher plants, green algae, and cyanobacteria," Plant Physiol., 92:1-11.

Canevascini et al., (1996). "Tissue-Specific Expression and Promoter Analysis of the Tobacco Ltp1 Gene," Plant Physiol., 112(2):513-524.

Capecchi, (1989). "Altering the genome by homologous recombination," Science, 244:1288-1292.

Casas et al., (1993). "Transgenic sorghum plants via microprojectile bombardment," Proc. Natl. Acad Sci. USA, 90:11212-11216.

Cermak et al., (2011). "Efficient design and assembly of custom TALEN and other TAL effector-based constructs for DNA targeting," Nucleic Acids Research, 39(12):e82, 11 pages.

Chalhoub et al., (2014). "Early allopolyploid evolution in the post-Neolithic *Brassica napus* oilseed genome," Science, 345:950-953.

Chan et al., (1999). "Targeted correction of an episomal gene in mammalian cells by a short DNA fragment tethered to a triplex-forming oligonucleotide," The Journal of biological chemistry, 274(17):11541-11548.

Chee et al., (1992). "Transformation of cucumber tissues by microprojectile bombardment: identification of plants containing functional and non-functional transferred genes," Gene, 118:255-260.

Cheng et al., (2013). "Multiplexed activation of endogenous genes by CRISPR-on, an RNA-guided transcriptional activator system," Cell Research, 23(10):1163-71.

Christensen et al, (1992). "Maize polyubiquitin genes: structure, thermal perturbation of expression and transcript splicing, and promoter activity following transfer to protoplasts by electroporation," Plant Mol. Biol. 18: 675-689.

Christensen et al., (1989). "Sequence analysis and transcriptional regulation by heat shock of polyubiquitin transcripts from maize," Plant Mol. Biol., 12:619-632.

Christou et al., (1992). "The development of a variety-independent gene-transfer method for rice," Trends in Biotechnology, 10:239-246.

Christou, (1993). "Philosophy and practice of variety-independent gene transfer into recalcitrant crops," In Vitro Cell. Dev. Biol.-Plant, 29:119-124.

Christou, (1994). "Genetic engineering of crop legumes and cereals: current status and recent advances," Agro. Food. Ind. Hi Tech., 5:17-27.

Chugh et al., (2008). "Cellular uptake of cell-penetrating peptides pVEC and transportan in plants," Journal of peptide science: an official publication of the European Peptide Society, 14(4):477-481.

Chuong et al., (1985). "A simple culture method for *Brassica hypototyl* protoplasts," Plant Cell Reports 4(1):4-6.

Clark et al., (1989). "Mutations at the transit peptide-mature protein junction separate two cleavage events during chloroplast import of the chlorophyll a/b-binding protein," J. Biol. Chem., 264:17544-17550.

Colombier et al., (1996). "Interstrand Cross-linking Reaction in Triplexes Containing a Monofunctional Transplatin-Adduct," Nucleic Acids Research, 24:4519-4524.

Cong et al., (2013). "Multiplex Genome Engineering Using CRISPR/Cas Systems," Science, 339:819-823.

Coumans et al., (1989). "Plant development from isolated microspores of *Zea mays* L.," Plant Cell Rep., 7:618-621.

Cousins et al., (1991). "Transformation of an Australian cotton cultivar: prospects for cotton improvement through genetic engineering," Functional Plant Biology, 18(5):481-494.

Datta et al., (1990). "Embryogenesis and plant regeneration from microspores of both 'Indica' and 'Japonica' rice (*Oryza sativa*)," Plant Sci., 67:83-88.

(56) References Cited

OTHER PUBLICATIONS

Davies et al., (1993). "Transformation of peas," Plant Cell Rep., 12:180-183.
De Block, (1988). "Genotype-independent leaf disc transformation of potato (Solanum tuberosum) using Agrobacterium tumefaciens," Theoretical and applied genetics, 76(5):767-774.
De Castro Silva Filho et al., (1996). "Mitochondrial and chloroplast targeting sequences in tandem modify protein import specificity in plant organelles," Plant molecular biology, 30(4):769-780.
Della-Cioppa et al., (1987). "Protein Trafficking in Plant Cells," Plant Physiol., 84:965-968.
Dervan et al., (1999). "Sequence-specific DNA recognition by polyamides," Curr Opin Chem Biol, 3:688-693.
D'Halluin et al., (1992). "Transformation of Sugarbeet (Beta vulgaris L.) and Evaluation of Herbicide Resistance in Transgenic Plants," Bio/Technol., 10:309-314.
Dhir et al., (1992). "Regeneration of Fertile Plants from Protoplasts of Soybean (Glycine max L. Merr.): genotypic differences in culture response," Plant Cell Reports, 11:285-289.
Dong et al., (1993). "Transgenic flax plants from Agro-bacterium mediated transformation: incidence of chimeric regenerans and inheritance of transgenic plants," Plant Sci. 91:139-148.
Eapen et al., (1994). "Agrobacterium tumefaciens mediated gene transfer in peanut (Arachis hypogaea L.)," Plant Cell Rep., 13:582-586.
Faruqi et al., (1996). "Recombination induced by triple-helix-targeted DNA damage in mammalian cells," Mol Cell Biol, 16:6820-6828.
Fennell et al., (1992). "Electroporation and PEG delivery of DNA into maize microspores," Plant Cell Reports, 11:567-570.
Fire et al., (1998). "Potent and specific genetic interference by double-stranded RNA in Caenorhabditis elegans," Nature, 391:806-811.
Folger et al., (1982). "Patterns of integration of DNA microinjected into cultured mammalian cells: evidence for homologous recombination between injected plasmid DNA molecules," Mol Cell Biol, 2:1372-1387.
Frame et al., (1994). "Production of fertile transgenic maize plants by silicon carbide whisker-mediated transformation," Plant J., 6:941-948.
Franklin et al., (1993). "Genetic transformation of green bean callus via Agrobacterium mediated DNA transfer," Plant Cell Report, 12:74-79.
Fry et al., (1987). "Transformation of Brassica napus with Agrobacterium tumefaciens based vectors," Plant Cell Rep., 6:321-325.
Gallie et al., (1987). "A comparison of eukaryotic viral 5'-leader sequences as enhancers of mRNA expression in vivo," Nucleic Acid Res., 15:8693-8711.
Gallie et al., (1994). "The Regulation of Gene Expression in Transformed Maize Aleurone and Endosperm Protoplasts," Plant Physiol., 106:929-939.
Genbank Accession No. AY036062 "Brassica napus Shatterproof1 (BnSHP1) mRNA,complete cds," Avalable online at <https://www.ncbi.nlm.nih.gov/nuccore/AY036062>, May 17, 2011, 2 pages.
Genbank Accession No. JQ973084 "Brassica nap us Shatterproof (SHP1 b) mRNA, complete cds," Available online at, <https://www.ncbi.nlm.nih.gov/nuccore/JQ973084>, Apr. 12, 2012, 1 page.
Genbank Accession No. JQ973085 "Brassica napus Shatterproof (SHP1 a) mRNA, complete eds," Available online at, <https://www.ncbi.nlm.nih.gov/nuccore/JQ973085>, Sep. 13, 2013, 1 page.
Golovkin et al., (1993). "Production of transgenic maize plants by direct DNA uptake into embryogenic protoplasts," Plant Sci., 90:41-52.
Guerineau et al., (1991). "Effect of deletions in the cauliflower mosaic virus polyadenylation sequence on the choice of the polyadenylation sites in tobacco protoplasts," Mol. Gen. Genet., 262:141-144.
Guevara-Garcia et al., (1993). "Tissue-specific and wound-inducible pattern of expression of the mannopine synthase promoter is determined by the interaction between positive and negative cis-regulatory elements," Plant J., 4(3):495-505.
Gustafsson et al., (2004). "Codon bias and heterologous protein expression," Trends Biotechnol, 22:346-353.
Hammond et al., (2001). "Post-transcriptional gene silencing by double-stranded RNA," Nature Rev Gen, 2:110-119.
Hansen et al., (1997). "Wound-inducible and organ-specific expression of ORF13 from Agrobacterium rhizogenes 8196 T-DNA in transgenic tobacco plants," Mol. Gen Genet., 254(3):337-343.
Hartman et al., (1994). "Herbicide Resistant Turfgrass (Agrostis palustris Huds.) by Biolistic Transformation," Bio/Technology, 12:919-923.
Havre et al., (1993). "Targeted mutagenesis of DNA using triple helix-forming oligonucleotides linked to psoralen," Proc Nat'l Acad Sci, U.S.A., 90:7879-7883.
Havre et al., (1993). "Targeted mutagenesis of simian virus 40 DNA mediated by a triple helix-forming oligonucleotide," J Virol, 67:7324-7331.
Henikoff et al., (1989). "Amino acid substitution matrices from protein blocks," Proc. Natl. Acad. Sci. USA, 89:10915-10919.
International Search Report and Written Opinion dated Jun. 14, 2019, for PCT Patent Application No. PCT/US2019/12938 filed on Jan. 9, 2019, 17 pages.
Jardinaud et al., (1993). "Transient GUS gene expression in Brassica napus electroporated microspores," Plant Sci., 93:177-184.
Jinek et al., (2012). "A Programmable Dual-RNA-Guided DNA Endonuclease in Adaptive Bacterial Immunity," Science, 337:816-821.
Joshi et al., (1987). "Putative polyadenylation signals in nuclear genes of higher plants: a compilation and analysis," Nucleic Acid Res., 15:9627-9639.
Kadkol, (Sep. 2009). "Brassica shatter-resistance research update," In Proceedings of the 16th Australian research assembly on Brassicas conference, Ballarat Victoria (pp. 104-109).
Kagale et al., (2011). "EAR motif-mediated transcriptional repression in plants: an underlying mechanism for epigenetic regulation of gene expression," Epigenetics, 6(2):141-146.
Kane et al., (1995). "Specific cleavage of a DNA triple helix by Fell.bleomycin," Biochemistry, 34(51):16715-16724.
Karlin et al., (1993). "Applications and Statistics for Multiple High-Scoring Segments in Molecular Sequences," Proc Natl Acad. Sci., 90:5873-5877.
Kartha et al., (1974). "In vitro Plant Formation from Stem Explants of Rape," Physiol. Plant, 31:217-220.
Kawamata et al., (1997). "Temporal and spatial pattern of expression of the pea phenylalanine ammonia-lyase gene1 promoter in transgenic tobacco," Plant & cell physiology, 38(7):792-803.
Kim et al., (1996). "Hybrid restriction enzymes: zinc finger fusions to Fok I cleavage domain," Proceedings of the National Academy of Sciences of the United States of America, 93(3):1156-1160.
Kim et al., (2004). "DNA . RNA heteroduplex containing 8-oxo-7,8-dihydroguanosine: base pairing, structures, and thermodynamic stability," Journal of biochemistry and molecular biology, 37(6):657-662.
Komatsuda et al. (1991). "Genotype X Sucrose Interactions for Somatic Embryogenesis in Soybeans," Crop Sci., 31:333-337.
Komatsuda et al., (1992). "Maturation and Germination of Somatic Embryos as Affected by Sucrose and Plant Growth Regulators in Soybeans Glycine gracilis Skvortz and Glycine max (L.) Merr." Plant Cell, Tissue and Organ Culture, 28:103-113.
Kunzelmann et al., (1996). "Gene targeting of CFTR DNA in CF epithelial cells," Gene therapy, 3(10):859-867.
Lam, (1994). "Analysis of tissue-specific elements in the CaMV 35S promoter," Results and problems in cell differentiation, 20:181-196.
Lamppa, (1988). "The chlorophyll a/b-binding protein inserts into the thylakoids independent of its cognate transit peptide," The Journal of biological chemistry, 263(29):14996-14999.
Lanza et al., (2014). "A condition-specific codon optimization approach for improved heterologous gene expression in Saccharomyces cerevisiae," BMC systems biology, 8:33.
Last et al., (1991). "pEmu: an improved promoter for gene expression in cereal cells," Theor. Appl. Genet., 81:581-8.

(56) References Cited

OTHER PUBLICATIONS

Lawrence et al., (1997). "Alterations in the Chlamydomonas plastocyanin transit peptide have distinct effects on in vitro import and in vivo protein accumulation," The Journal of biological chemistry, 272(33):20357-20363.
Li et al., (1982). "Somatic embryogenesis in quite a direct way in cultures of mesophyll protoplasts of *Brassica napus* L.," Plant Cell Reports, 1:209-211.
Liljegren et al., (2000). Shatterproof MADS-box genes control seed dispersal in *Arabidopsis*, Nature, 404(6779):766-770.
Lukhtanov et al., (1997). "Minor groove DNA alkylation directed by major groove triplex forming oligodeoxyribonucleotides," Nucleic acids research, 25(24):5077-5084.
Maeder et al., (2013). "CRISPR RNA-guided activation of endogenous human genes," Nature methods, 10(10):977-979.
Maheshwari et al., (1982). "Special Paper: Haploids From Pollen Grains—Retrospect and Prospect," American Journal of Botany, 69:865-879.
Mali et al., (2013). "CAS9 transcriptional activators for target specificity screening and paired nickases for cooperative genome engineering," Nature biotechnology, 31(9):833-838.
Maniatis et al., (1987). "Regulation of inducible and tissue-specific gene expression," Science (New York, N.Y.), 236(4806):1237-1245.
Martienssen, (1998). "Functional genomics: probing plant gene function and expression with transposons," Proceedings of the National Academy of Sciences of the United States of America, 95(5):2021-2026.
Matsuoka et al., (1993). "Tissue-specific light-regulated expression directed by the promoter of a C4 gene, maize pyruvate,orthophosphate dikinase, in a C3 plant, rice," Proceedings of the National Academy of Sciences of the United States of America, 90(20):9586-9590.
McBride et al., (1994). "Controlled expression of plastid transgenes in plants based on a nuclear DNA-encoded and plastid-targeted T7 RNA polymerase," Proceedings of the National Academy of Sciences of the United States of America, 91(15):7301-7305.
McElroy et al., (1990). "Isolation of an efficient actin promoter for use in rice transformation," Plant Cell, 2:163-171.
Mogen et al., (1990). "Upstream sequences other than AAUAAA are required for efficient messenger RNA 3'-end formation in plants," The Plant cell, 2(12):1261-1272.
Morlan et al., (2009). "Mutation detection by real-time PCR: a simple, robust and highly selective method," PloS one, 4(2):e4584.
Munroe et al., (1990). "Tales of poly(A): a review," Gene, 91(2):151-158.
Murray et al., (1989). "Codon usage in plant genes," Nucl. Acids Res., 17:477-98.
Myers et al., (1988). "Optimal alignments in linear space," Computer applications in the biosciences:CABIOS, 4(1):11-17.
Narasimhulu et al., (1988). "Species Specific Shoot Regeneration Response of Cotyledonary Explants of *Brassicas*," Plant Cell Reports, 7(2):104-106.
Needleman et al., (1970). "A general method applicable to the search for similarities in the amino acid sequence of two proteins," J. Mol. Biol., 48:443-53.
Nehlin et al., (1995). "Induction of secondary embryogenesis in microspore-derived embryos of *Brassica napus* L," Plant Sci., 111:219-227.
Núñez et al., (2000). "Long-range guanine oxidation in DNA restriction fragments by a triplex-directed naphthalene diimide intercalator," Biochemistry, 39(20):6190-6199.
Odell et al., (1985). "Identification of DNA sequences required for activity of the cauliflower mosaic virus 35S promoter," Nature, 313:810-2.
Oh et al., (1999). "Triple helix-forming oligonucleotides target psoralen adducts to specific chromosomal sequences in human cells," Nucleic acids research, 27(24):4734-4742.
Orozco et al., (1993). "Localization of light-inducible and tissue-specific regions of the spinach ribulose bisphosphate carboxylase/oxygenase (rubisco) activase promoter in transgenic tobacco plants," Plant molecular biology, 23(6):1129-1138.
Paddison et al., (2002). "Short hairpin RNAs (shRNAs) induce sequence-specific silencing in mammalian cells," Genes & development, 16(8):948-958.
Pandey et al., (1992). "Plant Regeneration from Leaf and Hypocotyl Explants of Glycine wightii (W. and A.) VERDC. var. *Longicauda*," Japan J. Breed. 42:1-5.
Pasupathy et al., (2008). "Direct plant gene delivery with a poly(amidoamine) dendrimer," Biotechnology journal, 3(8):1078-1082.
Pearson et al., (1988). "Improved tools for biological sequence comparison," Proc. Natl. Acad. Sci., 85:2444-48.
Perez-Pinera et al., (2013). "RNA-guided gene activation by CRISPR-Cas9-based transcription factors," Nature methods, 10(10):973-976.
Pilch et al., (1999). "The thermodynamics of polyamide—DNA recognition: hairpin polyamide binding in the Minor Groove of duplex DNA," Biochemistry, 38(7):2143-2151.
Proudfoot, (1991). "Poly(A) signals," Cell, 64(4):671-674.
Raemakers et al., (1995). "Secondary somatic embryogenesis and applications in plant breeding," Euphytica, 81:93-107.
Raghavan, (1987). "Developmental strategies of the angiosperm pollen: a biochemical perspective," Cell differentiation, 21(4):213-226.
Raman et al., (2014). "Genome-wide delineation of natural variation for pod shatter resistance in *Brassica napus*," PLoS One, 9(7):e101673, 13 pages.
Rinehart et al., (1996). "Tissue-specific and developmental regulation of cotton gene FbL2A. Demonstration of promoter activity in transgenic plants," Plant physiology, 112(3):1331-1341.
Ritala et al., (1994). "Fertile transgenic barley to particle bombardment of immature embryos," Plant molecular biology, 24(2):317-325.
Roeder et al., (2006). "Fruit development in *Arabidopsis*," The *Arabidopsis* Book/American Society of Plant Biologists, 4.
Römer et al., (1993). "Expression of the genes encoding the early carotenoid biosynthetic enzymes in Capsicum annuum," Biochemical and biophysical research communications, 196(3):1414-1421.
Rouet et al., (1994). "Expression of a site-specific endonuclease stimulates homologous recombination in mammalian cells," Proceedings of the National Academy of Sciences of the United States of America, 91(13):6064-6068.
Rubnitz et al., (1984). "The minimum amount of homology required for homologous recombination in mammalian cells," Molecular and cellular biology, 4(11):2253-2258.
Russell et al., (1997). "Tissue-specific expression in transgenic maize of four endosperm promoters from maize and rice," Transgenic research, 6(2):157-168.
Sanfaçon et al., (1991). "A dissection of the cauliflower mosaic virus polyadenylation signal," Genes & development, 5(1):141-149.
Schmidt et al., (1993). "A novel operon organization involving the genes for chorismate synthase (aromatic biosynthesis pathway) and ribosomal GTPase center proteins (L11, L1, L10, L12: rpIKAJL) in cyanobacterium Synechocystis PCC 6803," The Journal of biological chemistry, 268(36):27447-27457.
Schnell et al., (1991). "Signal peptide analogs derived from two chloroplast precursors interact with the signal recognition system of the chloroplast envelope," The Journal of biological chemistry, 266(5):3335-3342.
Segal et al., (1995). "Endonuclease-induced, targeted homologous extrachromosomal recombination in Xenopus oocytes," Proceedings of the National Academy of Sciences of the United States of America, 92(3):806-810.
Sergeyev et al., (1995). "Catalytic site-specific cleavage of a DNA-target by an oligonucleotide carrying bleomycin A5," Nucleic acids research, 23(21):4400-4406.
Shah et al., (1986). "Engineering herbicide tolerance in transgenic plants," Science, 233(4762):478-481.
Shetty et al., (1992). "Stimulation of In Vitro Shoot Organogenesis in Glycine max (Merrill.) by Allantoin and Amides," Plant Science, 81:245-251.
Skuzeski et al., (1990). "Analysis of leaky viral translation termination codons in vivo by transient expression of improved beta-glucuronidase vectors," Plant molecular biology, 15(1):65-79.

(56) References Cited

OTHER PUBLICATIONS

Smith et al., (1981). "Comparison of biosequences," Adv. Appl. Math., 2:482-9.
Sone et al., (2002). "A novel gene delivery system in plants with calcium alginate micro-beads. Journal of bioscience and bioengineering," 94(1):87-91.
Spence et al., (1996). "'Pod shatter' in *Arabidopsis thalianaBrassica napus* and *B. juncea*," Journal of Microscopy, 181(2):195-203.
Staub et al., (1993). "Accumulation of D1 polypeptide in tobacco plastids is regulated via the untranslated region of the psbA mRNA," The EMBO Journal, 12(2):601-606.
Stephens et al., (1991). "Agronomic Evaluation of Tissue-Culture-Derived Soybean Plants," Theor. Appl. Genet. 82:633-635.
Sun et al., (1998). "Cotyledon-derived diploid and haploid protoplast culture and diploid plant regeneration in *Brassica napus* cv. 'Topas'," Can. J. Bot. 76:530-541.
Svab et al., (1990). "Stable transformation of plastids in higher plants," Proceedings of the National Academy of Sciences of the United States of America, 87(21):8526-8530.
Svab et al., (1993). "High-frequency plastid transformation in tobacco by selection for a chimeric aadA gene," Proceedings of the National Academy of Sciences of the United States of America, 90(3):913-917.
Swanson et al., (1987). "Efficient isolation of microspores and the production of microspore-derived embryos from *Brassica napus*," Plant cell reports, 6(2):94-97.
Takasugi et al., (1991). "Sequence-specific photo-induced cross-linking of the two strands of double-helical DNA by a psoralen covalently linked to a triple helix-forming oligonucleotide," Proceedings of the National Academy of Sciences of the United States of America, 88(13):5602-5606.
Takeshita et al., (1987). "Oligodeoxynucleotides containing synthetic abasic sites. Model substrates for DNA polymerases and apurinic/apyrimidinic endonucleases," The Journal of biological chemistry, 262(21):10171-10179.
Thompson et al., (1994). "Clustal W: improving the sensitivity of progressive multiple sequence alignment through sequence weighting, position-specific gap penalties and weight matrix choice," Nucleic acids research, 22(22):4673-4680.
Timmons et al., (1998). "Specific interference by ingested dsRNA," Nature, 395(6705):854.
Torney et al., (2007). "Mesoporous silica nanoparticles deliver DNA and chemicals into plants," Nature nanotechnology, 2(5):295-300.
Van Camp et al., (1996). "Tissue-specific activity of two manganese superoxide dismutase promoters in transgenic tobacco," Plant physiology, 112(2):525-535.
Velten et al., (1984). "Isolation of a dual plant promoter fragment from the Ti plasmid of Agrobacterium tumefaciens," The EMBO journal, 3(12):2723-2730.
Von Heijne et al., (1991). "CHLPEP—A database of chloroplast transit peptides," Plant Mol Biol Rep 9:104-126.
Wan et al., (1994). "Generation of Large Numbers of Independently Transformed Fertile Barley Plants," Plant physiology, 104(1):37-48.
Wang et al., (1988). "Carcinogens can induce homologous recombination between duplicated chromosomal sequences in mouse L cells," Molecular and cellular biology, 8(1):196-202.
Wang et al., (1995). "Targeted mutagenesis in mammalian cells mediated by intracellular triple helix formation," Molecular and cellular biology, 15(3):1759-1768.
Wang et al., (1996). "Mutagenesis in mammalian cells induced by triple helix formation and transcription-coupled repair," Science, 271(5250):802-805.
Wang et al., (2008). "Hairpin RNAs derived from RNA polymerase II and polymerase III promoter-directed transgenes are processed differently in plants," RNA, 14(5):903-913.
Winkler et al., (1998). "PCR-based identification of T-DNA insertion mutants," Methods in molecular biology, 82:129-136.
Wong et al., (1987). "Homologous recombination between coinjected DNA sequences peaks in early to mid-S phase," Molecular and cellular biology, 7(6):2294-2295.
Yamamoto et al., (1994). "The promoter of a pine photosynthetic gene allows expression of a beta-glucuronidase reporter gene in transgenic rice plants in a light-independent but tissue-specific manner," Plant & cell physiology, 35(5):773-778.
Yamamoto et al., (1997). "Light-responsive elements of the tobacco PSI-D gene are located both upstream and within the transcribed region," The Plant journal : for cell and molecular biology, 12(2):255-265.
Zhang et al., (2013). "Transcription activator-like effector nucleases enable efficient plant genome engineering," Plant physiology, 161(1):20-27.
Zhao et al., (1995). "Immunological characterization and chloroplast localization of the tryptophan biosynthetic enzymes of the flowering plant *Arabidopsis thaliana*," The Journal of biological chemistry, 270(11):6081-6087.

\* cited by examiner

FIG. 1A

```
BnSHP-2C    ATGGAGGAAGGTGGGAGTAGTCACGACGCAGAGAGTAACAAGAAGCTAGTAAGAGGGAAG
BnSHP-2A    ATGGAGGAAGGTGGGAGTAGTCACGACGCAGAGAGTAGCAAGAAGCTAGTAAGAGGGAAG
AtSHP1      ATGGAGGAAGGTGGGAGTAGTCACGACGCAGAGAGTAGCAAGAAACTAGGGAGAGGGAAA
BnSHP-4A    ATGGAGGGTGGTGCGAGTGATGAAGTAGCAGAGAGCAGCAAGAAGATAGGGAGAGGGAAG
BnSHP-4C    ATGGAGGGTGGTGCGAGTGATGAGGTAGCAGAGAGCAGCAAGAAGATAGGGAGAGGGAAG
AtSHP2      ATGGAGGGTGGTGCGAGTAATGAAGTAGCAGAGAGCAGCAAGAAGATAGGGAGAGGGAAG
BnSHP-3A    ATGGAGGAAGGTGGGAGTAGTCACGACGCAGAGAGTAACAAGAAGCTAGTGAGAGGGAAG
BnSHP-3C    ATGGAGGAAGGTGGGAGTAGTCACGACGCAGAGAGTAACAAGAAGCTAGTGAGAGGGAAG
BnSHP-1A    ATGGATGAAGGTGGGAGTAGTCACGATGCAGAGAGTAGCAAGAAGATAGGTAGAGGGAAG
BnSHP-1C    ATGGATGAAAGTGGGAGTAGTCACGATGCAGAGAGTAGCAAGAAGATAGGTAGAGGGAAG
            *****  *  *** ****  *  *  *;  *******  * ******  ***   ********

BnSHP-2C    ATAGAGATAAAGAGGATAGAGAACACAACAAGTCGTCAAGTAACTTTCTGTAAACGACGC
BnSHP-2A    ATAGAGATAAAGAGGATAGAGAACACAACAAGTCGTCAAGTAACTTTCTGTAAACGACGC
AtSHP1      ATAGAGATAAAGAGGATAGAGAACACAACAAATCGTCAAGTTACTTTCTGCAAACGACGC
BnSHP-4A    ATAGAGATAAAGAGGATAGAGAACACCACGAATCGCCAAGTCACTTTCTGCAAAAGACGC
BnSHP-4C    ATAGAGATAAAGAGGATAGAGAACACCACGAATCGCCAAGTCACTTTCTGCAAAAGACGC
AtSHP2      ATAGAGATAAAGAGGATAGAGAACACTACGAATCGTCAAGTCACTTTCTGCAAACGACGC
BnSHP-3A    ATAGAGATAAAGAGGATAGAGAACACGACAAGTCGTCAGGTAACTTTCTGCAAACGACGC
BnSHP-3C    ATAGAGATAAAGAGGATAGAGAACACGACAAGTCGTCAAGTAACTTTCTGCAAACGACGC
BnSHP-1A    ATAGAGATAAAGAGGATAGAGAACACAACAAATCGTCAAGTAACCTTCTGCAAACGACGC
BnSHP-1C    ATAGAGATAAAGAGGATAGAGAACACAACAAATCGTCAAGTAACCTTCTGCAAACGACGC
            **************************  **.* *** ** **  **  *****  ***.*****

BnSHP-2C    AATGGTCTTCTTAAGAAAGCTTATGAGCTTTCTGTCTTGTGTGATGCTGAAGTTGCCCTC
BnSHP-2A    AATGGTCTTCTTAAGAAAGCTTATGAGCTTTCTGTCTTGTGTGATGCTGAAGTTGCCCTC
AtSHP1      AATGGTCTTCTCAAGAAAGCTTATGAACTCTCTGTCTTGTGTGATGCCGAAGTTGCCCTC
BnSHP-4A    AATGGTCTGCTCAAGAAAGCTTATGAGCTCTCTGTCTTGTGTGACGCTGAGGTTGCTCTT
BnSHP-4C    AATGGTCTGCTTAAGAAAGCTTATGAGCTCTCTGTCTTGTGTGACGCTGAGGTTGCTCTT
AtSHP2      AATGGTTTACTCAAGAAAGCTTATGAGCTCTCTGTCTTGTGTGACGCTGAGGTTGCTCTT
BnSHP-3A    AATGGTCTTCTCAAGAAAGCTTATGAGCTCTCTGTCTTGTGTGATGCGGAAGTTGCACTT
BnSHP-3C    AATGGTCTTCTCAAGAAAGCTTATGAGCTCTCTGTCTTGTGTGATGCGGAAGTTGCACTT
BnSHP-1A    AATGGTCTTCTCAAGAAAGCTTATGAGCTCTCTGTCTTGTGTGATGCTGAAGTTGCCCTC
BnSHP-1C    AATGGTCTTCTCAAGAAAGCTTATGAGCTCTCTGTCTTGTGTGATGCTGAAGTTGCCCTC
            ******  *  ** *************.**  ****************  **.******  **

BnSHP-2C    GTCATCTTCTCGACTCGTGGCCGTCTCTATGAGTACGCCAACAACAGG..
BnSHP-2A    GTCATCTTCTCCACTCGTGGCCGTCTCTATGAGTACGCCAACAACAGG..
AtSHP1      GTCATCTTCTCCACTCGTGGCCGTCTCTATGAGTACGCCAACAACAGC..
BnSHP-4A    GTCATCTTCTCCACTCGCGGTCGTCTCTACGAGTACGCCAACAACAGG..
BnSHP-4C    GTCATCTTCTCCACTCGAGGTCGTCTCTACGAGTACGCCAACAACAGG..
AtSHP2      GTCATCTTCTCCACTCGAGGCCGTCTCTACGAGTACGCCAACAACAGT..
BnSHP-3A    GTTGTCTTTTCCACTCGTGGCCGTCTCTATGAGTACGCTAACAACAGG..
BnSHP-3C    GTTGTCTTCTCCACTCGTGGCCGTCTCTATGAGTACGCTAACAACAGG..
BnSHP-1A    GTTATCTTCTCCACTCGTGGCCTTCTTTATGAGTACGCCAGCAACAGG..
BnSHP-1C    GTTATCTTCTCCACTCGTGGCCGTCTCTATGAATACGCCAGCAACAGG..
            **  .**** ** ****** **  *  *** ** **.****** *.******
```

FIG. 1B

```
AtSHP1     MEEGGSSHDAESSKKLGRGKIEIKRIENTTNRQVTFCKRRNGLLKKAYELSVLCDAEVALVIFSTRGRLYEYANNS_
AtSHP2     MEGGASNEVAESSKKIGRGKIEIKRIENTTNRQVTFCKRRNGLLKKAYELSVLCDAEVALVIFSTRGRLYEYANNS_
BnSHP-1A   MDEGGSSHDAESSKKIGRGKIEIKRIENTTNRQVTFCKRRNGLLKKAYELSVLCDAEVALVIFSTRGLLYEYASNR_
BnSHP-1C   MDESGSSHDAESSKKIGRGKIEIKRIENTTNRQVTFCKRRNGLLKKAYELSVLCDAEVALVIFSTRGRLYEYASNR_
BnSHP-2A   MEEGGSSHDAESSKKLVRGKIEIKRIENTTSRQVTFCKRRNGLLKKAYELSVLCDAEVALVIFSTRGRLYEYANNR_
BnSHP-2C   MEEGGSSHDAESNKKLVRGKIEIKRIENTTSRQVTFCKRRNGLLKKAYELSVLCDAEVALVIFSTRGRLYEYANNR_
BnSHP-3C   MEEGGSSHDAESNKKLVRGKIEIKRIENTTSRQVTFCKRRNGLLKKAYELSVLCDAEVALVVFSTRGRLYEYANNR_
BnSHP-3A   MEEGGSSHDAESNKKLVRGKIEIKRIENTTSRQVTFCKRRNGLLKKAYELSVLCDAEVALVVFSTRGRLYEYANNR_
BnSHP-4A   MEGGASDEVAESSKKIGRGKIEIKRIENTTNRQVTFCKRRNGLLKKAYELSVLCDAEVALVIFSTRGRLYEYANNR_
BnSHP-4C   MEGGASDEVAESSKKIGRGKIEIKRIENTTNRQVTFCKRRNGLLKKAYELSVLCDAEVALVIFSTRGRLYEYANNR_
           *.   *   *** **. ************** ****************************-***** ***** *
```

FIG. 7

| Line | SHP Gene KO Configuration (Genotype) | | | | | | | | Gene KO Description | C0 Greenhouse TissueLyser Frequency (Hz) | C1 Greenhouse TissueLyser Frequency (Hz) | C1 Field Test 1 TissueLyser Frequency (Hz) | C1/C2 Field Test 2 Geno/Grinder (rpm) |
|---|---|---|---|---|---|---|---|---|---|---|---|---|---|
| | 1A | 1C | 2A | 2C | 3A | 3C | 4A | 4C | | | | | |
| A05_0071 | 1 | 1 | 1 | -2 | 1 | 1 | 1 | -2 | 8KO | 17 | 22 | n/a | 1005 |
| A05_2013 | 1 | 1 | 1 | 1 | 1 | 1 | 1 | 1 | 8KO | 16.3 | 20 | n/a | 1065 |
| A05_1635 | 1 | 1 | 1 | 1 | -1 | wt | 1 | 1 | 7KO | 24 | 26 | n/a | 996 |
| A05_0342 | 1 | -1 | 1 | -2 | 1 | 1 | -2 | wt | 7KO | 18 | 22 | 20.3 | 1076 |
| A05_0113 | 1 | -2 | -2 | 1 | 1 | 1 | 1 | wt | 7KO | 16 | 20 | 19 | 1033 |
| A05_0277 | wt | 1 | -2 | 1 | 1 | 1 | 1 | wt | 6KO | 18 | 25 | 20.3 | 990 |
| A05_0272 | wt | 1 | 1 | 1 | wt | 1 | -2 | wt | 5KO | 16.7 | 19.3 | 19 | 978 |
| A05_1600 | wt | 1 | 1 | 1 | -1 | 1 | 1 | wt | 5KO | 15.7 | 20 | 20.3 | 900 |
| A05_0751 | wt | 1 | 1 | wt | -1 | 1 | 1 | wt | 5KO | 18.3 | 19.3 | n/a | 818 |
| A05_1894 | wt | wt | 1 | 1 | 1 | 1 | wt | -1 | 5KO | 16.5 | 19.3 | n/a | 966 |
| Commercial Line Check 1 | | | | | | | | | Positive check | 17.8 | 25.3 | 19.7 | 895 |
| Commercial Line Check 2 | | | | | | | | | Positive check | 17.5 | 25.3 | 19.7 | 970 |
| Wild-Type | | | | | | | | | Negative check | 14.3 | 16.7 | 16.7 | 744 |

SHATTERPROOF GENES AND MUTATIONS

CROSS-REFERENCE TO RELATED APPLICATIONS

This application is a national stage application under 35 U.S.C. § 371 of International Application No. PCT/US2019/012938, internationally filed on Jan. 9, 2019, which claims the benefit of U.S. Provisional Application No. 62/615,409, filed on Jan. 9, 2018, and U.S. Provisional Application No. 62/732,397, filed on Sep. 17, 2018, each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 165072000100SEQLIST.TXT, date recorded: Jun. 11, 2020, size: 90 KB).

FIELD

The present disclosure relates to compositions and methods pertaining to novel plant genes and gene products and also to plants having one or more gene mutations. In particular, the present disclosure provides shatterproof (SHP) genes and plants and/or plant cells bearing one or more mutations in a shatterproof gene; as well as methods of making and using such plants. In some embodiments the plant or plant cell is resistant to preharvest dehiscence.

BACKGROUND

Preharvest dehiscence of canola seed pods is a process of agronomic importance that causes significant yield loss as well as carry over of a crop into the subsequent growing season. Accordingly, there exists a need for improved methods of reducing or preventing preharvest dehiscence of seed pods, as well as for improved plants that exhibit improved resistance to or reduced susceptibility to preharvest dehiscence.

BRIEF SUMMARY

The present disclosure is based at least in part on the discovery that *Brassica* plants have eight shatterproof genes; and that causing mutations to one or more of such genes can reduce preharvest dehiscence in agriculture crops such as *Brassica* crops.

A shatterproof (SHP) gene as used herein means a gene having a sequence as represented by the *Brassica napus* SHP1A, SHP1C, SHP2A, SHP2C, SHP3A, SHP3C, SHP4A, SHP4C sequences as disclosed herein or in certain embodiments, homologs, variants or mutants thereof. The term "shatterproof homolog" or any variation refers to a shatterproof gene or shatterproof gene product found in another species that performs the same or substantially the same biological function as the *Brassica* genes and gene products disclosed herein and where the nucleic acid sequences of the coding region or polypeptide sequences (of the SHP gene product) are said to be "identical" or at least 50%, or at least 60%, or at least 70%, or at least 75%, or at least 80%, or at least 85%, or at least 90%, or at least 92%, or at least 95%, or at least 96%, or at least 97%, or at least 98% or at least 99% similar (also referred to as "percent identity" or "substantially identical") to one or more of SHP1A, SHP1C, SHP2A, SHP2C, SHP3A, SHP3C, SHP4A, SHP4C sequences as disclosed herein.

In a first aspect, provided is a method of preventing or reducing preharvest dehiscence in a plant, said method comprising mutating at least one endogenous shatterproof gene in a cell of said plant. In some embodiments the method includes (1) introducing into plant cells a gene repair oligonucleobase to produce plant cells with a mutant SHP gene; and (2) regenerating a non-transgenic plant having a mutated SHP gene from said selected plant cell. In some embodiments the method includes (1) introducing into plant cells a DNA cutter configured to specifically nick or cut a SHP gene to produce plant cells with a mutant SHP gene; and (2) regenerating a non-transgenic plant having a mutated SHP gene from said selected plant cell. In a related embodiment, provided is method comprising contacting a cell with a DNA cutter configured to specifically nick or cut a shatterproof gene. In a related aspect, provided are methods of making a mutation in a SHP gene. In some embodiments the method or methods as described herein may include exposing the cell to a DNA cutter and a GRON. In certain embodiments the methods include exposing a cell to a DNA cutter and a GRON wherein said GRON is modified with one or more of a Cy3 group, 3PS group, and a 2'O-methyl group. In some embodiments the method or methods may include exposing the cell to a DNA cutter without exposing the cell to a GRON. In some embodiments that include exposure to a DNA cutter, the DNA cutter specifically targets a SHP gene. In some embodiments the DNA cutter is one or more selected from a CRISPR which includes but is not limited to Cas9, Cpf1 and their corresponding homologues, orthologues and/or paralogues, a base editor, a TALEN, a zinc finger, meganuclease, and a DNA-cutting antibiotic. In some embodiments the DNA cutter can be plasmid (DNA), RNA and/or protein. In certain embodiments, the methods provided do not include contacting the plant or plant cell with any transgene. In some embodiments of any of the aspects and embodiments provided herein, the plant or plant cell is non-transgenic. In certain aspects, the mutation, alteration or modification to a SHP gene includes an insertion or deletion. In some embodiments the mutation, alteration or modification is or includes a nucleotide change or substitution. In some embodiments of the method, the alteration, mutation or modification introduces a premature stop codon. In some embodiments the alteration, mutation or modification introduces a frame shift mutation. In some embodiments of the compositions and methods provided herein, the mutation relative to a wildtype a SHP gene is an +1, −1, −2 nucleotide insertion or deletion (InDel). In certain embodiments of the compositions and methods provided herein, the mutation relative to a wildtype a SHP gene is an +1, −1, −2 nucleotide insertion or deletion (InDel) developed by a targeted mutation. In some embodiments of the methods provided herein, the mutation, modification or alteration in the SHP gene reduces or obviates the activity or expression of the SHP gene. In certain embodiments of the methods provided herein, at least one SHP gene; or at least two SHP genes; or at least three SHP genes; or at least four SHP genes; or at least five SHP genes; or at least six SHP genes; or at least seven SHP genes; or eight SHP genes are modified. In certain aspects, the mutation, alteration or modification includes an insertion or deletion. In some embodiments the mutation, alteration or modification includes a nucleotide change or substitution. In some embodiments of the method, the alteration, mutation or modification introduces a premature stop codon. In some embodiments of the methods provided herein, the mutation, modification or alteration in the SHP gene reduces or obviates the activity or expression of the SHP gene. In some embodiments, the plant or plant cell is a *Brassica* plant. In certain embodiments, provided is a plant or plant cell generated by the methods disclosed herein.

In one aspect provided is an isolated nucleic acid the sequence of SHP1A, SHP1C, SHP2A, SHP2C, SHP3A, SHP3C, SHP4A, or SHP4C as disclosed herein or a fragment thereof. In some embodiments, a fragment of one or more of the aforementioned SHP gene sequences includes at least 80%; or at least 85%, or at least 90%, or at least 92%, or at least 95%, or at least 96%, or at least 97%, or at least 98% or at least 99% of the entire sequence of the gene. In a related aspect, provided is an isolated amino acid sequence encoded by a SHP1A, SHP1C, SHP2A, SHP2C, SHP3A, SHP3C, SHP4A, or SHP4C nucleic acid sequence as disclosed herein or a fragment thereof.

In another aspect, provided is a plant or plant cell having at least three, or at least four, or at least five, or at least seven, or eight shatterproof genes having a sequence that is different than any naturally occurring shatterproof gene.

In one aspect, provided is a plant or plant cell having at least three, or at least four, or at least five, or at least seven, or eight endogenous shatterproof genes having a sequence that is different than any naturally occurring shatterproof gene.

In another aspect, provided is a canola plant or canola plant cell having at least one, or at least two, or at least three, or at least four, or at least five, or at least seven, or eight shatterproof genes having a sequence that is different than any naturally occurring shatterproof gene.

In certain aspects and embodiments, it is desirable to have dehiscence to occur (although not prematurely) and, thus, it may in some embodiments to retain a certain amount of activity of a gene product of one or more of the SHP1A, SHP1C, SHP2A, SHP2C, SHP3A, SHP3C, SHP4A, or SHP4C genes/loci. Accordingly, in one embodiment, provided is a plant or plant cell having three to seven SHP genes having a sequence that is different than any naturally occurring shatterproof gene. In another embodiment, provided is a plant or plant cell having three to six SHP genes having a sequence that is different than any naturally occurring shatterproof gene. In another embodiment, provided is a plant or plant cell having three to five SHP genes having a sequence that is different than any naturally occurring shatterproof gene. In another embodiment, provided is a plant or plant cell having four to six SHP genes having a sequence that is different than any naturally occurring shatterproof gene. In another embodiment, provided is a plant or plant cell having four or five SHP genes having a sequence that is different than any naturally occurring shatterproof gene. In another embodiment, provided is a plant or plant cell having three or four SHP genes having a sequence that is different than any naturally occurring shatterproof gene. In another embodiment, provided is a plant or plant cell having three SHP genes having a sequence that is different than any naturally occurring shatterproof gene. In another embodiment, provided is a plant or plant cell having four SHP genes having a sequence that is different than any naturally occurring shatterproof gene. In another embodiment, provided is a plant or plant cell having five SHP genes having a sequence that is different than any naturally occurring shatterproof gene. In another embodiment, provided is a plant or plant cell having six SHP genes having a sequence that is different than any naturally occurring shatterproof gene. In another embodiment, provided is a plant or plant cell having seven SHP genes having a sequence that is different than any naturally occurring shatterproof gene.

In a certain aspect, provided is a plant or plant cell having a mutation in a SHP1A, SHP1C, SHP2A, SHP2C, SHP3A, SHP3C, SHP4A, or SHP4C gene. In some embodiments of this aspect, the SHP gene is an endogenous SHP gene.

In another aspect, the present disclosure relates to a plant or part thereof including at least one mutation in at least one, at least two, at least three, at least four, at least five, at least six, at least seven, or eight nucleic acid sequences encoding SHATTERPROOF (SHP) genes. In some embodiments, the nucleic acid sequences have at least 90% sequence identity, at least 95% sequence identity, at least 98% sequence identity, or at least 99% sequence identity to nucleic acid sequences selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In some embodiments, the nucleic acid sequences are selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In some embodiments that may be combined with any of the preceding embodiments, the mutation is a frameshift mutation. In some embodiments, the frameshift mutation results in one or more nucleotide insertions or deletions as compared to the corresponding endogenous gene without the frameshift mutation. In some embodiments that may be combined with any of the preceding embodiments, the frameshift mutation results in a premature stop codon. In some embodiments that may be combined with any of the preceding embodiments, the mutation reduces or eliminates expression of the SHP gene and/or SHP polypeptide. In some embodiments that may be combined with any of the preceding embodiments, the plant exhibits reduced susceptibility to preharvest dehiscence. In some embodiments that may be combined with any of the preceding embodiments, the plant is selected from the group of *Brassica napus, Brassica rapa, Brassica oleracea, Brassica juncea, Brassica species, Raphanus sativus, Pisum sativum, Phaseolus vulgaris, Lens culinaris, Glycine max*, and *Fabaceae* species.

In another aspect, the present disclosure relates to a method of producing the plant or part thereof of any of the preceding embodiments, including the steps of: a) introducing mutations into plant cells, wherein the mutations are at least one mutation in at least one, at least two, at least three, at least four, at least five, at least six, at least seven, or eight nucleic acid sequences encoding SHP genes; b) selecting plant cells containing the mutations; and c) regenerating a plant having the mutations; wherein the plant exhibits reduced susceptibility to preharvest dehiscence. In some embodiments, wherein the mutations are introduced using one or more vectors, wherein the vectors include gene editing components selected from the group of a CRISPR/Cas9 system, a TALEN, a zinc finger, and a meganuclease designed to target a nucleic acid sequence encoding a SHP gene. In some embodiments, the mutations are introduced using a GRON system designed to target a nucleic acid sequence encoding a SHP gene. In some embodiments, the GRON system comprises one or more modifications selected from the group consisting of a Cy3 group, 3PS group, and a 2'O-methyl group. In some embodiments that may be combined with any of the preceding embodiments, the nucleic acid sequences have at least 90% sequence identity, at least 95% sequence identity, at least 98% sequence identity, or at least 99% sequence identity to nucleic acid sequences selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In some embodiments that may be combined with any of the preceding embodiments, the nucleic acid sequences are selected from the group of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8. In some embodiments that may be combined with any of the preceding embodiments, the mutation is selected from the group of a frameshift mutation, a frameshift mutation resulting in one or more nucleotide insertions or deletions as compared to the corresponding endogenous gene without the frameshift mutation, and a frameshift mutation resulting in a premature stop codon, and wherein the mutation reduces or eliminates expression of the SHP gene and/or SHP polypeptide. In some embodiments that may be combined with any of the preceding embodiments, the plant is selected from the group of *Brassica napus*, *Brassica rapa*, *Brassica oleracea*, *Brassica juncea*, *Brassica* species, *Raphanus sativus*, *Pisum sativum*, *Phaseolus vulgaris*, *Lens culinaris*, *Glycine max*, and *Fabaceae* species.

In another aspect, the present disclosure provides an $F_1$ plant, where the $F_1$ plant has the plant of any one of the preceding embodiments as a parent. In another aspect, the present disclosure provides a method of making plant seeds, the method including crossing the plant of any one of the preceding embodiments with another plant and harvesting seed therefrom. In another aspect, the present disclosure provides a method of making a plant of any one of the preceding embodiments, the method including selecting seeds from the cross of the plant of any one of the preceding embodiments with the plant of any one of the preceding embodiments to make the plant of any one of the preceding embodiments. In another aspect, the present disclosure provides a plant produced by growing the seed of any one of the preceding embodiments, where the plant has all the physiological and morphological characteristics of the plant of any one of the preceding embodiments.

BRIEF DESCRIPTION OF THE DRAWINGS

The patent or application file contains at least one drawing executed in color. Copies of this patent or patent application publication with color drawings will be provided by the office upon request and payment of the necessary fee.

FIGS. 1A-1B illustrate CLUSTAL multiple sequence alignments of partial nucleotide sequences and deduced amino acid sequences of *Brassica napus* SHATTERPROOF (BnSHP) genes and *Arabidopsis thaliana* SHP genes (AtSHP1 and AtSHP2). FIG. 1A illustrates CLUSTAL multiple sequence alignment of partial nucleotide sequences of BnSHP1A (SEQ ID NO: 30), BnSHP1C (SEQ ID NO: 31), BnSHP2A (SEQ ID NO: 23), BnSHP2C (SEQ ID NO: 22), BnSHP3A (SEQ ID NO: 28), BnSHP3C (SEQ ID NO: 29), BnSHP4A (SEQ ID NO: 25), BnSHP4C (SEQ ID NO: 26), AtSHP1 (SEQ ID NO: 24), and AtSHP2 (SEQ ID NO: 27) beginning at the start codon (*B. napus* nucleotide sequences obtained from gDNA of the BN2-SU line). FIG. 1B illustrates CLUSTAL multiple sequence alignment of deduced amino acid sequences of BnSHP1A (SEQ ID NO: 34), BnSHP1C (SEQ ID NO: 35), BnSHP2A (SEQ ID NO: 36), BnSHP2C (SEQ ID NO: 37), BnSHP3A (SEQ ID NO: 39), BnSHP3C (SEQ ID NO: 38), BnSHP4A (SEQ ID NO: 40), BnSHP4C (SEQ ID NO: 41), AtSHP1 (SEQ ID NO: 32), and AtSHP2 (SEQ ID NO: 33).

FIG. 2A illustrates developmental stages of fruit samples taken for SHP gene expression analysis: developmental stage 13=anthesis, when flowers open and self-pollinate; developmental stages 17-1, 17-2. 17-3, 17-4, and 17-5=fruits of increasing sizes during the elongation stage (Roeder and Yanofsky, 2006). FIG. 2B illustrates the percentage of total reads identified for each SHP gene at each fruit developmental stage after RT-PCR and NGS analysis (developmental stages shown from left to right for each SHP gene in the order 13, 17-1, 17-2, 17-3, 17-4, and 17-5).

FIG. 7 illustrates phenotype and genotype data of shatterproof KO canola lines and checks (controls).

DETAILED DESCRIPTION

Figure 2A:
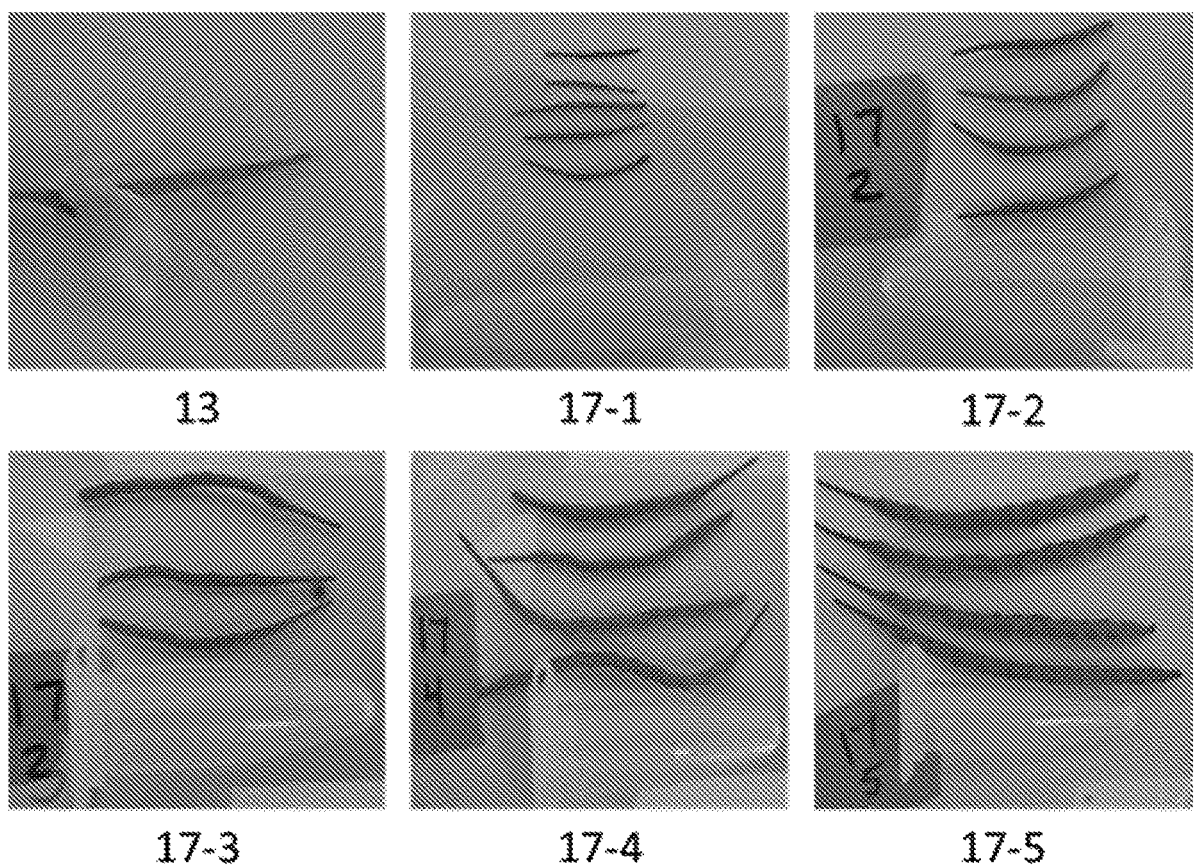
FIGS. 2A-2B illustrate SHP gene expression analysis by next generation sequencing (NGS).

Various aspects and embodiments of the present disclosure provide a plant having one or more SHP mutations and/or mutation combinations, methods of making such a plant, and methods for reducing preharvest dehiscence.

One skilled in the art readily appreciates that the present disclosure is well adapted to carry out the objects and obtain the ends and advantages mentioned, as well as those inherent therein. The examples provided herein are representative of preferred embodiments, are exemplary, and are not intended as limitations on the scope of the disclosure.

It will be readily apparent to a person skilled in the art that varying substitutions and modifications may be made to the disclosure disclosed herein without departing from the scope and spirit of the disclosure.

The disclosure illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

Thus, it should be understood that although the present disclosure has been specifically disclosed by preferred embodiments and optional features, modification, improvement, and variation of the disclosures disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Preharvest Dehiscence

Siliques or pods from *Brassica* plants release their seeds through a process called fruit dehiscence. Shedding of seed (also referred to as "seed shatter" or "pod shatter") by mature pods before or during crop harvest is a universal phenomenon with crops that develop dry dehiscent fruits. Premature seed shatter results in a reduced seed recovery, which represents a problem in crops that are grown primarily for the seeds, such as oil-producing *Brassica* plants, particularly oilseed rape. Another problem related to premature seed shattering is an increase in volunteer (weed) growth in the subsequent crop year.

Preharvest dehiscence of canola seed pods is a process of agronomic importance that causes significant yield loss as well as carryover of a crop into the subsequent growing season. In canola, pod shatter causes an annual yield loss of 20% and may result in losses of 50% when harvest is delayed, and under adverse weather conditions. Seed shattering occurs in ripe standing crops during hot and windy summers due to impact from other plants, and in windrows from the impact of harvest machinery (MacLeod, 1981; Child and Evans, 1989). In real terms, shatter results in a yield loss of $20-$25 per acre ($39M annual yield loss in the US) and swathing costs add an additional $6 per acre ($8.7 M annual additional direct cost; Barry Coleman, Northern Canola Growers Association).

Figure 4:
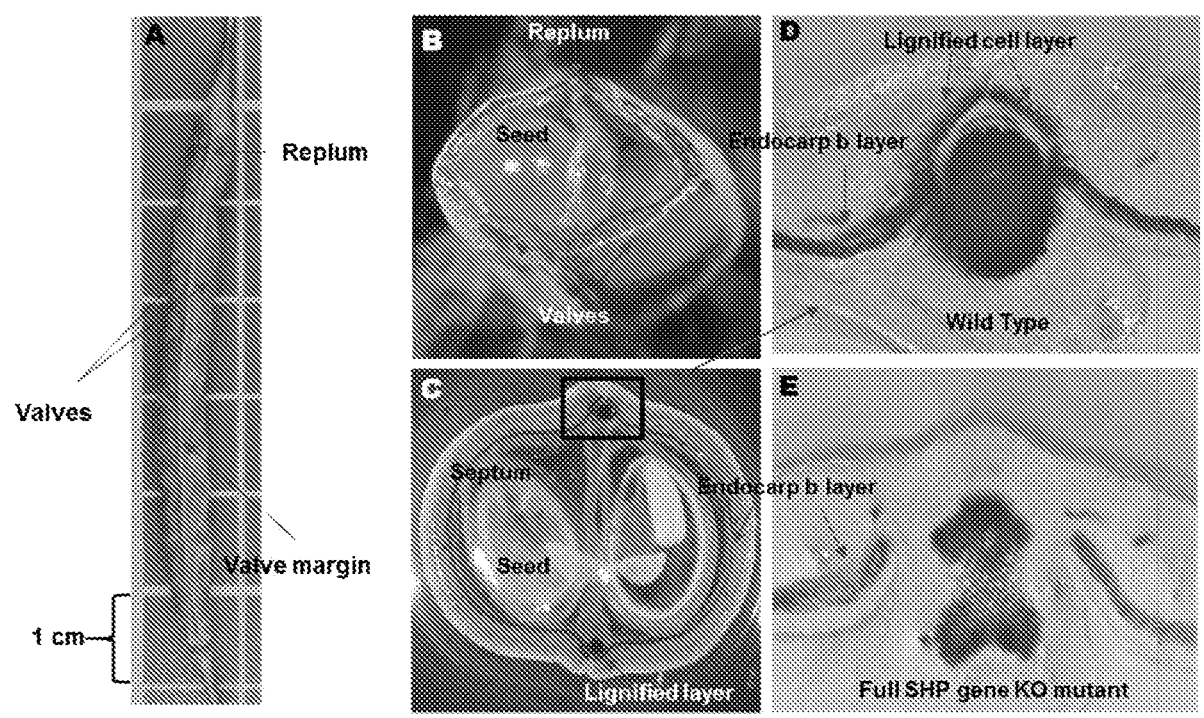
FIG. 4 illustrates phloroglucinol staining of lignified cell layers in canola pods (siliques). The left panel illustrates a silique (lengthwise image of full silique). Siliques are derived from two carpels that form two locules separated by the septum. The fruit walls are valves containing the seeds that are attached to the replum forming a suture. The top middle panel illustrates a transverse section of the silique valves containing the seeds attached to the septum. The bottom middle panel illustrates a transverse section of the silique valves containing the seeds attached to the septum stained with phloroglucinol, showing lignified cell layers in the region of attachment of the silique valve to the replum and the lignified endocarp-b cell layer. The top right panel illustrates lignified cell layers in a cross section of a wild type silique (phloroglucinol staining score=1). The bottom right panel illustrates the absence of lignified cell layer in a cross section of a pod from a full SHP knock-out (KO) mutant line (phloroglucinol staining score=5). The absence of the lignified cell layer in the region of attachment of the silique valve to the replum has been associated with a high level of shatter resistance in oilseed Brassicas.

As used herein, the fruit of the Brassicaceae develops from a gynoecium composed of two fused carpels, which, upon fertilization, grow to become a silique with two locules (valves) that contain the developing seeds (See FIG. 4, Example 4). The fruit walls are the valves that are attached to the replum (the persisting septa of the ovary) forming a suture, also called dehiscence zone (DZ), along the valve margins. The DZ typically consists of a thin layer of parenchyma cells that acts as a separation layer upon fruit ripening, when cell wall degrading enzymes, such as cellulases and polygalaturonases are secreted, reducing cellular cohesion, and predisposing pods to shattering by external mechanical forces (Meakin and Roberts, 1990a,b). The absence of the separation layer in the region of attachment of the silique valve to the replum has been associated with a high level of shatter resistance in oilseed Brassicas (Kadkol et al., 1986; Meakin and Roberts, 1990a,b; Liljegren et al., 2000).

The lignified cell layer, as used herein, refers to another layer of specialized cells along the valve margins that contribute to the opening of the fruit, in addition to the separation layer (See FIG. 4). At maturity, the lignified cell layer in the valve and the replum delimit the non-lignified separation layer in the valve margins. The stiffening of cell walls through lignification of the lignified margin layer, and the internal lignified endocarp b valve layer has been proposed to contribute mechanically to fruit opening (Spence et al., 1996). As the fruit dries, differential shrinkage of the remaining thin-walled valve cells relative to the rigid lignified margin and valve layers is thought to create internal tension, causing the shattering that is characteristic of fruit dehiscence.

SHATTERPROOF (SHP), as used herein, refer to transcription factors members of the MADS-box family involved in the differentiation of the DZ in developing pods in the Brassicaceae (Liljegren et al., 2000). Loss-of-function studies indicate that SHP promote cell wall lignification of the valve margin cells (i.e., lignified cell layer) in *Arabidopsis* fruit. *Arabidopsis* shp1shp2 double mutants develop a non-functional DZ that does not fully differentiate a layer of cells with lignified cell walls, nor a separation cell layer, and, as a consequence, the fruits are indehiscent and do not open at the end of development (Liljegren et al., 2000). SHP encoding genes are expressed at the valve margins from the early stages of gynoecium development, where they activate the expression of bHLH factors INDEHISCENT (IND), essential for both separation and lignified layer development, and ALCATRAZ (ALC), required only for separation layer formation (Roeder and Yanofsky, 2006).

As used herein, Oilseed Rape (syn. canola, rapeseed, *Brassica napus* L., spp. *oleifera*; genomes AACC, $2n=4\times=38$), also a member of the Brassicaceae, is an allopolyploid plant originated through spontaneous hybridization between turnip rape (*Brassica rapa* L.; genome AA, $2n=2\times=20$), and cabbage (*Brassica oleracea* L.; genome CC, $2n=2\times=18$) (Chalhoub et al., 2014). Homologs of *Arabidopsis* SHP1/2 (as well as other functionally-related transcription factors IND and ALC) have been found in canola, and molecular genetic research has previously shown several quantitative trait loci (QTL) associated with shattering with epistatic relationships between them (Gururaj, 2009; Raman et al, 2014).

Increased pod shatter resistance, as used herein, refers to the reduction of seed shattering of mature (dried) fruits, as a consequence of external mechanical forces in the laboratory and in the field. Laboratory tests simulate the process of pod shattering as it occurs under natural field conditions, and the results normally correlate with the field measurements. Field evaluation alone of shatter resistance can be inaccurate due to varying weather conditions during harvest time in different seasons and locations.

As used herein, fruit anatomical characters are associated with pod shatter resistance. Differentiation of the lignified valve margin cells and the separation cell layer determines the level of seed shattering. In *Arabidopsis*, the loss of phloroglucinol-stainable lignified valve margin cells positively correlates with a higher resistance of the pods to mechanical shatter. Phloroglucinol is a common dye used to stain cell wall lignin in plant tissue. After staining with phloroglucinol, lignified cell walls appear red-violet, and the intensity of the stain (color) positively correlates with the level of lignin deposition and differentiation of the cells. Lignified valve margin cells readily stain with phloroglucinol in cross sections of wild type fruits of *Arabidopsis* and Oil Seed Rape (OSR). The separation layer cells of the DZ do not contain lignin, and they are not stained with phloroglucinol. The fruits of *Arabidopsis* shp1shp2 double mutant plants do not differentiate valve margin cells with lignified cell walls, and therefore they are not stained with phloroglucinol (Liljegren et al., 2000).

A pod breaking test, as used herein, refers to a laboratory test that uses a tissue lyser to assess the shatter resistance of mature, fully dried pods. The shatterproof phenotype was determined by the level of valve separation found under controlled agitation of the pods. For this test, single pods are placed in a 96 well deep trough container and secured in the arms of a TissueLyser II (Qiagen, Germany). The single pod samples are run on the TissueLyser for 30 seconds at frequencies of 22, 23, 24, 25, 26, 27, 28, 29, and 30 Hz. Four single pods reps per plant are tested at each frequency. The phenotype is scored on a scale of 1-5 (See e.g. Example 4). An intact pod is given a score of one, a partially split pod with connected valves is scored a two, a score of three represents the separation of one valve, and a score of four indicates that both valves are separated from the replum. A high correlation is found between the shaking frequency to shatter score of dried pods and the phloroglucinol staining score of lignified layers of developing pods (r=0.797). This demonstrated that the lignified layer staining of fruits and the shaking frequency to shatter test could be used to effectively evaluate the shatterproof trait.

Pod shattering could also be determined using the Geno/Grinder 2010 (SPEX Sample Prep, USA). In this case, the shatterproof phenotype is determined by the level of valve separation found under controlled agitation of the pods. To test the valve separation, 12-24 pods are placed into a 96 well deep trough container and secured in the arms of a Geno/Grinder 2010. The containers holding pod samples are run for 20 seconds at different rpm (for example at 720, 750, 780, 810, 840, 870, 900, 930, 960, 990, 1020, 1050, 1080 rpm). At the end of the run, the container is taken off the machine and the shattering score is given to each pod according to the score table (see Example 4). When the average shattering score under the certain rpm is greater than 2.5, the rpm value will be the pod shattering value for the line.

Shatterproof (SHP) Genes

The present disclosure generally relates to plants having mutations in shatterproof (SHP) genes. In some embodiments, one or more mutations in one or more SHP genes results in increased resistance to/reduced susceptibility to preharvest dehiscence.

In some aspects, plants of the present disclosure are *Brassica napus* L., spp. *oleifera* (canola, oilseed rape) plants. Canola plants contain eight SHATTERPROOF (SHP) genes, designated BnSHP1A, BnSHP1C, BnSHP2A, BnSHP2C, BnSHP3A, BnSHP3C, BnSHP4A and BnSHP4C. In some aspects, plants of the present disclosure have at least one mutation in at least one SHP gene.

Certain aspects of the present disclosure relate to BnSHP1A. The nucleotide coding sequence of BnSHP1A is set forth in SEQ ID NO: 1. Provided herein are also homologs and orthologs of BnSHP1A. In some embodiments, a homolog or ortholog of BnSHP1A has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 1. In some embodiments, a nucleic acid sequence encoding a homolog or ortholog of BnSHP1A may also have one or more mutations.

Certain aspects of the present disclosure relate to BnSHP1C. The nucleotide coding sequence of BnSHP1C is set forth in SEQ ID NO: 2. Provided herein are also homologs and orthologs of BnSHP1C. In some embodiments, a homolog or ortholog of BnSHP1C has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 2. In some embodiments, a nucleic acid sequence encoding a homolog or ortholog of BnSHP1C may also have one or more mutations.

Certain aspects of the present disclosure relate to BnSHP2A. The nucleotide coding sequence of BnSHP2A is set forth in SEQ ID NO: 3. Provided herein are also homologs and orthologs of BnSHP2A. In some embodiments, a homolog or ortholog of BnSHP2A has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 3. In some embodiments, a nucleic acid sequence encoding a homolog or ortholog of BnSHP2A may also have one or more mutations.

Certain aspects of the present disclosure relate to BnSHP2C. The nucleotide coding sequence of BnSHP2C is set forth in SEQ ID NO: 4. Provided herein are also homologs and orthologs of BnSHP2C. In some embodiments, a homolog or ortholog of BnSHP2C has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:

4. In some embodiments, a nucleic acid sequence encoding a homolog or ortholog of BnSHP2C may also have one or more mutations.

Certain aspects of the present disclosure relate to BnSHP3A. The nucleotide coding sequence of BnSHP3A is set forth in SEQ ID NO: 5. Provided herein are also homologs and orthologs of BnSHP3A. In some embodiments, a homolog or ortholog of BnSHP3A has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 5. In some embodiments, a nucleic acid sequence encoding a homolog or ortholog of BnSHP3A may also have one or more mutations.

Certain aspects of the present disclosure relate to BnSHP3C. The nucleotide coding sequence of BnSHP3C is set forth in SEQ ID NO: 6. Provided herein are also homologs and orthologs of BnSHP3C. In some embodiments, a homolog or ortholog of BnSHP3C has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 6. In some embodiments, a nucleic acid sequence encoding a homolog or ortholog of BnSHP3C may also have one or more mutations.

Certain aspects of the present disclosure relate to BnSHP4A. The nucleotide coding sequence of BnSHP4A is set forth in SEQ ID NO: 7. Provided herein are also homologs and orthologs of BnSHP4A. In some embodiments, a homolog or ortholog of BnSHP4A has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 7. In some embodiments, a nucleic acid sequence encoding a homolog or ortholog of BnSHP4A may also have one or more mutations.

Certain aspects of the present disclosure relate to BnSHP4C. The nucleotide coding sequence of BnSHP4C is set forth in SEQ ID NO: 8. Provided herein are also homologs and orthologs of BnSHP4C. In some embodiments, a homolog or ortholog of BnSHP4C has a nucleic acid coding sequence that is at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO: 8. In some embodiments, a nucleic acid sequence encoding a homolog or ortholog of BnSHP4C may also have one or more mutations.

In some aspects, plants of the present disclosure have a mutation in BnSHP1A. In some embodiments, these plants may also have mutations in one or more SHP genes selected from BnSHP1C, BnSHP2A, BnSHP2C, BnSHP3A, BnSHP3C, BnSHP4A and BnSHP4C.

In some aspects, plants of the present disclosure have a mutation in BnSHP1C. In some embodiments, these plants may also have mutations in one or more SHP genes selected from BnSHP1A, BnSHP2A, BnSHP2C, BnSHP3A, BnSHP3C, BnSHP4A and BnSHP4C.

In some aspects, plants of the present disclosure have a mutation in BnSHP2A. In some embodiments, these plants may also have mutations in one or more SHP genes selected from BnSHP1A, BnSHP1C, BnSHP2C, BnSHP3A, BnSHP3C, BnSHP4A and BnSHP4C.

In some aspects, plants of the present disclosure have a mutation in BnSHP2C. In some embodiments, these plants may also have mutations in one or more SHP genes selected from BnSHP1A, BnSHP1C, BnSHP2A, BnSHP3A, BnSHP3C, BnSHP4A and BnSHP4C.

In some aspects, plants of the present disclosure have a mutation in BnSHP3A. In some embodiments, these plants may also have mutations in one or more SHP genes selected from BnSHP1A, BnSHP1C, BnSHP2A, BnSHP2C, BnSHP3C, BnSHP4A and BnSHP4C.

In some aspects, plants of the present disclosure have a mutation in BnSHP3C. In some embodiments, these plants may also have mutations in one or more SHP genes selected from BnSHP1A, BnSHP1C, BnSHP2A, BnSHP2C, BnSHP3A, BnSHP4A and BnSHP4C.

In some aspects, plants of the present disclosure have a mutation in BnSHP4A. In some embodiments, these plants may also have mutations in one or more SHP genes selected from BnSHP1A, BnSHP1C, BnSHP2A, BnSHP2C, BnSHP3A, BnSHP3C and BnSHP4C.

In some aspects, plants of the present disclosure have a mutation in BnSHP4C. In some embodiments, these plants may also have mutations in one or more SHP genes selected from BnSHP1A, BnSHP1C, BnSHP2A, BnSHP2C, BnSHP3A, BnSHP3C and BnSHP4A.

In some aspects, plants of the present disclosure have a mutation in at least one, at least two, at least three, at least four, at least five, at least six, at least seven, or eight of the SHP genes. In some aspects, plants of the present disclosure have a mutation in at least five, at least six, at least seven, or eight of the SHP genes.

In some aspects, the mutation may be a frameshift mutation, a frameshift mutation resulting in one or more nucleotide insertions or deletions as compared to the corresponding endogenous gene without the frameshift mutation, or a frameshift mutation resulting in a premature stop codon, wherein the mutation reduces or eliminates expression of the SHP gene and/or SHP polypeptide.

Methods of Identifying Sequence Similarity

Two polynucleotides or polypeptides are identical if the sequence of nucleotides or amino acid residues, respectively, in the two sequences is the same when aligned for maximum correspondence as described below. The terms "identical" or "percent identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. For polypeptides where sequences differ in conservative substitutions, the percent sequence identity may be adjusted upwards to correct for the conservative nature of the substitution. Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, Computer Applic. Biol. Sci. 4: 11-17 (1988) e.g., as implemented in the program PC/GENE (Intelligenetics, Mountain View, Calif., USA).

The phrases "substantially identical," and "percent identity" in the context of two nucleic acids or polypeptides, refer to sequences or subsequences that have at least 50%, advantageously 60%, preferably 70%, more preferably 80%, and most preferably 90-95% nucleotide or amino acid residue identity when aligned for maximum correspondence over a comparison window as measured using one of the following sequence comparison algorithms or by manual alignment and visual inspection. This definition also refers to the complement of a test sequence, which has substantial sequence or subsequence complementarity when the test sequence has substantial identity to a reference sequence.

One of skill in the art will recognize that two polypeptides can also be "substantially identical" if the two polypeptides are immunologically similar. Thus, overall protein structure may be similar while the primary structure of the two polypeptides displays significant variation. Therefore, a method to measure whether two polypeptides are substantially identical involves measuring the binding of monoclonal or polyclonal antibodies to each polypeptide. Two polypeptides are substantially identical if the antibodies specific for a first polypeptide bind to a second polypeptide with an affinity of at least one third of the affinity for the first polypeptide. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence relative to the reference sequence, based on the designated program parameters.

The percentage of "sequence similarity" is the percentage of amino acids or nucleotides which is either identical or changed viz. "sequence similarity"=percent sequence identity)+percent changes). Thus, whenever the term sequence "similarity" is used it embraces sequence "identity" and "changes" to the sequence at some percentage. In certain embodiments, the changes in a sequence permitted by the referenced percent sequence identity are all or nearly all conservative changes; that is, in those embodiments when a sequence is 90% identical, the remaining 10% are all or nearly all conservative changes. The term "nearly all" in this context refers to at least 75% of the permitted sequence changes are conservative changes, more preferably at least 85%, still more preferably at least 90%, and most preferably at least 95%.

Optimal alignment of sequences for comparison can be conducted, e.g., by the local homology algorithm of Smith & Waterman, 0.4dv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 5 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by software for alignments such as VECTOR NTI Version #11.5 by Life Technologies, Carlsbad, Calif., USA, by the procedures described in ClustalW, Thompson, J. D., Higgins, D. G. and Gibson, T. J. (1994) CLUSTALW: improving the sensitivity of progressive multiple sequence alignment through sequence weighting, position—specific gap penalties and weight matrix choice. Nucleic Acids Research, 22:4673-4680 or by visual inspection (see generally, Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1977) Nucleic Acids Res. 25: 33 89-3402, respectively. Software for performing BLAST analyses is publicly available through the National Center for Biotechnology Information (worldwide web address: ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1989)). In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Nucleic Acids and Delivery Thereof to Cells

Certain aspects of the present disclosure involve nucleic acids (e.g. SHP genes), as well as nucleic acids having one or more mutations. Various methods exist for inducing mutations in a nucleic acid, as described herein. In some embodiments, one or more nucleic acids may be delivered to a cell, as described herein.

Oligonucleobases

As used herein, an "oligonucleobase" is a polymer of nucleobases, which polymer can hybridize by Watson-Crick base pairing to a DNA having the complementary sequence.

Nucleobases comprise a base, which may be a purine, pyrimidine, or a derivative or analog thereof. Nucleobases include peptide nucleobases, the subunits of peptide nucleic acids, and morpholine nucleobases as well as nucleosides and nucleotides. Nucleosides are nucleobases that contain a pentosefuranosyl moiety, e.g., an optionally substituted riboside or 2'-deoxyriboside. Nucleosides can be linked by one of several linkage moieties, which may or may not contain phosphorus. Nucleosides that are linked by unsubstituted phosphodiester linkages are termed nucleotides.

An oligonucleobase chain may have a single 5' and 3' terminus, which are the ultimate nucleobases of the polymer. A particular oligonucleobase chain can contain nucleobases of all types. An oligonucleobase compound is a compound comprising one or more oligonucleobase chains that are complementary and hybridized by Watson-Crick base pairing. Nucleobases are either deoxyribo-type or ribo-type. Ribo-type nucleobases are pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

An oligonucleobase strand generically includes both oligonucleobase chains and segments or regions of oligonucleobase chains. An oligonucleobase strand has a 3' end and a 5' end. When an oligonucleobase strand is coextensive with a chain, the 3' and 5' ends of the strand are also 3' and 5' termini of the chain.

The oligonucleobase can be introduced into a plant cell using any method commonly used in the art, including but not limited to, microcarriers (biolistic delivery), microfibers (whiskers), electroporation, nucleofection, PEG-mediated delivery, direct DNA uptake and microinjection. Illustrative examples of an oligonucleobase are described below.

The description can be practiced with oligonucleobases having the conformations and chemistries described in the Kmiec I and Kmiec II patents which are incorporated herein by reference. Kmiec I teaches a method for introducing specific genetic alterations into a target gene. The oligonucleobases in Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; WO 99/40789; U.S. Pat. No. 6,870,075; and US Published Patent Application 20030084473, which are each hereby incorporated in their entirety, disclose additional molecules that can be used for the present description. The term "oligonucleobase" is used herein to denote the molecules that can be used in the methods of the present disclosure and include mixed duplex oligonucleotides, non-nucleotide containing molecules taught in Kmiec II, single stranded oligodeoxynucleotides and other molecules taught in the above noted patents and patent publications.

In one embodiment, the oligonucleobase is a mixed duplex oligonucleotide in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are incorporated herein by reference. As used herein, a 2'-fluoro, chloro or bromo derivative of a ribonucleotide or a ribonucleotide having a 2'-OH substituted with a substituent described in the Martin Applications or Sproat is termed a "2'-substituted ribonucleotide." As used herein the term "RNA-type nucleotide" means a 2'-hydroxyl or 2'-substituted nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a MDON by an unsubstituted phosphodiester linkage or any of the non-natural linkages taught by Kmiec I or Kmiec II.

In one embodiment of the present disclosure, the oligonucleobase or GRON is a mixed duplex oligonucleotide that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-substituted nucleotide. Particularly preferred embodiments of 2'-substituted ribonucleotides are 2'-fluoro, 2'-methoxy, 2'-propyloxy, 2'-allyloxy, 2'-hydroxylethyloxy, 2'-methoxyethyloxy, 2'-fluoropropyloxy and T-trifluoropropyloxy substituted ribonucleotides. More preferred embodiments of 2'-substituted ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotide having only a single type of 2'-substituted RNA-type nucleotide is more conveniently synthesized, the methods of the disclosure can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses such an "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target SHP gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identically the length of the heterologous region when a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

The change to be introduced into the target gene is encoded by the heterologous region. The change to be introduced into the SHP gene may be a change in one or more bases of the target gene sequence that changes the native amino acid in that position to the desired amino acid.

In another embodiment of the present disclosure, the oligonucleobase is a single stranded oligodeoxynucleotide mutational vector or SSOMV, which is disclosed in International Patent Application PCT/US00/23457, which is incorporated herein by reference in its entirety. The sequence of the SSOMV is based on the same principles as the mutational vectors described in U.S. Pat. Nos. 5,756,325; 5,871,984; 5,760,012; 5,888,983; 5,795,972; 5,780,296; 5,945,339; 6,004,804; and 6,010,907 and in International Publication Nos. WO 98/49350; WO 99/07865; WO 99/58723; WO 99/58702; WO 99/40789; U.S. Pat. No. 6,870,075; and US Published Patent Application 20030084473. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region will cause a substitution.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent, see supra. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotides be a pyrimidine. To the extent that is consistent with achieving the desired functional result it is preferred that both the mutator nucleotide and the targeted nucleotide in the complementary strand be pyrimidines. Particularly preferred are SSOMV that encode transversion mutations, i.e., a C or T mutator nucleotide is mismatched, respectively, with a C or T nucleotide in the complementary strand.

In addition to the oligodeoxynucleotide the SSOMV can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred as reagents to make SSOMV are the reagents sold as Cy3™ and Cy5™ by Glen Research, Sterling Va. (now GE Healthcare), which are blocked phosphoroamidites that upon incorporation into an oligonucleotide yield 3,3,3',3'-tetramethyl N,N'-isopropyl substituted indomonocarbocyanine and indodicarbocyanine dyes, respectively. Cy3 is the most preferred. When the indocarbocyanine is N-oxyalkyl substituted it can be conveniently linked to the 5' terminal of the oligodeoxynucleotide through as a phosphodiester with a 5' terminal phosphate. The chemistry of the dye linker between the dye and the oligodeoxynucleotide is not critical and is chosen for synthetic convenience. When the commercially available Cy3 phosphoramidite is used as directed the resulting 5' modification consists of a blocking substituent and linker together which are a N-hydroxypropyl, N'-phosphatidylpropyl 3,3,3',3'-tetramethyl indomonocarbocyanine.

In a preferred embodiment the indocarbocyanine dye is tetra substituted at the 3 and 3' positions of the indole rings. Without limitation as to theory these substitutions prevent the dye from being an intercalating dye. The identity of the substituents at these positions is not critical. The SSOMV can in addition have a 3' blocking substituent. Again the chemistry of the 3' blocking substituent is not critical.

In another embodiment the oligonucleotide may be a single-stranded oligodeoxynucleotide having a 3' end nucleotide, a 5' end nucleotide, having at least 25 deoxynucleotides and not more than 65 deoxynucleotides, and having a sequence comprising at least two regions each of at least 8 deoxynucleotides that are each, respectively, identical to at least two regions of the targeted chromosomal gene, which regions together are at least 24 nucleotides in length, and which regions are separated by at least one nucleotide in the sequence of the targeted chromosomal gene or in the sequence of the oligodeoxynucleotide or both such that the sequence of the oligodeoxynucleotide is not identical to the sequence of the targeted chromosomal gene. See U.S. Pat. No. 6,271,360 which is incorporated herein by reference.

The mutations herein described might also be obtained by mutagenesis (random, somatic or directed) and other DNA editing or nucleases using a repair template including, but not limited to, gene targeting using zinc finger nucleases, using Transcription Activator-Like Effector Nucleases (TALENs), using Clustered Regularly Interspaced Short Palindromic Repeats (CRISPRs). These nucleases can be plasmid (DNA) based, RNA and/or protein.

Microcarriers and Microfibers

The use of metallic microcarriers (microspheres) for introducing large fragments of DNA into plant cells having cellulose cell walls by projectile penetration is well known to those skilled in the relevant art (henceforth biolistic delivery). U.S. Pat. Nos. 4,945,050; 5,100,792 and 5,204,253 describe general techniques for selecting microcarriers and devices for projecting them. U.S. Pat. Nos. 5,484,956 and 5,489,520 describe the preparation of fertile transgenic corn using microprojectile bombardment of corn callus tissue. The biolistic techniques are also used in transforming immature corn embryos.

Specific conditions for using microcarriers in the methods of the present disclosure are described in International Publication WO 99/07865. In an illustrative technique, ice cold microcarriers (60 mg/ml), mixed duplex oligonucleotide (60 mg/ml) 2.5 M $CaCl_2$ and 0.1 M spermidine are added in that order; the mixture is gently agitated, e.g., by vortexing, for 10 minutes and let stand at room temperature for 10 minutes, whereupon the microcarriers are diluted in 5 volumes of ethanol, centrifuged and resuspended in 100% ethanol. Good results can be obtained with a concentration in the adhering solution of 8-10 µg/µl microcarriers, 14-17 µg/ml mixed duplex oligonucleotide, 1.1-1.4 M $CaCl_2$ and 18-22 mM spermidine. Optimal results were observed under the conditions of 8 µg/µl microcarriers, 16.5 µg/ml mixed duplex oligonucleotide, 1.3 M $CaCl_2$ and 21 mM spermidine.

Oligonucleobases can also be introduced into plant cells for the practice of the present disclosure using microfibers to penetrate the cell wall and cell membrane. U.S. Pat. No. 5,302,523 to Coffee, R., and Dunwell, J. M. (1994) describes the use of 30×0.5 µm and 10×0.3 µm silicon carbide fibers to facilitate transformation of suspension maize cultures of Black Mexican Sweet. Any mechanical technique that can be used to introduce DNA for transformation of a plant cell using microfibers can be used to deliver oligonucleobases for use in making the present SHP mutants. The process disclosed by Coffee, R., and Dunwell, J. M. (1994) in U.S. Pat. No. 5,302,523 can be employed with regenerable plant cell materials to introduce the present oligonucleobases to effect the mutation of the SHP gene.

An illustrative technique for microfiber delivery of an oligonucleobase is as follows: Sterile microfibers (2 µg) are suspended in 150 µl of plant culture medium containing about 10 µg of a mixed duplex oligonucleotide. A suspension culture is allowed to settle, and equal volumes of packed cells and the sterile fiber/nucleotide suspension are vortexed for 10 minutes and plated. Selective media are applied immediately or with a delay of up to about 120 hours as is appropriate for the particular trait.

Electroporation

In an alternative embodiment, the oligonucleobases can be delivered to the plant cell by electroporation of a protoplast derived from a plant part according to techniques that are well-known to one of ordinary skill in the art. See, e.g., Gallois et al., 1996, in Methods in Molecular Biology 55:89-107, Humana Press, Totowa, N.J.; Kipp et al., 1999, in Methods in Molecular Biology 133:213-221, Humana Press, Totowa, N.J.

Oligonucleobases can also be introduced into microspores by electroporation. Upon release of the tetrad, the microspore is uninucleate and thin-walled. It begins to enlarge and develops a germpore before the exine forms. A microspore at this stage is potentially more amenable to transformation with exogenous DNA than other plant cells. In addition, microspore development can be altered in vitro to produce either haploid embryos or embryogenic callus that can be regenerated into plants (Coumans et al., Plant Cell Rep. 7:618-621, 1989; Datta et al., Plant Sci. 67:83-88, 1990; Maheshwari et al., Am. J Bot. 69:865-879, 1982; Schaeffer, Adv. In Cell Culture 7:161-182, 1989; Swanson et al., Plant Cell Rep. 6:94-97, 1987). Thus, transformed microspores can be regenerated directly into haploid plants or dihaploid fertile plants upon chromosome doubling by standard methods. See also co-pending application U.S. Ser. No. 09/680,858 entitled Compositions and Methods for Plant Genetic Modification which is incorporated herein by reference.

Microspore electroporation can be practiced with any plant species for which microspore culture is possible, including but not limited to plants in the families Graminae, Leguminoceae, Cruciferaceae, Solanaceae, Cucurbitaceae, Rosaceae, Poaceae, Lilaceae, Rutaceae, Vitaceae, including such species as corn (*Zea mays*), wheat (*Triticum aestivum*), rice (*Oryza sativa*), oats, barley, canola (*Brassica napus, Brassica rapa, Brassica oleracea,* and *Brassica juncea*), cotton (*Gossypium hirsuitum* L.), various legume species (e.g., soybean (*Glycine max*), pea (*Pisum sativum*), etc.), grapes (*Vitis vinifera*), and a host of other important crop plants. Microspore embryogenesis, both from anther and microspore culture, has been described in more than 170 species, belonging to 68 genera and 28 families of dicotyledons and monocotyledons (Raghavan, Embryogenesis in Angiosperms: A Developmental and Experimental Study, Cambridge University Press, Cambridge, England, 1986; Rhagavan, Cell Differentiation 21:213-226, 1987; Raemakers et al., Euphytica 81:93-107, 1995). For a detailed discussion of microspore isolation, culture, and regeneration of double haploid plants from microspore-derived embryos (MDE) in *Brassica napus* L., see Nehlin, The Use of Rapeseed (*Brassica napus* L.) Microspores as a Tool for Biotechnological Applications, doctoral thesis, Swedish University of Agricultural Sciences, Uppsala, Sweden, 1999; also Nehlin et al., Plant Sci. 111:219-227, 1995, and Nehlin et al., Plant Sci. 111:219-227, 1995). Chromosome doubling from microspore or anther culture is a well-established technique for production of double-haploid homozygous plant lines in several crops (Heberle-Bors et al., In vitro pollen cultures: Progress and perspectives. In: Pollen Biotechnology. Gene expression and allergen characterization, vol. 85-109, ed. Mohapatra, S. S., and Knox, R. B., Chapman and Hall, New York, 1996).

Microspore electroporation methods are described in Jardinaud et al., Plant Sci. 93:177-184, 1993, and Fennell and Hauptman, Plant Cell Reports 11:567-570, 1992. Methods for electroporation of MDON into plant protoplasts can also be adapted for use in microspore electroporation.

Whiskers Technique

In yet another alternative embodiment, the oligonucleobase can be delivered to the plant cell by whiskers or microinjection of the plant cell. The so-called whiskers technique is performed essentially as described in Frame et al., 1994, Plant J. 6:941-948. The oligonucleobase is added to the whiskers and used to transform the plant cells. The oligonucleobase may be co-incubated with plasmids comprising sequences encoding proteins capable of forming recombinase complexes in plant cells such that recombination is catalyzed between the oligonucleotide and the target sequence in the SHP gene.

Other Delivery Methods

In an alternative embodiment, nucleic acids are embedded in microbeads composed of calcium alginate and taken up by plant protoplasts in the presence of the membrane-modifying agent polyethylene glycol (see, e.g., Sone et al., 2002; Liu et al., 2004).

In an alternative embodiment, nucleic acids frozen in water and introduced into plant cells by bombardment in the form of microparticles (see, e.g., Gilmore, 1991, U.S. Pat. No. 5,219,746; Brinegar et al.).

In an alternative embodiment, nucleic acids attached to nanoparticles are introduced into intact plant cells by incubation of the cells in a suspension containing the nanoparticle (see, e.g., Pasupathy et al., 2008) or by delivering them into intact cells through particle bombardment or into protoplasts by co-incubation (see, e.g., Torney et al., 2007).

In an alternative embodiment, nucleic acids complexed with penetrating peptides are delivered into cells by co-incubation (see, e.g., Chugh et al., 2008, WO 2008148223 A1; Eudes and Chugh).

In an alternative embodiment, nucleic acids are introduced into intact cells through electroporation (see, e.g., He et al., 1998, U.S. 2003/0115641 A1, Dobres et al.).

In an alternative embodiment, nucleic acids are delivered into cells of dry embryos by soaking them in a solution with nucleic acids (by soaking dry embryos in (see, e.g., Töpfer et al., 1989, Senaratna et al., 1991).

Targeted Gene Modification

Targeted genetic modification mediated by oligonucleotides is a valuable technique for use in the specific alteration of short stretches of DNA to create deletions, short insertions, and point mutations and may be used in conjunction with the disclosures herein, for example to cause one or more of the SHP mutations contemplated herein. These methods may in some embodiments involve DNA pairing/annealing, followed by a DNA repair event. First, the nucleic acid anneals with its complementary strand in the double-stranded DNA in a process mediated by cellular protein factors. This annealing creates a centrally located mismatched base pair (in the case of a point mutation), resulting in a structural perturbation that most likely stimulates the endogenous protein machinery to initiate the second step in the repair process: site-specific modification of the chromosomal sequence and/or that in organelles (e.g., mitochondria and chloroplasts). This newly introduced mismatch induces the DNA repair machinery to perform a second repair event, leading to the final revision of the target site. The present methods and compositions in various aspects and embodiments disclosed herein, may improve the methods by providing novel approaches which increase the availability of DNA repair components, thus increasing the efficiency and reproducibility of gene repair-mediated modifications to targeted nucleic acids.

Efficient methods for site-directed genomic modifications are desirable for research, clinical gene therapy, industrial microbiology and agriculture. One approach utilizes triplex-forming oligonucleotides (TFO) which bind as third strands to duplex DNA in a sequence-specific manner, to mediate directed mutagenesis. Such TFO can act either by delivering a tethered mutagen, such as psoralen or chlorambucil (Havre et al., Proc Nat'l Acad Sci, U.S.A. 90:7879-7883, 1993; Havre et al., J Virol 67:7323-7331, 1993; Wang et al., Mol Cell Biol 15:1759-1768, 1995; Takasugi et al., Proc Nat'l Acad Sci, U.S.A. 88:5602-5606, 1991; Belousov et al., Nucleic Acids Res 25:3440-3444, 1997), or by binding with sufficient affinity to provoke error-prone repair (Wang et al., Science 271:802-805, 1996).

Another strategy for genomic modification that may be used in conjunction with the compositions and methods herein involves the induction of homologous recombination between an exogenous DNA fragment and the targeted gene. This approach has been used successfully to target and disrupt selected genes in mammalian cells and has enabled the production of transgenic mice carrying specific gene knockouts (Capeechi et al., Science 244:1288-1292, 1989; Wagner, U.S. Pat. No. 4,873,191). This approach involves the transfer of selectable markers to allow isolation of the desired recombinants. Without selection, the ratio of homologous to non-homologous integration of transfected DNA in typical gene transfer experiments is low, usually in the range of 1:1000 or less (Sedivy et al., Gene Targeting, W. H. Freeman and Co., New York, 1992). This low efficiency of homologous integration limits the utility of gene transfer for experimental use or gene therapy. The frequency of targeted mutation can be enhanced by damage to the target site from UV irradiation and selected carcinogens (Wang et al., Mol Cell Biol 8:196-202, 1988) as well as by site-specific endonucleases (Sedivy et al, Gene Targeting, W. H. Freeman and Co., New York, 1992; Rouet et al., Proc Nat'l Acad Sci, U.S.A. 91:6064-6068, 1994; Segal et al., Proc Nat'l Acad Sci, U.S.A. 92:806-810, 1995). In addition, DNA damage induced by triplex-directed psoralen photoadducts can stimulate recombination within and between extrachromosomal vectors (Segal et al., Proc Nat'l Acad Sci, U.S.A. 92:806-810, 1995; Faruqi et al., Mol Cell Biol 16:6820-6828, 1996; Glazer, U.S. Pat. No. 5,962,426).

Linear donor fragments are more efficacious for targeted mutation than their circular counterparts (Folger et al., Mol Cell Biol 2:1372-1387, 1982). Recombination can in certain embodiments also be influenced by the length of uninterrupted homology between both the donor and target sites, with short fragments often appearing to be ineffective substrates (Rubnitz et al., Mol Cell Biol 4:2253-2258, 1984). Nonetheless, the use of short fragments of DNA or DNA/RNA hybrids for gene correction is the focus of various strategies. (Kunzelmann et al., Gene Ther 3:859-867, 1996).

"Nucleic acid sequence," "nucleotide sequence" and "polynucleotide sequence" as used herein refer to an oligonucleotide or polynucleotide, and fragments or portions thereof, and to DNA or RNA of genomic or synthetic origin which may be single- or double-stranded and represent the sense or antisense strand.

As used herein, the terms "oligonucleotide" and "oligomer" refer to a polymer of nucleobases. In some embodiments an "oligonucleotide" or "oligomer" may be of at least about 8 nucleobases or may have as many as about 1,500 nucleobases or more. In certain embodiments, an "oligonucleotide" or "oligomer" may be any length as contemplated herein.

The terms "DNA-modifying molecule" and "DNA-modifying reagent" as used herein refer to a molecule which is capable of recognizing and specifically binding to a nucleic acid sequence in the genome of a cell, and which is capable of modifying a target nucleotide sequence within the genome, wherein the recognition and specific binding of the DNA-modifying molecule to the nucleic acid sequence is protein-independent. The term "protein-independent" as used herein in connection with a DNA-modifying molecule means that the DNA-modifying molecule does not require the presence and/or activity of a protein and/or enzyme for the recognition of, and/or specific binding to, a nucleic acid sequence. DNA-modifying molecules are exemplified, but not limited to triplex forming oligonucleotides, peptide nucleic acids, polyamides, and oligonucleotides which are intended to promote gene conversion. The DNA-modifying molecules of the present disclosure are in certain embodiments distinguished from the prior art's nucleic acid sequences which are used for homologous recombination (Wong & Capecchi, Molec. Cell. Biol. 7:2294-2295, 1987) in that the prior art's nucleic acid sequences which are used for homologous recombination are protein-dependent. The term "protein-dependent" as used herein in connection with a molecule means that the molecule requires the presence and/or activity of a protein and/or enzyme for the recognition of, and/or specific binding of the molecule to, a nucleic acid sequence. Methods for determining whether a DNA-modifying molecule requires the presence and/or activity of a protein and/or enzyme for the recognition of, and/or specific binding to, a nucleic acid sequence are within the skill in the art (see, e.g., Dennis et al. Nucl. Acids Res. 27:4734-4742, 1999). For example, the DNA-modifying molecule may be incubated in vitro with the nucleic acid sequence in the absence of any proteins and/or enzymes. The detection of specific binding between the DNA-modifying molecule and the nucleic acid sequence demonstrates that the DNA-modifying molecule is protein-independent. On the other hand, the absence of specific binding between the DNA-modifying molecule and the nucleic acid sequence demonstrates that the DNA-modifying molecule is protein-dependent and/or requires additional factors.

"Triplex forming oligonucleotide" (TFO) is defined as a sequence of DNA or RNA that is capable of binding in the major grove of a duplex DNA or RNA helix to form a triple helix. Although the TFO is not limited to any particular length, a preferred length of the TFO is 250 nucleotides or less, 200 nucleotides or less, or 100 nucleotides or less, or from 5 to 50 nucleotides, or from 10 to 25 nucleotides, or from 15 to 25 nucleotides. Although a degree of sequence specificity between the TFO and the duplex DNA is necessary for formation of the triple helix, no particular degree of specificity is required, as long as the triple helix is capable of forming. Likewise, no specific degree of avidity or affinity between the TFO and the duplex helix is required as long as the triple helix is capable of forming. While not intending to limit the length of the nucleotide sequence to which the TFO specifically binds in one embodiment, the nucleotide sequence to which the TFO specifically binds is from 1 to 100, in some embodiments from 5 to 50, yet other embodiments from 10 to 25, and in other embodiments from 15 to 25, nucleotides. Additionally, "triple helix" is defined as a double-helical nucleic acid with an oligonucleotide bound to a target sequence within the double-helical nucleic acid. The "double-helical" nucleic acid can be any double-stranded nucleic acid including double-stranded DNA, double-stranded RNA and mixed duplexes of DNA and RNA. The double-stranded nucleic acid is not limited to any particular length. However, in preferred embodiments it has a length of greater than 500 bp, in some embodiments greater than 1 kb and in some embodiments greater than about 5 kb. In many applications the double-helical nucleic acid is cellular, genomic nucleic acid. The triplex forming oligonucleotide may bind to the target sequence in a parallel or anti-parallel manner.

"Peptide Nucleic Acids," "polyamides" or "PNA" are nucleic acids wherein the phosphate backbone is replaced with an N-aminoethylglycine-based polyamide structure. PNAs have a higher affinity for complementary nucleic acids than their natural counter parts following the Watson-Crick base-pairing rules. PNAs can form highly stable triple helix structures with DNA of the following stoichiometry: (PNA)2.DNA. Although the peptide nucleic acids and polyamides are not limited to any particular length, a preferred length of the peptide nucleic acids and polyamides is 200 nucleotides or less, in some embodiments 100 nucleotides or less, and in some embodiments from 5 to 50 nucleotides long. While not intending to limit the length of the nucleotide sequence to which the peptide nucleic acid and polyamide specifically binds, in one embodiment, the nucleotide sequence to which the peptide nucleic acid and polyamide specifically bind is from 1 to 100, in some embodiments from 5 to 50, yet other embodiments from 5 to 25, and other embodiments from 5 to 20, nucleotides.

The term "capable of modifying DNA" or "DNA modifying means" refers to procedures, as well as endogenous or exogenous agents or reagents that can induce, or can aid in the induction of, changes to the nucleotide sequence of a targeted segment of DNA. Such changes may be made by the deletion, addition or substitution of one or more bases on the targeted DNA segment. It is not necessary that the DNA sequence changes confer functional changes to any gene encoded by the targeted sequence. Furthermore, it is not necessary that changes to the DNA be made to any particular portion or percentage of the cells.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences that do not encode an mRNA or protein product (e.g., promoter sequence, enhancer sequence, polyadenylation sequence, termination sequence, regulatory RNAs such as miRNA, etc.).

"Amino acid sequence," "polypeptide sequence," "peptide sequence" and "peptide" are used interchangeably herein to refer to a sequence of amino acids.

"Target sequence," as used herein, refers to a double-helical nucleic acid comprising a sequence that is the subject of interest. In some embodiments a target sequence may be greater than 8 nucleotides in length and in some embodiments less than 1,500 nucleotides in length. In some embodiments, the target sequence is between 8 to 30 bases. In some embodiments the target sequence may be between about 75 and 250 bases in length. In certain embodiments the target sequence may be a length complimentary to the length of an oligonucleotide as contemplated herein. The target sequence, in general, is defined by the nucleotide sequence on one of the strands on the double-helical nucleic acid.

As used herein, a "purine-rich sequence" or "polypurine sequence" when made in reference to a nucleotide sequence on one of the strands of a double-helical nucleic acid sequence is defined as a contiguous sequence of nucleotides wherein greater than 50% of the nucleotides of the target sequence contain a purine base. However, it is preferred that the purine-rich target sequence contain greater than 60% purine nucleotides, in some embodiments greater than 75% purine nucleotides, in other embodiments greater than 90% purine nucleotides and yet other embodiments 100% purine nucleotides.

As used herein, a "pyrimidine-rich sequence" or "polypyrimidine sequence" when made in reference to a nucleotide sequence on one of the strands of a double-helical nucleic acid sequence is defined as a contiguous sequence of nucleotides wherein greater that 50% of the nucleotides of the target sequence contain a pyrimidine base. However, it is preferred that the pyrimidine-rich target sequence contain greater than 60% pyrimidine nucleotides and, in some embodiments, greater than 75% pyrimidine nucleotides. In some embodiments, the sequence contains greater than 90% pyrimidine nucleotides and, in other embodiments, is 100% pyrimidine nucleotides.

A "variant" of a first nucleotide sequence is defined as a nucleotide sequence which differs from the first nucleotide sequence (e.g., by having one or more deletions, insertions, or substitutions that may be detected using hybridization assays or using DNA sequencing). Included within this definition is the detection of alterations or modifications to the genomic sequence of the first nucleotide sequence. For example, hybridization assays may be used to detect (1) alterations in the pattern of restriction enzyme fragments capable of hybridizing to the first nucleotide sequence when comprised in a genome (i.e., RFLP analysis), (2) the inability of a selected portion of the first nucleotide sequence to hybridize to a sample of genomic DNA which contains the first nucleotide sequence (e.g., using allele-specific oligonucleotide probes), (3) improper or unexpected hybridization, such as hybridization to a locus other than the normal chromosomal locus for the first nucleotide sequence (e.g., using fluorescent in situ hybridization (FISH) to metaphase chromosomes spreads, etc.). One example of a variant is a mutated wild type sequence.

The terms "nucleic acid" and "unmodified nucleic acid" as used herein refer to any one of the known four deoxyribonucleic acid bases (i.e., guanine, adenine, cytosine, and thymine). The term "modified nucleic acid" refers to a nucleic acid whose structure is altered relative to the structure of the unmodified nucleic acid. Illustrative of such modifications would be replacement covalent modifications of the bases, such as alkylation of amino and ring nitrogens as well as saturation of double bonds.

As used herein, the terms "mutation" and "modification" and grammatical equivalents thereof when used in reference to a nucleic acid sequence are used interchangeably to refer to a deletion, insertion, substitution, strand break, and/or introduction of an adduct. A "deletion" is defined as a change in a nucleic acid sequence in which one or more nucleotides is absent. An "insertion" or "addition" is that change in a nucleic acid sequence which has resulted in the addition of one or more nucleotides. A "substitution" results from the replacement of one or more nucleotides by a molecule which is a different molecule from the replaced one or more nucleotides. For example, a nucleic acid may be replaced by a different nucleic acid as exemplified by replacement of a thymine by a cytosine, adenine, guanine, or uridine. Pyrimidine to pyrimidine (e.g. C to T or T to C nucleotide substitutions) or purine to purine (e.g. G to A or A to G nucleotide substitutions) are termed transitions, whereas pyrimidine to purine or purine to pyrimidine (e.g. G to T or G to C or A to T or A to C) are termed transversions. Alternatively, a nucleic acid may be replaced by a modified nucleic acid as exemplified by replacement of a thymine by thymine glycol. Mutations may result in a mismatch. The term "mismatch" refers to a non-covalent interaction between two nucleic acids, each nucleic acid residing on a different polynucleic acid sequence, which does not follow the base-pairing rules. For example, for the partially complementary sequences 5'-AGT-3' and 5'-AAT-3', a G-A mismatch (a transition) is present. The terms "introduction of an adduct" or "adduct formation" refer to the covalent or non-covalent linkage of a molecule to one or more nucleotides in a DNA sequence such that the linkage results in a reduction (in some embodiments from 10% to 100%, in other embodiments from 50% to 100%, and in some embodiments from 75% to 100%) in the level of DNA replication and/or transcription.

The term "DNA cutter" refers to a moiety that effects a strand break. Non-limited examples include meganucleases, TALEs/TALENs, antibiotics, zinc fingers and CRISPRs or CRISPR/Cas systems.

The term "strand break" when made in reference to a double stranded nucleic acid sequence includes a single-strand break and/or a double-strand break. A single-strand break (a nick) refers to an interruption in one of the two strands of the double stranded nucleic acid sequence. This contrasts with a double-strand break which refers to an interruption in both strands of the double stranded nucleic acid sequence, which may result in blunt or staggered ends. Strand breaks may be introduced into a double stranded nucleic acid sequence either directly (e.g., by ionizing radiation or treatment with certain chemicals) or indirectly (e.g., by enzymatic incision at a nucleic acid base). In certain embodiments, a DNA cutter may have selectivity for certain specific sequences, such as in the case of a CRISPR, a zinc finger, a meganuclease, a TALEN as described herein.

The terms "mutant cell" and "modified cell" refer to a cell which contains at least one modification in the cell's genomic sequence.

The term "portion" when used in reference to a nucleotide sequence refers to fragments of that nucleotide sequence. The fragments may range in size from 5 nucleotide residues to the entire nucleotide sequence minus one nucleic acid residue.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer one or more DNA segment from one cell to another.

The terms "in operable combination," "in operable order" and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that a functional protein is produced.

The term "transfection" as used herein refers to the introduction of foreign DNA into cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofectin, protoplast fusion, retroviral infection, biolistics (i.e., particle bombardment) and the like.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total". "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids. For the sake of convenience, the terms "polynucleotides" and "oligonucleotides" include molecules which include nucleosides.

The terms "homology" and "homologous" as used herein in reference to nucleotide sequences refer to a degree of complementarity with other nucleotide sequences. There may be partial homology or complete homology (i.e., identity). When used in reference to a double-stranded nucleic acid sequence such as a cDNA or genomic clone, the term "substantially homologous" refers to any nucleic acid sequence (e.g., probe) which can hybridize to either or both strands of the double-stranded nucleic acid sequence under conditions of low stringency as described above. A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested using a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 68° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 2.0×SSPE, 0.1% SDS at room temperature when a probe of about 100 to about 1000 nucleotides in length is employed.

In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5×SSPE, 1% SDS, 5×Denhardt's reagent and 100 µg/ml denatured salmon sperm DNA followed by washing in a solution comprising 0.1×SSPE and 0.1% SDS at 68° C. when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids.

As used herein the term "hybridization complex" refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: $Tm=81.5+0.41(\% G+C)$, when a nucleic acid is in aqueous solution at 1 M NaCl (see e.g., Anderson and Young, Quantitative Filter Hybridization, in Nucleic Acid Hybridization, 1985). Other references include more sophisticated computations which take structural as well as sequence characteristics into account for the calculation of Tm.

As used herein the term "stringency" is used in reference to the conditions of temperature, ionic strength, and the presence of other compounds such as organic solvents, under which nucleic acid hybridizations are conducted. "Stringency" typically occurs in a range from about Tm −5° C. (5° C. below the melting temperature of the probe) to about 20° C. to 25° C. below Tm. As will be understood by those of skill in the art, a stringent hybridization can be used to identify or detect identical polynucleotide sequences or to identify or detect similar or related polynucleotide sequences.

The terms "specific binding," "binding specificity," and grammatical equivalents thereof when made in reference to the binding of a first nucleotide sequence to a second nucleotide sequence, refer to the preferential interaction between the first nucleotide sequence with the second nucleotide sequence as compared to the interaction between the second nucleotide sequence with a third nucleotide sequence. Specific binding is a relative term that does not require absolute specificity of binding; in other words, the term "specific binding" does not require that the second nucleotide sequence interact with the first nucleotide sequence in the absence of an interaction between the second nucleotide sequence and the third nucleotide sequence. Rather, it is sufficient that the level of interaction between the first nucleotide sequence and the second nucleotide sequence is greater than the level of interaction between the second nucleotide sequence with the third nucleotide sequence. "Specific binding" of a first nucleotide sequence with a second nucleotide sequence also means that the interaction between the first nucleotide sequence and the second nucleotide sequence is dependent upon the presence of a particular structure on or within the first nucleotide sequence; in other words the second nucleotide sequence is recognizing and binding to a specific structure on or within the first nucleotide sequence rather than to nucleic acids or to nucleotide sequences in general. For example, if a second nucleotide sequence is specific for structure "A" that is on or within a first nucleotide sequence, the presence of a third nucleic acid sequence containing structure A will reduce the amount of the second nucleotide sequence which is bound to the first nucleotide sequence.

As used herein, the term "amplifiable nucleic acid" is used in reference to nucleic acids which may be amplified by any amplification method. It is contemplated that "amplifiable nucleic acid" will usually comprise "sample template."

The terms "heterologous nucleic acid sequence" or "heterologous DNA" are used interchangeably to refer to a nucleotide sequence which is ligated to a nucleic acid sequence to which it is not ligated in nature, or to which it is ligated at a different location in nature. Heterologous DNA is not endogenous to the cell into which it is introduced but has been obtained from another cell. Generally, although not necessarily, such heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

"Amplification" is defined as the production of additional copies of a nucleic acid sequence and is generally carried out using polymerase chain reaction technologies well known in the art (Dieffenbach, C. W. and G. S. Dveksler (1995) PCR Primer, a Laboratory Manual, Cold Spring Harbor Press, Plainview, N.Y.). As used herein, the term "polymerase chain reaction" ("PCR") refers to the method of K. B. Mullis U.S. Pat. Nos. 4,683,195, and 4,683,202, hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

One such preferred method, particularly for commercial applications, is based on the widely used TaqMan® real-time PCR technology and combines Allele-Specific PCR with a Blocking reagent (ASB-PCR) to suppress amplification of the wildtype allele. ASB-PCR can be used for detection of germ line or somatic mutations in either DNA or RNA extracted from any type of tissue, including formalin-fixed paraffin-embedded tumor specimens. A set of reagent design rules are developed enabling sensitive and selective detection of single point substitutions, insertions, or deletions against a background of wild-type allele in thousand-fold or greater excess. (Morlan J, Baker J, Sinicropi D Mutation Detection by Real-Time PCR: A Simple, Robust and Highly Selective Method. PLoS ONE 4(2): e4584, 2009)

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). In some embodiments, the primer is single stranded for maximum efficiency in amplification but may alternatively be double stranded. If double stranded, the primer is first treated to separate its strands before being used to prepare extension products. In some embodiments, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation, of particular gene sequences. It is contemplated that any probe used in the present disclosure will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present disclosure be limited to any particular detection system or label.

As used herein, the terms "restriction endonucleases" and "restriction enzymes" refer to bacterial enzymes, each of which cut or nick double- or single-stranded DNA at or near a specific nucleotide sequence, for example, an endonuclease domain of a type IIS restriction endonuclease (e.g., FokI can be used, as taught by Kim et al., 1996, Proc. Nat'l. Acad. Sci. USA, 6:1 156-60).

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Additionally, "an oligonucleotide having a nucleotide sequence encoding a gene" may include suitable control elements such as enhancers, promoters, splice junctions, polyadenylation signals, etc. if needed to permit proper initiation of transcription and/or correct processing of the primary RNA transcript. Further still, the coding region of the present disclosure may contain endogenous enhancers, splice junctions, intervening sequences, polyadenylation signals, etc.

Transcriptional control signals in eukaryotes comprise "enhancer" elements. Enhancers consist of short arrays of DNA sequences that interact specifically with cellular proteins involved in transcription (Maniatis, T. et al., Science 236:1237, 1987). Enhancer elements have been isolated from a variety of eukaryotic sources including genes in plant, yeast, insect and mammalian cells and viruses. The selection of a particular enhancer depends on what cell type is to be used to express the protein of interest.

The presence of "splicing signals" on an expression vector often results in higher levels of expression of the recombinant transcript. Splicing signals mediate the removal of introns from the primary RNA transcript and consist of a splice donor and acceptor site (Sambrook, J. et al., Molecular Cloning: A Laboratory Manual, 2nd ed., Cold Spring Harbor Laboratory Press, New York, pp. 16.7-16.8, 1989). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene.

The term "promoter," "promoter element" or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls and provides a site for specific binding by RNA polymerase and for initiation of transcription.

The term "promoter activity" when made in reference to a nucleic acid sequence refers to the ability of the nucleic acid sequence to initiate transcription of an oligonucleotide sequence into mRNA.

The term "tissue specific" as it applies to a promoter refers to a promoter that can direct selective expression of an oligonucleotide sequence to a specific type of tissue in the relative absence of expression of the same oligonucleotide in a different type of tissue. Tissue specificity of a promoter may be evaluated by, for example, operably linking a reporter gene to the promoter sequence to generate a reporter construct, introducing the reporter construct into the genome of a plant or an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic plant or animal. Selectivity need not be absolute. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter which is capable of directing selective expression of an oligonucleotide sequence in a specific type of cell in the relative absence of expression of the same oligonucleotide sequence in a different type of cell within the same tissue. The term "cell type specific" when applied to a promoter also means a promoter capable of promoting selective expression of an oligonucleotide in a region within a single tissue. Again, selectivity need not be absolute. Cell type specificity of a promoter may be assessed using methods well known in the art, e.g., immunohistochemical staining as described herein. Briefly, tissue sections are embedded in paraffin, and paraffin sections are reacted with a primary antibody which is specific for the polypeptide product encoded by the oligonucleotide sequence whose expression is controlled by the promoter. As an alternative to paraffin sectioning, samples may be cryosectioned. For example, sections may be frozen prior to and during sectioning thus avoiding potential interference by residual paraffin. A labeled (e.g., peroxidase conjugated) secondary antibody which is specific for the primary antibody is allowed to bind to the sectioned tissue and specific binding detected (e.g., with avidin/biotin) by microscopy.

The terms "selective expression," "selectively express" and grammatical equivalents thereof refer to a comparison of relative levels of expression in two or more regions of interest. For example, "selective expression" when used in connection with tissues refers to a substantially greater level of expression of a gene of interest in a particular tissue, or to a substantially greater number of cells which express the gene within that tissue, as compared, respectively, to the level of expression of, and the number of cells expressing, the same gene in another tissue (i.e., selectivity need not be absolute). Selective expression does not require, although it may include, expression of a gene of interest in a particular tissue and a total absence of expression of the same gene in another tissue. Similarly, "selective expression" as used herein in reference to cell types refers to a substantially greater level of expression of, or a substantially greater number of cells which express, a gene of interest in a particular cell type, when compared, respectively, to the expression levels of the gene and to the number of cells expressing the gene in another cell type.

The term "contiguous" when used in reference to two or more nucleotide sequences means the nucleotide sequences are ligated in tandem either in the absence of intervening sequences, or in the presence of intervening sequences which do not comprise one or more control elements.

As used herein, the terms "nucleic acid molecule encoding," "nucleotide encoding," "DNA sequence encoding" and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein, the term "purified" or "to purify" refers to the removal of one or more (undesired) components from a sample. For example, where recombinant polypeptides are expressed in bacterial host cells, the polypeptides are purified by the removal of host cell proteins thereby increasing the percent of recombinant polypeptides in the sample.

As used herein, the term "substantially purified" refers to molecules, either nucleic or amino acid sequences, that are removed from their natural environment, isolated or separated, and are at least 60% free, in some embodiments 75% free and other embodiments 90% free from other components with which they are naturally associated. An "isolated polynucleotide" is, therefore, a substantially purified polynucleotide.

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side generally by the nucleotide triplet "ATG" which encodes the initiator methionine and on the 3' side by one of the three triplets which specify stop codons (i.e., TAA, TAG, TGA).

By "coding sequence" is meant a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

By "non-coding sequence" is meant a sequence of a nucleic acid or its complement, or a part thereof that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

As used herein, the term "structural gene" or "structural nucleotide sequence" refers to a DNA sequence coding for RNA or a protein which does not control the expression of other genes. In contrast, a "regulatory gene" or "regulatory sequence" is a structural gene which encodes products (e.g., transcription factors) which control the expression of other genes.

As used herein, the term "regulatory element" refers to a genetic element which controls some aspect of the expression of nucleic acid sequences. For example, a promoter is a regulatory element which facilitates the initiation of transcription of an operably linked coding region. Other regulatory elements include splicing signals, polyadenylation signals, termination signals, etc.

As used herein, the term "peptide transcription factor binding site" or "transcription factor binding site" refers to a nucleotide sequence which binds protein transcription factors and, thereby, controls some aspect of the expression of nucleic acid sequences. For example, Sp-1 and API (activator protein 1) binding sites are examples of peptide transcription factor binding sites.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

A "non-human animal" refers to any animal which is not a human and includes vertebrates such as rodents, non-human primates, ovines, bovines, ruminants, lagomorphs, porcines, caprines, equines, canines, felines, ayes, etc. Preferred non-human animals are selected from the order Rodentia. "Non-human animal" additionally refers to amphibians (e.g. *Xenopus*), reptiles, insects (e.g. *Drosophila*) and other non-mammalian animal species.

As used herein, the term "transgenic" refers to an organism or cell that has DNA derived from another organism inserted into which becomes integrated into the genome either of somatic and/or germ line cells of the plant or animal. A "transgene" means a DNA sequence which is partly or entirely heterologous (i.e., not present in nature) to the plant or animal in which it is found, or which is homologous to an endogenous sequence (i.e., a sequence that is found in the animal in nature) and is inserted into the plant' or animal's genome at a location which differs from that of the naturally occurring sequence. Transgenic plants or animals which include one or more transgenes are within the scope of this disclosure. Additionally, a "transgenic" as used herein refers to an organism that has had one or more genes modified and/or "knocked out" (made non-functional or made to function at reduced level, e.g., a "knockout" mutation) by the disclosure's methods, by homologous recombination, TFO mutation or by similar processes. For example, in some embodiments, a transgenic organism or cell includes inserted DNA that includes a foreign promoter and/or coding region.

A "transformed cell" is a cell or cell line that has acquired the ability to grow in cell culture for multiple generations, the ability to grow in soft agar, and/or the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" includes but is not limited to such methods as transfection, microinjection, electroporation, nucleofection and lipofection (liposome-mediated gene transfer). Transformation may be accomplished through use of any expression vector. For example, the use of baculovirus to introduce foreign nucleic acid into insect cells is contemplated. The term "transformation" also includes methods such as P-element mediated germline transformation of whole insects. Additionally, transformation refers to cells that have been transformed naturally, usually through genetic mutation.

As used herein "exogenous" means that the gene encoding the protein is not normally expressed in the cell. Additionally, "exogenous" refers to a gene transfected into a cell to augment the normal (i.e. natural) level of expression of that gene.

A peptide sequence and nucleotide sequence may be "endogenous" or "heterologous" (i.e., "foreign"). The term "endogenous" refers to a sequence which is naturally found in the cell into which it is introduced so long as it does not contain some modification relative to the naturally-occurring sequence. The term "heterologous" refers to a sequence which is not endogenous to the cell into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell into which it is introduced, and which contains some modification relative to the naturally-occurring sequence. Generally, although not necessarily, heterologous DNA encodes heterologous RNA and heterologous proteins that are not normally produced by the cell into which it is introduced. Examples of heterologous DNA include reporter genes, transcriptional and translational regulatory sequences, DNA sequences which encode selectable marker proteins (e.g., proteins which confer drug resistance), etc.

In certain aspects and embodiments of the disclosures herein, provided are methods for introducing a gene repair oligonucleobase (GRON)-mediated mutation into a target deoxyribonucleic acid (DNA) sequence in a plant cell; for example, for the purpose of modifying an SHP gene such as provided herein. In certain embodiments the methods may include, inter alia, culturing the plant cell under conditions that increase one or more cellular DNA repair processes prior to, and/or coincident with, delivery of a GRON into the plant cell; and/or delivery of a GRON into the plant cell greater than 15 bases in length, the GRON optionally comprising one or more; or two or more; mutation sites (such as SHP mutation sites as provided herein) for introduction into the target DNA.

A "gene repair oligonucleotide" or "GRON" as used herein means an oligonucleobase (e.g., mixed duplex oligonucleotides, non-nucleotide containing molecules, single stranded oligodeoxynucleotides, double stranded oligodeoxynucleotides and other gene repair molecules) that can under certain conditions direct single, or in some embodiments multiple, nucleotide deletions, insertions or substitutions in a DNA sequence. This oligonucleotide-mediated gene repair editing of the genome may comprise both non-homology-based repair systems (e.g., non-homologous end joining) and homology-based repair systems (e.g., homology-directed repair). The GRON is typically designed to align in register with a genomic target except for the designed mismatch(es). These mismatches can be recognized and corrected by harnessing one or more of the cell's endogenous DNA repair systems. In some embodiments a GRON or oligonucleotide can be designed to contain multiple differences when compared to the organism's target sequence. These differences may not all affect the protein sequence translated from said target sequence and in one or more cases be known as silent changes. Numerous variations of GRON structure, chemistry and function are described elsewhere herein. In various embodiments, a GRON as used herein may have one or more modifications. For example, a GRON as used herein may have one or more modifications that attract DNA repair machinery to the targeted (mismatch) site and/or that prevent recombination of part or all of the GRON (other than the desired targeted deletions, insertions, substitutions or the like) into the genomic DNA of the target DNA sequence and/or that increase the stability of the GRON.

In various embodiments, a GRON may have both RNA and DNA nucleotides and/or other types of nucleobases. In some embodiments, one or more of the DNA or RNA nucleotides comprise a modification.

In one aspect, provided is a method of causing a genetic change in a plant cell (for example a genetic change in a SHP gene), wherein the method involves exposing the cell to a DNA cutter and a GRON, for example a GRON that is modified as contemplated herein. In some embodiments the GRON may be modified such as with a Cy3 group, 3PS group, a 2'O-methyl group or other modification such as contemplated herein. In another aspect, provided is a plant cell that includes a DNA cutter and a GRON (such as a GRON that binds and/or modifies a SHP gene), for example where the GRON is modified such as with a Cy3 group, 3PS group, a 2'O-methyl group or other modification. In some embodiments the DNA cutter is one or more selected from a CRISPR which includes but is not limited to Cas9, Cpf1 and their corresponding homologues, orthologues and/or paralogues, a base editor, a TALEN, a zinc finger, meganuclease, and a DNA-cutting antibiotic. In some embodiments, the DNA cutter is a CRISPR. In some embodiments, the DNA cutter is a TALEN. The DNA cutter can be plasmid (DNA) based, RNA and/or protein. In some embodiments, the GRON is between 15 and 60 nucleobases in length; or between 30 and 40 nucleobases in length; or between 35 and 45 nucleobases in length; or between 20 and 70 nucleobases in length; or between 20 and 200 nucleobases in length; or between 30 and 180 nucleobases in length; or between 50 and 160 nucleobases in length; or between 70 and 150 nucleobases in length; or between 80 and 120 nucleobases in length; or between 90 and 110 nucleobases in length; or between 95 and 105 nucleobases in length; or between 80 and 300 nucleobases in length; or between 90 and 250 nucleobases in length; or between 100 and 150 nucleobases in length; or between 100 and 300 nucleobases in length; or between 150 and 200 nucleobases in length; or between 200 and 300 nucleobases in length; or between 250 and 350 nucleobases in length; or between 50 and 110 nucleobases in length; or between 50 and 200 nucleobases in length; or between 150 and 210 nucleobases in length; or between 20 and 1000 nucleobases in length; or between 100 and 1000 nucleobases in length; or between 200 and 1000 nucleobases in length; or between 300 and 1000 nucleobases in length; or between 400 and 1000 nucleobases in length; or between 500 and 1000 nucleobases in length; or between 600 and 1000 nucleobases in length; or between 700 and 1000 nucleobases in length; or between 800 and 1000 nucleobases in length; or between 900 and 1000 nucleobases in length; or between 300 and 800 nucleobases in length; or between 400 and 600 nucleobases in length; or between 500 and 700 nucleobases in length; or between 600 and 800 nucleobases in length; or longer than 30 nucleobases in length; or longer than 35 nucleobases in length; or longer than 40 nucleobases in length; or longer than 50 nucleobases in length; or longer than 60 nucleobases in length; or longer than 65 nucleobases in length; or longer than 70 nucleobases in length; or longer than 75 nucleobases in length; or longer than 80 nucleobases in length; or longer than 85 nucleobases in length; or longer than 90 nucleobases in length; or longer than 95 nucleobases in length; or longer than 100 nucleobases in length; or longer than 110 nucleobases in length; or longer than 125 nucleobases in length; or longer than 150 nucleobases in length; or longer than 165 nucleobases in length; or longer than 175 nucleobases in length; or longer than 200 nucleobases in length; or longer than 250 nucleobases in length; or longer than 300 nucleobases in length; or longer than 350 nucleobases in length; or longer than 400 nucleobases in length; or longer than 450 nucleobases in length; or longer than 500 nucleobases in length; or longer than 550 nucleobases in length; or longer than 600 nucleobases in length; or longer than 700 nucleobases in length; or longer than 800 nucleobases in length; or longer than 900 nucleobases in length.

GRONs may be targeted at both non-coding (NC) and coding (C) regions of a target gene.

The term "CRISPR" as used herein refers to elements; i.e., a cas (CRISPR associated) gene, transcript (e.g., mRNA) and/or protein and at least one CRISPR spacer sequence (Clustered Regularly Interspaced Short Palindromic Repeats, also known as SPIDRs—SPacer Interspersed Direct Repeats); that when effectively present or expressed in a cell could effect cleavage of a target DNA sequence via CRISPR/CAS cellular machinery such as described in e.g., Cong, L. et al., Science, vol. 339 no 6121 pp. 819-823 (2013); Jinek et al., Science, vol. 337:816-821 (2013); Wang et al., RNA, vol. 14, pp. 903-913 (2008); Zhang et al., Plant Physiology, vol. 161, pp. 20-27 (2013), Zhang et al, PCT Application No. PCT/US2013/074743; and Charpentier et al., PCT Application No. PCT/US2013/032589. In some embodiments, such as for example a CRISPR for use in a eukaryotic cell, a CRISPR as contemplated herein may also include an additional element that includes a sequence for one or more functional nuclear localization signals. CRISPRs as contemplated herein can be expressed in, administered to and/or present in a cell (such as a plant cell) in any of many ways or manifestations. For example, a CRISPR as contemplated herein may include or involve one or more of a CRISPR on a plasmid, a CRISPR nickase on a plasmid, a CRISPRa on a plasmid, or a CRISPRi on a plasmid as follows:

CRISPR on a plasmid: A recombinant expression vector comprising:

(i) a nucleotide sequence encoding a DNA-targeting RNA (e.g., guide RNA), wherein the DNA-targeting RNA comprises:

a. a first segment comprising a nucleotide sequence that is complementary to a sequence in a target DNA (e.g., protospacer, spacer, or crRNA); and
b. a second segment that interacts with a site-directed modifying polypeptide (e.g., trans-activating crRNA or tracrRNA); and (ii) a nucleotide sequence encoding the site-directed modifying polypeptide (e.g., cas gene), wherein the site-directed polypeptide comprises:
a. an RNA-binding portion that interacts with the DNA-targeting RNA (e.g., REC lobe); and
b. an activity portion that causes double-stranded breaks within the target DNA (e.g., NUC lobe), wherein the site of the double-stranded breaks within the target DNA is determined by the DNA-targeting RNA.

CRISPR nickase on a plasmid. A recombinant expression vector comprising:

(i) a nucleotide sequence encoding a DNA-targeting RNA (e.g., guide RNA), wherein the DNA-targeting RNA comprises:
a. a first segment comprising a nucleotide sequence that is complementary to a sequence in a target DNA (e.g., protospacer, spacer, or crRNA); and
b. a second segment that interacts with a site-directed modifying polypeptide (e.g., trans-activating crRNA or tracrRNA); and (ii) a nucleotide sequence encoding the site-directed modifying polypeptide (e.g., cas gene), wherein the site-directed polypeptide comprises:
a. an RNA-binding portion that interacts with the DNA-targeting RNA (e.g., REC lobe); and
b. an activity portion that causes single-stranded breaks within the target DNA (e.g., NUC lobe), wherein the site of the single-stranded breaks within the target DNA is determined by the DNA-targeting RNA.

CRISPRa on a plasmid. A recombinant expression vector comprising:

(i) a nucleotide sequence encoding a DNA-targeting RNA (e.g., guide RNA), wherein the DNA-targeting RNA comprises:
a. a first segment comprising a nucleotide sequence that is complementary to a sequence in a target DNA (e.g., protospacer, spacer, or crRNA); and
b. a second segment that interacts with a site-directed modifying polypeptide (e.g., trans-activating crRNA or tracrRNA); and (ii) a nucleotide sequence encoding the site-directed modifying polypeptide (e.g., cas gene), wherein the site-directed polypeptide comprises:
a. an RNA-binding portion that interacts with the DNA-targeting RNA (e.g., REC lobe); and
b. an activity portion that modulates transcription (e.g., NUC lobe; in certain embodiments increases transcription) within the target DNA, wherein the site of the transcriptional modulation within the target DNA is determined by the DNA-targeting RNA.

CRISPRi on a plasmid. A recombinant expression vector comprising:

(i) a nucleotide sequence encoding a DNA-targeting RNA (e.g., guide RNA), wherein the DNA-targeting RNA comprises:
a. a first segment comprising a nucleotide sequence that is complementary to a sequence in a target DNA (e.g., protospacer, spacer, or crRNA); and
b. a second segment that interacts with a site-directed modifying polypeptide (e.g., trans-activating crRNA or tracrRNA); and (ii) a nucleotide sequence encoding the site-directed modifying polypeptide (e.g., cas gene), wherein the site-directed polypeptide comprises:
a. an RNA-binding portion that interacts with the DNA-targeting RNA (e.g., REC lobe); and
b. an activity portion that modulates transcription/translation (e.g., NUC lobe; in some embodiments decreases transcription/translation) within the target DNA, wherein the site of transcriptional/translational modulation within the target DNA is determined by the DNA-targeting RNA.

Each of the CRISPR on a plasmid, CRISPR nickase on a plasmid, CRISPRa on a plasmid, and CRISPRi on a plasmid may in some embodiments alternatively have one or more appropriate elements be administered, expressed or present in a cell as an RNA (e.g., mRNA) or a protein rather than on a plasmid. Delivery of protected mRNA may be as described in Kariko, et al, U.S. Pat. No. 8,278,036.

In some embodiments, each of the CRISPRi and CRISPRa may include a deactivated cas9 (dCas9). A deactivated cas9 still binds to target DNA, but does not have cutting activity. Nuclease-deficient Cas9 can result from D10A and H840A point mutations which inactivates its two catalytic domains.

In some embodiments, a CRISPRi inhibits transcription initiation or elongation via steric hindrance of RNA Polymerase II. CRISPRi can optionally be enhanced (CRISPRei) by fusion of a strong repressor domain to the C-terminal end of a dCas9 protein. In some embodiments, a repressor domain recruits and employs chromatin modifiers. In some embodiments, the repressor domain may include, but is not limited to domains as described in Kagale, S. et al., Epigenetics, vol. 6 no 2 pp 141-146 (2011):

```
(LxLxPP motif)                                    (SEQ ID NO: 17)
1. LDLNRPPPVEN - OsERF3 repressor domain (R/KLFGV motif)                                   (SEQ ID NO: 18)
2. LRLFGVNM - AtBRD repressor domain (R/KLFGV motif)                                   (SEQ ID NO: 19)
3. LKLFGVWL - AtHsfB1 repressor domain (EAR motif)                                       (SEQ ID NO: 20)
4. LDLELRLGFA - AtSUP repressor domain
```

```
(EAR motif)                                         (SEQ ID NO: 21)
5.ERSNSIELRNSFYGRARTSPWSYGDYDNCQQDHDYLLGFSWPPRSYTCSFCKRE
FRSAQALGGHMNVHRRDRARLRLQQSPSSSSTPSPPYPNPNYSYSTMANSPPPHH
SPLTLFPTLSPPSSPRYRAGLIRSLSPKSKHTPENACKTKKSSLLVEAGEATRFT
SKDACKILRNDEIISLELEIGLINESEQDLDLELRLGFA*-
full AtSUP gene containing repressor domain
```

In some embodiments, a CRISPRa activation of transcription achieved by use of dCas9 protein containing a fused C-terminal end transcriptional activator. In some embodiments, an activation may include, but is not limited to VP64 (4×VP16), AtERF98 activation domain, or AtERF98×4 concatemers such as described in Cheng, A W et al., Cell Research, pp 1-9 (2013); Perez-Pinera, P. et al., Nature Methods, vol. 10 pp 913-976 (2013); Maeder, M L. et al., Nature Methods, vol. 10 pp 977-979 (2013) and Mali, P., et al., Nature Biotech., vol. 31 pp 833-838 (2013).

In some embodiments the CRISPR includes a nickase. In certain embodiments, two or more CRISPR nickases are used. In some embodiments, the two or more nickases cut on opposite strands of target nucleic acid. In other embodiments, the two or more nickases cut on the same strand of target nucleic acid.

As used herein, "repressor protein" or "repressor" refers to a protein that binds to operator of DNA or to RNA to prevent transcription or translation, respectively.

As used herein, "repression" refers to inhibition of transcription or translation by binding of repressor protein to specific site on DNA or mRNA. In some embodiments, repression includes a significant change in transcription or translation level of at least 1.5 fold, in other embodiments at least two fold, and in other embodiments at least five fold.

As used herein, an "activator protein" or "activator" with regard to gene transcription and/or translation, refers to a protein that binds to operator of DNA or to RNA to enhance or increase transcription or translation, respectively.

As used herein with regard to gene transcription and/or translation, "activation" with regard to gene transcription and/or translation, refers to enhancing or increasing transcription or translation by binding of activator protein to specific site on DNA or mRNA. In some embodiments, activation includes a significant change in transcription or translation level of at least 1.5-fold, in some embodiments at least two-fold, and in some embodiments at least five fold.

In certain embodiments, conditions that increase one or more cellular DNA repair processes may include one or more of: introduction of one or more sites into the GRON or into the plant cell DNA that are targets for base excision repair, introduction of one or more sites into the GRON or into the plant cell DNA that are targets for non-homologous end joining, introduction of one or more sites into the GRON or into the plant cell DNA that are targets for microhomology-mediated end joining, introduction of one or more sites into the GRON or into the plant cell DNA that are targets for homologous recombination, and introduction of one or more sites into the GRON or into the plant cell DNA that are targets for effecting repair (e.g., base-excision repair (BER); homologous recombination repair (HR); mismatch repair (MMR); non-homologous end-joining repair (NHEJ) which include classical and alternative NHEJ; and nucleotide excision repair (NER)).

As described herein, GRONs for use herein may include one or more of the following (non-limiting) alterations from conventional RNA and DNA nucleotides:
  one or more abasic nucleotides;
  one or more 8'oxo dA and/or 8'oxo dG nucleotides;
  a reverse base at the 3' end thereof;
  one or more 2'O-methyl nucleotides;
  one or more RNA nucleotides;
  one or more RNA nucleotides at the 5' end thereof, and in some embodiments 2, 3, 4, 5, 6, 7, 8, 9, 10, or more; wherein one or more of the RNA nucleotides may further be modified; one or more RNA nucleotides at the 3' end thereof, and in some embodiments 2, 3, 4, 5, 6, 7, 8, 9, 10, or more; wherein one or more of the RNA nucleotides may further be modified;
  one or more 2'O-methyl RNA nucleotides at the 5' end thereof, and in some embodiments 2, 3, 4, 5, 6, 7, 8, 9, 10, or more;
  an intercalating dye;
  a 5' terminus cap;
  a backbone modification selected from the group consisting of a phosphothioate modification, a methyl phosphonate modification, a locked nucleic acid (LNA) modification, a O-(2-methoxyethyl) (MOE) modification, a di PS modification, and a peptide nucleic acid (PNA) modification;
  one or more intrastrand crosslinks;
  one or more fluorescent dyes conjugated thereto, and in some embodiments at the 5' or 3' end of the GRON; and
  one or more bases which increase hybridization energy.

The term "wobble base" as used herein refers to a change in a one or more nucleotide bases of a reference nucleotide sequence wherein the change does not change the sequence of the amino acid coded by the nucleotide relative to the reference sequence.

The term "non-nucleotide" or "abasic nucleotide" as use herein refers to any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine. It may have substitutions for a 2' or 3' H or OH as described in the art and herein.

As described herein, in certain embodiments GRON quality and conversion efficiency may be improved by synthesizing all or a portion of the GRON using nucleotide multimers, such as dimers, trimers, tetramers, etc. improving its purity.

In certain embodiments, the target deoxyribonucleic acid (DNA) sequence is within a plant cell, for example the target DNA sequence is in the plant cell genome. The plant cell may be non-transgenic or transgenic, and the target DNA sequence may be a transgene or an endogenous gene of the plant cell.

In certain embodiments, the conditions that increase one or more cellular DNA repair processes comprise introducing one or more compounds which induce single or double DNA strand breaks into the plant cell prior to, or coincident to, or after delivering the GRON into the plant cell. Exemplary compounds are described herein.

In certain embodiments, the methods further comprise regenerating a plant having a mutation introduced by the GRON from the plant cell, and may comprise collecting seeds from the plant.

In related aspects, the present disclosure relates to plant cells comprising a genomic modification introduced by a GRON according to the methods described herein, a plant comprising a genomic modification introduced by a GRON according to the methods described herein, or a seed comprising a genomic modification introduced by a GRON according to the methods described herein; or progeny of a seed comprising a genomic modification introduced by a GRON according to the methods described herein.

Constructs

The nucleic acid molecules disclosed herein (e.g., site specific nucleases, or guide RNA for CRISPRs) can be used in the production of recombinant nucleic acid constructs. In one embodiment, the nucleic acid molecules of the present disclosure can be used in the preparation of nucleic acid constructs, for example, expression cassettes for expression in the plant, microorganism, or animal of interest such as SHP expression constructs optionally having one or more mutations as described herein. This expression may be transient for instance when the construct is not integrated into the host genome or maintained under the control offered by the promoter and the position of the construct within the host's genome if it becomes integrated.

Expression cassettes may include regulatory sequences operably linked to the site-specific nuclease or guide RNA sequences disclosed herein. The cassette may additionally contain at least one additional gene to be co-transformed into the organism. Alternatively, the additional gene or genes can be provided on multiple expression cassettes.

The nucleic acid constructs may be provided with a plurality of restriction sites for insertion of the site-specific nuclease coding sequence to be under the transcriptional regulation of the regulatory regions. The nucleic acid constructs may additionally contain nucleic acid molecules encoding for selectable marker genes.

Any promoter can be used in the production of the nucleic acid constructs. The promoter may be native or analogous, or foreign or heterologous, to the plant, microbial, or animal host nucleic acid sequences disclosed herein. Additionally, the promoter may be the natural sequence or alternatively a synthetic sequence. Where the promoter is "foreign" or "heterologous" to the plant, microbial, or animal host, it is intended that the promoter is not found in the native plant, microbial, or animal into which the promoter is introduced. As used herein, a chimeric gene comprises a coding sequence operably linked to a transcription initiation region that is heterologous to the coding sequence.

The site directed nuclease sequences disclosed herein may be expressed using heterologous promoters.

Any promoter can be used in the preparation of constructs to control the expression of the site directed nuclease sequences, such as promoters providing for constitutive, tissue-preferred, inducible, or other promoters for expression in plants, microbes, or animals. Constitutive promoters include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812; 1985); rice actin (McElroy et al., Plant Cell 2:163-171, 1990); ubiquitin (Christensen et al., Plant Mol. Biol. 12:619-632, 1989 and Christensen et al., Plant Mol. Biol. 18:675-689, 1992); pEMU (Last et al., Theor. Appl. Genet. 81:581-588, 1991); MAS (Velten et al., EMBO J. 3:2723-2730, 1984); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to direct site directed nuclease expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al., Plant J. 12(2): 255-265, 1997; Kawamata et al., Plant Cell Physiol. 38(7): 792-803, 1997; Hansen et al., Mol. Gen Genet. 254(3):337-343, 1997; Russell et al., Transgenic Res. 6(2):157-168, 1997; Rinehart et al., Plant Physiol. 112(3):1331-1341, 1996; Van Camp et al., Plant Physiol. 112(2):525-535, 1996; Canevascini et al., Plant Physiol. 112(2): 513-524, 1996; Yamamoto et al., Plant Cell Physiol. 35(5):773-778, 1994; Lam, Results Probl. Cell Differ. 20:181-196, 1994; Orozco et al. Plant Mol Biol. 23(6):1129-1138, 1993; Matsuoka et al., Proc Nat'l. Acad. Sci. USA 90(20):9586-9590, 1993; and Guevara-Garcia et al., Plant J. 4(3):495-505, 1993.

The nucleic acid constructs may also include transcription termination regions. Where transcription terminations regions are used, any termination region may be used in the preparation of the nucleic acid constructs. For example, the termination region may be derived from another source (i.e., foreign or heterologous to the promoter). Examples of termination regions that are available for use in the constructs of the present disclosure include those from the Ti-plasmid of *A. tumefaciens*, such as the octopine synthase and nopaline synthase termination regions. See also Guerineau et al., Mol. Gen. Genet. 262:141-144, 1991; Proudfoot, Cell 64:671-674, 1991; Sanfacon et al., Genes Dev. 5:141-149, 1991; Mogen et al., Plant Cell 2:1261-1272, 1990; Munroe et al., Gene 91:151-158, 1990; Ballas et al., Nucleic Acids Res. 17:7891-7903, 1989; and Joshi et al., Nucleic Acid Res. 15:9627-9639, 1987.

In conjunction with any of the aspects, embodiments, methods and/or compositions disclosed herein, the nucleic acids may be optimized for increased expression in the transformed plant. That is, the nucleic acids encoding the site directed nuclease proteins can be synthesized using plant-preferred codons for improved expression. See, for example, Campbell and Gowri, (Plant Physiol. 92:1-11, 1990) for a discussion of host-preferred codon usage. Methods are available in the art for synthesizing plant-preferred genes. See, for example, U.S. Pat. Nos. 5,380,831, and 5,436,391, and Murray et al., Nucleic Acids Res. 17:477-498, 1989. See also e.g., Lanza et al., BMC Systems Biology 8:33-43, 2014; Burgess-Brown et al., Protein Expr. Purif. 59:94-102, 2008; Gustafsson et al., Trends Biotechnol 22:346-353, 2004.

In addition, other sequence modifications can be made to the nucleic acid sequences disclosed herein. For example, additional sequence modifications are known to enhance gene expression in a cellular host. These include elimination of sequences encoding spurious polyadenylation signals, exon/intron splice site signals, transposon-like repeats, and other such well-characterized sequences that may be deleterious to gene expression. The G-C content of the sequence may also be adjusted to levels average for a target cellular host, as calculated by reference to known genes expressed in the host cell. In addition, the sequence can be modified to avoid predicted hairpin secondary mRNA structures.

Other nucleic acid sequences may also be used in the preparation of the constructs of the present disclosure, for example to enhance the expression of the site directed nuclease coding sequence. Such nucleic acid sequences include the introns of the maize AdhI, intronl gene (Callis et al., Genes and Development 1:1183-1200, 1987), and leader sequences, (W-sequence) from the Tobacco Mosaic virus (TMV), Maize Chlorotic Mottle Virus and Alfalfa Mosaic Virus (Gallie et al., Nucleic Acid Res. 15:8693-8711, 1987; and Skuzeski et al., Plant Mol. Biol. 15:65-79, 1990). The first intron from the shrunken-1 locus of maize has been shown to increase expression of genes in chimeric gene constructs. U.S. Pat. Nos. 5,424,412 and 5,593,874 disclose the use of specific introns in gene expression constructs, and Gallie et al. (Plant Physiol. 106:929-939, 1994) also have shown that introns are useful for regulating gene expression on a tissue specific basis. To further enhance or to optimize site directed nuclease gene expression, the plant expression vectors disclosed herein may also contain DNA sequences containing matrix attachment regions (MARs). Plant cells transformed with such modified expression systems, then, may exhibit overexpression or constitutive expression of a nucleotide sequence of the disclosure.

The expression constructs disclosed herein can also include nucleic acid sequences capable of directing the expression of the site directed nuclease sequence to the chloroplast or other organelles and structures in both prokaryotes and eukaryotes. Such nucleic acid sequences include chloroplast targeting sequences that encodes a chloroplast transit peptide to direct the gene product of interest to plant cell chloroplasts. Such transit peptides are known in the art. With respect to chloroplast-targeting sequences, "operably linked" means that the nucleic acid sequence encoding a transit peptide (i.e., the chloroplast-targeting sequence) is linked to the site directed nuclease nucleic acid molecules disclosed herein such that the two sequences are contiguous and in the same reading frame. See, for example, Von Heijne et al., Plant Mol. Biol. Rep. 9:104-126, 1991; Clark et al., J. Biol. Chem. 264:17544-17550, 1989; Della-Cioppa et al., Plant Physiol. 84:965-968, 1987; Romer et al., Biochem. Biophys. Res. Commun. 196:1414-1421, 1993; and Shah et al., Science 233:478-481, 1986.

Chloroplast targeting sequences are known in the art and include the chloroplast small subunit of ribulose-1,5-bisphosphate carboxylase (Rubisco) (de Castro Silva Filho et al., Plant Mol. Biol. 30:769-780, 1996; Schnell et al., J. Biol. Chem. 266(5):3335-3342, 1991); 5-(enolpyruvyl)shikimate-3-phosphate synthase (EPSPS) (Archer et al., J. Bioenerg. Biomemb. 22(6):789-810, 1990); tryptophan synthase (Zhao et al., J. Biol. Chem. 270(11):6081-6087, 1995); plastocyanin (Lawrence et al., J. Biol. Chem. 272(33):20357-20363, 1997); chorismate synthase (Schmidt et al., J. Biol. Chem. 268(36):27447-27457, 1993); and the light harvesting chlorophyll a/b binding protein (LHBP) (Lamppa et al., J. Biol. Chem. 263:14996-14999, 1988). See also Von Heijne et al., Plant Mol. Biol. Rep. 9:104-126, 1991; Clark et al., J. Biol. Chem. 264:17544-17550, 1989; Della-Cioppa et al., Plant Physiol. 84:965-968, 1987; Romer et al., Biochem. Biophys. Res. Commun. 196:1414-1421, 1993; and Shah et al., Science 233: 478-481, 1986.

In conjunction with any of the aspects, embodiments, methods and/or compositions disclosed herein, the nucleic acid constructs may be prepared to direct the expression of the mutant site directed nuclease coding sequence from the plant cell chloroplast. Methods for transformation of chloroplasts are known in the art. See, for example, Svab et al., Proc. Nat'l. Acad. Sci. USA 87:8526-8530, 1990; Svab and Maliga, Proc. Nat'l. Acad. Sci. USA 90:913-917, 1993; Svab and Maliga, EMBO J. 12:601-606, 1993. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. Proc. Nat'l. Acad. Sci. USA 91:7301-7305, 1994.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The nucleic acid constructs can be used to transform plant cells and regenerate transgenic plants comprising the site directed nuclease coding sequences. Numerous plant transformation vectors and methods for transforming plants are available. See, for example, U.S. Pat. No. 6,753,458, An, G. et al., Plant Physiol., 81:301-305, 1986; Fry, J. et al., Plant Cell Rep. 6:321-325, 1987; Block, M., Theor. Appl Genet. 76:767-774, 1988; Hinchee et al., Stadler. Genet. Symp. 203212.203-212, 1990; Cousins et al., Aust. J. Plant Physiol. 18:481-494, 1991; Chee, P. P. and Slightom, J. L., Gene. 118:255-260, 1992; Christou et al., Trends. Biotechnol. 10:239-246, 1992; D'Halluin et al., Bio/Technol. 10:309-314, 1992; Dhir et al., Plant Physiol. 99:81-88, 1992; Casas et al., Proc. Nat'l. Acad Sci. USA 90:11212-11216, 1993; Christou, P., In Vitro Cell. Dev. Biol.-Plant 29P:119-124, 1993; Davies et al., Plant Cell Rep. 12:180-183, 1993; Dong, J. A. and Mc Hughen, A., Plant Sci. 91:139-148, 1993; Franklin, C. I., Trieu, T. N., Cassidy, B. G., Dixon, R. A., Nelson, R. S. 1993, Plant Cell Report 12, 74-79; Golovkin et al., Plant Sci. 90:41-52, 1993; Guo Chin Sci. Bull. 38:2072-2078; Asano et al., Plant Cell Rep. 13, 1994; Ayeres, N. M. and Park, W. D., Crit. Rev. Plant. Sci. 13:219-239, 1994; Barcelo et al., Plant. J. 5:583-592, 1994; Becker et al., Plant. J. 5:299-307, 1994; Borkowska et al., Acta. Physiol Plant. 16:225-230, 1994; Christou, P., Agro. Food. Ind. Hi Tech. 5:17-27, 1994; Eapen et al., Plant Cell Rep. 13:582-586, 1994; Hartman et al., Bio-Technology 12:919923, 1994; Ritala et al., Plant. Mol. Biol. 24:317-325, 1994; and Wan, Y. C. and Lemaux, P. G., Plant Physiol. 104:3748, 1994. The constructs may also be transformed into plant cells using homologous recombination.

The term "wild-type" when made in reference to a peptide sequence and nucleotide sequence refers to a peptide sequence and nucleotide sequence (locus/gene/allele), respectively, which has the characteristics of that peptide sequence and nucleotide sequence when isolated from a naturally occurring source. A wild-type peptide sequence and nucleotide sequence is that which is most frequently observed in a population and is thus arbitrarily designated the "normal" or "wild-type" form of the peptide sequence and nucleotide sequence, respectively. "Wild-type" may also refer to the sequence at a specific nucleotide position or positions, or the sequence at a particular codon position or positions, or the sequence at a particular amino acid position or positions.

"Consensus sequence" is defined as a sequence of amino acids or nucleotides that contain identical amino acids or nucleotides or functionally equivalent amino acids or nucleotides for at least 25% of the sequence. The identical or functionally equivalent amino acids or nucleotides need not be contiguous.

A nucleobase is a base, which in certain preferred embodiments is a purine, pyrimidine, or a derivative or analog thereof. Nucleosides are nucleobases that contain a pentose-furanosyl moiety, e.g., an optionally substituted riboside or 2'-deoxyriboside. Nucleosides can be linked by one of several linkage moieties, which may or may not contain phosphorus. Nucleosides that are linked by unsubstituted phosphodiester linkages are termed nucleotides. The term "nucleobase" as used herein includes peptide nucleobases, the subunits of peptide nucleic acids, and morpholine nucleobases as well as nucleosides and nucleotides.

An oligonucleobase is a polymer comprising nucleobases; in some embodiments at least, a portion of which can hybridize by Watson-Crick base pairing to a DNA having the complementary sequence. An oligonucleobase chain may have a single 5' and 3' terminus, which are the ultimate nucleobases of the polymer. A particular oligonucleobase chain can contain nucleobases of all types. An oligonucleobase compound is a compound comprising one or more oligonucleobase chains that may be complementary and hybridized by Watson-Crick base pairing. Ribo-type nucleobases include pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

In certain embodiments, an oligonucleobase strand may include both oligonucleobase chains and segments or regions of oligonucleobase chains. An oligonucleobase strand may have a 3' end and a 5' end, and when an oligonucleobase strand is coextensive with a chain, the 3' and 5' ends of the strand are also 3' and 5' termini of the chain.

As used herein the term "codon" refers to a sequence of three adjacent nucleotides (either RNA or DNA) constituting the genetic code that determines the insertion of a specific amino acid in a polypeptide chain during protein synthesis or the signal to stop protein synthesis. The term "codon" is also used to refer to the corresponding (and complementary) sequences of three nucleotides in the messenger RNA into which the original DNA is transcribed.

As used herein, the term "homology" refers to sequence similarity among proteins and DNA. The term "homology" or "homologous" refers to a degree of identity. There may be partial homology or complete homology. A partially homologous sequence is one that has less than 100% sequence identity when compared to another sequence.

"Heterozygous" refers to having different alleles at one or more genetic loci in homologous chromosome segments. As used herein "heterozygous" may also refer to a sample, a cell, a cell population or an organism in which different alleles at one or more genetic loci may be detected. Heterozygous samples may also be determined via methods known in the art such as, for example, nucleic acid sequencing. For example, if a sequencing electropherogram shows two peaks at a single locus and both peaks are roughly the same size, the sample may be characterized as heterozygous. Or, if one peak is smaller than another, but is at least about 25% the size of the larger peak, the sample may be characterized as heterozygous. In some embodiments, the smaller peak is at least about 15% of the larger peak. In other embodiments, the smaller peak is at least about 10% of the larger peak. In other embodiments, the smaller peak is at least about 5% of the larger peak. In other embodiments, a minimal amount of the smaller peak is detected.

As used herein, "homozygous" refers to having identical alleles at one or more genetic loci in homologous chromosome segments. "Homozygous" may also refer to a sample, a cell, a cell population or an organism in which the same alleles at one or more genetic loci may be detected. Homozygous samples may be determined via methods known in the art, such as, for example, nucleic acid sequencing. For example, if a sequencing electropherogram shows a single peak at a particular locus, the sample may be termed "homozygous" with respect to that locus.

The term "hemizygous" refers to a gene or gene segment being present only once in the genotype of a cell or an organism because the second allele is deleted, or is not present on the homologous chromosome segment. As used herein "hemizygous" may also refer to a sample, a cell, a cell population or an organism in which an allele at one or more genetic loci may be detected only once in the genotype.

The term "zygosity status" as used herein refers to a sample, a cell population, or an organism as appearing heterozygous, homozygous, or hemizygous as determined by testing methods known in the art and described herein. The term "zygosity status of a nucleic acid" means determining whether the source of nucleic acid appears heterozygous, homozygous, or hemizygous. The "zygosity status" may refer to differences in at a single nucleotide position in a sequence. In some methods, the zygosity status of a sample with respect to a single mutation may be categorized as homozygous wild-type, heterozygous (i.e., one wild-type allele and one mutant allele), homozygous mutant, or hemizygous (i.e., a single copy of either the wild-type or mutant allele).

As used herein, the term "RTDS" refers to The Rapid Trait Development System™ (RTDS™) developed by Cibus. RTDS is a site-specific gene modification system that is effective at making precise changes in a gene sequence without the incorporation of foreign genes or control sequences.

The term "about" as used herein means in quantitative terms plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

RTDS and Repair Oligonucleotides (GRONs)

Various aspects and embodiments of the methods and compositions contemplated herein include methods to improve the efficiency of the targeting of modifications to specific locations in genomic or other nucleotide sequences (for example modifications to an SHP gene such as contemplated herein).

RTDS in some embodiments is based on altering a targeted gene by utilizing the cell's own gene repair system to specifically modify the gene sequence in situ and not insert foreign DNA and gene expression control sequences. This procedure can effect a precise change in the genetic sequence while the rest of the genome is left unaltered. In some embodiments, in contrast to conventional transgenic GMOs, there is no integration of foreign genetic material, nor is any foreign genetic material left in the plant. The changes in the genetic sequence introduced by RTDS are not randomly inserted. Since affected genes remain in their native location, no random, uncontrolled or adverse pattern of expression occurs.

The molecule that effects this change is a chemically synthesized oligonucleotide (GRON) as described herein which may be composed of both DNA and modified RNA bases as well as other chemical moieties, and is designed to hybridize at the targeted gene location to create a mismatched base-pair. This mismatched base-pair acts as a signal to attract the cell's own natural gene repair system to that site and correct (replace, insert or delete) the designated nucleotide or nucleotides within the gene. Once the correction process is complete the GRON molecule is degraded and the now-modified or repaired gene is expressed under that gene's normal endogenous control mechanisms.

The methods and compositions disclosed herein can be practiced or made with "gene repair oligonucleobases" (GRON) having the conformations and chemistries as described in detail herein and below. The "gene repair oligonucleobases" as contemplated herein have also been described in published scientific and patent literature using other names including "recombinagenic oligonucleobases;" "RNA/DNA chimeric oligonucleotides;" "chimeric oligonucleotides;" "mixed duplex oligonucleotides" (MDONs); "RNA DNA oligonucleotides (RDOs);" "gene targeting oligonucleotides;" "genoplasts;" "single stranded modified oligonucleotides;" "Single stranded oligodeoxynucleotide mutational vectors" (SSOMVs); "duplex mutational vectors;" and "heteroduplex mutational vectors." The gene repair oligonucleobase can be introduced into a plant cell using any method commonly used in the art, including but not limited to, microcarriers (biolistic delivery), microfibers, polyethylene glycol (PEG)-mediated uptake, electroporation, and microinjection.

In one embodiment, the gene repair oligonucleobase is a mixed duplex oligonucleotides (MDON) in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are hereby incorporated by reference. As used herein, a 2'-fluoro, chloro or bromo derivative of a ribonucleotide or a ribonucleotide having a T-OH substituted with a substituent described in the Martin Applications or Sproat is termed a "T-substituted ribonucleotide." As used herein the term "RNA-type nucleotide" means a T-hydroxyl or 2'-substituted nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a T-H, which can be linked to other nucleotides of a gene repair oligonucleobase by an unsubstituted phosphodiester linkage or any of the non-natural linkages taught by Kmiec I or Kmiec II.

In particular embodiments of the present disclosure, the gene repair oligonucleobase may be a mixed duplex oligonucleotide (MDON) that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particular preferred embodiments of 2'-Substituted Ribonucleotides are 2'-fluoro, T-methoxy, 2'-propyloxy, 2'-allyloxy, 2'-hydroxylethyloxy, 2'-methoxyethyloxy, T-fluoropropyloxy and 2'-trifluoropropyloxy substituted ribonucleotides. More preferred embodiments of 2'-Substituted Ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotides (MDONs) having only a single type of 2'-substituted RNA-type nucleotide are more conveniently synthesized, the methods of the disclosure can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses terms such as "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides in some embodiments have fewer than 100 nucleotides and other embodiments fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target gene/allele, i.e., have the same sequence as the target gene/allele. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene/allele. Alternatively, the heterologous region can also contain an insertion or one, two, three or of five or fewer nucleotides. Alternatively, the sequence of the mixed duplex oligonucleotide may differ from the sequence of the target gene/allele only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identical to the length of the heterologous region where a substitution or substitutions is intended. When the heterologous region contains an insertion, the homologous regions are thereby separated in the mixed duplex oligonucleotide farther than their complementary homologous fragments are in the gene/allele, and the converse is applicable when the heterologous region encodes a deletion.

The RNA segments of the mixed duplex oligonucleotides are each a part of a homologous region, i.e., a region that is identical in sequence to a fragment of the target gene, which segments together in some embodiments contain at least 13 RNA-type nucleotides and in some embodiments from 16 to 25 RNA-type nucleotides or yet other embodiments 18-22 RNA-type nucleotides or in some embodiments 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

In another embodiment of the methods and compositions of the present disclosure, a gene repair oligonucleobase (GRON) is a single stranded oligodeoxynucleotide mutational vector (SSOMV), such as disclosed in International Patent Application PCT/USOO/23457, U.S. Pat. Nos. 6,271, 360, 6,479,292, and 7,060,500 which is incorporated by reference in its entirety. The sequence of the SSOMV is based on the same principles as the mutational vectors described in U.S. Pat. Nos. 5,756,325; 5,871,984; 5,760, 012; 5,888,983; 5,795,972; 5,780,296; 5,945,339; 6,004, 804; and 6,010,907 and in International Publication Nos. WO 98/49350; WO 99/07865; WO 99/58723; WO 99/58702; and WO 99/40789. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region can cause a substitution. Alternatively, the homologous regions in the SSOMV can be contiguous to each other, while the regions in the target gene having the same sequence are separated by one, two or more nucleotides. Such an SSOMV causes a deletion from the target gene of the nucleotides that are absent from the SSOMV. Lastly, the sequence of the target gene that is identical to the homologous regions may be adjacent in the target gene but separated by one, two, or more nucleotides in the sequence of the SSOMV. Such an SSOMV causes an insertion in the sequence of the target gene. In certain embodiments, a SSOMV does not anneal to itself.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotide and the targeted nucleotide be a pyrimidine. To the extent that is consistent with achieving the desired functional result, it is preferred that both the mutator nucleotide and the targeted nucleotide in the complementary strand be pyrimidines. Particularly preferred are SSOMVs that encode transversion mutations, i.e., a C or T mutator nucleotide is mismatched, respectively, with a C or T nucleotide in the complementary strand.

2'-OME GRON Design. In various embodiments, a GRON may have both RNA and DNA nucleotides and/or other types of nucleobases. In some embodiments, one or more of the DNA or RNA nucleotides comprise a modification. In certain embodiments, the first 5' nucleotide is an RNA nucleotide and the remainder of the nucleotides are DNA. In still further embodiments, the first 5' RNA nucleotide is modified with a 2-O-Me. In other embodiments, the first two, three, four, five, six, seven, eight, nine, ten or more 5' nucleotides are an RNA nucleotide and the remainder of the nucleotides are DNA. In still further embodiments, one or more of the first two, three, four, five, six, seven, eight, nine, ten or more 5' RNA nucleotide are modified with a 2'-0-Me. In plant cells, double-strand beaks in DNA are typically repaired by the NHEJ DNA repair pathway. This pathway does not require a template to repair the DNA and is therefore error prone. The advantage of using this pathway to repair DNA for a plant cell is that it is quick, ubiquitous and most importantly can occur at times when a cell is not undergoing DNA replication. Another DNA repair pathway that functions in repairing double-strand breaks outside of the replication fork in plant cells is called templated repair; however, unlike the NHEJ pathway this type of repair is precise and requires the use of a DNA template (GRON).

Improving Efficiency

The present disclosure may include any of a number of approaches to increase the effectiveness of conversion of a target gene using repair oligonucleotides, and which may be used alone or in combination with one another. These include, for example:

1. Introducing modifications to the repair oligonucleotides which attract DNA repair machinery to the targeted (mismatch) site.
    A. Introduction of one or more abasic sites in the oligonucleotide (e.g., within 10 bases, and in some embodiments with 5 bases of the desired mismatch site) generates a lesion which is an intermediate in base excision repair (BER), and which attracts BER machinery to the vicinity of the site targeted for conversion by the repair oligonucleotide. dSpacer (abasic furan) modified oligonucleotides may be prepared as described in, for example, Takeshita et al., *J. Biol. Chem.*, 262:10171-79, 1987.
    B. Inclusion of compounds which induce single or double strand breaks, either into the oligonucleotide or together with the oligonucleotide, generates a lesion which is repaired by NHEJ, microhomology-mediated end joining (MMEJ), and homologous recombination. By way of example, the bleomycin family of antibiotics, zinc fingers, FokI (or any type IIS class of restriction enzyme) and other nucleases may be covalently coupled to the 3' or 5' end of repair oligonucleotides, in order to introduce double strand breaks in the vicinity of the site targeted for conversion by the repair oligonucleotide. The bleomycin family of antibiotics are DNA cleaving glycopeptides which include bleomycin, zeocin, phleomycin, tallysomycin, pepleomycin and others.
    C. Introduction of one or more 8'oxo dA or dG incorporated in the oligonucleotide (e.g., within 10 bases, and in some embodiments with 5 bases of the desired mismatch site) generates a lesion which is similar to lesions created by reactive oxygen species. These lesions induce the so-called "pushing repair" system. See, e.g., Kim et al., J. Biochem. Mol. Biol. 37:657-62, 2004.
2. Increase stability of the repair oligonucleotides:
    Introduction of a reverse base (idC) at the 3' end of the oligonucleotide to create a 3' blocked end on the repair oligonucleotide.

Introduction of one or more 2'O-methyl nucleotides or bases which increase hybridization energy (see, e.g., WO2007/073149) at the 5' and/or 3' of the repair oligonucleotide.

Introduction of one or a plurality of 2'O-methyl RNA nucleotides at the 5' end of the repair oligonucleotide, leading into DNA bases which provide the desired mismatch site, thereby creating an Okazaki Fragment-like nucleic acid structure.

Conjugated (5' or 3') intercalating dyes such as acridine, psoralen, ethidium bromide and Syber stains.

Introduction of a 5' terminus cap such as a T/A clamp, a cholesterol moiety, SIMA (HEX), riboC and amidite.

Backbone modifications such as phosphothioate, 2'-O methyl, methyl phosphonates, locked nucleic acid (LNA), MOE (methoxyethyl), di PS and peptide nucleic acid (PNA).

Crosslinking of the repair oligonucleotide, e.g., with intrastrand crosslinking reagents agents such as cisplatin and mitomycin C.

Conjugation with fluorescent dyes such as Cy3, DY547, Cy3.5, Cy3B, Cy5 and DY647.

3. Increase hybridization energy of the repair oligonucleotide through incorporation of bases which increase hybridization energy (see, e.g., WO2007/073149).

4. Increase the quality of repair oligonucleotide synthesis by using nucleotide multimers (dimers, trimers, tetramers, etc.) as building blocks for synthesis. This results in fewer coupling steps and easier separation of the full-length products from building blocks.

5. Use of long repair oligonucleotides (i.e., greater than 55 nucleotides in length, for example such as the lengths described herein, for example having one or more mutations or two or more mutations targeted in the repair oligonucleotide.

Examples of the foregoing approaches are provided in Table A.

TABLE A

Exemplary GRON chemistries

| Oligo type | | Modifications |
|---|---|---|
| 5' mods | T/A clamp | T/A clamp |
| Backbone modifications | Phosphothioate | PS |
| Intercalating dyes | 5' Acridine 3' | idC Acridine, idC |
| 2'-O-methyl | | DNA/RNA |
| Cy3 replacements | | DY547 |
| Facilitators | 2'-O-Me oligos designed 5' and 3' of the converting oligo | 2'-O-Me |
| Abasic | Abasic site placed in various locations 5' and 3' to the converting base. 44 mer | Abasic 2 |
| Assist | Assist approach Overlap: 2 oligos: 1 with Cy3/idC, 1 unmodified repair oligo | Cy3, idC on one, none on the other: |
| Assist | Assist approach No overlap: 2 oligos: 1 with Cy3/idC, 1 unmodified repair oligo | only make the unmodified oligo |
| Abasic | THF site placed in various locations 5' and 3' to the converting base. 44 mer | Tetrahydrofuran (dspacer) |

TABLE A-continued

Exemplary GRON chemistries

| Oligo type | | Modifications |
|---|---|---|
| Backbone modifications 9 | | 2'-O-Me |
| Trimers | | Trimer amidites, Cy3. idC |
| Pushing repair | | 8'oxo dA, 5' Cy3, idC |
| Pushing repair | | 8'oxo dA, 5' Cy3, idC |
| Double Strand Break | | Bleomycin |
| Crosslinker | | Cisplatin |
| Crosslinker | | Mitomycin C |
| Facilitators | super bases 5' and 3' of converting oligo | 2 amino dA and 2-thio T |
| Super oligos | | 2'amino d, 5' Cy3, idC |
| Super oligos | | 2-thio T, 5' Cy3, idC |
| Super oligos | | 7-deaza A, 5' Cy3, idC |
| Super oligos | | 7-deaza G, 5' Cy3, idC |
| Super oligos | | propanyl dC, 5' Cy3, idC |
| Intercalating dyes | 5' Psoralen/3' idC | Psoralen, idC |
| Intercalating dyes | 5' Ethidium bromide | Ethidium bromide |
| Intercalating dyes | 5' Syber stains | Syber stains |
| 5' mods | 5' Choi/3' idC | Cholesterol |
| Double mutation | Long oligo (55+ bases) w/2 mutation | Any modification |
| 5' mods | 5' SIMA HEX/3'idC | SIMA HEX, idC |
| Backbone modifications 9 | | Methyl phosphonates |
| Backbone modifications | | LNA |
| Backbone modifications 1 | | MOE (methoxyethyl) |
| Cy3 replacements | | Cy3.5 |
| Cy3 replacements | | Cy5 |
| Backbone modifications | | di PS |
| 5' mods | | riboC for branch nm |
| Backbone modifications | | PNA |
| Cy3 replacements | | DY647 |
| 5' mods | 5' branch | symmetric branch amidite/idC |

The foregoing modifications may also include known nucleotide modifications such as methylation, 5' intercalating dyes, modifications to the 5' and 3' ends, backbone modifications, crosslinkers, cyclization and 'caps' and substitution of one or more of the naturally occurring nucleotides with an analog such as inosine. Modifications of nucleotides include the addition of acridine, amine, biotin, cascade blue, cholesterol, Cy3@, Cy5@, Cy5.5@ Daboyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S", SE, BODIPY®, Marina Blue@, Pacific Blue@, Oregon Green@, Rhodamine Green@, Rhodamine Red@, Rhodol Green@ and Texas Red@. Polynucleotide backbone modifications include methylphosphonate, 2'-OMe-methylphosphonate RNA, phosphorothioate, RNA, 2'-OMeRNA. Base modifications include 2-amino-dA, 2-aminopurine, 3'-(ddA), 3'dA (cordycepin), 7-deaza-dA, 8-Br-dA, 8-oxo-dA, N6-Me-dA, abasic site (dSpacer), biotin dT, 2'-OMe-5Me-C, 2'-OMe-propynyl-C, 3'-(5-Me-dC), 3'-(ddC), 5-Br-dC, 5-1-duc, 5-Me-dC, 5-F-dC, carboxy-dT, convertible dA, convertible dC, convertible dG, convertible dT, convertible dU, 7-deaza-dG, 8-Br-dG, 8-oxo-dG, 06-Me-dG, S6-DNP-dG, 4-methyl-indole, 5-nitroindole, 2'-OMe-inosine, 2'-dI, o6-phenyl-dI, 4-methyl-indole, 2'-deoxynebularine, 5-nitroindole, 2-aminopurine, dP (purine analogue), dK (pyrimidine analogue), 3-nitropyrrole, 2-thio-dT, 4-thio-dT, biotin-dT, carboxy-dT, 04-Me-dT, 04-triazol dT, 2'-OMe-propynyl-U, 5-Br-dU, 2'-dU, 5-F-dU, 5-1-dU, 04-triazol dU. Said terms also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors.

Oligonucleobases may have nick(s), gap(s), modified nucleotides such as modified oligonucleotide backbones, abasic nucleotides, or other chemical moieties. In a further embodiment, at least one strand of the oligonucleobase includes at least one additional modified nucleotide, e.g., a 2'-O-methyl modified nucleotide such as a MOE (methoxyethyl), a nucleotide having a 5'-phosphorothioate group, a terminal nucleotide linked to a cholesteryl derivative, a 2'-deoxy-2'-fluoro modified nucleotide, a 2'-deoxy-modified nucleotide, a locked nucleotide, an abasic nucleotide (the nucleobase is missing or has a hydroxyl group in place thereof (see, e.g., Glen Research, worldwide web address: glenresearch.com/GlenReports/GR21-14.html)), a 2'-amino-modified nucleotide, a 2'-alkyl-modified nucleotide, a morpholino nucleotide, a phosphoramidite, and a non-natural base comprising nucleotide. Various salts, mixed salts and free acid forms are also included.

Preferred modified oligonucleotide backbones include, for example, phosphorothioates, chiral phosphorothioates, phosphoro-dithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkyl-phosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). The most common use of a linkage inversion is to add a 3'-3' linkage to the end of an antisense oligonucleotide with a phosphorothioate backbone. The 3'-3' linkage further stabilizes the antisense oligonucleotide to exonuclease degradation by creating an oligonucleotide with two 5'-OH ends and no 3'-OH end. Linkage inversions can be introduced into specific locations during oligonucleotide synthesis through use of "reversed phosphoramidites". These reagents have the phosphoramidite groups on the 5'-OH position and the dimethoxytrityl (DMT) protecting group on the 3'-OH position. Normally, the DMT protecting group is on the 5'-OH and the phosphoramidite is on the 3'-OH.

Examples of modified bases include, but are not limited to, 2-aminopurine, 2'-amino-butyryl pyrene-uridine, 2'-aminouridine, 2'-deoxyuridine, 2'-fluoro-cytidine, 2'-fluoro-uridine, 2,6-diaminopurine, 4-thio-uridine, 5-bromo-uridine, 5-fluoro-cytidine, 5-fluorouridine, 5-indo-uridine, 5-methyl-cytidine, inosine, N3-methyl-uridine, 7-deaza-guanine, 8-aminohexyl-amino-adenine, 6-thio-guanine, 4-thio-thymine, 2-thio-thymine, 5-iodo-uridine, 5-iodo-cytidine, 8-bromo-guanine, 8-bromo-adenine, 7-deaza-adenine, 7-diaza-guanine, 8-oxo-guanine, 5,6-dihydro-uridine, and 5-hydroxymethyl-uridine. These synthetic units are commercially available; (for example, purchased from Glen Research Company) and can be incorporated into DNA by chemical synthesis.

Examples of modification of the sugar moiety are 3'-deoxylation, 2'-fluorination, and arabanosidation, however, it is not to be construed as being limited thereto. Incorporation of these into DNA is also possible by chemical synthesis.

Examples of the 5' end modification are 5'-amination, 5'-biotinylation, 5'-fluoresceinylation, 5'-tetrafluoro-fluoreceinyaltion, 5'-thionation, and 5'-dabsylation, however it is not to be construed as being limited thereto.

Examples of the 3' end modification are 3'-amination, 3'-biotinylation, 2,3-dideoxidation, 3'-thionation, 3'-dabsylation, 3'-carboxylation, and 3'-cholesterylation, however, it is not to be construed as being limited thereto.

In one preferred embodiment, the oligonucleobase can contain a 5' blocking substituent that is attached to the 5' terminal carbons through a linker. The chemistry of the linker is not critical other than its length, which should in some embodiments be at least 6 atoms long and that the linker should be flexible. A variety of non-toxic substituents such as biotin, cholesterol or other steroids or a non-intercalating cationic fluorescent dye can be used. Particularly preferred reagents to make oligonucleobases are the reagents sold as Cy3™ and Cy5™ by Glen Research, Sterling Va. (now GE Healthcare), which are blocked phosphoroamidites that upon incorporation into an oligonucleotide yield 3,3,3',3'-tetramethyl N,N'-isopropyl substituted indomonocarbocyanine and indodicarbocyanine dyes, respectively. Cy3 is particularly preferred. When the indocarbocyanine is N-oxyalkyl substituted it can be conveniently linked to the 5' terminal of the oligodeoxynucleotide as a phosphodiester with a 5' terminal phosphate. When the commercially available Cy3 phosphoramidite is used as directed, the resulting 5' modification consists of a blocking substituent and linker together which are a N-hydroxypropyl, N'-phosphatidylpropyl 3,3,3',3'-tetramethyl indomonocarbocyanine. Other dyes contemplated include Rhodamine6G, Tetramethylrhodamine, Sulforhodamine 101, Merocyanine 540, Atto565, Atto550 26, Cy3.5, Dy547, Dy548, Dy549, Dy554, Dy555, Dy556, Dy560, mStrawberry and mCherry.

In a preferred embodiment the indocarbocyanine dye is tetra substituted at the 3 and 3' positions of the indole rings. Without limitations as to theory these substitutions prevent the dye from being an intercalating dye. The identity of the substituents at these positions is not critical.

The oligo designs herein described might also be used as more efficient donor templates in combination with other DNA editing or recombination technologies including, but not limited to, gene targeting using site-specific homologous recombination by zinc finger nucleases, meganucleases, Transcription Activator-Like Effector Nucleases (TALENs) or Clustered Regularly Interspaced Short Palindromic Repeats (CRISPRs).

The present disclosure in certain aspects and embodiments may include methods and compositions relating to methods for the efficient modification of genomic cellular DNA and/or recombination of DNA into the genomic DNA of cells. Although not limited to any particular use, some methods provided herein may in certain embodiments be useful in, for example, introducing a modification into the genome of a cell for the purpose of determining the effect of the modification on the cell. For example, a modification may be introduced into the nucleotide sequence which encodes an enzyme to determine whether the modification alters the enzymatic activity of the enzyme, and/or determine the location of the enzyme's catalytic region. Alternatively, the modification may be introduced into the coding sequence of a DNA-binding protein to determine whether the DNA binding activity of the protein is altered, and thus to delineate the particular DNA-binding region within the protein. Yet another alternative is to introduce a modification into a non-coding regulatory sequence (e.g., promoter, enhancer, regulatory RNA sequence (miRNA), etc.) in order to determine the effect of the modification on the level of expression of a second sequence which is operably linked to the non-coding regulatory sequence. This may be desirable to, for example, define the particular sequence which possesses regulatory activity.

DNA Cutters

One strategy for producing targeted gene disruption is through the generation of single strand or double strand DNA breaks using a DNA cutter such as a site-specific endonuclease. Endonucleases are most often used for targeted gene disruption in organisms that have traditionally been refractive to more conventional gene targeting methods, such as algae, plants, and large animal models, including humans. For example, there are currently human clinical trials underway involving zinc finger nucleases for the treatment and prevention of HIV infection. Additionally, endonuclease engineering is currently being used in attempts to disrupt genes that produce undesirable phenotypes in crops.

Certain aspects of the present disclosure related to introducing one or more mutations into a targeted nucleic acid using a DNA endonuclease. In some embodiments, the DNA endonuclease is an RNA-guided DNA endonuclease. Exemplary RNA-guided DNA endonucleases include Cas9, Cpf1, and the like. RNA-guided DNA endonucleases suitable for use in the methods and compositions described herein will be readily apparent to one of skill in the art. Additional DNA endonucleases for use in the methods and compositions of the present disclosure are described herein.

Zinc Fingers

One class of artificial endonucleases is the zinc finger endonucleases. Zinc finger endonucleases combine a non-specific cleavage domain, typically that of FokI endonuclease, with zinc finger protein domains that are engineered to bind to specific DNA sequences. The modular structure of the zinc finger endonucleases makes them a versatile platform for delivering site-specific double-strand breaks to the genome. As FokI endonuclease cleaves as a dimer, one strategy to prevent off-target cleavage events has been to design zinc finger domains that bind at adjacent 9 base pair sites. See also U.S. Pat. Nos. 7,285,416; 7,521,241; 7,361,635; 7,273,923; 7,262,054; 7,220,719; 7,070,934; 7,013,219; 6,979,539; 6,933,113; 6,824,978; each of which is hereby herein incorporated by reference in its entirety.

TALENs

TALENs are targetable nucleases are used to induce single- and double-strand breaks into specific DNA sites, which are then repaired by mechanisms that can be exploited to create sequence alterations at the cleavage site.

The fundamental building block that is used to engineer the DNA-binding region of TALENs is a highly conserved repeat domain derived from naturally occurring TALEs encoded by *Xanthomonas* spp. proteobacteria. DNA binding by a TALEN is mediated by arrays of highly conserved 33-35 amino acid repeats that are flanked by additional TALE-derived domains at the amino-terminal and carboxy-terminal ends of the repeats.

These TALE repeats specifically bind to a single base of DNA, the identity of which is determined by two hyper-variable residues typically found at positions 12 and 13 of the repeat, with the number of repeats in an array corresponded to the length of the desired target nucleic acid, the identity of the repeat selected to match the target nucleic acid sequence. In some embodiments, the target nucleic acid is between 15 and 20 base pairs in order to maximize selectivity of the target site. Cleavage of the target nucleic acid typically occurs within 50 base pairs of TALEN binding. Computer programs for TALEN recognition site design have been described in the art. See, e.g., Cermak et al., Nucleic Acids Res. 2011 July; 39(12): e82.

Once designed to match the desired target sequence, TALENs can be expressed recombinantly and introduced into protoplasts as exogenous proteins, or expressed from a plasmid within the protoplast or administered as mRNA or as protein.

Meganucleases

The homing endonucleases, also known as meganucleases, are sequence specific endonucleases that generate double strand breaks in genomic DNA with a high degree of specificity due to their large (e.g., >14 bp) cleavage sites. While the specificity of the homing endonucleases for their target sites allows for precise targeting of the induced DNA breaks, homing endonuclease cleavage sites are rare and the probability of finding a naturally occurring cleavage site in a targeted gene is low.

Another class of artificial endonucleases is the engineered meganucleases. Engineered homing endonucleases are generated by modifying the specificity of existing homing endonucleases. In one approach, variations are introduced in the amino acid sequence of naturally occurring homing endonucleases and then the resultant engineered homing endonucleases are screened to select functional proteins which cleave a targeted binding site. In another approach, chimeric homing endonucleases are engineered by combining the recognition sites of two different homing endonucleases to create a new recognition site composed of a half site of each homing endonuclease. See e.g., U.S. Pat. Nos. 8,338,157, and 8,445,251.

CRISPRs or CRISPR/cas Systems

CRISPR-Cas system contains three basic design components: 1) Cas gene, transcript (e.g., mRNA) or protein; 2) guide RNA (gRNA); and 3) crRNAs (CRISPR RNA) are RNA segments processed from RNA transcripts encoding the CRISPR repeat arrays, which harbor a "protospacer" region that are complementary to a foreign DNA site (e.g., endogenous DNA target region) and a part of the CRISPR repeat. See e.g., PCT Application Nos WO/2014/093661 and WO/2013/176772.

Cas (CRISPR Associated) Gene, Transcript (e.g., mRNA) or Protein

Transient Cas expression from a plasmid vector, direct delivery of Cas protein and or direct delivery of Cas mRNA into plant cells. Cas genes are codon optimized for expression in higher plants, algae or yeast and are driven by either a constitutive, inducible, tissue-specific or species-specific promoter when applicable. Cas transcript termination and polyadenlyation signals are either NosT, RBCT, HSP18.2T or other gene specific or species-specific terminators. Cas gene cassettes may contain introns, either native or in combination with gene-specific promoters and or synthetic promoters. Cas protein may contain one or more nuclear localization signal sequences (NLS), mutations, deletions, alterations or truncations. In transient expression systems, Cas gene cassettes may be combined with other components of the CRISPR-Cas system such as gRNA cassettes on the same transient expression vector. Alternatively, Cas gene cassettes may be located and expressed from constructs independent of gRNA cassettes or from other components of the CRISPR-Cas system. CRISPR associated (Cas) gene—encode for proteins with a variety of predicted nucleic acid-manipulating activities such as nucleases, helicases and polymerase. Cas genes include Cas9. Cas9 is a gene encoding a large protein containing a predicted RuvC-like and HNH endonuclease domains and is associated with the CRISPR adaptive immunity system that is present in most archaea and many bacteria. Cas9 protein consists of two lobes:

1) Recognition (REC) lobe—consists of three domains:
a) BH (bridge helix)
b) REC1—facilitates RNA-guided DNA targeting
c) REC2—facilitates RNA-guided DNA targeting 2) Nuclease (NUC) lobe—consists of three domains:
a) RuvC—facilitates RNA-guided DNA targeting; endonuclease activity
b) HNH—endonuclease activity
c) PI—PAM interacting In other embodiments, the Cas gene may be a homolog of Cas9 in which the RuvC, HNH, REC and BH domains are highly conserved. In some embodiments, Cas genes are those from the following species listed in Table B.

TABLE B

Exemplary Cas Genes

| Locus ID/ GI | Species | Cas profile ID | Cas gene |
|---|---|---|---|
| 352684361 | *Acidaminococcus_intestini*_RyC_MR95_uid74445 | mkCas0193 | cas9 |
| 117929158 | *Acidothermus_cellulolyticus*_11B_uid58501 | cd09643 | cas9 |
| 326315085 | *Acidovorax_avenae*_ATCC_19860_uid42497 | cd09643 | cas9 |
| 222109285 | *Acidovorax_ebreus*_TPSY_uid59233 | COG3513 | cas9 |
| 152978060 | *Actinobacillus_succinogenes*_130Z_uid58247 | COG3513 | cas9 |
| 407692091 | *Actinobacillus_suis*_H91_0380_uid176363 | COG3513 | cas9 |
| 187736489 | *Akkermansia_muciniphila*_ATCC_BAA_835_uid58985 | cd09643 | cas9 |
| 319760940 | *Alicycliphilus_denitrificans*_BC_uid49953 | cd09643 | cas9 |
| 330822845 | *Alicycliphilus_denitrificans*_K601_uid66307 | cd09643 | cas9 |
| 288957741 | *Azospirillum*_B510_uid46085 | cd09643 | cas9 |
| 549484339 | *Bacteroides*_CF50_uid222805 | cd09643, COG3513 | cas9 |
| 375360193 | *Bacteroides_fragilis*_638R_uid84217 | COG3513, COG3513 | cas9 |
| 60683389 | *Bacteroides_fragilis*_NCTC_9343_uid57639 | COG3513, COG3513 | cas9 |
| 471261880 | *Bdellovibrio_exovorus*_JSS_uid194119 | COG3513 | cas9 |
| 390944707 | *Belliella_baltica*_DSM_15883_uid168182 | cd09643, COG3513 | cas9 |
| 470166767 | *Bibersteinia_trehalosi*_192_uid193709 | COG3513 | cas9 |
| 310286728 | *Bifidobacterium_bifidum*_S17_uid59545 | mkCas0193 | cas9 |
| 283456135 | *Bifidobacterium_dentium*_Bd1_uid43091 | cd09643 | cas9 |
| 189440764 | *Bifidobacterium_longum*_DJO10A_uid58833 | cd09643 | cas9 |
| 384200944 | *Bifidobacterium_longum*_KACC_91563_uid158861 | cd09643 | cas9 |
| 479188345 | *Butyrivibrio_fibrisolvens*_uid197155 | cd09643 | cas9 |
| 544063172 | *Campylobacter_jejuni*_00_2425_uid219359 | COG3513 | cas9 |
| 543948719 | *Campylobacter_jejuni*_00_2426_uid219324 | COG3513 | cas9 |
| 543946932 | *Campylobacter_jejuni*_00_2538_uid219325 | C0G3513 | cas9 |
| 543950499 | *Campylobacter_jejuni*_00_2544_uid219326 | COG3513 | cas9 |
| 549693479 | *Campylobacter_jejuni*_4031_uid222817 | COG3513 | cas9 |
| 157415744 | *Campylobacter_jejuni*_81116_uid58771 | COG3513 | cas9 |
| 384448746 | *Campylobacter_jejuni*_IA3902_uid159531 | COG3513 | cas9 |
| 384442102 | *Campylobacter_jejuni*_M1_uid159535 | C0G3513 | cas9 |
| 384442103 | *Campylobacter_jejuni*_M1_uid159535 | C0G3513 | cas9 |
| 403056243 | *Campylobacter_jejuni*_NCTC_11168_BN148_uid174152 | COG3513 | cas9 |
| 218563121 | *Campylobacter_jejuni*_NCTC_11168_ATCC_700819_uid57587 | COG3513 | cas9 |
| 407942868 | *Campylobacter_jejuni*_PT14_uid176499 | COG3513 | cas9 |
| 153952471 | *Campylobacter_jejuni_doylei*_269_97_uid58671 | COG3513 | cas9 |
| 294086111 | *Candidatus_Puniceispirillum_marinum*_IMCC1322_uid47081 | cd09643 | cas9 |
| 340622236 | *Capnocytophaga_canimorsus*_Cc5_uid70727 | COG3513, cd09643 | cas9 |
| 220930482 | *Clostridium_cellulolyticum*_H10_uid58709 | COG3513 | cas9 |
| 479136975 | *Coprococcus_catus*_GD_7_uid197174 | mkCas0193 | cas9 |
| 328956315 | *Coriobacterium_glomerans*_PW2_uid65787 | mkCas0193 | cas9 |
| 375289763 | *Corynebacterium_diphtheriae*_241_uid83607 | cd09643 | cas9 |
| 376283539 | *Corynebacterium_diphtheriae*_31A_uid84309 | cd09643 | cas9 |
| 376286566 | *Corynebacterium_diphtheriae*_BH8_uid84311 | cd09643 | cas9 |
| 376289243 | *Corynebacterium_diphtheriae*_C7_beta_uid84313 | cd09643 | cas9 |
| 376244596 | *Corynebacterium_diphtheriae*_HC01_uid84297 | cd09643 | cas9 |
| 376292154 | *Corynebacterium_diphtheriae*_HC02_uid84317 | cd09643 | cas9 |
| 38232678 | *Corynebacterium_diphtheriae*_NCTC_13129_uid57691 | cd09643 | cas9 |
| 376256051 | *Corynebacterium_diphtheriae*_VA01_uid84305 | cd09643 | cas9 |
| 159042956 | *Dinoroseobacter_shibae*_DFL_12_uid58707 | cd09643 | cas9 |
| 339445983 | *Eggerthella*_YY7918_uid68707 | mkCas0193 | cas9 |
| 187250660 | *Elusimicrobium_minutum*_Pei191_uid58949 | cd09643 | cas9 |
| 479180325 | *Enterococcus*_7L76_uid197170 | cd09643 | cas9 |
| 397699066 | *Enterococcus_faecalis*_D32_uid171261 | mkCas0193 | cas9 |
| 384512368 | *Enterococcus_faecalis*_OG1RF_uid54927 | mkCas0193 | cas9 |
| 392988474 | *Enterococcus_hirae*_ATCC_9790_uid70619 | mkCas0193 | cas9 |
| 558685081 | *Enterococcus_mundtii*_QU_25_uid229420 | mkCas0193 | cas9 |
| 238924075 | *Eubacterium_rectale*_ATCC_33656_uid59169 | cd09643 | cas9 |
| 385789535 | *Fibrobacter_succinogenes*_S85_uid161919 | cd09643, cd09643 | cas9 |
| 261414553 | *Fibrobacter_succinogenes*_S85_uid41169 | cd09643, cd09643 | cas9 |
| 374307738 | *Filifactor_alocis*_ATCC_35896_uid46625 | mkCas0193 | cas9 |
| 169823755 | *Finegoldia_magna*_ATCC_29328_uid58867 | mkCas0193 | cas9 |
| 150025575 | *Flavobacterium_psychrophilum*_JIP02_86_uid61627 | cd09643, cd09643 | cas9 |
| 327405121 | *Fluviicola_taffensis*_DSM_16823_uid65271 | cd09643, cd09643 | cas9 |

TABLE B-continued

Exemplary Cas Genes

| Locus ID/ GI | Species | Cas profile ID | Cas gene |
|---|---|---|---|
| 387824704 | Franciscella_cf_novicida_3523_uid162107 | cd09704 | cas9 |
| 118497352 | Franciscella_novicida_U112_uid58499 | cd09704 | cas9 |
| 134302318 | Franciscella_tularensis_WY96_3418_uid58811 | cd09704 | cas9 |
| 89256630 | Franciscella_tularensis_holarctica_LVS_uid58595 | cd09704 | cas9 |
| 89256631 | Franciscella_tularensis_holarctica_LVS_uid58595 | cd09704 | cas9 |
| 534508854 | Fusobacterium_3_1_36A2_uid55995 | mkCas0193 | cas9 |
| 530600688 | Geobacillus_JF8_uid215234 | COG3513 | cas9 |
| 209542524 | Gluconacetobacter_diazotrophicus_PA1_5_uid59075 | COG3513 | cas9 |
| 162147907 | Gluconacetobacter_diazotrophicus_PA1_5_uid61587 | COG3513 | cas9 |
| 479173968 | Gordonibacter_pamelaeae_7_10_1_b_uid197167 | mkCas0193 | cas9 |
| 345430422 | Haemophilus_parainfluenzae_T3T1_uid72801 | COG3513 | cas9 |
| 471315929 | Helicobacter_cinaedi_ATCC_BAA_847_uid193765 | COG3513 | cas9 |
| 386762035 | Helicobacter_cinaedi_PAGU611_uid162219 | COG3513 | cas9 |
| 291276265 | Helicobacter_mustelae_12198_uid46647 | COG3513 | cas9 |
| 385811609 | Ignavibacterium_album_JCM_16511_uid162097 | cd09643, COG3513 | cas9 |
| 310780384 | Ilyobacter_polytropus_DSM_2926_uid59769 | COG3513 | cas9 |
| 331702228 | Lactobacillus_buchneri_NRRL_B_30929_uid66205 | mkCas0193 | cas9 |
| 406027703 | Lactobacillus_buchneri_uid73657 | mkCas0193 | cas9 |
| 385824065 | Lactobacillus_casei_BD_II_uid162119 | mkCas0193 | cas9 |
| 191639137 | Lactobacillus_casei_BL23_uid59237 | mkCas0193 | cas9 |
| 385820880 | Lactobacillus_casei_LC2W_uid162121 | mkCas0193 | cas9 |
| 523514789 | Lactobacillus_casei_LOCK919_uid210959 | mkCas0193 | cas9 |
| 409997999 | Lactobacillus_casei_W56_uid178736 | mkCas0193 | cas9 |
| 301067199 | Lactobacillus_casei_Zhang_uid50673 | mkCas0193 | cas9 |
| 385815562 | Lactobacillus_delbrueckii_bulgaricus_2038_uid161929 | mkCas0193 | cas9 |
| 385815563 | Lactobacillus_delbrueckii_bulgaricus_2038_uid161929 | mkCas0193 | cas9 |
| 385815564 | Lactobacillus_delbrueckii_bulgaricus_2038_uid161929 | mkCas0193 | cas9 |
| 385826041 | Lactobacillus_johnsonii_DPC_6026_uid162057 | mkCas0193 | cas9 |
| 532357525 | Lactobacillus_paracasei_8700_2_uid55295 | mkCas0193 | cas9 |
| 448819853 | Lactobacillus_plantarum_ZJ316_uid188689 | mkCas0193 | cas9 |
| 385828839 | Lactobacillus_rhamnosus_GG_uid161983 | mkCas0193 | cas9 |
| 258509199 | Lactobacillus_rhamnosus_GG_uid59313 | mkCas0193 | cas9 |
| 523517690 | Lactobacillus_rhamnosus_LOCK900_uid210957 | mkCas0193 | cas9 |
| 385839898 | Lactobacillus_salivarius_CECT_5713_uid162005 | mkCas0193 | cas9 |
| 385839899 | Lactobacillus_salivarius_CECT_5713_uid162005 | mkCas0193 | cas9 |
| 385839900 | Lactobacillus_salivarius_CECT_5713_uid162005 | mkCas0193 | cas9 |
| 90961083 | Lactobacillus_salivarius_UCC118_uid58233 | mkCas0193 | cas9 |
| 90961084 | Lactobacillus_salivarius_UCC118_uid58233 | mkCas0193 | cas9 |
| 347534532 | Lactobacillus_sanfranciscensis_TMW_1_1304_uid72937 | mkCas0193 | cas9 |
| 54296138 | Legionella_pneumophila_Paris_uid58211 | cd09704 | cas9 |
| 406600271 | Leuconostoc_gelidum_JB7_uid175682 | mkCas0193 | cas9 |
| 16801805 | Listeria_innocua_Clip11262_uid61567 | cd09643, COG3513 | cas9 |
| 386044902 | Listeria_monocytogenes_10403S_uid54461 | COG3513, COG3513 | cas9 |
| 550898770 | Listeria_monocytogenes_EGD_uid223288 | COG3513, COG3513 | cas9 |
| 386048324 | Listeria_monocytogenes_J0161_uid54459 | COG3513, COG3513 | cas9 |
| 405756714 | Listeria_monocytogenes_SLCC2540_uid175106 | COG3513, COG3513 | cas9 |
| 404411844 | Listeria_monocytogenes_SLCC5850_uid175110 | COG3513, COG3513 | cas9 |
| 404282159 | Listeria_monocytogenes_serotype_1_2b_SLCC2755_uid52455 | COG3513, COG3513 | cas9 |
| 404287973 | Listeria_monocytogenes_serotype_7_SLCC2482_uid174871 | COG3513, COG3513 | cas9 |
| 433625054 | Mycoplasma_cynos_C142_uid184824 | cd09643 | cas9 |
| 401771107 | Mycoplasma_gallisepticum_CA06_2006_052_5_2P_uid172630 | cd09643 | cas9 |
| 385326554 | Mycoplasma_gallisepticum_F_uid162001 | cd09643 | cas9 |
| 401767318 | Mycoplasma_gallisepticum_NC95_13295_2_2P_uid172625 | cd09643 | cas9 |
| 401768090 | Mycoplasma_gallisepticum_NC96_1596_4_2P_uid172626 | cd09643 | cas9 |
| 401768851 | Mycoplasma_gallisepticum_NY01_2001_047_5_1P_uid172627 | cd09643 | cas9 |
| 385325798 | Mycoplasma_gallisepticum_R_high_uid161999 | cd09643 | cas9 |
| 294660600 | Mycoplasma_gallisepticum_R_low_uid57993 | cd09643 | cas9 |
| 565627373 | Mycoplasma_gallisepticum_S6_uid200523 | cd09643 | cas9 |
| 401769598 | Mycoplasma_gallisepticum_WI01_2001_043_13_2P_uid172628 | cd09643 | cas9 |
| 47458868 | Mycoplasma_mobile_163K_uid58077 | cd09643 | cas9 |
| 71894592 | Mycoplasma_synoviae_53_uid58061 | cd09643 | cas9 |
| 313669044 | Neisseria_lactamica_020_06_uid60851 | COG3513 | cas9 |
| 161869390 | Neisseria_meningitidis_053442_uid58587 | COG3513 | cas9 |
| 385324780 | Neisseria_meningitidis_8013_uid161967 | COG3513 | cas9 |
| 385337435 | Neisseria_meningitidis_WUE_2594_uid162093 | COG3513 | cas9 |
| 218767588 | Neisseria_meningitidis_Z2491_uid57819 | COG3513 | cas9 |
| 254804356 | Neisseria_meningitidis_alpha14_uid61649 | COG3513 | cas9 |
| 319957206 | Nitratifractor_salsuginis_DSM_16511_uid62183 | cd09643 | cas9 |
| 325983496 | Nitrosomonas_AL212_uid55727 | COG3513 | cas9 |
| 302336020 | Olsenella_uli_DSM_7084_uid51367 | mkCas0193 | cas9 |
| 392391493 | Ornithobacterium_rhinotracheale_DSM_15997_uidl68256 | cd09643 | cas9 |
| 154250555 | Parvibaculum_lavamentivorans_DS_1_uid58739 | cd09643 | cas9 |
| 15602992 | Pasteurella_multocida_Pm70_uid57627 | COG3513 | cas9 |
| 557607382 | Pediococcus_pentosaceus_SL4_uid227215 | mkCas0193 | cas9 |
| 294674019 | Prevotella_ruminicola_23_uid47507 | COG3513 | cas9 |

TABLE B-continued

Exemplary Cas Genes

| Locus ID/ GI | Species | Cas profile ID | Cas gene |
|---|---|---|---|
| 408489713 | Psychroflexus_torquis_ATCC_700755_uid54205 | cd09643, cd09643 | cas9 |
| 90425961 | Rhodopseudomonas_palustris_BisB18_uid58443 | COG3513 | cas9 |
| 91975509 | Rhodopseudomonas_palustris_BisB5_uid58441 | COG3513 | cas9 |
| 83591793 | Rhodospirillum_rubrum_ATCC_11170_uid57655 | cd09643 | cas9 |
| 386348484 | Rhodospirillum_rubrum_F11_uid162149 | cd09643 | cas9 |
| 383485594 | Riemerella_anatipestifer_ATCC_11845_DSM_15868_uid159857 | COG3513, cd09643 | cas9 |
| 407451859 | Riemerella_anatipestifer_RA_CH_1_uid175469 | COG3513, cd09643 | cas9 |
| 442314523 | Riemerella_anatipestifer_RA_CH_2_uid186548 | COG3513, cd09643 | cas9 |
| 386321727 | Riemerella_anatipestifer_RA_GD_uid162013 | COG3513, cd09643 | cas9 |
| 479204792 | Roseburia_intestinalis_uid197164 | COG3513 | cas9 |
| 470213512 | Sphingomonas_MM_1_uid193771 | COG3513 | cas9 |
| 325972003 | Spirochaeta_Buddy_uid63633 | cd09643 | cas9 |
| 563693590 | Spiroplasma_apis_B31_uid230613 | cd09643 | cas9 |
| 507384108 | Spiroplasma_syrphidicola_EA_1_uid205054 | cd09643 | cas9 |
| 556591142 | Staphylococcus_pasteuri_SP1_uid226267 | cd09643 | cas9 |
| 386318630 | Staphylococcus_pseudintermedius_ED99_uid162109 | mkCas0193 | cas9 |
| 269123826 | Streptobacillus_moniliformis_DSM_12112_uid41863 | COG3513 | cas9 |
| 552737657 | Streptococcus_I_G2_uid224251 | cd09643 | cas9 |
| 512539130 | Streptococcus_agalactiae_09mas018883_uid208674 | mkCas0193 | cas9 |
| 22537057 | Streptococcus_agalactiae_2603V_R_uid57943 | mkCas0193 | cas9 |
| 494703075 | Streptococcus_agalactiae_2_22_uid202215 | mkCas0193 | cas9 |
| 76788458 | Streptococcus_agalactiae_A909_uid57935 | mkCas0193 | cas9 |
| 406709383 | Streptococcus_agalactiae_GD201008_001_uid175780 | mkCas0193 | cas9 |
| 512544670 | Streptococcus_agalactiae_ILRI005_uid208676 | mkCas0193 | cas9 |
| 512698372 | Streptococcus_agalactiae_ILRI112_uid208675 | mkCas0193 | cas9 |
| 25010965 | Streptococcus_agalactiae_NEM316_uid61585 | mkCas0193 | cas9 |
| 410594450 | Streptococcus_agalactiae_SA20_06_uid178722 | mkCas0193 | cas9 |
| 538370328 | Streptococcus_anginosus_C1051_uid218003 | cd09643 | cas9 |
| 410494913 | Streptococcus_dysgalactiae_equisimilis_AC_2713_uid178644 | COG3513 | cas9 |
| 386317166 | Streptococcus_dysgalactiae_equisimilis_ATCC_12394_uid161979 | COG3513 | cas9 |
| 251782637 | Streptococcus_dysgalactiae_equisimilis_GGS_124_uid59103 | COG3513 | cas9 |
| 408401787 | Streptococcus_dysgalactiae_equisimilis_RE378_uid176684 | COG3513 | cas9 |
| 195978435 | Streptococcus_equi_zooepidemicus_MGCS10565_uid59263 | COG3513 | cas9 |
| 386338081 | Streptococcus_gallolyticus_ATCC_43143_uid162103 | cd09643 | cas9 |
| 386338091 | Streptococcus_gallolyticus_ATCC_43143_uid162103 | mkCas0193 | cas9 |
| 325978669 | Streptococcus_gallolyticus_ATCC_BAA_2069_uid63617 | mkCas0193 | cas9 |
| 288905632 | Streptococcus_gallolyticus_UCN34_uid46061 | cd09643 | cas9 |
| 288905639 | Streptococcus_gallolyticus_UCN34_uid46061 | mkCas0193 | cas9 |
| 157150687 | Streptococcus_gordonii_Challis_substr_CH1_uid57667 | cd09643 | cas9 |
| 379705580 | Streptococcus_infantarius_CJ18_uid87033 | mkCas0193 | cas9 |
| 508127396 | Streptococcus_iniae_SF1_uid206041 | mkCas0193 | cas9 |
| 508127399 | Streptococcus_iniae_SF1_uid206041 | COG3513 | cas9 |
| 538379999 | Streptococcus_intermedius_B196_uid218000 | cd09643 | cas9 |
| 527330434 | Streptococcus_lutetiensis_033_uid213397 | mkCas0193 | cas9 |
| 374338350 | Streptococcus_macedonicus_ACA_DC_198_uid81631 | cd09643 | cas9 |
| 397650022 | Streptococcus_mutans_GS_5_uid169223 | mkCas0193 | cas9 |
| 387785882 | Streptococcus_mutans_LJ23_uid162197 | mkCas0193 | cas9 |
| 290580220 | Streptococcus_mutans_NN2025_uid46353 | mkCas0193 | cas9 |
| 24379809 | Streptococcus_mutans_UA159_uid57947 | mkCas0193 | cas9 |
| 336064611 | Streptococcus_pasteurianus_ATCC_43144_uid68019 | cd09643 | cas9 |
| 410680443 | Streptococcus_pyogenes_A20_uid178106 | COG3513 | cas9 |
| 470200927 | Streptococcus_pyogenes_M1_476_uid193766 | COG3513 | cas9 |
| 15675041 | Streptococcus_pyogenes_M1_GAS_uid57845 | COG3513 | cas9 |
| 94990395 | Streptococcus_pyogenes_MGAS10270_uid58571 | COG3513 | cas9 |
| 94994317 | Streptococcus_pyogenes_MGAS10750_uid58575 | COG3513 | cas9 |
| 383479946 | Streptococcus_pyogenes_MGA515252_uid158037 | C0G3513 | cas9 |
| 383493861 | Streptococcus_pyogenes_MGAS1882_uid158061 | COG3513 | cas9 |
| 94992340 | Streptococcus_pyogenes_MGA52096_uid58573 | COG3513 | cas9 |
| 21910213 | Streptococcus_pyogenes_MGAS315_uid57911 | COG3513 | cas9 |
| 71910582 | Streptococcus_pyogenes_MGAS5005_uid58337 | COG3513 | cas9 |
| 71903413 | Streptococcus_pyogenes_MGAS6180_uid58335 | COG3513 | cas9 |
| 94988516 | Streptococcus_pyogenes_MGA59429_uid58569 | COG3513 | cas9 |
| 209559356 | Streptococcus_pyogenes_NZ131_uid59035 | C0G3513 | cas9 |
| 28896088 | Streptococcus_pyogenes_SSI_1_uid57895 | COG3513 | cas9 |
| 387783792 | Streptococcus_salivarius_JIM8777_uid162145 | cd09643 | cas9 |
| 386584496 | Streptococcus_suis_D9_uid162125 | cd09643 | cas9 |
| 389856936 | Streptococcus_suis_ST1_uid167482 | mkCas0193 | cas9 |
| 330833104 | Streptococcus_suis_ST3_uid66327 | cd09643 | cas9 |
| 55822627 | Streptococcus_thermophilus_CNRZ1066_uid58221 | cd09643 | cas9 |
| 386344353 | Streptococcus_thermophilus_JIM_8232_uid162157 | cd09643 | cas9 |
| 116627542 | Streptococcus_thermophilus_LMD_9_uid58327 | cd09643 | cas9 |
| 116628213 | Streptococcus_thermophilus_LMD_9_uid58327 | mkCas0193 | cas9 |
| 55820735 | Streptococcus_thermophilus_LMG_18311_uid58219 | cd09643 | cas9 |
| 387909441 | Streptococcus_thermophilus_MN_ZLW_002_uid166827 | cd09643 | cas9 |
| 387910220 | Streptococcus_thermophilus_MN_ZLW_002_uid166827 | mkCas0193 | cas9 |

TABLE B-continued

Exemplary Cas Genes

| Locus ID/ GI | Species | Cas profile ID | Cas gene |
|---|---|---|---|
| 386086348 | Streptococcus_thermophilus_ND03_uid162015 | cd09643 | cas9 |
| 386087120 | Streptococcus_thermophilus_ND03_uid162015 | mkCas0193 | cas9 |
| 389874754 | Tistrella_mobilis_KA081020_065_uid167486 | COG3513 | cas9 |
| 42525843 | Treponema_denticola_ATCC_35405_uid57583 | mkCas0193 | cas9 |
| 530892607 | Treponema_pedis_T_A4_uid215715 | COG3513, COG3513 | cas9 |
| 121608211 | Verminephrobacter_eiseniae_EF01_2_uid58675 | cd09643 | cas9 |
| 525888882 | Vibrio_parahaemolyticus_O1_K33_CDC_K4557_uid212977 | COG3513, COG3513 | cas9 |
| 525913263 | Vibrio_parahaemolyticus_O1_K33_CDC_K4557_uid212977 | COG3513 | cas9 |
| 525919586 | Vibrio_parahaemolyticus_O1_K33_CDC_K4557_uid212977 | COG3513, COG3513 | cas9 |
| 525927253 | Vibrio_parahaemolyticus_O1_K33_CDC_K4557_uid212977 | COG3513, COG3513 | cas9 |
| 325955459 | Weeksella_virosa_DSM_16922_uid63627 | cd09643, cd09643 | cas9 |
| 34557790 | Wolinella_succinogenes_DSM_1740_uid61591 | cd09643 | cas9 |
| 34557932 | Wolinella_succinogenes_DSM_1740_uid61591 | cd09704 | cas9 |
| 295136244 | Zunongwangia_profunda_SM_A87_uid48073 | COG3513, cd09643 | cas9 |
| 304313029 | gamma_proteobacterium_HdN1_uid51635 | cd09643 | cas9 |
| 189485058 | uncultured_Termite_group_1_bacterium_phylotype_Rs_D17_uid59059 | cd09643 | cas9 |
| 189485059 | uncultured_Termite_group_1_bacterium_phylotype_Rs_D17_uid59059 | cd09643 | cas9 |
| 189485225 | uncultured_Termite_group_1_bacterium_phylotype_Rs_D17_uid59059 | COG3513 | cas9 |
| 347536497 | Flavobacterium_branchiophilum_FL_15_uid73421 | COG3513, cd09643, COG3513 | cas9, cas9 |
| 365959402 | Flavobacterium_columnare_ATCC_49512_uid80731 | COG3513, cd09643, COG3513 | cas9, cas9 |
| 387132277 | Prevotella_intermedia_17_uid163151 | cd09643, COG3513, COG0188 | cas9, Type IIA topoisomerase |

Guide RNA (gRNA)

gRNA or sgRNA (single guide RNA) is engineered as a fusion between a crRNA and part of the transactivating CRISPR RNA (tracrRNA) sequence, which guides the Cas9 to a specific target DNA sequence that is complementary to the protospacer region. Guide RNA may include an expression cassette containing a chimeric RNA design with a long tracrRNA hybrid, short tracrRNA hybrid or a native CRISPR array+tracrRNA conformation. Chimeric gRNA combines the targeting specificity of the crRNA with the scaffolding properties of the tracrRNA into a single transcript. gRNA transient expression is controlled by species-specific higher plant RNA Polymerase III promoters such as those from the U6 or U3 snRNA gene family (Wang et al., 2008). gRNA transcript termination is controlled by a 6-20 nucleotide tract of poly dT as per Wang et al., 2008. gRNA expression cassettes are located on the same or different transient expression vectors from other components of the CRISPR-Cas system. gRNA transcripts may be synthesized in vitro and delivered directly into plant cells, independent of or in combination with gRNA transient expression vectors.

In some embodiments, the native S. pyogenes type II CRISPR-Cas system consists of a Crispr ASsociated (Cas9) nuclease and two disparate non-coding RNAs, trans-activating RNA (tracrRNA) and CRISPR RNA (crRNA). The RNA components of this system direct Cas9 nuclease to a sequence specific target in a genome. All three components can be expressed separately as tracrRNA and crRNA and Cas9 protein. The crRNA provides the target specificity and consists of a spacer sequence of 20 bases that are complementary to the target DNA (protospacer sequence) that is cleaved by Cas9 (Le Cong et al., 2013). The tracrRNA acts as an RNA scaffold when associated with crRNA by way of RNA:RNA base pairing and it is this complex that associates with Cas9. The tracrRNA can be engineered to be shorter than 89 bases, as is the case in the Alt-R™ system developed by Integrated DNA Technologies (IDT). In this system tracrRNA as short as 67 bases have increased on-target performance when compare to native tracrRNA. When the crRNA and tracrRNA are artificially combined into a single fused functional RNA or single guide RNA (sgRNA) targeting of Cas9 protein can be greatly simplified over the native system. Similar to the native tracerRNA:crRNA complex, the engineered sgRNA guides the Cas9 to a specific target DNA sequence.

Target Region

Guide RNAs contain two components that define specificity to a DNA target region, a proto-spacer and a proto-spacer adjacent motif (PAM). Proto-spacer sequence, typically 20 nucleotides but can vary based on the DNA target, provides DNA sequence specificity for the CRISPR-Cas complex. DNA targets also contain a NNG or NAG trinucleotide sequence (PAM) where N denotes any nucleotide, immediately 3' or downstream of the proto-spacer.

One Component Approach

Similar to Le Cong et al. (2013) and others, a simplified "one component approach" to CRISPR-Cas gene editing wherein a single transient expression construct contains all components of the CRISPR-Cas complex, i.e. both the gRNA and the Cas expressions cassettes. This allows for an easy modular design for targeting single or multiple loci in any given plant or crop. Targeting multiple loci can be achieved by simply swapping in the target-specific gRNA cassettes. Additionally, species specific promoters, terminators or other expressing enhancing elements can easily be shuttled in and out of "one component approach" transient vectors allowing for optimal expression of both gRNA and Cas protein in a species-specific manner.

Two Component Approach

In the two-component approach, Cas and gRNA expression cassettes are located on different transient expression vectors. This allows for delivery of a CRISPR-Cas editing components separately, allowing for different ratios of gRNA to Cas within the same cell. Similar to the one component approach, the two-component approach also allows for promoters, terminators or other elements affecting expression of CRISPR-Cas components to be easily altered and allow targeting of DNA in a species-specific manner.

Antibiotics

Another class of endonucleases are antibiotics which are DNA cleaving glycopeptides such as the bleomycin family of antibiotics are DNA cleaving glycopeptides which include bleomycin, zeocin, phleomycin, tallysomycin, pepleomycin and others which are further described herein.

Other DNA-Modifying Molecules

Other DNA-modifying molecules may be used in targeted gene recombination. For example, peptide nucleic acids may be used to induce modifications to the genome of the target cell or cells (see, e.g., Ecker, U.S. Pat. No. 5,986,053 herein incorporated by reference). In brief, synthetic nucleotides comprising, at least, a partial peptide backbone is used to target a homologous genomic nucleotide sequence. Upon binding to the double-helical DNA, or through a mutagen ligated to the peptide nucleic acid, modification of the target DNA sequence and/or recombination is induced to take place. Targeting specificity is determined by the degree of sequence homology between the targeting sequence and the genomic sequence.

In some embodiments of the methods and compositions of the present disclosure genes (such as the SHP gene) may be targeted using triple helix forming oligonucleotides (TFO). TFOs may be generated synthetically, for example, by PCR or by use of a gene synthesizer apparatus. Additionally, TFOs may be isolated from genomic DNA if suitable natural sequences are found. TFOs may be used in a number of ways, including, for example, by tethering to a mutagen such as, but not limited to, psoralen or chlorambucil (see, e.g., Havre et al., Proc Nat'l Acad Sci, U.S.A. 90:7879-7883, 1993; Havre et al., J Virol 67:7323-7331, 1993; Wang et al., Mol Cell Biol 15:1759-1768, 1995; Takasugi et al., Proc Nat'l Acad Sci, U.S.A. 88:5602-5606, 1991; Belousov et al., Nucleic Acids Res 25:3440-3444, 1997). Furthermore, for example, TFOs may be tethered to donor duplex DNA (see, e.g., Chan et al., J Biol Chem 272:11541-11548, 1999). TFOs can also act by binding with sufficient affinity to provoke error-prone repair (Wang et al., Science 271:802-805, 1996).

The methods disclosed herein are not necessarily limited to the nature or type of DNA-modifying reagent which is used. For example, such DNA-modifying reagents release radicals which result in DNA strand breakage. Alternatively, the reagents alkylate DNA to form adducts which would block replication and transcription. In another alternative, the reagents generate crosslinks or molecules that inhibit cellular enzymes leading to strand breaks. Examples of DNA-modifying reagents which have been linked to oligonucleotides to form TFOs include, but are not limited to, indolocarbazoles, napthalene diimide (NDI), transplatin, bleomycin, analogues of cyclopropapyrroloindole, and phenanthodihydrodioxins. In particular, indolocarbazoles are topoisomerase I inhibitors. Inhibition of these enzymes results in strand breaks and DNA protein adduct formation (Arimondo et al., Bioorganic and Medicinal Chem. 8, 777-784, 2000). NDI is a photooxidant that can oxidize guanines which could cause mutations at sites of guanine residues (Nunez et al., Biochemistry, 39, 6190-6199, 2000). Transplatin has been shown to react with DNA in a triplex target when the TFO is linked to the reagent. This reaction causes the formation of DNA adducts which would be mutagenic (Columbier et al., Nucleic Acids Research, 24: 4519-4524, 1996). Bleomycin is a DNA breaker, widely used as a radiation mimetic. It has been linked to oligonucleotides and shown to be active as a breaker in that format (Sergeyev, Nucleic Acids Research 23, 4400-4406, 1995; Kane et al., Biochemistry, 34, 16715-16724, 1995). Analogues of cyclopropapyrroloindole have been linked to TFOs and shown to alkylate DNA in a triplex target sequence. The alkylated DNA would then contain chemical adducts which would be mutagenic (Lukhtanov et al., Nucleic Acids Research, 25, 5077-5084, 1997). Phenanthodihydrodioxins are masked quinones that release radical species upon photoactivation. They have been linked to TFOs and have been shown to introduce breaks into duplex DNA on photoactivation (Bendinskas et al., Bioconjugate Chem. 9, 555-563, 1998).

Other methods of inducing modifications and/or recombination are contemplated by the present disclosure. For example, another embodiment involves the induction of homologous recombination between an exogenous DNA fragment and the targeted gene (see e.g., Capecchi et al., Science 244:1288-1292, 1989) or by using peptide nucleic acids (PNA) with affinity for the targeted site. Still other methods include sequence specific DNA recognition and targeting by polyamides (see e.g., Dervan et al., Curr Opin Chem Biol 3:688-693, 1999; Biochemistry 38:2143-2151, 1999) and the use nucleases with site specific activity (e.g., zinc finger proteins, TALENs, Meganucleases and/or CRISPRs).

The present disclosure is not limited to any particular frequency of modification and/or recombination. In some embodiments the methods disclosed herein result in a frequency of modification in the target nucleotide sequence of from 0.01% to 3%. Nonetheless, any frequency (i.e., between 0% and 100%) of modification and/or recombination is contemplated to be within the scope of the present disclosure. The frequency of modification and/or recombination is dependent on the method used to induce the modification and/or recombination, the cell type used, the specific gene targeted, and the DNA mutating reagent used, if any. Additionally, the method used to detect the modification and/or recombination, due to limitations in the detection method, may not detect all occurrences of modification and/or recombination. Furthermore, some modification and/or recombination events may be silent, giving no detectable indication that the modification and/or recombination has taken place. The inability to detect silent modification and/or recombination events gives an artificially low estimate of modification and/or recombination. Because of these reasons, and others, the disclosure is not necessarily limited to any particular modification and/or recombination frequency. In one embodiment, the frequency of modification and/or recombination is between 0.01% and 100%. In another embodiment, the frequency of modification and/or recombination is between 0.01% and 50%. In yet another embodiment, the frequency of modification and/or recombination is between 0.1% and 10%. In still yet another embodiment, the frequency of modification and/or recombination is between 0.1% and 5%.

The term "frequency of mutation" as used herein in reference to a population of cells which are treated with a DNA-modifying molecule that is capable of introducing a mutation into a target site in the cells' genome, refers to the number of cells in the treated population which contain the mutation at the target site as compared to the total number of cells which are treated with the DNA-modifying molecule. For example, with respect to a population of cells which is treated with the DNA-modifying molecule TFO tethered to psoralen which is designed to introduce a mutation at a target site in the cells' genome, a frequency of mutation of 5% means that of a total of 100 cells which are treated with TFO-psoralen, 5 cells contain a mutation at the target site.

Although the present disclosure is not necessarily limited to any degree of precision in the modification and/or recombination of DNA in the cell, it is contemplated that some embodiments of the present disclosure require higher degrees of precision, depending on the desired result. For example, the specific sequence changes required for gene repair (e.g., particular base changes) require a higher degree of precision as compared to producing a gene knockout wherein only the disruption of the gene is necessary. With the methods of the present disclosure, achievement of higher levels of precision in modification and/or homologous recombination techniques is greater than with prior art methods.

Delivery of Gene Repair Oligonucleobases into Plant Cells

Any commonly known method used to transform a plant cell can be used for delivering the gene repair oligonucleobases. Illustrative methods are listed below. The methods and compositions herein may involve any of many methods to transfect the cells with the DNA-modifying reagent or reagents. Methods for the introduction of DNA modifying reagents into a cell or cells are well known in the art and include, but are not limited to, microinjection, electroporation, passive adsorption, calcium phosphate-DNA co-precipitation, DEAE-dextran-mediated transfection, polybrene-mediated transfection, liposome fusion, lipofectin, nucleofection, protoplast fusion, retroviral infection, biolistics (i.e., particle bombardment) and the like.

The use of metallic microcarriers (microspheres) for introducing large fragments of DNA into plant cells having cellulose cell walls by projectile penetration is well known to those skilled in the relevant art (henceforth biolistic delivery). U.S. Pat. Nos. 4,945,050; 5,100,792 and 5,204,253 describe general techniques for selecting microcarriers and devices for projecting them.

Specific conditions for using microcarriers in the methods disclosed herein may include the conditions described in International Publication WO 99/07865. In an illustrative technique, ice cold microcarriers (60 mg/mL), mixed duplex oligonucleotide (60 mg/mL) 2.5 M $CaCl_2$ and 0.1 M spermidine are added in that order; the mixture gently agitated, e.g., by vortexing, for 10 minutes and then left at room temperature for 10 minutes, whereupon the microcarriers are diluted in 5 volumes of ethanol, centrifuged and resuspended in 100% ethanol. Good results can be obtained with a concentration in the adhering solution of 8-10 µg/µL microcarriers, 14-17 µg/mL mixed duplex oligonucleotide, 1.1-1.4 M $CaCl_2$ and 18-22 mM spermidine. Optimal results were observed under the conditions of 8 µg/µL microcarriers, 16.5 µg/mL mixed duplex oligonucleotide, 1.3 M $CaCl_2$ and 21 mM spermidine.

Gene repair oligonucleobases can also be introduced into plant cells using microfibers to penetrate the cell wall and cell membrane. U.S. Pat. No. 5,302,523 to Coffee, R., and Dunwell, J. M. (1994) describes the use of silicon carbide fibers to facilitate transformation of suspension maize cultures of Black Mexican Sweet. Any mechanical technique that can be used to introduce DNA for transformation of a plant cell using microfibers can be used to deliver gene repair oligonucleobases for transmutation.

An illustrative technique for microfiber delivery of a gene repair oligonucleobase is as follows: Sterile microfibers (2 µg) are suspended in 150 µL of plant culture medium containing about 10 µg of a mixed duplex oligonucleotide. A suspension culture is allowed to settle, and equal volumes of packed cells and the sterile fiber/nucleotide suspension are vortexed for 10 minutes and plated. Selective media are applied immediately or with a delay of up to about 120 hours as is appropriate for the particular trait.

In an alternative embodiment, the gene repair oligonucleobases can be delivered to the plant cell by electroporation of a protoplast derived from a plant part. The protoplasts are formed by enzymatic treatment of a plant part, particularly a leaf, according to techniques well known to those skilled in the art. See, e.g., Gallois et al., 1996, in Methods in Molecular Biology 55:89-107, Humana Press, Totowa, N.J.; Kipp et al., 1999, in Methods in Molecular Biology 133: 213-221, Humana Press, Totowa, N.J. The protoplasts need not be cultured in growth media prior to electroporation. Illustrative conditions for electroporation are 300,000 protoplasts in a total volume of 0.3 mL with a concentration of gene repair oligonucleobase of between 0.6-4 µg/mL.

In an alternative embodiment, nucleic acids are taken up by plant protoplasts in the presence of the membrane-modifying agent polyethylene glycol, according to techniques well known to those skilled in the art. In another alternative embodiment, the gene repair oligonucleobases can be delivered by injecting it with a microcapillary into plant cells or into protoplasts.

In an alternative embodiment, nucleic acids are embedded in microbeads composed of calcium alginate and taken up by plant protoplasts in the presence of the membrane-modifying agent polyethylene glycol (see, e.g., Sone et al., Journal of Bioscience and Bioengineering, 94(1):87-91, 2002; Liu et al., 2004).

In an alternative embodiment, nucleic acids frozen in water and introduced into plant cells by bombardment in the form of microparticles (see, e.g., Gilmore, 1991, U.S. Pat. No. 5,219,746; Brinegar et al.).

In an alternative embodiment, nucleic acids attached to nanoparticles are introduced into intact plant cells by incubation of the cells in a suspension containing the nanoparticle (see, e.g., Pasupathy et al., Biotechnology Journal: Healthcare Nutrition Technology, 3(8), 1078-1082, 2008) or by delivering them into intact cells through particle bombardment or into protoplasts by co-incubation (see, e.g., Torney et al., Nature nanotechnology, 2(5), 295, 2007).

In an alternative embodiment, nucleic acids complexed with penetrating peptides and delivered into cells by co-incubation (see, e.g., Chugh and Eudes, Journal of peptide science: an official publication of the European Peptide Society, 14(4), 477-481, 2008; WO 2008148223 A1).

In an alternative embodiment, nucleic acids are introduced into intact cells through electroporation (see, e.g., He et al., 1998, US 2003/0115641 A1, Dobres et al.).

In an alternative embodiment, nucleic acids are delivered into cells of dry embryos by soaking them in a solution with nucleic acids (see, e.g., Töpfer et al., 1989, Senaratna et al., 1991) or in other embodiments are introduced by Cellsqueeze (SQZ Biotech).

Methods of Reducing Polypeptide Activity and Other Mutagenesis Techniques

Certain aspects of the present disclosure relate to reducing levels and/or activity of a polypeptide (e.g. an SHP polypeptide). Methods of modifying decreasing the quantity/level or the activity of one or more polypeptides of the present disclosure are well-known in the art and are described herein.

Cells (e.g. plant cells) of the present disclosure may contain one or more polypeptides with decreased activity as compared to a corresponding control cell, such as a wild-type cell. In some embodiments, one or more SHP proteins have decreased activity in a host cell as compared to a corresponding control cell. Methods of decreasing the expression, abundance, and/or activity of a polypeptide are well-known in the art and are described herein.

In some embodiments, decreasing the activity of a polypeptide such as, for example, one or more SHP proteins involves decreasing the expression of a nucleic acid encoding the polypeptide.

Decreasing the expression of a nucleic acid may be accomplished by introducing a genetic mutation into a target nucleic acid. Mutagenesis approaches may be used to disrupt or "knockout" the expression of a target gene by generating mutations. In some embodiments, the mutagenesis results in a partial deletion of the target gene. In other embodiments, the mutagenesis results in a complete deletion of the target gene. Methods of mutagenizing microorganisms are well known in the art and include, for example, random mutagenesis and site-directed mutagenesis to induce mutations. Examples of methods of random mutagenesis include, for example, chemical mutagenesis (e.g., using ethane methyl sulfonate), insertional mutagenesis, and irradiation. In some embodiments, mutagenic techniques may be used to introduce a premature stop codon into a nucleic acid of the present disclosure (e.g. an SHP gene). This could be accomplished via, for example, a targeted single nucleotide change into the target nucleic acid at a location that creates a premature stop codon.

In some embodiments, nucleic acids of the present disclosure (e.g. SHP genes) may be edited in a manner that does not result in a shift of the open reading frame or that does not substantially eliminate expression of the nucleic acid and/or the polypeptide it encodes, such as, for example introducing a single nucleotide change into the nucleic acid. Various techniques may be used to accomplish such an edit such as, for example, targeted introduction of a point mutation in the nucleic acid. Such edits may, for example, reduce the expression of the nucleic acid and/or reduce the expression and/or activity of the polypeptide it encodes. For example, a point mutation may be introduced into an SHP gene that results in an amino acid change in the encoded polypeptide sequence. In some embodiments, such an amino acid change may be in a region important for the function of the SHP gene, such that the encoded mutant SHP polypeptide has reduced activity and/or altered function.

One method for reducing or inhibiting the expression of a target gene is by genetically modifying the target gene and introducing it into the genome of a host cell to replace the wild-type version of the gene by homologous recombination (for example, as described in U.S. Pat. No. 6,924,146).

Another method for reducing or inhibiting the expression of a target gene is by insertion mutagenesis using the T-DNA of *Agrobacterium tumefaciens*, or transposons (see Winkler et al., Methods Mol. Biol. 82:129-136, 1989, and Martienssen Proc. Natl. Acad. Sci. 95:2021-2026, 1998). After generating the insertion mutants, the mutants can be screened to identify those containing the insertion in a target gene. Methods to disrupt a target gene by insertional mutagenesis are described in for example, U.S. Pat. No. 5,792,633. Methods to disrupt a target gene by transposon mutagenesis are described in for example, U.S. Pat. No. 6,207,384.

A further method to disrupt a target gene is by use of the cre-lox system (for example, as described in U.S. Pat. No. 4,959,317).

Another method to disrupt a target gene is by use of PCR mutagenesis (for example, as described in U.S. Pat. No. 7,501,275).

Endogenous gene expression may also be reduced or inhibited by means of RNA interference (RNAi), which uses a double-stranded RNA having a sequence identical or similar to the sequence of the target gene. RNAi may include the use of micro RNA, such as artificial miRNA, to suppress expression of a gene.

RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA.

Thus, in some embodiments, reduction or inhibition of gene expression is achieved using RNAi techniques. For example, to achieve reduction or inhibition of the expression of a DNA encoding a protein using RNAi, a double-stranded RNA having the sequence of a DNA encoding the protein, or a substantially similar sequence thereof (including those engineered not to translate the protein) or fragment thereof, is introduced into a host cell of interest. As used herein, RNAi and dsRNA both refer to gene-specific silencing that is induced by the introduction of a double-stranded RNA molecule, see e.g., U.S. Pat. Nos. 6,506,559 and 6,573,099, and includes reference to a molecule that has a region that is double-stranded, e.g., a short hairpin RNA molecule. The resulting cells may then be screened for a phenotype associated with the reduced expression of the target gene, e.g., reduced cellulase expression, and/or by monitoring steady-state RNA levels for transcripts of the target gene. Although the sequences used for RNAi need not be completely identical to the target gene, they may be at least 70%, 80%, 90%, 91%, 92%, 93%, 94%, 95%, 96%, 97%, 98%, 99%, or more identical to the target gene sequence. See, e.g., U.S. Patent Application Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Application Publication No. 2003/0221211.

The RNAi nucleic acids may encompass the full-length target RNA or may correspond to a fragment of the target RNA. In some cases, the fragment will have fewer than 100, 200, 300, 400, or 500 nucleotides corresponding to the target sequence. In addition, in some aspects, these fragments are at least, e.g., 50, 100, 150, 200, or more nucleotides in length. Interfering RNAs may be designed based on short duplexes (i.e., short regions of double-stranded sequences). Typically, the short duplex is at least about 15, 20, or 25-50 nucleotides in length (e.g., each complementary sequence of the double stranded RNA is 15-50 nucleotides in length), often about 20-30 nucleotides, e.g., 20, 21, 22, 23, 24, 25, 26, 27, 28, 29, or 30 nucleotides in length. In some cases, fragments for use in RNAi will correspond to regions of a target protein that do not occur in other proteins in the organism or that have little similarity to other transcripts in the organism, e.g., selected by comparison to sequences in analyzing publicly-available sequence databases. Similarly, RNAi fragments may be selected for similarity or identity with a conserved sequence of a gene family of interest, such as those described herein, so that the RNAi targets multiple different gene transcripts containing the conserved sequence.

RNAi may be introduced into a host cell as part of a larger DNA construct. Often, such constructs allow stable expression of the RNAi in cells after introduction, e.g., by integration of the construct into the host genome. Thus, expression vectors that continually express RNAi in cells transfected with the vectors may be employed for this disclosure. For example, vectors that express small hairpin or stem-loop structure RNAs, or precursors to microRNA, which get processed in vivo into small RNAi molecules capable of carrying out gene-specific silencing (Brummelkamp et al, Science 296:550-553, (2002); and Paddison, et al., Genes & Dev. 16:948-958, (2002)) can be used. Post-transcriptional gene silencing by double-stranded RNA is discussed in further detail by Hammond et al., Nature Rev Gen 2: 110-119, (2001); Fire et al., Nature 391: 806-811, (1998); and Timmons and Fire, Nature 395: 854, (1998).

Methods for selection and design of sequences that generate RNAi are well-known in the art (e.g. U.S. Pat. Nos. 6,506,559; 6,511,824; and 6,489,127).

A reduction or inhibition of gene expression in a host cell of a target gene may also be obtained by introducing into host cells antisense constructs based on a target gene nucleic acid sequence. For antisense suppression, a target sequence is arranged in reverse orientation relative to the promoter sequence in the expression vector. The introduced sequence need not be a full length cDNA or gene, and need not be identical to the target cDNA or a gene found in the cell to be transformed. Generally, however, where the introduced sequence is of shorter length, a higher degree of homology to the native target sequence is used to achieve effective antisense suppression. In some aspects, the introduced antisense sequence in the vector will be at least 30 nucleotides in length, and improved antisense suppression will typically be observed as the length of the antisense sequence increases. In some aspects, the length of the antisense sequence in the vector will be greater than 100 nucleotides. Transcription of an antisense construct as described results in the production of RNA molecules that are the reverse complement of mRNA molecules transcribed from an endogenous target gene. Suppression of a target gene expression can also be achieved using a ribozyme. The production and use of ribozymes are disclosed in U.S. Pat. Nos. 4,987,071 and 5,543,508.

Expression cassettes containing nucleic acids that encode target gene expression inhibitors, e.g., an antisense or siRNA, can be constructed using methods well known in the art. Constructs include regulatory elements, including promoters and other sequences for expression and selection of cells that express the construct. Typically, fungal and/or bacterial transformation vectors include one or more cloned coding sequences (genomic or cDNA) under the transcriptional control of 5' and 3' regulatory sequences and a dominant selectable marker. Such transformation vectors typically also contain a promoter (e.g., a regulatory region controlling inducible or constitutive, environmentally- or developmentally-regulated expression), a transcription initiation start site, an RNA processing signal (such as intron splice sites), a transcription termination site, and/or a polyadenylation signal.

In certain embodiments, a portion of the target nucleic acid may be modified, such as the region encoding the catalytic domain, the coding region, or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification may include, for example, a leader sequence, a propeptide sequence, a signal sequence, a transcription terminator, and a transcriptional activator.

Plants of the Present Disclosure

The methods and compositions described herein may in certain aspects and embodiments be applicable to plants generally. For example, in some aspects and/or embodiments a plant species may be selected from the Brassicaceae family, including a number of important crops such as *Brassica napus* (canola, oilseed rape), *Brassica rapa* (e.g., turnip, Chinese cabbage), *Brassica oleracea* (broccoli, cabbage, cauliflower, etc.), *Brassica juncea* (mustard), or *Raphanus sativus* (common radish), as well as many important legume crops such as peas, beans, lentils, and soybeans.

According to the present description, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild type SHP protein.

According to the present description, substantially normal development of a plant, plant organ, plant tissue or plant cell is defined as the occurrence of one or more developmental events in the plant, plant organ, plant tissue or plant cell that are substantially the same as those occurring in a corresponding plant, plant organ, plant tissue or plant cell expressing the wild type SHP protein.

According to the present description plant organs include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Plants of the present disclosure include those plants that have the potential to exhibit pod shatter. For example, the present disclosure includes *Brassica* spp. plants that exhibit pod shatter.

In various embodiments, plants as disclosed herein are principally focused on monocotyledonous plants including any woody plant species that grows as a tree or shrub, any herbaceous species, or any species that produces edible fruits, seeds or vegetables, or any species that produces colorful or aromatic flowers. For example, the plant maybe selected from a species of plant from the group consisting of canola, sunflower, corn, tobacco, sugar beet, cotton, maize, wheat, barley, rice, alfalfa, barley, sorghum, tomato, mango, peach, apple, pear, strawberry, banana, melon, cassava, potato, carrot, lettuce, onion, soy bean, soya spp, sugar cane, pea, chickpea, field pea, fava bean, lentils, turnip, rutabaga, brussel sprouts, lupin, cauliflower, kale, field beans, poplar, pine, *eucalyptus*, grape, citrus, triticale, alfalfa, rye, oats, turf and forage grasses, flax, oilseed rape, mustard, cucumber, morning glory, balsam, pepper, eggplant, marigold, lotus, cabbage, daisy, carnation, tulip, iris, lily, and nut producing plants insofar as they are not already specifically mentioned.

Plants and plant cells can be tested for resistance preharvest dehiscence using commonly known methods in the art.

In some embodiments, plants of the present disclosure have one or more mutations in one or more SHP genes have increased resistance/reduced susceptibility to preharvest dehiscence as compared to a corresponding control plant (e.g. a plant of the same species that does not have any mutations in any SHP genes, such as a wild-type plant). The incidence of pod shattering in plants having increased resistance/reduced susceptibility to preharvest dehiscence may be, for example, at least about 5%, at least about 10%, at least about 15%, at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% lower or reduced as compared to a corresponding control.

As used herein, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild-type protein of interest.

As used herein, substantially normal development of a plant, plant organ, plant tissue or plant cell is defined as the occurrence of one or more development events in the plant, plant organ, plant tissue or plant cell that are substantially the same as those occurring in a corresponding plant, plant organ, plant tissue or plant cell expressing the wild-type protein.

In certain embodiments plant organs provided herein include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Generation of Plants

Tissue culture of various tissues of plant species and regeneration of plants therefrom is known. For example, the propagation of a canola cultivar by tissue culture is described in any of the following but not limited to any of the following: Li et al., "Somatic embryogenesis in quite a direct way in cultures of mesophyll protoplasts of *Brassica napus* L.", Plant Cell Reports 1: 209-211, 1982; Chuong et al., "A Simple Culture Method for *Brassica* hypocotyls Protoplasts," Plant Cell Reports 4:4-6, 1985; Barsby et al., "A Rapid and Efficient Alternative Procedure for the Regeneration of Plants from Hypocotyl Protoplasts of *Brassica napus*," Plant Cell Reports (Spring, 1996); Kartha et al., "In vitro Plant Formation from Stem Explants of Rape," Physiol. Plant, 31:217-220, 1974; Narasimhulu et al., "Species Specific Shoot Regeneration Response of Cotyledonary Explants of Brassicas," Plant Cell Reports (Spring 1988); Sun et al., "Cotyledon-derived diploid and haploid protoplast culture and diploid plant regeneration in *Brassica napus* cv. 'Topas'," Can. J. Bot. 76: 530-541, 1998; Swanson, E., "Microspore Culture in *Brassica*," Methods in Molecular Biology, Vol. 6, Chapter 17, p. 159, 1990.

Further reproduction of the variety can occur by tissue culture and regeneration. Tissue culture of various tissues of soybeans and regeneration of plants therefrom is well known and widely published. For example, see Komatsuda et al., "Genotype X Sucrose Interactions for Somatic Embryogenesis in Soybeans," Crop Sci. 31:333-337, 1991; Stephens et al., "Agronomic Evaluation of Tissue-Culture-Derived Soybean Plants," Theor. Appl. Genet. 82:633-635, 1991; Komatsuda et al., "Maturation and Germination of Somatic Embryos as Affected by Sucrose and Plant Growth Regulators in Soybeans *Glycine gracilis* L. Skvortz and *Glycine max* L. Merr." Plant Cell, Tissue and Organ Culture, 28:103-113, 1992; Dhir et al., "Regeneration of Fertile Plants from Protoplasts of Soybean (*Glycine max* L. Merr.); Genotypic Differences in Culture Response," Plant Cell Reports 11:285-289, 1992; Pandey et al., "Plant Regeneration from Leaf and Hypocotyl Explants of *Glycine wightii* (W. and A.) VERDC. var. *longicauda*," Japan J. Breed. 42:1-5, 1992; and Shetty et al., "Stimulation of In Vitro Shoot Organogenesis in *Glycine max* L. Merrill. by Allantoin and Amides," Plant Science 81:245-251, 1992. The disclosures of U.S. Pat. No. 5,024,944 issued Jun. 18, 1991 to Collins et al., and U.S. Pat. No. 5,008,200 issued Apr. 16, 1991 to Ranch et al., are hereby incorporated herein in their entirety by reference.

Certain aspects of the present disclosure also related to plants derived from plants having one or more mutations in a nucleic acid (e.g. an SHP gene) of the present disclosure. For example, plants having one or more SHP mutations may be crossed with the same or different plants to give rise to an $F_1$ progeny plant, where at least one of the parents of the $F_1$ progeny plant had the one or more SHP mutations. These $F_1$ plants can be further self-crossed or crossed with a different plant line, and resulting $F_2$ progeny can be screened for one or more SHP mutations.

EXAMPLES

The following examples are provided to further illustrate aspects of the present disclosure. These examples are non-limiting and should not be construed as limiting any aspect of the present disclosure.

Example 1: Identification and Characterization of SHP1A, SHP1C, SHP2A, SHP2C, SHP3A, SHP3C, SHP4A and SHP4C Genes Molecular Characterization of BnSHP Genes Eight BnSHP genes found in the *Brassica* genome database (Genoscope) were characterized. The SHP canola genes are herein designated BnSHP1A, BnSHP1C, BnSHP2A, BnSHP2C, BnSHP3A, BnSHP3C, BnSHP4A and BnSHP4C. It appears that each half of the genes were contributed by the *B. rapa* (AA) and the *B. oleracea* (CC) parental subgenomes. The respective chromosomal location of each gene in *B. napus* genome is presented in Table 1, as well as the nucleotide sequence of the coding regions of all eight SHP genes found in Genoscope (SEQ ID NO: 1-8, see Table 1) and the genomic DNA sequence of all eight SHP genes found in Genoscope (SEQ ID NO: 9-16, see Table 1). The partial sequence of the 5' UTR promoter region, along with some of the 5' coding sequence of each BnSHP gene was cloned and sequenced from genomic DNA obtained from the BN2-SU plant line. All 8 genes were found to have unique promoters. The 5'-UTR of the BnSHP1A gene revealed an insertion of ~5 kb that appeared to be a translocated transposable element, which is not present in the reference sequence in Genoscope, and may be line-specific. FIG. 1A shows the alignment of the partial nucleotide sequences, while FIG. 1B shows the corresponding translated amino acid sequences obtained from the gene characterization of the 5' genomic region of the BN2-SU SHP genes, and compared to the corresponding *Arabidopsis* AtSHP1 and AtSHP2 sequences. The level of homology among all BnSHP genes and the AtSHP genes at the nucleotide and the amino acid levels is very high (>80%).

TABLE 1

Shatterproof genes, chromosomal location (source: Genoscope), source genome, nucleotide coding sequence, and genomic DNA sequence

| SHP Gene Cibus Name | Chromosome | Position Chromosome | Genome | Coding Sequence, SEQ ID NO: | Genomic DNA Sequence, SEQ ID NO: |
|---|---|---|---|---|---|
| BnSHP-1A | A09 | 3139589-3143645 | A | 1 | 9 |
| BnSHP-1C | C08 | 29697543-29700152 | C | 2 | 10 |
| BnSHP-2A | A07 | 14877625-14881448 | A | 3 | 11 |
| BnSHP-2C | C06 | 19706214-19709351 | C | 4 | 12 |
| BnSHP-3A | A04 | 1164261-1165954 | A | 5 | 13 |
| BnSHP-3C | C04 | 24456162-24474692 | C | 6 | 14 |
| BnSHP-4A | A05 | 1619288-1623119 | A | 7 | 15 |
| BnSHP-4C | Unknown | Unknown | C | 8 | 16 |

Cloning and Further Molecular Characterization of BnSHP Genes

SHP1 and 2 genes in *Arabidopsis thaliana* are highly homologous to the Canola SHP genes having 80% nucleotide identity. Using the publicly available cDNA and genomic sequences of *Arabidopsis thaliana* SHP1 and SHP2 and those for *Brassica napus*, PCR primers were designed and used to amplify the BnSHP gene sequences from genomic DNA from elite canola lines BN2 and BN-17. PCR-amplified SHP genomic fragments were cloned and sequenced. Additional sequencing of the genomic DNA fragments was performed by Next Generation Sequencing to complete this analysis. Forward and reverse primers unique to each of the eight SHP genes were used to PCR amplify a fragment from the 5' UTR through to the region of the SHP genes that encodes for the MADS box domain. Genomic DNA isolated from the haploid *B. napus* line BN2-SU was used to PCR amplify each gene fragment. The products were cloned into a TOPO TA cloning vector, transformed into competent bacterial cells and plated on LB plates. A minimum of ten colonies for each gene was cloned and sequenced and the resulting sequence was compared to the reference sequences located in GenBank and Genoscope.

Gene Expression Analysis

Canola pods from 6 stages of development were harvested (FIG. 2A). Total RNA was isolated from each sample using gene specific RT-PCR primers to amplify the expressed SHP genes/alleles from cDNA synthesized from total RNA extractions. The cDNA of each sample was then sequenced by NGS to determine the relative expression of each SHP gene at each developmental stage tested.

Figure 2B:
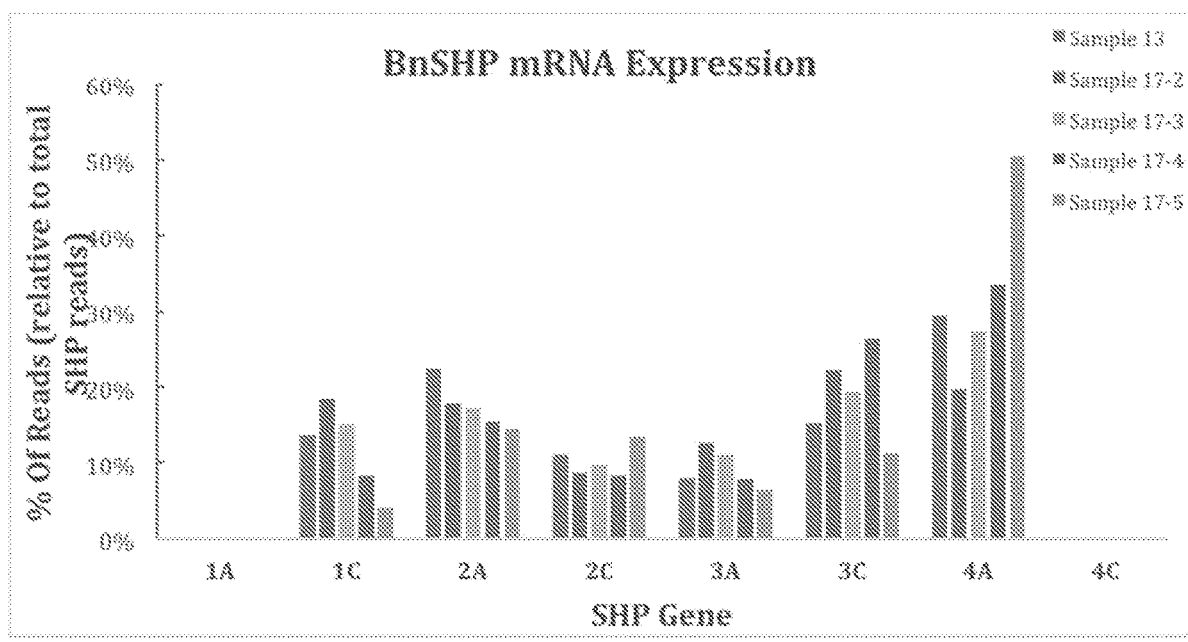

The expression of all 8 BnSHP genes was investigated to gain insight into which genes are important for the pod shatter reduction phenotype. Expression analysis using gene specific primers resulted in at least 6 of the 8 BnSHP genes expressed in developing siliques (FIG. 2A and FIG. 2B). Sequences corresponding to genes BnSHP1A and BnSHP4C were not represented in these data.

REFERENCES

Roeder, A. H. K. and Yanofsky, M. F. (2006) Fruit Development in *Arabidopsis*. In, The *Arabidopsis* Book, American Society of Plant Biologists, doi: e0075. 10.1199/tab.0075

Liljegren, S. J., Ditta, G. S., Eshed, Y., Savidge, B., Bowman, J. L., and Yanofsky, M. F. (2000) SHATTERPROOF MADS-box genes control seed dispersal in *Arabidopsis*. Nature 404, 776-770.

Raman H, Raman R, Kilian A, Detering F, Carling J, et al. (2014) Genome-Wide Delineation of Natural Variation for Pod Shatter Resistance in *Brassica napus*. PLoS ONE 9(7): e101673. doi:10.1371/journal.pone.0101673.

Gururaj K. (2009) *Brassica* shatter-resistance research update. In, 16th Australian Research Assembly on Brassicas. Ballarat, Victoria, 2009

Chalhoub, B. et al., (2014) Early allopolyploid evolution in the post-Neolithic *Brassica napus* oilseed genome. Science 345, 950-953.

Example 2: Generation of Shatterproof Gene Knock-Out Lines in the BN2-SU-H Canola Line Using CRISPR/Cas9 Plasmid Delivery into Protoplasts In this Example, sulphonylurea-tolerant canola plant lines with non-functional (KO) Shatterproof (SHP) genes using CRISPR/Cas9 were generated. The CRISPR/Cas9 gene and sgRNAs contained within plasmids were delivered to protoplasts isolated from leaves of haploid plants to knock down the BnSHP genes. The sgRNA is a fusion of CRISPR RNA (crRNA) and trans-activating crRNA (tracrRNA). The crRNA guides the Cas9 to the target genes, where Cas9 makes a double-stranded break in each of the BnSHP gene in a site-directed manner. The double-stranded breaks in the BnSHP gene when repaired by the ubiquitous, error-prone NHEJ pathway will cause InDels (nucleotide Insertions or Deletions) to form around the cleavage site. Loss of function alleles of the BnSHP genes occur when these InDels created by Cas9 shift the reading frame of the SHP genes.

Figure 3:
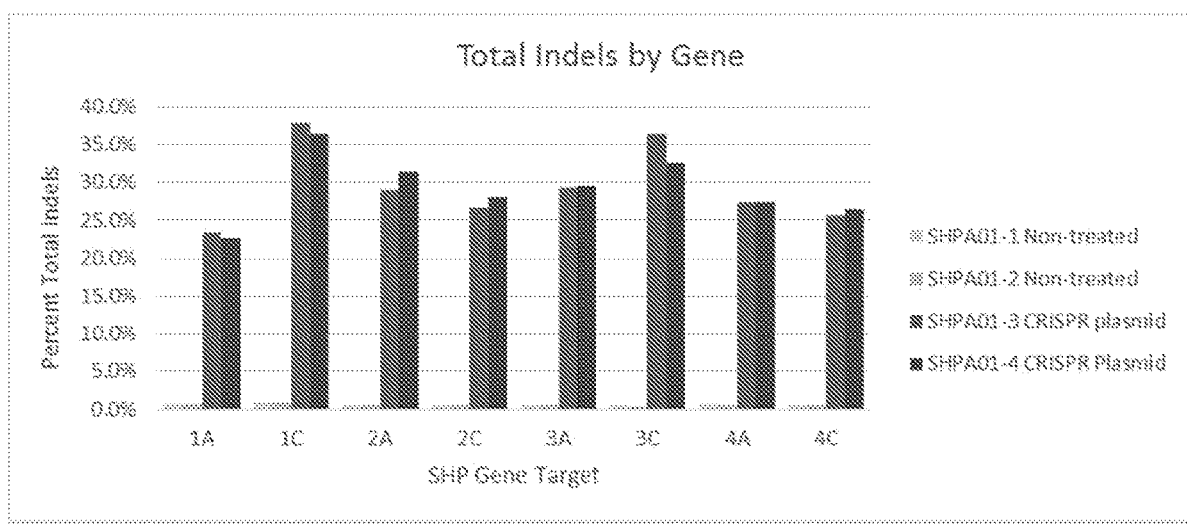
FIG. 3 illustrates the total percentage of insertions and deletions (InDels) identified by NGS in each of the SHP genes in shoots regenerated from control non-treated protoplasts (SHPA01-1 and SHPA01-2, lighter gray bars shown on left for each SHP gene), and protoplasts treated with CRISPR/Cas9 plasmid (SHPA01-3 and SHPA01-4, darker gray bars shown on right for each SHP gene). Treatments were performed in duplicate.

The percentage of InDel formation in each of the 8 SHP gene targets in shoots regenerated from protoplasts treated with CRISPR/Cas9 was between 20 to 40%, as determined by Next Generation Sequencing (FIG. 3). The most common InDels identified were +1 insertions (up to 10%), and −1 and −2 deletions (5% and 1.5% respectively; data not shown). Shoots with mutations in 1 through 8 of the genes were identified with different frequencies (Table 2). Approximately 70% of the shoots contained InDels in at least one SHP gene. Sequence analysis of the target region (around the Cas9 cleavage site) in each gene indicated that not all of the InDels in these genes resulted in a non-functional (KO) allele due to a frame shift. The majority of the plants had between 2 and 5 gene KOs (Table 2). Out of this experiment, 80 independent plant lines were regenerated containing InDels in 2 to 8 of the BnSHP genes, showing that Cas9 is active and able to cleave all 8 target SHP genes in *B. napus* and form InDels. Moreover, these InDels can generate non-functional gene KOs after the CRISPR/Cas9 plasmid was introduced, by shifting the reading frame of the SHP genes.

TABLE 2

Frequency of BnSHP genes with InDels and non-functional gene KOs in regenerated shoots screened by NGS

| SHP Genes with InDels | Shoots # | % | SHP Gene KOs* | Shoots # | % |
|---|---|---|---|---|---|
| 0 | 133 | 29 | 0 | 149 | 33 |
| 1 | 40 | 9 | 1 | 36 | 8 |
| 2 | 38 | 8 | 2 | 62 | 14 |
| 3 | 49 | 11 | 3 | 80 | 18 |
| 4 | 57 | 12 | 4 | 62 | 14 |
| 5 | 50 | 11 | 5 | 40 | 9 |
| 6 | 57 | 12 | 6 | 14 | 3 |
| 7 | 19 | 3 | 7 | 8 | 2 |
| 8 | 11 | 2 | 8 | 3 | 1 |
| Total Shoots | 454 | 100 | Total Shoots | 454 | 100 |

*Number of non-functional alleles of BnSHP genes due to shift in the reading frame caused by InDels Methods Canola protoplasts were isolated from leaves of in vitro-grown BN2-SU haploid plants derived from microspore culture (Sun et al., 1998; Swanson, E., 1990). The CRISPR/Cas9 encoded plasmids contains pMas::Cas9 with a pea rbcSE9 terminator and AtU6P::sgRNA with a poly-$T_{10}$ terminator. Sequences of features are as follows: amino acid sequence of Cas9 (SEQ ID NO: 50), nucleotide sequence of Mas promoter (SEQ ID NO: 51), nucleotide sequence of rbcSE9 terminator (SEQ ID NO: 52), nucleotide sequence of AtU6 promoter (SEQ ID NO: 53), and nucleotide sequence of poly-$T_{10}$ terminator (SEQ ID NO: 54).

The CRISPR/Cas9 plasmids were introduced into protoplasts by PEG mediated delivery at a final concentration of 0.05 µg/µL. Protoplasts were cultured in liquid medium ($2.5 \times 10^5$ cells/mL) and incubated in the dark at 25° C. Cell samples were obtained after one week and analyzed by NGS. After 6-8 weeks, protoplast-derived microcalli were plated over solid regeneration medium, and shoots started differentiating from regenerated calli after about 2-4 weeks. Leaf samples from fully differentiated shoots were analyzed by NGS to determine the occurrence of InDels in targeted SHP genes. Elongated shoots were micropropagated and rooted plants were transferred to soil and hardened in a growth chamber for 2-4 weeks until the plants were well established.

The CRISPR/Cas9 consists of two components: the plant codon-optimized *Streptococcus pyogenes* Cas9 (SpCas9) and sgRNAs were expressed from separated plasmids. The sgRNA is a fusion of CRISPR RNA (crRNA) and trans-activating crRNA (tracrRNA). The crRNA region contains the spacer sequences described in Table 3, which were used to guide the Cas9 nuclease to the target gene. In this experiment the CRISPR/Cas9 targets the BnSHP genes.

TABLE 3 gRNAs targeting BnSHP genes

| gRNA Name | gRNA Sequence (5' to 3') | BnSHP Gene Target |
|---|---|---|
| BnSHP-2 | GTAGCAAGAAGATAGGTAGA (SEQ ID NO: 42) | 1A, 1C |
| BnSHP-3 | GTAACAAGAAGCTAGTGAGA (SEQ ID NO: 43) | 3A, 3C |
| BnSHP-4 | GTAGCAAGAAGCTAGTAAGA (SEQ ID NO: 44) | 2A, 2C, 3A, 3C |
| BnSHP-5 | GCAGCAAGAAGATAGGGAGA (SEQ ID NO: 45) | 4A, 4C |
| BnSHP-9 | CAGAAGCAATGGATGAAGGT (SEQ ID NO: 46) | 1A, 1C |
| BnSHP-10 | CAGAATCAATGGAGGAAGGT (SEQ ID NO: 47) | 2A, 2C, 3A, 3C |
| BnSHP-11 | GGGTTGATATAAATGGAGGG (SEQ ID NO: 48) | 4A, 4C |
| BnSHP-12 | CAGAAGCAATGGATGAAAGT (SEQ ID NO: 49) | 1A, 1C |

REFERENCES

Sun et al., "Cotyledon-derived diploid and haploid protoplast culture and diploid plant regeneration in *Brassica napus* cv. 'Topas'," Can. J. Bot. 76: 530-541, 1998.

Swanson, E., "Microspore Culture in *Brassica*," Methods in Molecular Biology, Vol. 6, Chapter 17, p. 159-69, 1990.

Example 3: Generation of Shatterproof Gene Knock-Out Canola Lines by Delivering CRISPR/Cas9 Ribonucleoprotein (RNP) to Protoplasts Similar to the previous Example 2, the purpose of this Example is to generate SU-tolerant canola plant lines with non-functional (KO) Shatterproof (SHP) genes using CRISPR/Cas9. The CRISPR/Cas9 used to knock down the BnSHP genes in the *B. napus* genome are delivered to leaf derived protoplasts as Cas9 protein complexed with gRNAs (RNPs), in combination with single-stranded oligonucleotides (ssODNs or GRONs, Table 4) targeting three specific InDel mutations (+1 insertion, −1, and −2 deletions) to disrupt the function of each of the 8 BnSHP paralogous genes. Before delivery to protoplasts, recombinant Cas9 protein (commercially available) is complexed in vitro with the gRNA (Table 5), which is in vitro synthesized from a plasmid DNA template to generate a fusion of CRISPR RNA (crRNA) and trans-activating crRNA (tracrRNA). Once within the cells, the crRNA guides the Cas9 to the target genes, where Cas9 makes a double-strand break in each of the BnSHP gene in a site-directed manner. In the presence of the GRONs, the double-stranded breaks in the BnSHP genes could be repaired by the Homologous Direct Repair (HDR) pathway, in addition to the NHEJ pathway. The HDR pathway can use the GRONs as DNA templates, introducing targeted mutations specified in the GRON sequences (i.e., n+1, n−1, and n−2). Loss of function alleles of the BnSHP genes occur when these InDels shift the reading frame of the SHP genes, leading to truncated and non-functional gene products (mRNA and proteins, Table 6).

Results

InDel formation in 1 and up to 8 of the SHP genes were observed in over 95% of the shoots regenerated from protoplasts treated with CRISPR/Cas9, as determined by Next Generation Sequencing. GRON targeted mutations (+1,−1,−2 nucleotide insertion or deletions) were found in over 90% of the shoots with InDels in SHP genes. Shoots with mutations in each of the 8 SHP genes, and with combinations of multiple gene KOs were identified with different frequencies. Out of 5395 shoots screened from three consecutive experiments, 1127 independent plant lines were regenerated containing targeted InDels in 1 to 8 of the BnSHP genes, including a total of 153 unique KO genotypes (out of 255 possible). Plant KO lines representing each of the SHP KO genotypes were successfully transferred to soil and grown to maturity in the greenhouse for phenotypic analyses.

Methods

Canola protoplasts are isolated from leaves of in vitro microprogated haploid plants. Cas9 protein complexed with gRNAs (Table 5), along with single-stranded oligonucleotides (ssODNs; GRONs) make precise gene specific mutations in each of the 8 BnSHP paralogous genes (Table 4). Cas9 protein complexed with gRNAs and GRONs is introduced into protoplasts by PEG mediated delivery at a final concentration of 0.05 µg/µL and 0.5 µM, respectively. Protoplasts are cultured in liquid medium ($1.25 \times 10^5$ cells/mL) and incubated in the dark at 25° C. Cell samples are obtained after one week and analyzed by NGS. After 6-8 weeks, protoplast-derived microcalli are transferred to solid regeneration medium, and shoots start differentiating from regenerated calli after about 2-4 weeks. Leaf samples from fully differentiated shoots are analyzed by NGS to determine the occurrence of InDels in targeted SHP genes. Elongated shoots are micropropagated, and rooted plants are transferred to soil and hardened in a growth chamber for 2-4 weeks until the plants are well established.

The GRONs used with the Cas9 RNP contain the coding sequence of the targeted SHP genes around the site of conversion and are labeled with a 2'-O-Me group at the first 5' base of the GRON which is an RNA base instead of a DNA base (Table 4). The CRISPR/Cas9 consists of two components: the plant codon-optimized *Streptococcus pyogenes* Cas9 (SpCas9) and sgRNAs are expressed as protein and RNA respectively. The sgRNA is in vitro transcribed from a DNA template, and it is a fusion of CRISPR RNA (crRNA) and trans-activating crRNA (tracrRNA). The crRNA region contains the spacer sequences described in Table 5, which are used to guide the Cas9 nuclease protein to the target gene. In this Example the CRISPR/Cas9 targets the BnSHP genes.

TABLE 4

Sequence of ssODNs (GRONs)

| ID | Sequence (5' to 3') |
|---|---|
| BnSHP(-1;CR2-5)/C/41 | A*GAGAGYARCAAGAAGMTAGKAGAGGGAAGATAGAGATAAA (SEQ ID NO: 55) |
| BnSHP(-2R;CR2-5)/C/41 | A*GAGAGYARCAAGAAGMTAGAGAGGGAAGATAGAGATAAAG (SEQ ID NO: 56) |
| BnSHP(+1;CR2-5)/C/42 | A*GAGAGYARCAAGAAGMTAGKDNAGAGGGAAGATAGAGATAAA (SEQ ID NO: 57) |

TABLE 5 gRNAs targeting BnSHP genes

| gRNA Name | gRNA Sequence (5' to 3') | BnSHP Gene Target |
|---|---|---|
| BnSHP-2 | GTAGCAAGAAGATAGGTAGA (SEQ ID NO: 42) | 1A, 1C |
| BnSHP-3 | GTAACAAGAAGCTAGTGAGA (SEQ ID NO: 43) | 3A, 3C |
| BnSHP-4 | GTAGCAAGAAGCTAGTAAGA (SEQ ID NO: 44) | 2A, 2C, 3A, 3C |
| BnSHP-5 | GCAGCAAGAAGATAGGGAGA (SEQ ID NO: 45) | 4A, 4C |

TABLE 6

Size of predicted truncated, non-functional protein products generated by the introduction of targeted mutation n − 1, n − 2, and n + 1 (A, G, C, and T) in each of the SHP genes

| SHP Gene | WT Reference | n − 2 | n − 1 | n + 1 (A, G, C) | n + 1 (T) |
|---|---|---|---|---|---|
| 1A | 276 | 48 | 21 | 49 | 18 |
| 1C | 136 | 48 | 21 | 49 | 18 |
| 2A | 250 | 37 | 21 | 38 | 18 |
| 2C | 249 | 37 | 21 | 38 | 18 |
| 3A | 277 | 48 | 21 | 49 | 18 |
| 3C | 276 | 48 | 21 | 49 | 18 |
| 4A | 245 | 48 | 21 | 49 | 18 |
| 4C | 245 | 44 | 21 | 45 | 18 |

Example 4: Phenotyping of Shatterproof Mutant Canola Lines

In *Arabidopsis thaliana*, SHATTERPROOF 1 AND 2 (SHP1/SHP2) are transcription factors members of the MADS-box family involved in the formation of the dehiscent zone (DZ), a layer of cells between fruit valves responsible for the shatter of mature pods (Liljegren et al., 2000; Roeder and Yanofsky, 2006). The differentiation of the DZ in developing pods is characterized by the formation of a layer of cells with lignified cell walls, and a separation cell layer. *Arabidopsis thaliana* shp1 shp2 double mutants fail to develop a functional DZ, which does not lignify or has a defined separation layer, and, as a consequence, the fruits are indehiscent and do not open at the end of development. In canola (*Brassica napus*), Applicant has identified and characterized 8 genes that are highly homologous to the *Arabidopsis* SHP1/SHP2. The BnSHP genes also appear to be involved in the differentiation of the DZ and play a similar role in controlling the shattering of mature pods in canola.

Results

Loss-of-function studies indicate that SHP1 and SHP2 promote lignification of a subset of valve margin cells in *Arabidopsis* fruit. The lignification patterns of fruits obtained from different BnSHP KO $C_0$ lines were analyzed and compared to wild-type fruit. There is a clear reduction in valve margin cell lignification in fruits of BnSHP KO lines (FIG. 4). In mutated lines with 7-8 BnSHP gene KOs, no valve margin lignification was observed at the base of fruits, whereas lignified valve margin cells stained with phloroglucinol are present in wild type fruits, as well as in fruit from mutant plant lines with low number of gene KOs (FIG. 4).

Figure 5:
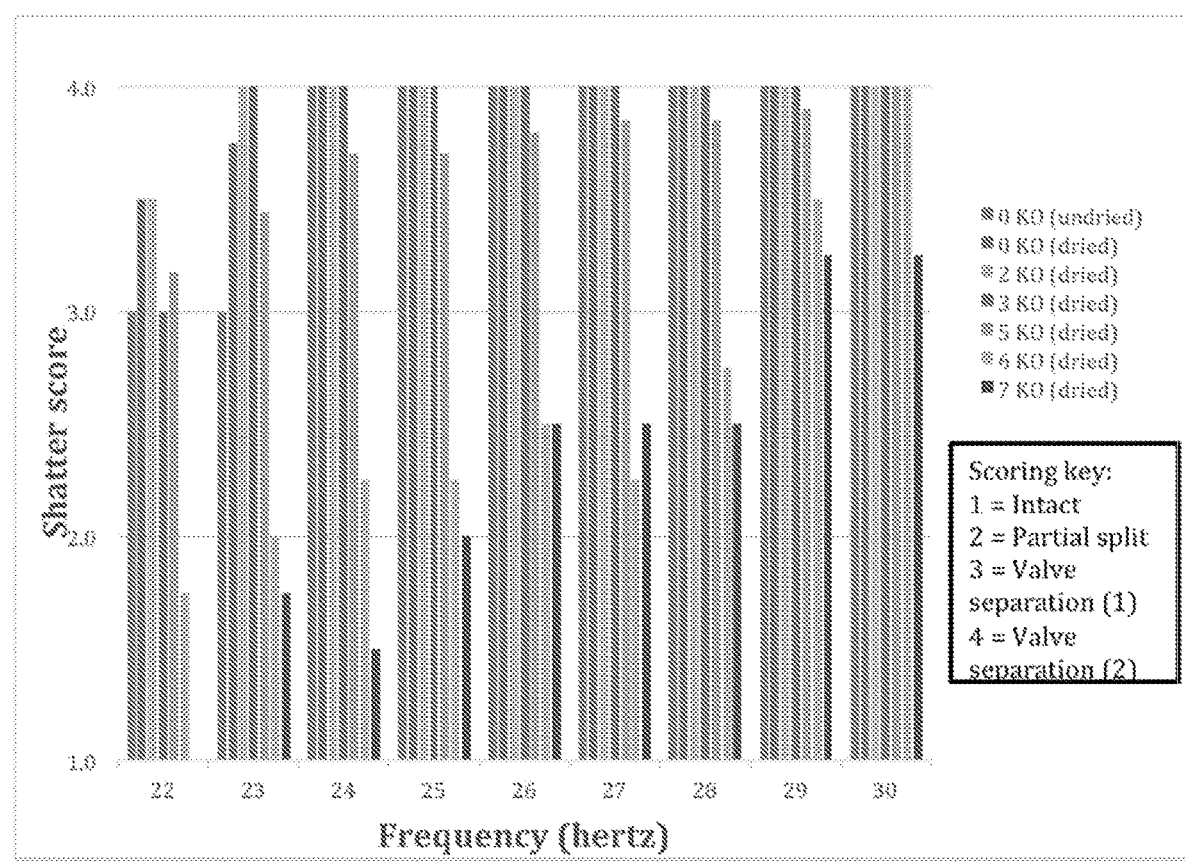
FIG. 5 illustrates a pod shattering test of selected KO plants ($C_0$) with different numbers of BnSHP gene KOs. Dried and undried mature pods were obtained from wild type (0 KO) plants and KO plants with 2, 3, 5, 6, or 7 SHP gene KOs (KOs shown from left to right at each frequency shown in order 0 KO (undried), 0 KO (dried), 2 KO (dried), 3 KO (dried), 5 KO (dried), 6 KO (dried), and 7 KO (dried)).

A pod breaking test using a TissueLyser and a Geno/Grinder was also used to assess shatter resistance in mature dried pods. The two tests show a correlation between the number of BnSHP gene KOs and pod shatter reduction (FIG. 5). A correlation (r=0.86) is also found between shaking frequency to pod shatter reduction and staining score of lignified layers (Table 7A). A separate experiment with different KO lines showed similar results (Table 7B).

TABLE 7A

Comparison of pod shattering test and lignified layer staining results-Experiment 1

| Candidate Line ID | Staining Score of Lignified Layer ($C_0$) | Shaking Frequency to Shatter ($C_1$) | Gene KO Description | Genotype |
|---|---|---|---|---|
| Control (WT) | 1 | 16 | N/A | N/A |
| A02-0230 | 1 | 18 | 2 KO | 4A/4C |
| A01-1013 | 2 | 16 | 2 KO | 1C/2C |
| A01-0151 | 1 | 16 | 3 KO | 2A/3A/4C |
| A02-0232 | 1 | 20 | 4 KO | 1A/1C/4A/4C |
| A01-0037 | 1 | 18 | 4 KO | 1C/2A/3C/4C |
| A01-0164 | 4 | 18 | 6 KO | 1A/2A/3A/3C/4A/4C |
| A01-1315 | 1 | 20 | 6 KO | 1C/2C/3A/3C/4A/4C |
| A01-0069 | 4 | 30 | 7 KO | 1C/2A/2C/3A/3C/4A/4C |
| A01-1291 | 4 | 24 | 7 KO | 1C/2A/2C/3A/3C/4A/4C |
| A01-1166 | 3 | 30 | 7 KO | 1A/2A/2C/3A/3C/4A/4C |
| A01-0222 | 5 | 30 | 8 KO | 1A/1C/2A/2C/3A/3C/4A/4C |
| A01-1187 | 5 | 30 | 8 KO | 1A/1C/2A/2C/3A/3C/4A/4C |

TABLE 7A-continued

Comparison of pod shattering test and lignified layer staining results-Experiment 1

| Candidate Line ID | Staining Score of Lignified Layer ($C_0$) | Shaking Frequency to Shatter ($C_1$) | Gene KO Description | Genotype |
|---|---|---|---|---|
| A01-0025 | 4 | 30 | 8 KO | 1A/1C/2A/2C/3A/3C/4A/4C |
| A01-0022 | 4 | 30 | 8 KO | 1A/1C/2A/2C/3A/3C/4A/4C |

TABLE 7B

Comparison of Pod shattering test and lignified layer staining results-Experiment 2

| Line ID | Staining Score of Lignified Layer ($C_0$) | Shaking Frequency to Shatter ($C_0$) | Gene KO Description | Genotype (SHP Gene KO) |
|---|---|---|---|---|
| Control (WT) | 1 | 14.0 | N/A | N/A |
| A05_1098 | 1 | 14.3 | 1KO | 1A |
| A05_1884 | 1 | 15.3 | 1KO | 4C |
| A05_0085 | 1 | 15.0 | 2KO | 1A/3A |
| A05_0641 | 1 | 14.3 | 2KO | 3C/4A |
| A05_1094 | 1 | 14.0 | 2KO | 3A/3C |
| A05_0375 | 1 | 14.0 | 3KO | 1C/3A/3C |
| A05_2790 | 1 | 14.5 | 3KO | 2A/4A/4C |
| A05_0102 | 2 | 16.0 | 4KO | 3A/3C/4A/4C |
| A05_0129 | 1 | 16.0 | 4KO | 1C/3A/3C/4A |
| A05_0415 | 1 | 16.3 | 4KO | 1C/2A/2C/3C |
| A06_0387 | 1 | 16.5 | 4KO | 2A/3A/3C/4C |
| A08_0780 | 1 | 15.3 | 4KO | 1C/2C/3C/4A |
| A05_0751 | 3 | 18.3 | 5KO | 1C/2A/3A/3C/4A |
| A05_1608 | 4 | 19.0 | 5KO | 2A/3A/3C/4A/4C |
| A05_1894 | 2 | 16.5 | 5KO | 2A/2C/3A/3C/4C |
| A08_0068 | 2 | 17.0 | 5KO | 1A/2C/3C/4A/4C |
| A05_0277 | 2 | 18.0 | 6KO | 1C/2A/2C/3A/3C/4A |
| A05_1217 | 2 | 17.0 | 6KO | 1C/2A/2C/3A/3C/4C |
| A05_0342 | 3 | 18.0 | 7KO | 1A/1C/2A/2C/3A/3C/4A |
| A05_1635 | 4 | 24.0 | 7KO | 1A/1C/2A/2C/3A/4A/4C |
| A05_3484 | 3 | 22.0 | 7KO | 1A/1C/2A/2C/3A/3C/4C |

Methods

Phloroglucinol staining of lignified cell layer in the valve dehiscent zone. Developing fruit from wild-type BN2-SU and different SHP KO lines ($C_0$ plants) are collected to examine the lignification pattern of fruits. For lignin staining, cross sections of fruits are obtained with a razor blade and the sections are stained for 2 min in a 2% phloroglucinol solution in 95% ethanol, then photographed in 66% perchloric acid. The intensity of the phloroglucinol staining of the lignified cell layer correlates with the amount of lignin in the cell walls (Liljegren et al., 2000; Roeder and Yanofsky, 2006), and it is scored as shown in Table 8 below.

TABLE 8

Lignification score summary

| Phloroglucinol staining result | Score |
|---|---|
| Very dark stained lignified layer | 1 |
| Medium dark stained lignified layer | 2 |
| Light stained lignified layer | 3 |
| Very light stained, Partial absent the lignified layer | 4 |
| Totally absent lignified layer | 5 |

Pod shattering test using a TissueLyser. Candidate lines are transplanted into 3.5" pots using Sunshine Mix 4 media and kept under T12 fluorescent grow lights at a 14-hour photoperiod. After three weeks the lines are transplanted into 5.5" pots and moved the greenhouse, where the maximum cooling temperature is set at 78° F. Plants are grown under standard canola maintenance conditions and perforated pollen bags are employed to prevent outcrossing and contamination. The plants are taken off water at a 30% seed color change, and continued to dry down in the greenhouse until the seeds reach a 100% color change, when the plants are fully desiccated. The pods are collected and placed in an oven at 30° C. for 1 h to ensure uniform levels of moisture across all samples.

The following candidate lines are selected to phenotype using the shatterproof breakage test (See also FIG. 5): BN2 Diploid WT (undried), BN2 Diploid WT (dried), SHP-A01-0151 (2 KO), SHP-A01-0037 (3 KO), SHP-A01-1098 (5 KO), SHP-A01-0154 (6 KO), SHP-A01-0222 (7 KO).

The shatterproof phenotype is determined by the level of valve separation found under controlled agitation of the pods. To test the valve separation, single pods are placed into a 96 well deep trough container and secured in the arms of a TissueLyser II (Qiagen, Germany). The single pod samples are run on the TissueLyser for 30 seconds at frequencies of 22, 23, 24, 25, 26, 27, 28, 29, and 30 Hz. Per line, four single pods reps were tested at each frequency. The phenotype was scored on a scale of 1-4. An intact pod was given a score of one, a partially split pod with connected valves was scored a two, a score of three represented the separation of one valve, and a score of four indicated that both valves were separated from the replum.

Pod shattering test of C generation of KO lines. Canola seeds ($C_1$) are germinated in plugs, where they remain for 3 weeks. Plants are then transferred into 4" pots and moved to the greenhouse under 14-h photoperiod with 23-25° C. Day/19-21° C. Night temperatures. Pods are collected from fully mature plants, and then dried in plastic containers with holes for about 3 weeks. The pods are completely dry before testing. Three uniform pods are chosen and placed in 3 separated cells of a modified shaking box. The box is then loaded onto a TissueLyser II. The frequency of shaking is set to a certain frequency setting (starting from 12 Hz), with a shaking time set to 30 seconds. When the shaking stopped, the box is unloaded, and pods are evaluated using a shattering score. Each frequency setting is tested on 12 pods per plant. The average score from the 12 pods is used as the final score for each frequency. When the shaking score is greater than 2.5, the corresponding frequency represents the pod shattering frequency set point.

Pod shattering test using the Geno/Grinder 2010 (SPEX Sample Prep, USA). Candidate lines are transplanted into 3.5" pots using Sunshine Mix 1 media and kept under T12 growth lights at a 16 h photoperiod and 21° C./19° C. day/night temperature for hardening. After three weeks, the lines are transplanted into 5.5" pots and moved the greenhouse, where the maximum cooling temperature is set at 78° F. Plants are grown under standard canola maintenance conditions and perforated pollen bags are employed to prevent outcrossing and contamination. The plants are taken off water at a 30% seed color change and continue to dry down in the greenhouse until the seeds reach a 100% color change and the plants are fully desiccated. The pods from each individual plant are collected in a plastic container with a cover with a hole in the center, which is placed in an oven at 40° C. for at least 12 h to ensure uniform levels of moisture across all samples.

Figure 6:
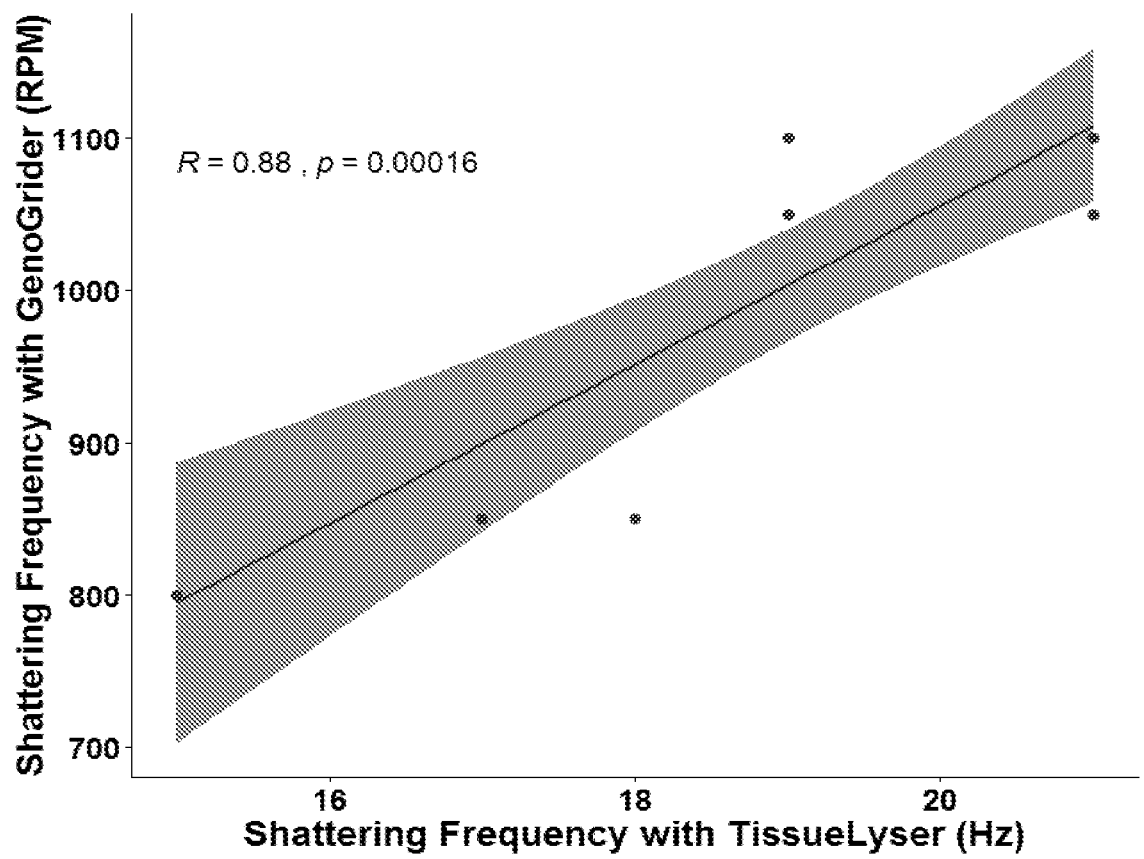
FIG. 6 illustrates the correlation between the shattering frequency determined with the TissueLyser (Hz) and the shattering frequency determined with the Geno/Grinder (RPM). R value=0.88; p value=0.00016.

The shatterproof phenotype is determined by the level of valve separation found under controlled agitation of the pods. To test the valve separation, 12-24 pods are placed into a 96 well deep trough container and secured in the arms of a Geno/Grinder 2010 (SPEX Sample Prep, USA). The containers holding pod samples are run for 20 sec at different rpm (for example at 720, 750, 780, 810, 840, 870, 900, 930, 960, 990, 1020, 1050, 1080 rpm). At the end of the run, the container is taken off the machine and the shattering score is given to each pod according to the score table (Table 9). When the average shattering score under the certain rpm is greater than 2.5, the rpm value will be the pod shattering value for the line. This method can handle more pods at one time and is much faster to run than the TissueLyser test. In order to validate the Geno/Grinder Method, the negative check and positive checks, along with a few lines were run using both TissueLyser and Geno/Grinder. The corresponding shattering scores were collected. The R value of the both data sets is 0.88, which indicates the data collected using both methods are highly correlated (FIG. 6).

TABLE 9

Shattering Score Summary

| Shaking Assay Result | Score |
|---|---|
| Intact pod that has no cracks or damage visible | 1 |
| Pod has a small crack at the end, no seeds have escaped. | 2 |
| There is a visible crack that is greater than half the pod, the two valves are still attached to the septum. Seeds might have escaped | 3 |

TABLE 9-continued

Shattering Score Summary

| Shaking Assay Result | Score |
|---|---|
| One of the valves has separated from the septum. Seeds have escaped | 4 |
| Both valves have separated from septum and pod has fully shattered. | 5 |

Example 5: Generation and Field Testing of Shatterproof KO Lines

This Example shows the evaluation and selection of top performing SHP KO lines. Since pod shattering traits are controlled by multiple genes and could be affected by environmental factors (e.g., biotic and abiotic), it is important to evaluate the pod shattering trait in multiple environments and years.

Results

Pod shatter resistance of SHP KO lines was evaluated first in the greenhouse ($C_0$ generation), and then in two different locations over a two-year period ($C_1$ and $C_2$ generations). Selected lines with 5 to 8 SHP gene KOs consistently showed much better performance than the negative WT control (FIG. 7). The KO lines also showed similar or better pod shatter reduction phenotypes compared to the commercial shatterproof lines checks (positive controls). For example, A05_1635, A05_0342, A05_0277, A05_2013 and A05_0071 were very stable, and they did not show any abnormal growth phenotype in any of the tested environments. These KO lines could be considered true shatterproof lines.

The SHP genes (either mutant or wild type) in each line were sequenced to confirm presence of the mutation in the respective SHP gene where applicable. The sequence of the full target amplicon of the area around the target region is presented in Table 10 below.

TABLE 10

SHP Sequences in Mutant Lines

| Line | SHP Gene SEQ ID NO: | | | | | | | |
|---|---|---|---|---|---|---|---|---|
| | 1A | 1C | 2A | 2C | 3A | 3C | 4A | 4C |
| A05_0071 | 62 | 72 | 82 | 92 | 102 | 112 | 122 | 132 |
| A05_2013 | 63 | 73 | 83 | 93 | 103 | 113 | 123 | 133 |
| A05_1635 | 64 | 74 | 84 | 94 | 104 | 114 | 124 | 134 |
| A05_0342 | 65 | 75 | 85 | 95 | 105 | 115 | 125 | 135 |
| A05_0113 | 66 | 76 | 86 | 96 | 106 | 116 | 126 | 136 |
| A05_0277 | 67 | 77 | 87 | 97 | 107 | 117 | 127 | 137 |
| A05_0272 | 68 | 78 | 88 | 98 | 108 | 118 | 128 | 138 |
| A05_1600 | 69 | 79 | 89 | 99 | 109 | 119 | 129 | 139 |
| A05_0751 | 70 | 80 | 90 | 100 | 110 | 120 | 130 | 140 |
| A05_1894 | 71 | 81 | 91 | 101 | 111 | 121 | 131 | 141 |

Methods

CRISPR/Cas9 protein complexed with gRNAs (RNPs, Table 5), along with single-stranded oligonucleotides (GRONs) (Table 4) are used to knock out BnSHP genes in an otherwise wild-type background canola line. The CRISPR/Cas9 consists of two components: the plant codon-optimized *Streptococcus pyogenes* Cas9 (SpCas9) and sgRNAs that are expressed as protein and RNA respectively. The sgRNA is in vitro transcribed from a DNA template, and it is a fusion of CRISPR RNA (crRNA) and trans-activating crRNA (tracrRNA). The crRNA region contains the spacer sequences described in Table 5, which are used to guide the Cas9 nuclease protein to each of the target SHP genes. The GRONs contain the coding sequence of the targeted SHP genes around the site of conversion, carry precise gene specific mutations (n+1, n−1, and n−2), and are labeled with a 2'-O-Me group at the first 5' base, which is a RNA base instead of a DNA base (Table 4).

RNPs and GRONs were introduced into protoplasts by PEG mediated delivery at a final concentration of 1.0 µg/µL and 0.05 µM, respectively. Before delivery to protoplasts, the recombinant Cas9 protein was complexed in vitro with the gRNA. Canola protoplasts were isolated from leaves of in vitro micropropagated plants, following a standard protocol. Protoplasts were cultured in liquid medium ($1.25 \times 10^5$ cells/mL) and incubated in the dark at 25° C. Cell samples were obtained after one or three weeks, and analyzed by deep sequencing, to determine the frequency of mutations in target genes. After 6-8 weeks, protoplast-derived microcalli were transferred to solid regeneration medium, and shoots started differentiating from regenerated calli after about 2-4 weeks. Leaf samples from fully differentiated shoots were analyzed by NGS to determine the occurrence of targeted mutations in each of the 8 SHP genes. Shoots with targeted mutations in individual and multiple genes, covering all 255 possible gene KO combinations or genotypes were then screened for ploidy. Diploid plants were micropropagated in vitro, and transferred to soil in a growth chamber. Hardened ($C_0$) plants were transferred to the greenhouse and grown to maturation (seed setting).

Seeds harvested from $C_0$ plants are called $C_1$ generation. At least 3 $C_0$ plants for each KO combination were selected and grown as stated in Example 4. During the hardening process, leaf samples were collected and the genotypes of $C_0$ plants were confirmed by NGS. $C_1$ seeds were germinated in plugs (5 plants per line), and leaf samples were collected 10-12 days after planting for genotype confirmation. Three weeks after planting, the $C_1$ plants were transferred into 5.5" pots and moved to the greenhouse, where the maximum cooling temperature is set at 78° F. Plants were grown under standard canola maintenance conditions and perforated pollen bags were employed to prevent outcrossing and contamination. The plants were taken off water at a 30% seed color change and continued to dry down in the greenhouse until the seeds reached a 100% color change and the plants were fully desiccated. The pods from either $C_0$ plants or $C_1$ plants grown in the greenhouse were collected and placed in an oven at 40° C. for at least 12 h to ensure uniform levels of moisture across all samples. Pod shattering was evaluated using the TissueLyser Method. The selected lines were also tested under field conditions in two different locations: one in California and one in North Dakota. A randomized complete block design (RCBD) with three replications was used to design the experiments. $C_1$ and $C_2$ seeds were treated with fungicide (Helix, Bayer Crop Science) and directly sowed in the soil. Under the growing environments, plants grew to maturity, and the pods were collected as a bulk sample for each line from each replication. Pod shattering phenotypes were evaluated using either the TissueLyser or the Geno/Grinder. The data were collected and analyzed.

REFERENCES

Bohanec B (2003) Ploidy determination using flow cytometry. In: Maluszynski M, Kasha K J, Forster B P, Szarejko I (eds) Doubled haploid production in crop plants: a manual. Kluwer, Dordrechts, pp 397-403.

I claim:

1. A *Brassica napus* plant or part thereof comprising a homozygous loss-of-function mutation in at least three, at least four, at least five, at least six, at least seven, or eight endogenous genes encoding SHATTERPROOF (SHP) polypeptides, wherein the endogenous genes comprise a coding sequence that has at least 90% sequence identity to a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

2. The plant or part thereof of claim 1, wherein the endogenous genes comprise a coding sequence having at least 95% sequence identity, at least 98% sequence identity, or at least 99% sequence identity to a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

3. The plant or part thereof of claim 1, wherein the endogenous genes comprise a coding sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

4. The plant or part thereof of claim 1, wherein the mutation is a frameshift mutation.

5. The plant or part thereof of claim 4, wherein the frameshift mutation results in one or more nucleotide insertions or deletions as compared to the corresponding endogenous gene without the frameshift mutation.

6. The plant or part thereof of claim 4, wherein the frameshift mutation results in a premature stop codon.

7. The plant or part thereof of claim 1, wherein the plant exhibits reduced susceptibility to preharvest dehiscence.

8. A method of producing the plant of claim 1, comprising the steps of:
   a) introducing mutations into *Brassica napus* plant cells, wherein the mutations are homozygous loss-of-function mutations in at least three, at least four, at least five, at least six, at least seven, or eight endogenous genes encoding SHP polypeptides, wherein the endogenous genes comprise a coding sequence that has at least 90% sequence identity to a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8;
   b) selecting plant cells containing the mutations; and
   c) regenerating a plant having the mutations;
   wherein the *Brassica napus* plant exhibits reduced susceptibility to preharvest dehiscence.

9. The method of claim 8, wherein the mutations are introduced using one or more vectors, wherein the vectors comprise gene editing components selected from the group consisting of a nuclease, an RNA-guided DNA endonuclease, a CRISPR/Cas9 system, a TALEN, a zinc finger, and a meganuclease designed to target a nucleic acid sequence encoding a SHP gene.

10. The method of claim 8, wherein the mutations are introduced using a GRON system designed to target a nucleic acid sequence encoding a SHP gene.

11. The method of claim 10, wherein the GRON system comprises one or more modifications selected from the group consisting of a Cy3 group, 3PS group, and a 2'O-methyl group.

12. The method of claim 8, wherein the endogenous genes comprise a coding sequence having at least 95% sequence identity, at least 98% sequence identity, or at least 99% sequence identity to a nucleic acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

13. The method of claim 8, wherein the endogenous genes comprise a coding sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8.

14. The method of claim 8, wherein the mutation is selected from the group consisting of a frameshift mutation, a frameshift mutation resulting in one or more nucleotide insertions or deletions as compared to the corresponding endogenous gene without the frameshift mutation, and a frameshift mutation resulting in a premature stop codon.

15. An F1 *Brassica napus* plant, wherein the F1 plant has the plant of claim 1 as a parent.

16. A method of making plant seeds, the method comprising crossing the plant of claim 1 with another *Brassica napus* plant and harvesting seed therefrom.

17. A *Brassica napus* plant produced by growing the seed of claim 16, wherein the plant has all the physiological and morphological characteristics of the *Brassica napus* plant comprising the homozygous loss-of-function mutations of the plant of claim 1.

18. The plant or part thereof of claim 1, wherein the homozygous loss-of-function mutation is in at least five to eight of the endogenous genes encoding SHP polypeptides.

19. The method of claim 8, wherein the homozygous loss-of-function mutations are in at least five to eight of the endogenous genes encoding SHP polypeptides.

\* \* \* \* \*

SEQUENCE LISTING

<160> NUMBER OF SEQ ID NOS: 141

<210> SEQ ID NO 1
<211> LENGTH: 828
<212> TYPE: DNA
<213> ORGANISM: Brassica napus

<400> SEQUENCE: 1

```
atggatgaag gtgggagtag tcactatgca gagagtagca agaagatagg tagagggaag      60
atagagataa agaggataga gaacacaaca aatcgtcaag taaccttctg caaacgacgc     120
aatggtcttc tcaagaaagc ttatgagctc tctgtcttgt gtgatgcgga agttgccctc     180
gttatctttt ccactcgtgg ccgtctttat gagtacgcca gcaacagctt ctataaaata     240
cttttatctc gacgacccat actatgtctt tctttaaata ttattagggt ttcgtcagta     300
aaaaaaaact ggggtacaat tgaaaggtac aagaaagctt gttccgatgc cgttaaccct     360
cctactgtca ctgaagctaa tactaagtac tatcagcaag aagcctctaa gcttcggagg     420
cagattcggg acattcagaa ttcgaacagg catattgttg gagaatcact tggttcattg     480
aacttcaagg aactcaaaaa cctagaagga cggcttgaaa aaggaatcag ccgcgtccga     540
tccaagaaga gtgaactttt agtggcagag atagagtata tgcagaagag ggaaatggag     600
ttgcagcacg ataacatgta cctaagagct aagatagaac aaggcgcgag attgaatccg     660
gaacagcatg gatccggtgt aatacaaggg acggcggttt atgagtccgg tctgtcttct     720
tctcatgatc agtcgcagca ttataatcgg aattatattc cggttaacct tcttgaaccg     780
```

```
aatcaacaat tctccggtca agaccaacct cctcttcaac ttgtttaa        828
```

<210> SEQ ID NO 2
<211> LENGTH: 408
<212> TYPE: DNA
<213> ORGANISM: Brassica napus

<400> SEQUENCE: 2

```
atggatgaaa gtgggagtag tcacgatgca gagagtagca agaagatagg tagagggaag    60
atagagataa agaggataga gaacacaaca atcgtcaag  taaccttctg caaacgacgc   120
aatggtcttc tcaagaaagc ttatgagctc tctgtcttgt gtgatgctga agttgccctc   180
gttatcttct ccactcgtgg ccgtctctat gaatacgcca gcaacagtgt gaagggtaca   240
attgaaaggt ataagaaagc ttgttccgat gccgttaacc ctcctactgt caccgaagct   300
aatactcagt actatcagca agaagcctct aagcttcgga ggcagattcg ggacattcag   360
aattcgaaca ggattgttag tttggttaac ttactcggaa ttgtttga               408
```

<210> SEQ ID NO 3
<211> LENGTH: 747
<212> TYPE: DNA
<213> ORGANISM: Brassica napus

<400> SEQUENCE: 3

```
atggaggaag gtgggagtag tcacgacgca gagagtagca agaagctagt aagagggaag    60
atagagataa agaggataga gaacacaaca agtcgtcaag taactttctg taaacgacgc   120
aatggtcttc ttaagaaagc ttatgagctt tctgtcttgt gtgatgctga agttgccctc   180
gtcatcttct ccactcgtgg ccgtctctat gagtacgcca acaacagcgt gaagggtaca   240
attgaaagat acaagaaagc ttgttccgat gccgttaacc ctccttctgt caccgaagct   300
aatactcagt actatcagca agaagcatct aagcttcgga ggcagattcg tgacattcag   360
aattctaaca ggcatatagt tggggaatca cttggttcct tgaacttcaa ggaactcaaa   420
aacctcgaag acgtcttga  aaaggaatc  agccgtgtcc gatccaagaa gaatgagctg   480
ttaatggcag agatagagta tatgcagaag agggaaatgg agttgcaaca cgataacatg   540
tacctgcgag ctaagatatc acaaggtgcg agattgaatc cggagcagca ggattcgagt   600
gtaatacaag aacagcggt  ttacgaatcc ggtttatctt cccatgatca gtcacagcat   660
tataaccgga actatattcc ggttaacctt cttgaaccga atcaacaatt ctccggtcaa   720
gaccaacctc ctctccaact tgtctaa                                        747
```

<210> SEQ ID NO 4
<211> LENGTH: 747
<212> TYPE: DNA
<213> ORGANISM: Brassica napus

<400> SEQUENCE: 4

```
atggaggaag gtgggagtag tcacgacgca gagagtaaca agaagctagt aagagggaag    60
atagagataa agaggataga gaacacaaca agtcgtcaag taactttctg taaacgacgc   120
aatggtcttc ttaagaaagc ttatgagctt tctgtcttgt gtgatgctga agttgccctc   180
gtcatcttct cgactcgtgg ccgtctctat gagtacgcca acaacagcgt gaagggtaca   240
attgaaagat acaagaaagc ttgttccgat gccgttaacc ctccttctgt caccgaagct   300
aatactcagt actatcagca agaagcctct aagcttcgga ggcagattcg tgacattcaa   360
aattctaaca ggcatatagt tggggaatca cttggttcct tgaacttcaa ggaactcaaa   420
```

```
aacctcgaag gacgtcttga aaaaggaatc aaccgtgtcc gatccaagaa gaatgagctg      480
ttaatggcag agatagagta tatgcagaag agggaaatgg agttgcaaca cgataacatg      540
tacctgcgag ctaagatatc acaaggtgcg agattgaatc cggagcagca ggattcgagt      600
gtaatacaag gaacagcggt ttacgaaccc ggtctatctt cccatgacca gtcacagcat      660
tataaccgga actatattcc ggttaacctt cttgaaccga atctacattt ctccggtcaa      720
gaccaacctc ctcttcaact tgtctaa                                         747

<210> SEQ ID NO 5
<211> LENGTH: 831
<212> TYPE: DNA
<213> ORGANISM: Brassica napus

<400> SEQUENCE: 5
atggaggaag gtgggagtag tcacgacgca gagagtaaca agaagctagt gagagggaag       60
atagagataa agaggataga gaacacgaca agtcgtcagg taactttctg caaacgacgc      120
aatggtcttc tcaagaaagc ttatgagctc tctgtcttgt gtgatgcgga agttgcactt      180
gttgtctttt ccactcgtgg ccgtctctat gagtacgcta acaacaggaa atatttgtct      240
tgtcttctca actcgttagc cgttttagt ttcactcgtt ttatgaaaca ttggaacctg      300
atgcatgtct gtgtgaaggg tacaattgaa aggtacaaga agcttgttc cgatgccgtc      360 aaccctccta ctgtgaccga agctaatact cagtattatc agcaagaagc tctaagctt      420 cggaggcaga ttcgggacat tcaaaattct aacaggcata ttgttggaga atcacttggt      480
tccttgaact tcaaggaact caaaaaccta aaggaaggc ttgaaaaagg aataaaccgc      540
gtccgatcca agaagaatga gttgttagtg gcagagcttg agtatatgca agaggggag      600 atagagttgc aacatgataa catgtacctg agagctaaga taacacactg cgctaggctg      660
gatccggaac aacaggaatc gagtgtgata caaggaactg cggtttatga atctggtctg      720
tcttctcatg atcagtcgca gaattataac cggagctata ttccggtgaa ccttcttgaa      780
ccgaatcaac aattctccgg tcaagaccaa cctcctcttc aacttgttta a               831

<210> SEQ ID NO 6
<211> LENGTH: 828
<212> TYPE: DNA
<213> ORGANISM: Brassica napus

<400> SEQUENCE: 6
atggaggaag gtgggagtag tcacgacgca gagagtaaca agaagctagt gagagggaag       60
atagagataa agaggataga gaacacgaca agtcgtcaag taactttctg caaacgacgc      120
aatggtcttc tcaagaaagc ttatgagctc tctgtcttgt gtgatgcgga agttgcactt      180
gttgtcttct ccactcgtgg ccgtctctat gagtacgcta acaacagaaa tcagttacta      240
ttatgtaata aattgtcgtg tgcatataaa tcaaactatc actcttggtt attcacaatc      300
attttaggtg tgaagggtac aattgaaagg tacaagaaag cttgttccga tgccgtcaac      360
cctcctacta tcaccgaagc taatactcag tattatcagc aagaagcctc taagcttcgg      420
aggcagattc gggacattca aaattctaac aggcatattg ttggagaatc acttggttcc      480
ttgaacttca aggaactcaa aaacctagaa ggaaggcttg aaaaggaat aaaccgcgtc      540 cgatccaaga gaatgagtt gttagtggca gagcttgagt atatgcagaa gagggagatg      600
gagttgcaac atgataacat gtacctgaga gctcagatag gaaactgcgc taggctggat      660
```

```
ccggaacaac aggaatcgag tgtgatacaa ggaactgcgg tttatgaatc tggtctgtct    720
tctcatgatc agtcacagaa ttataaccgg agctatattc cggtgaacct tcttgaaccg    780
aatcaacaat tctccggtca agaccaacct cctcttcagc ttgttttaa                828

<210> SEQ ID NO 7
<211> LENGTH: 735
<212> TYPE: DNA
<213> ORGANISM: Brassica napus

<400> SEQUENCE: 7
atggagggtg gtgcgagtga tgaagtagca gagagcagca agaagatagg gagagggaag     60
atagagataa agaggataga gaacaccacg aatcgccaag tcactttctg caaaagacgc    120
aatggtctgc tcaagaaagc ttatgagctc tctgtcttgt gtgacgctga ggttgctctt    180
gtcatcttct ccactcgcgg tcgtctctac gagtacgcca acaacagtgt aagaggaacg    240
atcgaaaggt acaagaaagc ttgctccgac gctgttaatc ctccttccgt caccgaagct    300
aatactcaat actatcagca agagtcatct aagctacgga gacagatccg ggacattcag    360
aatctgaaca gacacattct tggtgaatct ctcggttcct tgaacctcaa ggaactcaag    420
aacctcgaag gtaggcttga aaaaggcatc ggtcgtgtcc gctccaagaa gcatgagatg    480
ctagttgcag agatagagta catgcaaaaa agggagatcg agcttcaaaa cgataacatg    540
tatctccgat ccaagattaa tgaaagagcg ggaatgcagc agcaggaagc gagtgtgata    600
catcaacaag ggacggttta cgagtcatct tctcatcagt cggagcagta caaccggaac    660
tatattccgg ttaaccttct tgaaccaaat cagaactcct ccgaccaaaa ccaaccacct    720
ctccaacttg tttaa                                                     735

<210> SEQ ID NO 8
<211> LENGTH: 735
<212> TYPE: DNA
<213> ORGANISM: Brassica napus

<400> SEQUENCE: 8
atggagggtg gtgcgagtga tgaggtagca gagagcagca agaagatagg gagagggaag     60
atagagataa agaggataga gaacaccacg aatcgccaag tcactttctg caaaagacgc    120
aatggtctgc ttaagaaagc ttatgagctc tctgtcttgt gtgacgctga ggttgctctt    180
gtcatcttct ccactcgagg tcgtctctac gagtacgcca acaacagtgt aagaggaacg    240
attgaaaggt acaagaaagc ttgctccgac gctgttaatc ctccttccgt caccgaagct    300
aatactcagt actatcagca agaatcgtct aagctacgga gacagatccg ggacattcag    360
aatctgaaca gacacattct tggtgaatct cttggttcct tgaacctcaa ggagctcaag    420
aacctggaag gtaggcttga aaaggcatc ggtcgtgtcc gctccaagaa gcatgagatg    480
ctagttgcag agatagagta catgcaaaaa agggagatcg agcttcaaaa cgacaacatg    540
tatcttcgat ccaagattag tgaaagagca ggaatgcagc agcaggaagc gagtgtgata    600
catcaacaag ggacggttta cgagtcgtct tcccatcagt cggagcagta caaccggaac    660
tatattccgg ttaaccttct tgaaccaaat cagaactcct ccgaccaaaa ccaaccacct    720
ctccaacttg tttaa                                                     735

<210> SEQ ID NO 9
<211> LENGTH: 5801
<212> TYPE: DNA
<213> ORGANISM: Brassica napus
```

<220> FEATURE:
<221> NAME/KEY: misc_feature
<222> LOCATION: 4907
<223> OTHER INFORMATION: n = A,T,C or G

<400> SEQUENCE: 9

| | | | | | |
|---|---|---|---|---|---|
| cattagtaac | ttctccgtgt | gtactgatct | ccaggtaagg | ttgtgaatga | tacagtatat | 60 |
| atattaacct | aaaaacaagg | tttatgataa | aatatctgat | ccttgattta | acaattcgtg | 120 |
| ggtctgatat | cgttcttggt | ttgtttattt | attatgtata | aagaggttga | gaagatatat | 180 |
| aattcgataa | tcgtttctgt | cttattcact | caagacctca | aggtccttat | atacaagcta | 240 |
| tgttgtccta | ctcctatcaa | tacaaggaaa | gctaatataa | tcataataag | gaaatataat | 300 |
| ctaatagata | aacatgtcta | gatgtttatc | ctaatacccc | ccctcaagtt | ggagcgtata | 360 |
| gatttcgaat | gcccaacttg | tataggaaaa | tgtcaaactc | ttttcgtcct | agagctttgg | 420 |
| tcaaaatgtc | tgccaactga | tctttagtcg | tcacatgagc | agtagagatc | gttttgttga | 480 |
| tgatgtgatc | gcgaataaaa | tgacattcag | cttcgatgtg | cttcgttctt | tcgtgaaaaa | 540 |
| tcgggttctt | tgtcaagtag | atcgcagatt | gattatcaca | cattaatgtc | attggcgctg | 600 |
| cgtggttgat | tccaaaatcg | tgtaaaagac | ctttaatcca | tttgagttct | ttaacagcct | 660 |
| ctgtcatggc | tctgtactcg | gcttctgtgg | aggataaagc | aactgtatcc | tgcttttgag | 720 |
| tcttccaaga | aactatagac | gatccaatt | gcatgatcca | accagttagc | gatcgtcgtg | 780 |
| ttaaggggca | tccttcccaa | tctgagtcag | accaccctgt | tatgtgtata | ggaggagcag | 840 |
| cgcgcaacat | aataccctgc | ccaagagttc | cttttaaata | gcggataaca | tgcatggctg | 900 |
| cgtcccaatg | agctgtctct | ggtttctgca | tgaactgagt | gagaacatgg | atagaatacg | 960 |
| ccaagtctgg | tcgagttgca | gctaagtata | ctagtcggcc | aacgagtcgt | cgataacgtc | 1020 |
| ctgggtcagg | aaaaggtgac | ccgttagcca | aggcgagacc | gtgtttctga | tctatgggaa | 1080 |
| aaccagccgg | cttgcatcct | aacattccca | cttcggtgag | tacgtcacta | caatatttcc | 1140 |
| gttggcatat | ataaaaccca | tcagtgttgc | gagctacttc | gagtccaaga | aaatatttga | 1200 |
| gatggccgag | gtctttcatt | cgaaaacatg | aagagagata | agctttgaac | tcagtgatag | 1260 |
| atgatgtcga | gtttccagag | atgataagat | catcaacgta | tactaggaca | cgaagagtaa | 1320 |
| cgccaccttt | agtggataca | aagaacgagt | aatcacttcg | tgattgcgta | aaaccgaacg | 1380 |
| cgcggagagc | catggtgagt | tttgcaaacc | aacaacgtgg | tgcctgtcgt | aaaccataga | 1440 |
| gagatttgcg | taatcgacaa | acccttgtat | ctgattctga | tcgaaaaccg | ggcggcagtt | 1500 |
| tcatatatac | ctcttcgtcg | agatcgccat | gcaggaaagc | gttatgaaca | tccatctgat | 1560 |
| gtacttcata | atcttgtttg | gcagcaatgt | caagaaatat | acggaccgtt | gtcatcttcg | 1620 |
| cgactggtgc | aaatgtctct | tcatagtcaa | taccttcgat | ttggttgttg | cctagaacta | 1680 |
| ccagacgaga | tttgtgacgt | tcgagtgtgc | cgtctgcttt | gagtttgatt | cgataaaccc | 1740 |
| atttacatcc | cagtgcgacc | ttgcctggag | gcaagttgac | taattcccat | gtatggttaa | 1800 |
| gctctaaagc | atcgatctca | tgtcgcattg | attgtttcca | aacgtcatat | tgcatagctt | 1860 |
| ctttgtagga | tctcggttca | atagccgtgg | acagggccgt | taagaagcta | caatgggatg | 1920 |
| cagaaaaacg | atcacatgta | taatagtcag | tgagaggata | aaccgtacct | gaggatgccg | 1980 |
| atggatgacg | ggttgcaaga | ggagtgagag | agactgtatt | aatgacgaaa | tcggtgaggc | 2040 |
| gtgtagaagg | tttcttagct | cttaaaccgg | ggcctaattc | tgtagtttgt | tcgttagcag | 2100 |
| aggtcgacgt | agaaggttgc | atgtctgtta | ctgtagtttc | gataatagtc | gtgtcagttg | 2160 |

```
tcgatggtgt agtaatcgga gagtcggtcg aagtgtcttc ctcgatgtag ttattggtcg    2220
tggagctgat caaaggtatg actgttgttt ggtcggtcgc agcgggttgt gggttgtgat    2280
aagggaatat tttctcttgg aacaagacat ctcgtgaggt aaaggtttct tctttgtcga    2340
gatcgtataa tcgccatcct ttcttgccgt atgtatagcc taaaaatatg catcgtcgac    2400
ttctagaagc aaatttatcg cctccatgat tctgattgtg tgcgtagcat aagcaaccaa    2460
agacacgaag ttgatcaaag gccggttgtc gtttgtaaag catctcataa ggcgttttgt    2520
cgttgagaag ctttgatggt gttcgattaa tcaggtagca agcggttaag gcacattctg    2580
cccaaaaatc gattggtaac cctgcttgaa accgtagggc tcgagcaacg tttaagatat    2640
gtcgatgctt gcgttcgaca cgtccgtttt gttgtggagt tcccacgcaa gaggtttcat    2700
ggatgatgcc ttgttcttga agaattttg tcaagcacat aaattctgta ccattgtcgc     2760
ttcgaagaat cttcacgtga caatcaaatt gtcgtttgac gagtgcaaga aactcacgta    2820
ttcggttaga tacattgact ttgtcgggca aagatatag ccaaactgct ctggaatagt     2880
catcgacgat agtcaaaaaa taacgtgagc cacagaatgc agcggtgcgg tatggtcccc    2940
aaaggtcaca gtgaattagc tcaaaagatc gagatgcttt attataacta tcgggaaaag    3000
ggtttcgtgt ttgttttgat ctaagacaaa catcacacgt agataaagaa agcgcgacac    3060
tactagactt gagtttaaca ccaggaatta agttgataac gcgagaagac ggatgtccga    3120
gacgtagatg ccataaaaca ccttcatcac ttgtcgtagt attgaaagca gttacagttt    3180
cgaagccgcg gaattgatac agtccctctt tctctctttc acccgctcca atcagcgtcc    3240
tcgtgatgcg gtcctgtaaa acaacaagtc tatcagtgac ttgaccaacc aaaggattat    3300
cagtaagtag ttggccaaaa gatataaggt tcgtgtgaaa tccatcaaca tgatacacat    3360
tcttcaagag tatatgtgat gtaagttgaa tcattccacg ttgagtggtc aagacattag    3420
cacccgcagg caatgtaacc gatattgggt aaacatgctc aatgtctttt aataaatcga    3480
gtcggccagt catgtgatga gtagcgcctg tatccaggat ccacacggga tcgttagtct    3540
taccacttag acgatttccg tctgagtttg ctttcggtgg gtttaagagt ttcaccaatg    3600
tttgccactg agcatcagag aaacctgtta accctgtct gtcggcgtcg gttaaggtga     3660
gattggcgcc aatgccagtt gttgatccaa ttatctgaga agagtttgca cgtggagcag    3720
agttgtgtcc agaagattgt gtatttgctt gtccttcttg ataattgttg cggtttcgag    3780
gtctcgttcc ccaccactcc ggaaacccaa tcacacgaaa acatgaacta gctcgatgtc    3840
ctagcctgcc acaactagta catgtaacgt ttgcgtctgg atttggaggt cgtgggcggt    3900
agttgtcggt ttgtcgagtt gtcgaagaat gtcgagagtg ctccgagttg tgttgttgtg    3960
ttggtgcttg agcagcaaaa ctcaacacgg cgggagtctc agttttgcat tgagttgcac    4020
ggtttcgttt tgcactattg tctgatatgc tgagtcgaga tctggtagag gtatttgtgc    4080
acagatttgt gatcgtacgg agctatgtac ttcatcaaga ccaaacagaa aatcatgaac    4140
acgaatggtt tcacgttcag tatcatgagc gttgaccaaa tcgcattcac actttccgca    4200
gctacaggtc ttagttgata agcactcagc cattgaatcc caaattttcg tcaatctgcc    4260
gaaataatct tcaacggtgg aaccaacctg tcggcagttt gcaagagaag ctctgagttg    4320
ttgatatcga gcgccacttt tgagtgcaaa ccgcttttg atatgatccc aaagatcttt     4380
agctgtttct ttatgagata tatttgatcg aagtttcggt tctattgtca gcttggtcca    4440
tgtgacaagc agatgattgt tagccgtcca atcttcaagg tctggtgagt cagcagcggg    4500
tttcggtatt gtgccgtcga tgaaaccgaa tttctttcga gcacttaggg caactcgaaa    4560
```

```
attttgagcc cattcatcat agttacgtcc gttgagtaga ggttgagaga taaccgctcc    4620
ggggttatcg ttcgccgtta ggtcgtatgg agagatcgtt cgtcgtgtcg gtttcgttgt    4680
tgtaagaggt ccggacatga ttgaactggt tcgaggtcgt gagttgatga gaaaaaatca    4740
agagtcgagg tcgcaaatct tatgttatca gtttcgtagc tctgatacca tgagaagata    4800
tataattcga taatcgtttc tgtcttattc actcaagacc tcaaggtcct tatatacaag    4860
ctatgttgtc ctactcctat caatacaagg aaagctaata taatcanata aggaaatata    4920
atctaataga taaacatgtc tagatgttta tcctaataga ggtcggatca ttatacagtt    4980
gaaatcaacc ctaaaatccc aaatttggag ttcaaagttt ttttatttgt ttgaattaca    5040
atctcagctg attgattttt tagtgaccaa atcatttgat atatttattt aattttgcct    5100
ctcttgatct gcaaaaatat ttgatcataa acttgaatag catcgctctc tagttcaata    5160
tctctcccac ttcttttcgg tggtttattc atttggtgac gatatcacag aagcaatgga    5220
tgaaggtggg agtagtcacg atgcagagag tagcaagaag ataggtagag ggaagataga    5280 gataagagg atagagaaca caacaaatcg tcaagtaacc ttctgcaaac gacgcaatgg    5340
tcttctcaag aaagcttatg agctctctgt cttgtgtgat gctgaagttg ccctcgttat    5400
cttctccact cgtggccttc tttatgagta cgccagcaac aggtatgctt ctcctaccca    5460
caccttgatc tagctttctt gattaattta ctactacaat cctagttaat atgagccaag    5520
attagggttt tgtttaaatt acaatcctga attttctatt ttttatataa aaattagatc    5580
tcaatagggc taccattgtc tctctagatc tgtgtatatc caaataatga agacggaaga    5640
aatctgtctt gtcttctcaa cttctcgtta gtctgatctt tgttagtttc actcttttc    5700 tgcagatcac tagaacctgt ttcatgtcat gtcagcttct ataaaatgct tttatcttga    5760
cgacccatac tatgtctttc tttaaatatt attagggttt c                        5801
```

<210> SEQ ID NO 10
<211> LENGTH: 1489
<212> TYPE: DNA
<213> ORGANISM: Brassica napus

<400> SEQUENCE: 10

```
caatctaaca tctcacttgt atatatctat ataaatattc gtatctatttt atatgcatgt      60 ctagaggata aaagtgtga gctttgttgt gtatatgtgc ttttgacag ttgctagata      120 attggtatgc ctgttttct ttttctgcta tttataaata catctcagct aagaagaac      180 ttgtaaccct ctgttttctg caagtgggt caaatacct tcagagaaat attctttcaa      240
gtgaaactcg taaccaaaa aaaaatttac acaagaaag agagatattt ttcaagaaca      300
ttattattac gaaagcagaa ccaagactta agttacactg agatcaataa taattataat      360
atatattatc gcttcaaaac cagtttctca ttagtaactt ctccttgtgt cctgatctcc      420
aggtaaggtt gtgaatgata cagtatata ttaacccta aaaacaaggt ttatgataaa      480
atatctgatc cttgatttaa caattcgtgg gtctgatatc gttcttggtt tatttgttta      540
taatgtataa attaaagagt tctactgatt attatacagt tgaaattaac cctaaaatcc      600
caaatttgga gttcaaagtt ttttttctttg tttgaattac aatctcagct gattgatttt      660
ttgagtgacc aaatcatttg atatatttct tttgcctctc ttgatctgca aaatatttg      720 atcataaact taaatagcta ttttcaaaa aaaacttaa atagcatcgc tctcaagttc      780 aatctcccctc ccccttcttt tggtggtttt attcatttag tgacgatatc acagaagcaa    840
```

```
tggatgaaag tgggagtagt cacgatgcag agagtagcaa aagataggt agagggaaga      900 tagagataaa gaggatagag aacacaacaa atcgtcaagt aaccttctgc aaacgacgca      960
atggtcttct caagaaagct tatgagctct ctgtcttgtg tgatgctgaa gttgccctcg     1020
ttatcttctc cactcgtggc cgtctctatg aatacgccag caacaggtat gcttttctca     1080
cgtacacctt gatcctgctt taattacttg attaatttac tactacaaaa aatcttagtc     1140
aaaatgagcc aagattaggg ttttgttaa tttaaaaatg aaccaaaaat cttatatagt     1200
taattttgaa ccaagattag ggttttttgtt aaattcgaat cctgaactttt ctatttttta     1260 tataaaaaat tagatctcaa tagagctacc attatctctc tagatctgta ctatatgcaa     1320
ataatgaaga cggaagaaag ctgtcttgtc ttctcaactt ctcgttaggc tgatcttaat     1380
tagtttcact ctttttctgc aaatcattag aacctgtgca tgtcatgtca gcttctataa     1440
aacactttta tcttgacgac ccatactata gttgggtact tcttgacac               1489
```

```
<210> SEQ ID NO 11
<211> LENGTH: 1476
<212> TYPE: DNA
<213> ORGANISM: Brassica napus

<400> SEQUENCE: 11
gtttatatat ttgtcgagta tgtttgtttt gacaattggt atataattta tctgcttatt       60
atagatgtac gtaaatat atttcagcta agaaaaactt gtaaacttct gtgtgttctg      120
caagtggggt cttaataacct tcaaaaaata gtccttcaaa tgaaactgat cataaaccaa      180
atttgaaaag agagagatgt attttttcaaa aacgacataa ttattagaaa agcagaaaaa      240
aacagttaag tgatactgag atcaataata atatatagta tctcttcaag aacaatatct      300
cattacccac ttctccttg tgctgatcta tcataaactt taaaccccag gtaaggttct       360
gaatgttata cagtttatat agaataactc taatatcaaa tatttatatt cggagttctt      420
ttcatttctt tttcaattca atatctgatc ctttgttacc tagatttgat atgtttattt      480
attattgttt atctgcaaag agatttgatc attttaaccc taaacctaag tttcgtaccc      540
aaatcatacg atctatcttt tggttattct tgatctgcaa aatgattaat ttaatcatca      600
atcttaatta gcttctctag agcaatattt ttttttcttaa agctttgctc tagatcaatc      660
tctctccctc ttattatgtt atttttattca tctggtgata tcacagaatc aatggaggaa      720
ggtgggagta gtcacgacgc agagagtagc aagaagctag taagagggaa gatagagata      780
aagaggatag agaacacaac aagtcgtcaa gtaactttct gtaaacgacg caatggtctt      840
cttaagaaag cttatgagct ttctgtcttg tgtgatgctg aagttgccct cgtcatcttc      900
tccactcgtg gccgtctcta tgagtacgcc aacaacaggt acgcttctcc tgcacctttg      960
atctttgctt tcttggtttta ctactactac tacaagaaaa tcttagttaa atgtatggag     1020
aagtgacttg tagagtcaag attagggttt ttgttaaatt acaatcctgg ttttttcccc     1080
atgccaaaaa aaaaaaaatc ctgggttttt ttgtttttttc taaattaaat atcgatctct     1140
ctagagctac cataactatg tgtgtgtgtg tgtttgtgta agcaagtaat gaagaaggaa     1200
gaaagctgtc ttgtcttctc aacttctagt tagccttctc gttagccttt tttggtgtca     1260
ctctttttct gcaaatcatt agaacctgat gcatgtcagc ttctccatga aatttcttta     1320
ttcaaattca aattagggtt tgatcagtaa acaagttggg tactttcttg gcacgaaata     1380
gcatgtatat tatataaata tgcaagactt atgttaccct ctgcctagtg taacttggga     1440
caaagcctaa tgaccatttg tcacttgtca ctagct                              1476
```

<210> SEQ ID NO 12
<211> LENGTH: 1454
<212> TYPE: DNA
<213> ORGANISM: Brassica napus

<400> SEQUENCE: 12

```
gttatatagc tgtcgagtat ttccgttttg acaattggta gataatttat ctgtttttta      60
tatatgtata aatatatttc agctaagaaa aacttgtaaa cttctgtgtt tctgcaagtg     120
gggtcttaat accttcaaaa aatagtcctt caaatgaaac tgatcataaa ccaaatttga     180
aagagagatg tattttttcaa aaacgacaat tattagaaaa gcagaaaaaa agcagttaag    240
tgatactgag atcaataata atatatagta tctcttcaag aacaatatct cattacccac     300
ttctcctttg tgctgatcta tcataagctt taaaccccag gtacggttct gaatattata     360
caatttatat agaataactc taatatacaa gatttatatt cagagttctt ttcattttca     420
ttttcaattc aatatctgat cctttgttac ctagatttga tatgtttatt tattattgtt     480
tacaaagaga tttgatcatt ttaaccctaa acctaagttt tgtacccaaa tcatatgatc     540
tatcttttgg ttattcttga tctgcaaaat gattaatttg atcatcaatc ttaattatat     600
tctctataac aatcttttttt tttattaagc tttgctctga tcaatctctc tccctcttat    660
tatgttattt tattcatctg gtgatatcac agaatcaatg gaggaaggtg ggagtagtca     720
cgacgcagag agtaacaaga agctagtaag agggaagata gagataaaga ggatagagaa     780
cacaacaagt cgtcaagtaa ctttctgtaa acgacgcaat ggtcttctta agaaagctta    840
tgagctttct gtcttgtgtg atgctgaagt tgccctcgtc atcttctcga ctcgtggccg     900
tctctatgag tacgccaaca acaggtacgc ttctcctgca ccttcttgat ctttgctttc    960
ttggtttatt actactacaa gaaaatctta gttaaatgta tggagaagtg acttgtcgag    1020
tcaagattag ggttttttgtt aatttacaat cctgggtttt tttcccatgc caaaaaacaa    1080
aatcctgggt tttcttgttt tcctaaatta aatatctctc tagagctacc ataactatgt    1140
gtgtgtgtgt gtttgtgtaa gcaaataatg aagaaggaag aaagctgtct tgtcttctca    1200
acttctagtt agccttctcg ttagcctttt ttggtgtcac tcttttttctg caaatcattg    1260
aaacctgatg catgccagct tctccatgaa atttctttac tcaaattaat actagggttt    1320
aatcagtaaa caagttgggt actttcttga cacgaaatag catgtatatt atataaatat    1380
gcaagactta tgtaaccctc tgtctagtgt aacttgggac agagcctaat gatcagttgt    1440
cactagctag ggat                                                      1454
```

<210> SEQ ID NO 13
<211> LENGTH: 1301
<212> TYPE: DNA
<213> ORGANISM: Brassica napus

<400> SEQUENCE: 13

```
tagataaatt ggtctgctta ctgcttttcc gatttctttt tatgtataaa tacagttcag      60
ctaacaaaaa cgtgtaacct tctgttttct gaaagtgggg tcttataccct gcacaacaat    120
attccttcaa atgaaactca gaaccaaaa cagaaataac aaaaataaag agagatattt      180
ttacaagaac aacatacttt ttagaaaagc agaagcagca gttaagtgat attgagataa    240
ataataaat attatctctt caaaagagtt tctcattagt aacttctcct ttgtgctgat     300
ctatcatata atcttcaaaa cccaggtaag gttttgaata ctatacatta gagactaacc     360
```

| | |
|---|---|
| ctaaaaatac aaagtttatt tgttttttaat tcagtttctg atctttgagt taccaattcg | 420 |
| tgggtttgat atgtttcttg gttattgttt attgtttatc tacaaagaga tttgatcatt | 480 |
| atacagcaga acattaatta gttaacccta aaacaccaag ttttttgatg aaagtttttt | 540 |
| tcccttttgaa gtaacaatct cttttaattt ttgaatgacc taatcaacta tgatctgtta | 600 |
| atttctaggc tattcttgat ctgcaaaaat atttaatcat caagcttacc taccctcgct | 660 |
| ctctctagat caatcatctc cctcctcttt tgttgttttt tattcatttc ttgatattac | 720 |
| agaatcaatg gaggaaggtg ggagtagtca cgacgcagag agtaacaaga agctagtgag | 780 |
| agggaagata gagataaaga ggatagagaa cacgacaagt cgtcaggtaa ctttctgcaa | 840 |
| acgacgcaat ggtcttctca agaaagctta tgagctctct gtcttgtgtg atgcggaagt | 900 |
| tgcacttgtt gtctttttcca ctcgtggccg tctctatgag tacgctaaca acaggtacgc | 960 |
| ttctcctaca ccattgattg atctgctact gcaaataata ttagttatttt tattagtgat | 1020 |
| gatggacacg agaggtttag agccaagatt agggtttttta ttagttacaa tcctggatttt | 1080 |
| ttttaaatta aattttaccaa ttatctctct agatttctttt atatatttttt ttttgaacaa | 1140 |
| gatttcttta tatttatgtg tatgtgtgtg tatgcaaaat atgagaagga aatatttgtc | 1200 |
| ttgtcttctc aactcgttag ccgttttttag tttcactcgt tttatgaaac attggaacct | 1260 |
| gatgcatgtc tggttacgtt ctatacaaca cttaattagt t | 1301 |

<210> SEQ ID NO 14
<211> LENGTH: 1302
<212> TYPE: DNA
<213> ORGANISM: Brassica napus

<400> SEQUENCE: 14

| | |
|---|---|
| gataattggt ctgcttttttc gattttcttt tatgtataaa tacagttcag ctaacaaaaa | 60 |
| cgtgtaacct tctgttttct gaaagtgggg tcttatacct gcacaacaat attccttcaa | 120 |
| atgaaactca gaaaccaaaa cagaaataac aaaaataaag agagatattt ttacaagaac | 180 |
| aacataattt ttagaaaagc agaagcagca attaagtgat actgagatta ataataatat | 240 |
| attatctctt caaagagtt tctcattagt aacttcccct ttgtgctgat ctatcatata | 300 |
| atcttcaaaa cccaggtaag gttgtgaata ctatacatta aagactaacc ctaaaataca | 360 |
| aagtttatttt gttttaattt cagtgtctga tctttgagtt accaattcgt gggtttgata | 420 |
| tgtttcttgg ttattgttta ttttttatct acaaagagat ttgatcatta tacagcagaa | 480 |
| cattaattag ttaaccctaa aacaccaagt ttttgatga agttttttt ccctttgaag | 540 |
| taacaatctc ttttaatttt tgaatgacct aatcaactat gatctgttaa tttctaggct | 600 |
| attcttgatc tgcaaaaata tttaatcatc aagcttactt agcctcgctc tctctagatc | 660 |
| aatcatctcc ctcctctttt tgttgttttt attcatttct tgatattaca gaatcaatgg | 720 |
| aggaaggtgg gagtagtcac gacgcagaga gtaacaagaa gctagtgaga gggaagatag | 780 |
| agataaagag gatagagaac acgacaagtc gtcaagtaac tttctgcaaa cgacgcaatg | 840 |
| gtcttctcaa gaaagcttat gagctctctg tcttgtgtga tgcggaagtt gcacttgttg | 900 |
| tcttctccac tcgtggccgt ctctatgagt acgctaacaa caggtacgaa aaaaaaacaa | 960 |
| aaaaaaaaa aaaccaacag gtacgcttct cctacaccat tgattgatct gctactacaa | 1020 |
| ataatattgg ttattttatt agtgatgatg gacacgagag gtttagagcc aagattaggg | 1080 |
| tttttattag ttacaatcct ggattttttt taaaattaaa tttaccatt atctctctag | 1140 |
| atttctttat atttatgtgt atgtgtgtgt atgcaaaata tgagaaggaa aaaattgtct | 1200 |

```
tgtcttctca atttctcgtt agccgttttt agtttcactc ggtttatgaa acattggaac    1260
ctgatgcatg tctggttcta tacaacattt aattagtttt ga                      1302

<210> SEQ ID NO 15
<211> LENGTH: 1425
<212> TYPE: DNA
<213> ORGANISM: Brassica napus

<400> SEQUENCE: 15
actaccaaac cttctgtttt ctgcaagtgg gttttaaat actttcaagg aaatattcct      60
ttaagagaaa ttgtaaacca aaacagaaat cgaaacaaaa ataaagtggg aagcagcagt    120
taagtggtac tgaattaatt aataagaata gtatctttag ccaagaacat tttaattctc    180
ttagctagat ttcatcttcc cttctcactt ctccttcttt tatttctgat cacagtcata    240
caaacccagg tataacaatt acactaagtt aacctaaaaa ctcaagtttt ataatcagag    300
gttcttcctt ttttcttca tccaatcctt gaatcttgga gtgttttca tttcatctct      360 tgcttttctc ccttgagatc gatcttagaa cctagatagt agctagctat agtagatgga    420
gtccaaaaag attttatttg atctctctca gcttgtgtgt agtgtttgac cgtgtttggt    480
ttatctttaa gctatagggt tgatataaat ggagggtggt gcgagtgatg aagtagcaga    540
gagcagcaag aagataggga gagggaagat agagataaag aggatagaga acaccacgaa    600
tcgccaagtc actttctgca aaagacgcaa tggtctgctc aagaaagctt atgagctctc    660
tgtcttgtgt gacgctgagg ttgctcttgt catcttctcc actcgcggtc gtctctacga    720
gtacgccaac aacaggtaag ataagcatct attaacttct tttagatctt gattgtttgt    780
tttctctggg ttttgaatct ttatgggttt tctcttgtg gtttcttttc tcttctttta     840
aagtttctct gagtctcaac tctttgctga aaactttgat ttatatgtgt gtaccaaaat    900
tagggtttgt acccaagaac cctagttttg ctttggggaa aactctaatc tatttgcttc    960
tctctcttga aaaagctgtg aggtcttcta tgataataat taattagcat ctccatacct   1020
tgtaccagtc acttttttt tcttttacta gatcttata gtacagccta tctgtatcta     1080
tctatgtatg tcagttctac atgacatttc gataaatttg atgacccatc aggtttattt   1140
ctgcagattg atcataatta ggattccatc atagtagtga aaaagtagg gttcttgaca     1200 aaatataata ttatatatca tataatggct atataaagct aagtagattc cttaaaaaaa   1260
tgatacacta gctaggggga gacgggtgtt ttgtcttctg acacttctct ataaaaccag    1320
tgatttgatc tgttaaatca agaaatgttt aggggacaaa gcttgtggtt gtgtcactaa    1380
ttaattaatc atcaatcaat caaaaaataa aaataaacag aaaat                   1425

<210> SEQ ID NO 16
<211> LENGTH: 1457
<212> TYPE: DNA
<213> ORGANISM: Brassica napus

<400> SEQUENCE: 16
actaccaaac cttctgtttt ctgcaagtgg ggttttaaat actttcaagg aaatattctt      60
ttaacagaaa ttgtaaacca aaacagaaat caaaacaaaa ataaagtgcg aagcagcagt    120
taagtggtac tgaattaatt aataagaata gtatctttag ccaagaacat tttaattctc    180
ttagctagat ttcatcttcc cttctcactt ctccttcttt tatttctgat cacagtctta    240
caaacccagg tataacaatt aatatgacgc acactaagtt aacctaaaaa ctcaagtttt    300
```

-continued

```
ataatcagag gttcttcctt ttttttcttc atccaattct tgaatcttgg agtgttttc      360 atttcatctt ctttttttgg taatcatacg ctcttgcttt tctcccttga gatcgatctt      420
agaacctaga tagtagctag ctaccctag ctatagtaga tggagtccaa aaatatttta      480
tttgatctct ctcagcttgt gtgtagtgtt tgactgtgtt tggtttatct ttaagctata      540
gggttgatat aaatggaggg tggtgcgagt gatgaggtag cagagagcag caagaagata      600
gggagaggga agatagagat aaagaggata gagaacacca cgaatcgcca agtcactttc      660
tgcaaaagac gcaatggtct gcttaagaaa gcttatgagc tctctgtctt gtgtgacgct      720
gaggttgctc ttgtcatctt ctccactcga ggtcgtctct acgagtacgc caacaacagg      780
taagataaac atctattaac ttcttttaga tcttgattgt ttgttttctc tgggttttga      840
atctttatgg tttctttcct cttcttttaa agtttctctg agcctcaact ctttgttgaa      900
aactttgatt tatatgtgtg taccaaaatt agggtttgta cccaagaacc ctagttttgc      960
tttgggggaa actctagtct atttgcttct ctttcttgaa aaagctgtga ggtcttctat     1020
gataataatt aataagcatc tccataccttt gtaccagtca cttttctttt tcttttacta     1080
gatctttata gtacagccta tctgtatgta tctatgtatg tcagttctac atgacatttc     1140
gataaatttg atgacccatc aggtttattt ctgcagattg atcataatta ggattccatc     1200
atagtattga aaaagtagg gttcttgaca aaatataata ttatatgtca tcatatatgg     1260
ctatataaag ctaagtagat tccttaaaaa cttgatacac tagctagggg gagacgggtg     1320
ttttgtcttc tgacacttct ctataaaacc agtcatttga tctgttaaat caagaaatgt     1380
ttaggggaca aagcttgtgg ttgtgtcact aattaattaa tcatcaatca atcaaaaaat     1440
aaaaataaac agaaaat                                                    1457
```

<210> SEQ ID NO 17
<211> LENGTH: 11
<212> TYPE: PRT
<213> ORGANISM: Artificial Sequence
<220> FEATURE:
<223> OTHER INFORMATION: Synthetic Construct

<400> SEQUENCE: 17

Leu Asp Leu Asn Arg Pro Pro Pro Val Glu Asn
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

Leu Arg Leu Phe Gly Val Asn Met
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Leu Lys Leu Phe Gly Val Trp Leu
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

```
Leu Asp Leu Glu Leu Arg Leu Gly Phe Ala
1               5                   10
```

<210> SEQ ID NO 21
<211> LENGTH: 203
<212> TYPE: PRT
<213> ORGANISM: Artificial Sequence
<220> FEATURE:
<223> OTHER INFORMATION: Synthetic Construct

<400> SEQUENCE: 21

```
Glu Arg Ser Asn Ser Ile Glu Leu Arg Asn Ser Phe Tyr Gly Arg Ala
1               5                   10                  15

Arg Thr Ser Pro Trp Ser Tyr Gly Asp Tyr Asp Asn Cys Gln Gln Asp
            20                  25                  30

His Asp Tyr Leu Leu Gly Phe Ser Trp Pro Pro Arg Ser Tyr Thr Cys
        35                  40                  45

Ser Phe Cys Lys Arg Glu Phe Arg Ser Ala Gln Ala Leu Gly Gly His
    50                  55                  60

Met Asn Val His Arg Arg Asp Arg Ala Arg Leu Arg Leu Gln Gln Ser
65                  70                  75                  80

Pro Ser Ser Ser Thr Pro Ser Pro Pro Tyr Pro Asn Pro Asn Tyr
                85                  90                  95

Ser Tyr Ser Thr Met Ala Asn Ser Pro Pro His His Ser Pro Leu
            100                 105                 110

Thr Leu Phe Pro Thr Leu Ser Pro Pro Ser Ser Pro Arg Tyr Arg Ala
        115                 120                 125

Gly Leu Ile Arg Ser Leu Ser Pro Lys Ser Lys His Thr Pro Glu Asn
    130                 135                 140

Ala Cys Lys Thr Lys Lys Ser Ser Leu Leu Val Glu Ala Gly Glu Ala
145                 150                 155                 160

Thr Arg Phe Thr Ser Lys Asp Ala Cys Lys Ile Leu Arg Asn Asp Glu
                165                 170                 175

Ile Ile Ser Leu Glu Leu Glu Ile Gly Leu Ile Asn Glu Ser Glu Gln
            180                 185                 190

Asp Leu Asp Leu Glu Leu Arg Leu Gly Phe Ala
        195                 200
```

<210> SEQ ID NO 22
<211> LENGTH: 228
<212> TYPE: DNA
<213> ORGANISM: Brassica napus

<400> SEQUENCE: 22

```
atggaggaag gtgggagtag tcacgacgca gagagtaaca agaagctagt aagagggaag      60
atagagataa agaggataga gaacacaaca agtcgtcaag taactttctg taaacgacgc     120
aatggtcttc ttaagaaagc ttatgagctt tctgtcttgt gtgatgctga agttgccctc     180
gtcatcttct cgactcgtgg ccgtctctat gagtacgcca acaacagg                 228
```

```
<210> SEQ ID NO 23
<211> LENGTH: 228
<212> TYPE: DNA
<213> ORGANISM: Brassica napus

<400> SEQUENCE: 23
atggaggaag gtgggagtag tcacgacgca gagagtagca agaagctagt aagagggaag      60
atagagataa agaggataga gaacacaaca agtcgtcaag taactttctg taaacgacgc     120
aatggtcttc ttaagaaagc ttatgagctt tctgtcttgt gtgatgctga agttgccctc     180
gtcatcttct ccactcgtgg ccgtctctat gagtacgcca acaacagg                  228

<210> SEQ ID NO 24
<211> LENGTH: 228
<212> TYPE: DNA
<213> ORGANISM: Arabidopsis thaliana

<400> SEQUENCE: 24
atggaggaag gtgggagtag tcacgacgca gagagtagca agaaactagg gagagggaaa      60
atagagataa agaggataga gaacacaaca aatcgtcaag ttactttctg caaacgacgc     120
aatggtcttc tcaagaaagc ttatgaactc tctgtcttgt gtgatgccga agttgccctc     180
gtcatcttct ccactcgtgg ccgtctctat gagtacgcca acaacagc                  228

<210> SEQ ID NO 25
<211> LENGTH: 228
<212> TYPE: DNA
<213> ORGANISM: Brassica napus

<400> SEQUENCE: 25
atggagggtg gtgcgagtga tgaagtagca gagagcagca agaagatagg gagagggaag      60
atagagataa agaggataga gaacaccacg aatcgccaag tcactttctg caaaagacgc     120
aatggtctgc tcaagaaagc ttatgagctc tctgtcttgt gtgacgctga ggttgctctt     180
gtcatcttct ccactcgcgg tcgtctctac gagtacgcca acaacagg                  228

<210> SEQ ID NO 26
<211> LENGTH: 228
<212> TYPE: DNA
<213> ORGANISM: Brassica napus

<400> SEQUENCE: 26
atggagggtg gtgcgagtga tgaggtagca gagagcagca agaagatagg gagagggaag      60
atagagataa agaggataga gaacaccacg aatcgccaag tcactttctg caaaagacgc     120
aatggtctgc ttaagaaagc ttatgagctc tctgtcttgt gtgacgctga ggttgctctt     180
gtcatcttct ccactcgagg tcgtctctac gagtacgcca acaacagg                  228

<210> SEQ ID NO 27
<211> LENGTH: 228
<212> TYPE: DNA
<213> ORGANISM: Arabidopsis thaliana

<400> SEQUENCE: 27
atggagggtg gtgcgagtaa tgaagtagca gagagcagca agaagatagg gagagggaag      60
atagagataa agaggataga gaacactacg aatcgtcaag tcactttctg caaacgacgc     120
aatggtttac tcaagaaagc ttatgagctc tctgtcttgt gtgacgctga ggttgctctt     180
gtcatcttct ccactcgagg ccgtctctac gagtacgcca acaacagt                  228
```

<210> SEQ ID NO 28
<211> LENGTH: 228
<212> TYPE: DNA
<213> ORGANISM: Brassica napus

<400> SEQUENCE: 28

| | |
|---|---|
| atggaggaag gtgggagtag tcacgacgca gagagtaaca agaagctagt gagagggaag | 60 |
| atagagataa agaggataga gaacacgaca agtcgtcagg taactttctg caaacgacgc | 120 |
| aatggtcttc tcaagaaagc ttatgagctc tctgtcttgt gtgatgcgga agttgcactt | 180 |
| gttgtctttt ccactcgtgg ccgtctctat gagtacgcta acaacagg | 228 |

<210> SEQ ID NO 29
<211> LENGTH: 228
<212> TYPE: DNA
<213> ORGANISM: Brassica napus

<400> SEQUENCE: 29

| | |
|---|---|
| atggaggaag gtgggagtag tcacgacgca gagagtaaca agaagctagt gagagggaag | 60 |
| atagagataa agaggataga gaacacgaca agtcgtcaag taactttctg caaacgacgc | 120 |
| aatggtcttc tcaagaaagc ttatgagctc tctgtcttgt gtgatgcgga agttgcactt | 180 |
| gttgtcttct ccactcgtgg ccgtctctat gagtacgcta acaacagg | 228 |

<210> SEQ ID NO 30
<211> LENGTH: 228
<212> TYPE: DNA
<213> ORGANISM: Brassica napus

<400> SEQUENCE: 30

| | |
|---|---|
| atggatgaag gtgggagtag tcacgatgca gagagtagca agaagatagg tagagggaag | 60 |
| atagagataa agaggataga gaacacaaca aatcgtcaag taaccttctg caaacgacgc | 120 |
| aatggtcttc tcaagaaagc ttatgagctc tctgtcttgt gtgatgctga agttgccctc | 180 |
| gttatcttct ccactcgtgg ccttctttat gagtacgcca gcaacagg | 228 |

<210> SEQ ID NO 31
<211> LENGTH: 228
<212> TYPE: DNA
<213> ORGANISM: Brassica napus

<400> SEQUENCE: 31

| | |
|---|---|
| atggatgaaa gtgggagtag tcacgatgca gagagtagca agaagatagg tagagggaag | 60 |
| atagagataa agaggataga gaacacaaca aatcgtcaag taaccttctg caaacgacgc | 120 |
| aatggtcttc tcaagaaagc ttatgagctc tctgtcttgt gtgatgctga agttgccctc | 180 |
| gttatcttct ccactcgtgg ccgtctctat gaatacgcca gcaacagg | 228 |

<210> SEQ ID NO 32
<211> LENGTH: 76
<212> TYPE: PRT
<213> ORGANISM: Arabidopsis thaliana

<400> SEQUENCE: 32

Met Glu Glu Gly Gly Ser Ser His Asp Ala Glu Ser Ser Lys Lys Leu
1               5                   10                  15

Gly Arg Gly Lys Ile Glu Ile Lys Arg Ile Glu Asn Thr Thr Asn Arg
            20                  25                  30

Gln Val Thr Phe Cys Lys Arg Arg Asn Gly Leu Leu Lys Lys Ala Tyr

```
                    35                  40                  45

Glu Leu Ser Val Leu Cys Asp Ala Glu Val Ala Leu Val Ile Phe Ser
        50                  55                  60

Thr Arg Gly Arg Leu Tyr Glu Tyr Ala Asn Asn Ser
65                  70                  75

<210> SEQ ID NO 33
<211> LENGTH: 76
<212> TYPE: PRT
<213> ORGANISM: Arabidopsis thaliana

<400> SEQUENCE: 33

Met Glu Gly Gly Ala Ser Asn Glu Val Ala Glu Ser Ser Lys Lys Ile
1               5                   10                  15

Gly Arg Gly Lys Ile Glu Ile Lys Arg Ile Glu Asn Thr Thr Asn Arg
                20                  25                  30

Gln Val Thr Phe Cys Lys Arg Arg Asn Gly Leu Leu Lys Lys Ala Tyr
                    35                  40                  45

Glu Leu Ser Val Leu Cys Asp Ala Glu Val Ala Leu Val Ile Phe Ser
        50                  55                  60

Thr Arg Gly Arg Leu Tyr Glu Tyr Ala Asn Asn Ser
65                  70                  75

<210> SEQ ID NO 34
<211> LENGTH: 76
<212> TYPE: PRT
<213> ORGANISM: Brassica napus

<400> SEQUENCE: 34

Met Asp Glu Gly Gly Ser Ser His Asp Ala Glu Ser Ser Lys Lys Ile
1               5                   10                  15

Gly Arg Gly Lys Ile Glu Ile Lys Arg Ile Glu Asn Thr Thr Asn Arg
                20                  25                  30

Gln Val Thr Phe Cys Lys Arg Arg Asn Gly Leu Leu Lys Lys Ala Tyr
                    35                  40                  45

Glu Leu Ser Val Leu Cys Asp Ala Glu Val Ala Leu Val Ile Phe Ser
        50                  55                  60

Thr Arg Gly Leu Leu Tyr Glu Tyr Ala Ser Asn Arg
65                  70                  75

<210> SEQ ID NO 35
<211> LENGTH: 76
<212> TYPE: PRT
<213> ORGANISM: Brassica napus

<400> SEQUENCE: 35

Met Asp Glu Ser Gly Ser Ser His Asp Ala Glu Ser Ser Lys Lys Ile
1               5                   10                  15

Gly Arg Gly Lys Ile Glu Ile Lys Arg Ile Glu Asn Thr Thr Asn Arg
                20                  25                  30

Gln Val Thr Phe Cys Lys Arg Arg Asn Gly Leu Leu Lys Lys Ala Tyr
                    35                  40                  45

Glu Leu Ser Val Leu Cys Asp Ala Glu Val Ala Leu Val Ile Phe Ser
        50                  55                  60

Thr Arg Gly Arg Leu Tyr Glu Tyr Ala Ser Asn Arg
65                  70                  75

<210> SEQ ID NO 36
```

<211> LENGTH: 76
<212> TYPE: PRT
<213> ORGANISM: Brassica napus

<400> SEQUENCE: 36

Met Glu Glu Gly Gly Ser Ser His Asp Ala Glu Ser Ser Lys Lys Leu
1               5                   10                  15

Val Arg Gly Lys Ile Glu Ile Lys Arg Ile Glu Asn Thr Thr Ser Arg
            20                  25                  30

Gln Val Thr Phe Cys Lys Arg Arg Asn Gly Leu Leu Lys Lys Ala Tyr
        35                  40                  45

Glu Leu Ser Val Leu Cys Asp Ala Glu Val Ala Leu Val Ile Phe Ser
    50                  55                  60

Thr Arg Gly Arg Leu Tyr Glu Tyr Ala Asn Asn Arg
65                  70                  75

<210> SEQ ID NO 37
<211> LENGTH: 76
<212> TYPE: PRT
<213> ORGANISM: Brassica napus

<400> SEQUENCE: 37

Met Glu Glu Gly Gly Ser Ser His Asp Ala Glu Ser Asn Lys Lys Leu
1               5                   10                  15

Val Arg Gly Lys Ile Glu Ile Lys Arg Ile Glu Asn Thr Thr Ser Arg
            20                  25                  30

Gln Val Thr Phe Cys Lys Arg Arg Asn Gly Leu Leu Lys Lys Ala Tyr
        35                  40                  45

Glu Leu Ser Val Leu Cys Asp Ala Glu Val Ala Leu Val Ile Phe Ser
    50                  55                  60

Thr Arg Gly Arg Leu Tyr Glu Tyr Ala Asn Asn Arg
65                  70                  75

<210> SEQ ID NO 38
<211> LENGTH: 76
<212> TYPE: PRT
<213> ORGANISM: Brassica napus

<400> SEQUENCE: 38

Met Glu Glu Gly Gly Ser Ser His Asp Ala Glu Ser Asn Lys Lys Leu
1               5                   10                  15

Val Arg Gly Lys Ile Glu Ile Lys Arg Ile Glu Asn Thr Thr Ser Arg
            20                  25                  30

Gln Val Thr Phe Cys Lys Arg Arg Asn Gly Leu Leu Lys Lys Ala Tyr
        35                  40                  45

Glu Leu Ser Val Leu Cys Asp Ala Glu Val Ala Leu Val Val Phe Ser
    50                  55                  60

Thr Arg Gly Arg Leu Tyr Glu Tyr Ala Asn Asn Arg
65                  70                  75

<210> SEQ ID NO 39
<211> LENGTH: 76
<212> TYPE: PRT
<213> ORGANISM: Brassica napus

<400> SEQUENCE: 39

Met Glu Glu Gly Gly Ser Ser His Asp Ala Glu Ser Asn Lys Lys Leu
1               5                   10                  15

Val Arg Gly Lys Ile Glu Ile Lys Arg Ile Glu Asn Thr Thr Ser Arg

```
            20                  25                  30
Gln Val Thr Phe Cys Lys Arg Arg Asn Gly Leu Leu Lys Lys Ala Tyr
            35                  40                  45

Glu Leu Ser Val Leu Cys Asp Ala Glu Val Ala Leu Val Phe Ser
        50                  55                  60

Thr Arg Gly Arg Leu Tyr Glu Tyr Ala Asn Asn Arg
65                  70                  75
```

<210> SEQ ID NO 40
<211> LENGTH: 76
<212> TYPE: PRT
<213> ORGANISM: Brassica napus

<400> SEQUENCE: 40

```
Met Glu Gly Gly Ala Ser Asp Glu Val Ala Glu Ser Ser Lys Lys Ile
1               5                   10                  15

Gly Arg Gly Lys Ile Glu Ile Lys Arg Ile Glu Asn Thr Thr Asn Arg
            20                  25                  30

Gln Val Thr Phe Cys Lys Arg Arg Asn Gly Leu Leu Lys Lys Ala Tyr
            35                  40                  45

Glu Leu Ser Val Leu Cys Asp Ala Glu Val Ala Leu Val Ile Phe Ser
        50                  55                  60

Thr Arg Gly Arg Leu Tyr Glu Tyr Ala Asn Asn Arg
65                  70                  75
```

<210> SEQ ID NO 41
<211> LENGTH: 76
<212> TYPE: PRT
<213> ORGANISM: Brassica napus

<400> SEQUENCE: 41

```
Met Glu Gly Gly Ala Ser Asp Glu Val Ala Glu Ser Ser Lys Lys Ile
1               5                   10                  15

Gly Arg Gly Lys Ile Glu Ile Lys Arg Ile Glu Asn Thr Thr Asn Arg
            20                  25                  30

Gln Val Thr Phe Cys Lys Arg Arg Asn Gly Leu Leu Lys Lys Ala Tyr
            35                  40                  45

Glu Leu Ser Val Leu Cys Asp Ala Glu Val Ala Leu Val Ile Phe Ser
        50                  55                  60

Thr Arg Gly Arg Leu Tyr Glu Tyr Ala Asn Asn Arg
65                  70                  75
```

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
gtagcaagaa gataggtaga                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic Construct

<400> SEQUENCE: 43

-continued gtaacaagaa gctagtgaga                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct

<400> SEQUENCE: 44
gtagcaagaa gctagtaaga                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic Construct

<400> SEQUENCE: 45
gcagcaagaa gatagggaga                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic Construct

<400> SEQUENCE: 46
cagaagcaat ggatgaaggt                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic Construct

<400> SEQUENCE: 47
cagaatcaat ggaggaaggt                                              20

<210> SEQ ID NO 48
<211> LENGTH: 20
<212> TYPE: DNA
<213> ORGANISM: Artificial Sequence
<220> FEATURE:
<223> OTHER INFORMATION: Synthetic Construct

<400> SEQUENCE: 48
gggttgatat aaatggaggg                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct

<400> SEQUENCE: 49
cagaagcaat ggatgaaagt                                              20

<210> SEQ ID NO 50
<211> LENGTH: 1417
<212> TYPE: PRT
<213> ORGANISM: Artificial Sequence
<220> FEATURE:
<223> OTHER INFORMATION: Synthetic Construct

<400> SEQUENCE: 50

```
Met Ala Ser Ser Gly Gly Arg Met Asp Tyr Lys Asp His Asp Gly Asp
1               5                   10                  15

Tyr Lys Asp His Asp Ile Asp Tyr Lys Asp Asp Asp Asp Lys Met Ala
            20                  25                  30

Pro Lys Lys Lys Arg Lys Val Asp Lys Lys Tyr Ser Ile Gly Leu Asp
            35                  40                  45

Ile Gly Thr Asn Ser Val Gly Trp Ala Val Ile Thr Asp Glu Tyr Lys
        50                  55                  60

Val Pro Ser Lys Lys Phe Lys Val Leu Gly Asn Thr Asp Arg His Ser
65                  70                  75                  80

Ile Lys Lys Asn Leu Ile Gly Ala Leu Leu Phe Asp Ser Gly Glu Thr
                85                  90                  95

Ala Glu Ala Thr Arg Leu Lys Arg Thr Ala Arg Arg Arg Tyr Thr Arg
            100                 105                 110

Arg Lys Asn Arg Ile Cys Tyr Leu Gln Glu Ile Phe Ser Asn Glu Met
        115                 120                 125

Ala Lys Val Asp Asp Ser Phe Phe His Arg Leu Glu Glu Ser Phe Leu
130                 135                 140

Val Glu Glu Asp Lys Lys His Glu Arg His Pro Ile Phe Gly Asn Ile
145                 150                 155                 160

Val Asp Glu Val Ala Tyr His Glu Lys Tyr Pro Thr Ile Tyr His Leu
                165                 170                 175

Arg Lys Lys Leu Val Asp Ser Thr Asp Lys Ala Asp Leu Arg Leu Ile
            180                 185                 190

Tyr Leu Ala Leu Ala His Met Ile Lys Phe Arg Gly His Phe Leu Ile
        195                 200                 205

Glu Gly Asp Leu Asn Pro Asp Asn Ser Asp Val Asp Lys Leu Phe Ile
    210                 215                 220

Gln Leu Val Gln Thr Tyr Asn Gln Leu Phe Glu Glu Asn Pro Ile Asn
225                 230                 235                 240

Ala Ser Gly Val Asp Ala Lys Ala Ile Leu Ser Ala Arg Leu Ser Lys
                245                 250                 255

Ser Arg Arg Leu Glu Asn Leu Ile Ala Gln Leu Pro Gly Glu Lys Lys
            260                 265                 270

Asn Gly Leu Phe Gly Asn Leu Ile Ala Leu Ser Leu Gly Leu Thr Pro
        275                 280                 285

Asn Phe Lys Ser Asn Phe Asp Leu Ala Glu Asp Ala Lys Leu Gln Leu
    290                 295                 300

Ser Lys Asp Thr Tyr Asp Asp Asp Leu Asp Asn Leu Leu Ala Gln Ile
305                 310                 315                 320

Gly Asp Gln Tyr Ala Asp Leu Phe Leu Ala Ala Lys Asn Leu Ser Asp
                325                 330                 335

Ala Ile Leu Leu Ser Asp Ile Leu Arg Val Asn Thr Glu Ile Thr Lys
            340                 345                 350

Ala Pro Leu Ser Ala Ser Met Ile Lys Arg Tyr Asp Glu His His Gln
        355                 360                 365

Asp Leu Thr Leu Leu Lys Ala Leu Val Arg Gln Gln Leu Pro Glu Lys
    370                 375                 380

Tyr Lys Glu Ile Phe Phe Asp Gln Ser Lys Asn Gly Tyr Ala Gly Tyr
385                 390                 395                 400
```

```
Ile Asp Gly Gly Ala Ser Gln Glu Glu Phe Tyr Lys Phe Ile Lys Pro
                405                 410                 415

Ile Leu Glu Lys Met Asp Gly Thr Glu Leu Leu Val Lys Leu Asn
            420                 425                 430

Arg Glu Asp Leu Leu Arg Lys Gln Arg Thr Phe Asp Asn Gly Ser Ile
        435                 440                 445

Pro His Gln Ile His Leu Gly Glu Leu His Ala Ile Leu Arg Arg Gln
    450                 455                 460

Glu Asp Phe Tyr Pro Phe Leu Lys Asp Asn Arg Glu Lys Ile Glu Lys
465                 470                 475                 480

Ile Leu Thr Phe Arg Ile Pro Tyr Tyr Val Gly Pro Leu Ala Arg Gly
                485                 490                 495

Asn Ser Arg Phe Ala Trp Met Thr Arg Lys Ser Glu Glu Thr Ile Thr
            500                 505                 510

Pro Trp Asn Phe Glu Glu Val Val Asp Lys Gly Ala Ser Ala Gln Ser
        515                 520                 525

Phe Ile Glu Arg Met Thr Asn Phe Asp Lys Asn Leu Pro Asn Glu Lys
    530                 535                 540

Val Leu Pro Lys His Ser Leu Leu Tyr Glu Tyr Phe Thr Val Tyr Asn
545                 550                 555                 560

Glu Leu Thr Lys Val Lys Tyr Val Thr Glu Gly Met Arg Lys Pro Ala
                565                 570                 575

Phe Leu Ser Gly Glu Gln Lys Lys Ala Ile Val Asp Leu Leu Phe Lys
            580                 585                 590

Thr Asn Arg Lys Val Thr Val Lys Gln Leu Lys Glu Asp Tyr Phe Lys
        595                 600                 605

Lys Ile Glu Cys Phe Asp Ser Val Glu Ile Ser Gly Val Glu Asp Arg
    610                 615                 620

Phe Asn Ala Ser Leu Gly Thr Tyr His Asp Leu Leu Lys Ile Ile Lys
625                 630                 635                 640

Asp Lys Asp Phe Leu Asp Asn Glu Glu Asn Glu Asp Ile Leu Glu Asp
                645                 650                 655

Ile Val Leu Thr Leu Thr Leu Phe Glu Asp Arg Glu Met Ile Glu Glu
            660                 665                 670

Arg Leu Lys Thr Tyr Ala His Leu Phe Asp Asp Lys Val Met Lys Gln
        675                 680                 685

Leu Lys Arg Arg Arg Tyr Thr Gly Trp Gly Arg Leu Ser Arg Lys Leu
    690                 695                 700

Ile Asn Gly Ile Arg Asp Lys Gln Ser Gly Lys Thr Ile Leu Asp Phe
705                 710                 715                 720

Leu Lys Ser Asp Gly Phe Ala Asn Arg Asn Phe Met Gln Leu Ile His
                725                 730                 735

Asp Asp Ser Leu Thr Phe Lys Glu Asp Ile Gln Lys Ala Gln Val Ser
            740                 745                 750

Gly Gln Gly Asp Ser Leu His Glu His Ile Ala Asn Leu Ala Gly Ser
        755                 760                 765

Pro Ala Ile Lys Lys Gly Ile Leu Gln Thr Val Lys Val Val Asp Glu
    770                 775                 780

Leu Val Lys Val Met Gly Arg His Lys Pro Glu Asn Ile Val Ile Glu
785                 790                 795                 800

Met Ala Arg Glu Asn Gln Thr Thr Gln Lys Gly Gln Lys Asn Ser Arg
                805                 810                 815
```

-continued

Glu Arg Met Lys Arg Ile Glu Glu Gly Ile Lys Glu Leu Gly Ser Gln
            820                 825                 830

Ile Leu Lys Glu His Pro Val Glu Asn Thr Gln Leu Gln Asn Glu Lys
            835                 840                 845

Leu Tyr Leu Tyr Tyr Leu Gln Asn Gly Arg Asp Met Tyr Val Asp Gln
        850                 855                 860

Glu Leu Asp Ile Asn Arg Leu Ser Asp Tyr Asp Val Asp His Ile Val
865                 870                 875                 880

Pro Gln Ser Phe Leu Lys Asp Asp Ser Ile Asp Asn Lys Val Leu Thr
                885                 890                 895

Arg Ser Asp Lys Asn Arg Gly Lys Ser Asp Asn Val Pro Ser Glu Glu
            900                 905                 910

Val Val Lys Lys Met Lys Asn Tyr Trp Arg Gln Leu Leu Asn Ala Lys
            915                 920                 925

Leu Ile Thr Gln Arg Lys Phe Asp Asn Leu Thr Lys Ala Glu Arg Gly
        930                 935                 940

Gly Leu Ser Glu Leu Asp Lys Ala Gly Phe Ile Lys Arg Gln Leu Val
945                 950                 955                 960

Glu Thr Arg Gln Ile Thr Lys His Val Ala Gln Ile Leu Asp Ser Arg
                965                 970                 975

Met Asn Thr Lys Tyr Asp Glu Asn Asp Lys Leu Ile Arg Glu Val Lys
            980                 985                 990

Val Ile Thr Leu Lys Ser Lys Leu Val Ser Asp Phe Arg Lys Asp Phe
            995                 1000                1005

Gln Phe Tyr Lys Val Arg Glu Ile Asn Asn Tyr His His Ala His Asp
        1010                1015                1020

Ala Tyr Leu Asn Ala Val Val Gly Thr Ala Leu Ile Lys Lys Tyr Pro
1025                1030                1035                1040

Lys Leu Glu Ser Glu Phe Val Tyr Gly Asp Tyr Lys Val Tyr Asp Val
                1045                1050                1055

Arg Lys Met Ile Ala Lys Ser Glu Gln Glu Ile Gly Lys Ala Thr Ala
            1060                1065                1070

Lys Tyr Phe Phe Tyr Ser Asn Ile Met Asn Phe Phe Lys Thr Glu Ile
        1075                1080                1085

Thr Leu Ala Asn Gly Glu Ile Arg Lys Arg Pro Leu Ile Glu Thr Asn
1090                1095                1100

Gly Glu Thr Gly Glu Ile Val Trp Asp Lys Gly Arg Asp Phe Ala Thr
1105                1110                1115                1120

Val Arg Lys Val Leu Ser Met Pro Gln Val Asn Ile Val Lys Lys Thr
            1125                1130                1135

Glu Val Gln Thr Gly Gly Phe Ser Lys Glu Ser Ile Leu Pro Lys Arg
            1140                1145                1150

Asn Ser Asp Lys Leu Ile Ala Arg Lys Lys Asp Trp Asp Pro Lys Lys
        1155                1160                1165

Tyr Gly Gly Phe Asp Ser Pro Thr Val Ala Tyr Ser Val Leu Val Val
        1170                1175                1180

Ala Lys Val Glu Lys Gly Lys Ser Lys Lys Leu Lys Ser Val Lys Glu
1185                1190                1195                1200

Leu Leu Gly Ile Thr Ile Met Glu Arg Ser Ser Phe Glu Lys Asn Pro
                1205                1210                1215

Ile Asp Phe Leu Glu Ala Lys Gly Tyr Lys Glu Val Lys Lys Asp Leu
            1220                1225                1230

Ile Ile Lys Leu Pro Lys Tyr Ser Leu Phe Glu Leu Glu Asn Gly Arg

Lys Arg Met Leu Ala Ser Ala Gly Glu Leu Gln Lys Gly Asn Glu Leu
1250                1255                1260

Ala Leu Pro Ser Lys Tyr Val Asn Phe Leu Tyr Leu Ala Ser His Tyr
1265            1270                1275                1280

Glu Lys Leu Lys Gly Ser Pro Glu Asp Asn Glu Gln Lys Gln Leu Phe
            1285                1290                1295

Val Glu Gln His Lys His Tyr Leu Asp Glu Ile Ile Glu Gln Ile Ser
        1300                1305                1310

Glu Phe Ser Lys Arg Val Ile Leu Ala Asp Ala Asn Leu Asp Lys Val
            1315                1320                1325

Leu Ser Ala Tyr Asn Lys His Arg Asp Lys Pro Ile Arg Glu Gln Ala
            1330                1335                1340

Glu Asn Ile Ile His Leu Phe Thr Leu Thr Asn Leu Gly Ala Pro Ala
1345                1350                1355                1360

Ala Phe Lys Tyr Phe Asp Thr Thr Ile Asp Arg Lys Arg Tyr Thr Ser
            1365                1370                1375

Thr Lys Glu Val Leu Asp Ala Thr Leu Ile His Gln Ser Ile Thr Gly
            1380                1385                1390

Leu Tyr Glu Thr Arg Ile Asp Leu Ser Gln Leu Gly Gly Asp Ser Arg
            1395                1400                1405

Ala Asp Pro Lys Lys Lys Arg Lys Val
            1410                1415

<210> SEQ ID NO 51
<211> LENGTH: 668
<212> TYPE: DNA
<213> ORGANISM: Artificial Sequence
<220> FEATURE:
<223> OTHER INFORMATION: Synthetic Construct

<400> SEQUENCE: 51
aattctggcg ttcccctttt gcattgagac cgatgttcgt tccggaacct tgcacgcccc      60
agagcttctc accgttcacg acaatttcct tctcgttgag gtcggtcgcg ccatgtcgga     120
tgaaataaaa acttttgata ccagcggggg ccttcgcaga gccgaggtag gtctgagaaa     180
ttggcatttt cacgtgtgga agatatgaat ttttttgaga aactagataa gattaatgaa     240
tatcggtgtt ttggtttttt cttgtggccg tctttgttta tattgagatt ttcaaatca      300 gtgcgcaaga cgtgacgtaa gtatccgagt cagtttttat ttttctacta atttggtcgt     360
ttatttcggc gtgtaggaca tggcaaccgg gcctgaattt cgcgggtatt ctgtttctat     420
tccaactttt tcttgatccg cagccattaa cgactttga atagatacgc tgacacgcca      480
agcctcgcta gtcaaaagtg taccaaacaa cgctttacag caagaacgga atgcgcgtga     540
cgctcgcggt gacgccattt cgccttttca gaaatggata aatagccttg cttcctatta     600
tatcttccca aattaccaat acattacact agcatctgaa tttcataacc aatctcgata     660
caccaaac                                                              668

<210> SEQ ID NO 52
<211> LENGTH: 642
<212> TYPE: DNA
<213> ORGANISM: Artificial Sequence
<220> FEATURE:
<223> OTHER INFORMATION: Synthetic Construct

<400> SEQUENCE: 52

```
gagctttcgt tcgtatcatc ggtttcgaca acgttcgtca agttcaatgc atcagtttca    60
ttgcgcacac accagaatcc tactgagttc gagtattatg gcattgggaa acatgttttt   120
cttgtaccat ttgttgtgct tgtaatttac tgtgttttt attcggtttt cgctatcgaa    180
ctgtgaaatg gaaatggatg gagaagagtt aatgaatgat atggtccttt tgttcattct   240
caaattaata ttatttgttt tttctcttat ttgttgtgtg ttgaatttga aaatataaga   300
gatatgcaaa cattttgttt tgagtaaaaa tgtgtcaaat cgtggcctct aatgaccgaa   360
gttaatatga ggagtaaaac acttgtagtt gtaccattat gcttattcac taggcaacaa   420
atatattttc agacctagaa aagctgcaaa tgttactgaa tacaagtatg tcctcttgtg   480
ttttagacat ttatgaactt ccttttatgt aattttccag aatccttgtc agattctaat   540
cattgcttta taattatagt tatactcatg gatttgtagt tgagtatgaa aatatttttt   600
aatgcatttt atgacttgcc aattgattga caacatgcat ca                      642

<210> SEQ ID NO 53
<211> LENGTH: 445
<212> TYPE: DNA
<213> ORGANISM: Artificial Sequence
<220> FEATURE:
<223> OTHER INFORMATION: Synthetic Construct

<400> SEQUENCE: 53
cttcgttgaa caacggaaac tcgacttgcc ttccgcacaa tacatcattt cttcttagct    60
ttttttcttc ttcttcgttc atacagtttt tttttgttta tcagcttaca ttttcttgaa   120
ccgtagcttt cgttttcttc tttttaactt tccattcgga gtttttgtat cttgtttcat   180
agtttgtccc aggattagaa tgattaggca tcgaaccttc aagaatttga ttgaataaaa   240
catcttcatt cttaagatat gaagataatc ttcaaaaggc ccctgggaat ctgaaagaag   300
agaagcaggc ccatttatat gggaaagaac aatagtattt cttatatagg cccatttaag   360
ttgaaaacaa tcttcaaaag tcccacatcg cttagataag aaaacgaagc tgagtttata   420
tacagctaga gtcgaagtag tgatt                                         445

<210> SEQ ID NO 54
<211> LENGTH: 10
<212> TYPE: DNA
<213> ORGANISM: Artificial Sequence
<220> FEATURE:
<223> OTHER INFORMATION: Synthetic Construct

<400> SEQUENCE: 54
tttttttttt                                                           10

<210> SEQ ID NO 55
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: labeled with a 2'-O-Me group

<400> SEQUENCE: 55
agagagyarc aagaagmtag kagagggaag atagagataa a                        41

<210> SEQ ID NO 56
<211> LENGTH: 41
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: labeled with a 2'-O-Me group

<400> SEQUENCE: 56
agagagyarc aagaagmtag agagggaaga tagagataaa g          41

<210> SEQ ID NO 57
<211> LENGTH: 43
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1
<223> OTHER INFORMATION: labeled with a 2'-O-Me group
<220> FEATURE:
<221> NAME/KEY: misc_feature
<222> LOCATION: 23
<223> OTHER INFORMATION: n = A,T,C or G

<400> SEQUENCE: 57
agagagyarc aagaagmtag kdnagaggga agatagagat aaa        43

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62
<211> LENGTH: 270
<212> TYPE: DNA
<213> ORGANISM: Brassica napus

<400> SEQUENCE: 62
ttttgcctct cttgatctgc aaaaatattt gatcataaac ttgaatagca tcgctctcta    60
gttcaatatc tctcccactt cttttcggtg gtttattcat ttggtgacga tatcacagaa   120
gcaatggatg aaggtgggag tagtcacgat gcagagagta gcaagaagat aggttagagg   180
gaagatagag ataaagagga tagagaacac aacaaatcgt caagtaacct tctgcaaacg   240
acgcaatggt cttctcaaga aagcttatga                                   270
```

<210> SEQ ID NO 63
<211> LENGTH: 270
<212> TYPE: DNA
<213> ORGANISM: Brassica napus

<400> SEQUENCE: 63
ttttgcctct cttgatctgc aaaaatattt gatcataaac ttgaatagca tcgctctcta      60
gttcaatatc tctcccactt cttttcggtg gtttattcat ttggtgacga tatcacagaa     120
gcaatggatg aaggtgggag tagtcacgat gcagagagta gcaagaagat aggtaagagg     180
gaagatagag ataaagagga tagagaacac aacaaatcgt caagtaacct tctgcaaacg     240
acgcaatggt cttctcaaga aagcttatga                                      270

<210> SEQ ID NO 64
<211> LENGTH: 270
<212> TYPE: DNA
<213> ORGANISM: Brassica napus

<400> SEQUENCE: 64
ttttgcctct cttgatctgc aaaaatattt gatcataaac ttgaatagca tcgctctcta      60
gttcaatatc tctcccactt cttttcggtg gtttattcat ttggtgacga tatcacagaa     120
gcaatggatg aaggtgggag tagtcacgat gcagagagta gcaagaagat aggttagagg     180
gaagatagag ataaagagga tagagaacac aacaaatcgt caagtaacct tctgcaaacg     240
acgcaatggt cttctcaaga aagcttatga                                      270

<210> SEQ ID NO 65
<211> LENGTH: 270
<212> TYPE: DNA
<213> ORGANISM: Brassica napus

<400> SEQUENCE: 65
ttttgcctct cttgatctgc aaaaatattt gatcataaac ttgaatagca tcgctctcta      60
gttcaatatc tctcccactt cttttcggtg gtttattcat ttggtgacga tatcacagaa     120
gcaatggatg aaggtgggag tagtcacgat gcagagagta gcaagaagat aggttagagg     180
gaagatagag ataaagagga tagagaacac aacaaatcgt caagtaacct tctgcaaacg     240
acgcaatggt cttctcaaga aagcttatga                                      270

<210> SEQ ID NO 66
<211> LENGTH: 270
<212> TYPE: DNA
<213> ORGANISM: Brassica napus

<400> SEQUENCE: 66
ttttgcctct cttgatctgc aaaaatattt gatcataaac ttgaatagca tcgctctcta      60
gttcaatatc tctcccactt cttttcggtg gtttattcat ttggtgacga tatcacagaa     120
gcaatggatg aaggtgggag tagtcacgat gcagagagta gcaagaagat aggtgagagg     180
gaagatagag ataaagagga tagagaacac aacaaatcgt caagtaacct tctgcaaacg     240
acgcaatggt cttctcaaga aagcttatga                                      270

<210> SEQ ID NO 67
<211> LENGTH: 269
<212> TYPE: DNA
<213> ORGANISM: Brassica napus

<400> SEQUENCE: 67

```
ttttgcctct cttgatctgc aaaaatattt gatcataaac ttgaatagca tcgctctcta    60
gttcaatatc tctcccactt cttttcggtg gtttattcat ttggtgacga tatcacagaa   120
gcaatggatg aaggtgggag tagtcacgat gcagagagta gcaagaagat aggtagaggg   180
aagatagaga taaagaggat agagaacaca acaaatcgtc aagtaaccct ctgcaaacga   240
cgcaatggtc ttctcaagaa agcttatga                                     269
```

<210> SEQ ID NO 68
<211> LENGTH: 269
<212> TYPE: DNA
<213> ORGANISM: Brassica napus

<400> SEQUENCE: 68

```
ttttgcctct cttgatctgc aaaaatattt gatcataaac ttgaatagca tcgctctcta    60
gttcaatatc tctcccactt cttttcggtg gtttattcat ttggtgacga tatcacagaa   120
gcaatggatg aaggtgggag tagtcacgat gcagagagta gcaagaagat aggtagaggg   180
aagatagaga taaagaggat agagaacaca acaaatcgtc aagtaaccct ctgcaaacga   240
cgcaatggtc ttctcaagaa agcttatga                                     269
```

<210> SEQ ID NO 69
<211> LENGTH: 269
<212> TYPE: DNA
<213> ORGANISM: Brassica napus

<400> SEQUENCE: 69

```
ttttgcctct cttgatctgc aaaaatattt gatcataaac ttgaatagca tcgctctcta    60
gttcaatatc tctcccactt cttttcggtg gtttattcat ttggtgacga tatcacagaa   120
gcaatggatg aaggtgggag tagtcacgat gcagagagta gcaagaagat aggtagaggg   180
aagatagaga taaagaggat agagaacaca acaaatcgtc aagtaaccct ctgcaaacga   240
cgcaatggtc ttctcaagaa agcttatga                                     269
```

<210> SEQ ID NO 70
<211> LENGTH: 269
<212> TYPE: DNA
<213> ORGANISM: Brassica napus

<400> SEQUENCE: 70

```
ttttgcctct cttgatctgc aaaaatattt gatcataaac ttgaatagca tcgctctcta    60
gttcaatatc tctcccactt cttttcggtg gtttattcat ttggtgacga tatcacagaa   120
gcaatggatg aaggtgggag tagtcacgat gcagagagta gcaagaagat aggtagaggg   180
aagatagaga taaagaggat agagaacaca acaaatcgtc aagtaaccct ctgcaaacga   240
cgcaatggtc ttctcaagaa agcttatga                                     269
```

<210> SEQ ID NO 71
<211> LENGTH: 269
<212> TYPE: DNA
<213> ORGANISM: Brassica napus

<400> SEQUENCE: 71

```
ttttgcctct cttgatctgc aaaaatattt gatcataaac ttgaatagca tcgctctcta    60
gttcaatatc tctcccactt cttttcggtg gtttattcat ttggtgacga tatcacagaa   120
gcaatggatg aaggtgggag tagtcacgat gcagagagta gcaagaagat aggtagaggg   180
```
aagatagaga taaagaggat agagaacaca acaaatcgtc aagtaacctt ctgcaaacga    240
cgcaatggtc ttctcaagaa agcttatga                                      269

<210> SEQ ID NO 72
<211> LENGTH: 297
<212> TYPE: DNA
<213> ORGANISM: Brassica napus

<400> SEQUENCE: 72
ttttgcctct cttgatctgc aaaaatattt gatcataaac ttaaatagct attttttcaaa   60 aaaaaactta aatagcatcg ctctcaagtt caatctccct cccccttctt tttggtggtt   120
tattcattta gtgacgatat cacagaagca atggatgaaa gtgggagtag tcacgatgca   180
gagagtagca agaagatagg ttagagggaa gatagagata aagaggatag agaacacaac   240
aaatcgtcaa gtaaccttct gcaaacgacg caatggtctt ctcaagaaag cttatga       297

<210> SEQ ID NO 73
<211> LENGTH: 297
<212> TYPE: DNA
<213> ORGANISM: Brassica napus

<400> SEQUENCE: 73
ttttgcctct cttgatctgc aaaaatattt gatcataaac ttaaatagct attttttcaaa   60 aaaaaactta aatagcatcg ctctcaagtt caatctccct cccccttctt tttggtggtt   120
tattcattta gtgacgatat cacagaagca atggatgaaa gtgggagtag tcacgatgca   180
gagagtagca agaagatagg ttagagggaa gatagagata aagaggatag agaacacaac   240
aaatcgtcaa gtaaccttct gcaaacgacg caatggtctt ctcaagaaag cttatga       297

<210> SEQ ID NO 74
<211> LENGTH: 297
<212> TYPE: DNA
<213> ORGANISM: Brassica napus

<400> SEQUENCE: 74
ttttgcctct cttgatctgc aaaaatattt gatcataaac ttaaatagct attttttcaaa   60 aaaaaactta aatagcatcg ctctcaagtt caatctccct cccccttctt tttggtggtt   120
tattcattta gtgacgatat cacagaagca atggatgaaa gtgggagtag tcacgatgca   180
gagagtagca agaagatagg ttagagggaa gatagagata aagaggatag agaacacaac   240
aaatcgtcaa gtaaccttct gcaaacgacg caatggtctt ctcaagaaag cttatga       297

<210> SEQ ID NO 75
<211> LENGTH: 297
<212> TYPE: DNA
<213> ORGANISM: Brassica napus

<400> SEQUENCE: 75
ttttgcctct cttgatctgc aaaaatattt gatcataaac ttaaatagct attttttcaaa   60 aaaaaactta aatagcatcg ctctcaagtt caatctccct cccccttctt tttggtggtt   120
tattcattta gtgacgatat cacagaagca atggatgaaa gtgggagtag tcacgatgca   180
gagagtagca agaagatagg ttagagggaa gatagagata aagaggatag agaacacaac   240
aaatcgtcaa gtaaccttct gcaaacgacg caatggtctt ctcaagaaag cttatga       297

<210> SEQ ID NO 76
<211> LENGTH: 294

```
<212> TYPE: DNA
<213> ORGANISM: Brassica napus

<400> SEQUENCE: 76
ttttgcctct cttgatctgc aaaaatattt gatcataaac ttaaatagct attttttcaaa    60 aaaaaactta aatagcatcg ctctcaagtt caatctccct cccccttctt tttggtggtt   120
tattcattta gtgacgatat cacagaagca atggatgaaa gtgggagtag tcacgatgca   180
gagagtagca agaagataga gagggaagat agagataaag aggatagaga acacaacaaa   240
tcgtcaagta accttctgca acgacgcaa tggtcttctc aagaaagctt atga           294

<210> SEQ ID NO 77
<211> LENGTH: 297
<212> TYPE: DNA
<213> ORGANISM: Brassica napus

<400> SEQUENCE: 77
ttttgcctct cttgatctgc aaaaatattt gatcataaac ttaaatagct attttttcaaa    60 aaaaaactta aatagcatcg ctctcaagtt caatctccct cccccttctt tttggtggtt   120
tattcattta gtgacgatat cacagaagca atggatgaaa gtgggagtag tcacgatgca   180
gagagtagca agaagatagg ttagagggaa gatagagata aagaggatag agaacacaac   240
aaatcgtcaa gtaaccttct gcaaacgacg caatggtctt ctcaagaaag cttatga     297

<210> SEQ ID NO 78
<211> LENGTH: 297
<212> TYPE: DNA
<213> ORGANISM: Brassica napus

<400> SEQUENCE: 78
ttttgcctct cttgatctgc aaaaatattt gatcataaac ttaaatagct attttttcaaa    60 aaaaaactta aatagcatcg ctctcaagtt caatctccct cccccttctt tttggtggtt   120
tattcattta gtgacgatat cacagaagca atggatgaaa gtgggagtag tcacgatgca   180
gagagtagca agaagatagg ttagagggaa gatagagata aagaggatag agaacacaac   240
aaatcgtcaa gtaaccttct gcaaacgacg caatggtctt ctcaagaaag cttatga     297

<210> SEQ ID NO 79
<211> LENGTH: 297
<212> TYPE: DNA
<213> ORGANISM: Brassica napus

<400> SEQUENCE: 79
ttttgcctct cttgatctgc aaaaatattt gatcataaac ttaaatagct attttttcaaa    60 aaaaaactta aatagcatcg ctctcaagtt caatctccct cccccttctt tttggtggtt   120
tattcattta gtgacgatat cacagaagca atggatgaaa gtgggagtag tcacgatgca   180
gagagtagca agaagatagg taagagggaa gatagagata aagaggatag agaacacaac   240
aaatcgtcaa gtaaccttct gcaaacgacg caatggtctt ctcaagaaag cttatga     297

<210> SEQ ID NO 80
<211> LENGTH: 297
<212> TYPE: DNA
<213> ORGANISM: Brassica napus

<400> SEQUENCE: 80
ttttgcctct cttgatctgc aaaaatattt gatcataaac ttaaatagct attttttcaaa    60
```

```
aaaaaaactta aatagcatcg ctctcaagtt caatctccct cccccttctt tttggtggtt    120
tattcattta gtgacgatat cacagaagca atggatgaaa gtgggagtag tcacgatgca    180
gagagtagca agaagatagg taagagggaa gatagagata aagaggatag agaacacaac    240
aaatcgtcaa gtaaccttct gcaaacgacg caatggtctt ctcaagaaag cttatga      297
```

<210> SEQ ID NO 81
<211> LENGTH: 296
<212> TYPE: DNA
<213> ORGANISM: Brassica napus

<400> SEQUENCE: 81

```
ttttgcctct cttgatctgc aaaatatttt gatcataaac ttaaatagct atttttcaaa    60
aaaaaactta aatagcatcg ctctcaagtt caatctccct cccccttctt tttggtggtt   120
tattcattta gtgacgatat cacagaagca atggatgaaa gtgggagtag tcacgatgca   180
gagagtagca agaagatagg tagagggaag atagagataa agaggataga gaacacaaca   240
aatcgtcaag taaccttctg caaacgacgc aatggtcttc tcaagaaagc ttatga       296
```

<210> SEQ ID NO 82
<211> LENGTH: 294
<212> TYPE: DNA
<213> ORGANISM: Brassica napus

<400> SEQUENCE: 82

```
tattcttgat ctgcaaaatg attaatttaa tcatcaatct taattagctt ctctagagca    60 atatttttt ttcttaagct tgctctaga tcaatctctc tccctcttat tatgttattt    120
tattcatctg gtgatatcac agaatcaatg gaggaaggtg ggagtagtca cgacgcagag   180
agtagcaaga agctagtata gagggaagat agagataaag aggatagaga acacaacaag   240
tcgtcaagta actttctgta aacgacgcaa tggtcttctt aagaaagctt atga         294
```

<210> SEQ ID NO 83
<211> LENGTH: 294
<212> TYPE: DNA
<213> ORGANISM: Brassica napus

<400> SEQUENCE: 83

```
tattcttgat ctgcaaaatg attaatttaa tcatcaatct taattagctt ctctagagca    60 atatttttt ttcttaagct tgctctaga tcaatctctc tccctcttat tatgttattt    120
tattcatctg gtgatatcac agaatcaatg gaggaaggtg ggagtagtca cgacgcagag   180
agtagcaaga agctagtata gagggaagat agagataaag aggatagaga acacaacaag   240
tcgtcaagta actttctgta aacgacgcaa tggtcttctt aagaaagctt atga         294
```

<210> SEQ ID NO 84
<211> LENGTH: 294
<212> TYPE: DNA
<213> ORGANISM: Brassica napus

<400> SEQUENCE: 84

```
tattcttgat ctgcaaaatg attaatttaa tcatcaatct taattagctt ctctagagca    60 atatttttt ttcttaagct tgctctaga tcaatctctc tccctcttat tatgttattt    120
tattcatctg gtgatatcac agaatcaatg gaggaaggtg ggagtagtca cgacgcagag   180
agtagcaaga agctagtaaa gagggaagat agagataaag aggatagaga acacaacaag   240
tcgtcaagta actttctgta aacgacgcaa tggtcttctt aagaaagctt atga         294
```

<210> SEQ ID NO 85
<211> LENGTH: 294
<212> TYPE: DNA
<213> ORGANISM: Brassica napus

<400> SEQUENCE: 85
tattcttgat ctgcaaaatg attaatttaa tcatcaatct taattagctt ctctagagca    60
atattttttt ttcttaagct tgctctagat caatctctc tccctcttat tatgttattt    120
tattcatctg gtgatatcac agaatcaatg gaggaaggtg ggagtagtca cgacgcagag    180
agtagcaaga agctagtaaa gagggaagat agagataaag aggatagaga acacaacaag    240
tcgtcaagta actttctgta acgacgcaa tggtcttctt aagaaagctt atga         294

<210> SEQ ID NO 86
<211> LENGTH: 292
<212> TYPE: DNA
<213> ORGANISM: Brassica napus

<400> SEQUENCE: 86
tattcttgat ctgcaaaatg attaatttaa tcatcaatct taattagctt ctctagagca    60
atattttttt ttcttaagct tgctctagat caatctctc tccctcttat tatgttattt    120
tattcatctg gtgatatcac agaatcaatg gaggaaggtg ggagtagtca cgacgcagag    180
agtagcaaga agctagtaga gggaagatag agataaagag gatagagaac acaacaagtc    240
gtcaagtaac tttctgtaaa cgacgcaatg gtcttcttaa gaaagcttat ga           292

<210> SEQ ID NO 87
<211> LENGTH: 291
<212> TYPE: DNA
<213> ORGANISM: Brassica napus

<400> SEQUENCE: 87
tattcttgat ctgcaaaatg attaatttaa tcatcaatct taattagctt ctctagagca    60
atattttttt ttcttaagct tgctctagat caatctctc tccctcttat tatgttattt    120
tattcatctg gtgatatcac agaatcaatg gaggaaggtg ggagtagtca cgacgcagag    180
agtagcaaga agctagtgag ggaagataga gataaagagg atagagaaca caacaagtcg    240
tcaagtaact ttctgtaaac gacgcaatgg tcttcttaag aaagcttatg a            291

<210> SEQ ID NO 88
<211> LENGTH: 291
<212> TYPE: DNA
<213> ORGANISM: Brassica napus

<400> SEQUENCE: 88
tattcttgat ctgcaaaatg attaatttaa tcatcaatct taattagctt ctctagagca    60
atattttttt ttcttaagct tgctctagat caatctctc tccctcttat tatgttattt    120
tattcatctg gtgatatcac agaatcaatg gaggaaggtg ggagtagtca cgacgcagag    180
agtagcaaga agctagtgag ggaagataga gataaagagg atagagaaca caacaagtcg    240
tcaagtaact ttctgtaaac gacgcaatgg tcttcttaag aaagcttatg a            291

<210> SEQ ID NO 89
<211> LENGTH: 294
<212> TYPE: DNA
<213> ORGANISM: Brassica napus

```
<400> SEQUENCE: 89
tattcttgat ctgcaaaatg attaatttaa tcatcaatct taattagctt ctctagagca    60 atatttttt ttcttaagct tgctctaga tcaatctctc tccctcttat tatgttattt    120
tattcatctg gtgatatcac agaatcaatg gaggaaggtg ggagtagtca cgacgcagag    180
agtagcaaga agctagtaaa gagggaagat agagataaag aggatagaga acacaacaag    240
tcgtcaagta actttctgta aacgacgcaa tggtcttctt aagaaagctt atga         294

<210> SEQ ID NO 90
<211> LENGTH: 294
<212> TYPE: DNA
<213> ORGANISM: Brassica napus

<400> SEQUENCE: 90
tattcttgat ctgcaaaatg attaatttaa tcatcaatct taattagctt ctctagagca    60 atatttttt ttcttaagct tgctctaga tcaatctctc tccctcttat tatgttattt    120
tattcatctg gtgatatcac agaatcaatg gaggaaggtg ggagtagtca cgacgcagag    180
agtagcaaga agctagtata gagggaagat agagataaag aggatagaga acacaacaag    240
tcgtcaagta actttctgta aacgacgcaa tggtcttctt aagaaagctt atga         294

<210> SEQ ID NO 91
<211> LENGTH: 294
<212> TYPE: DNA
<213> ORGANISM: Brassica napus

<400> SEQUENCE: 91
tattcttgat ctgcaaaatg attaatttaa tcatcaatct taattagctt ctctagagca    60 atatttttt ttcttaagct tgctctaga tcaatctctc tccctcttat tatgttattt    120
tattcatctg gtgatatcac agaatcaatg gaggaaggtg ggagtagtca cgacgcagag    180
agtagcaaga agctagtata gagggaagat agagataaag aggatagaga acacaacaag    240
tcgtcaagta actttctgta aacgacgcaa tggtcttctt aagaaagctt atga         294

<210> SEQ ID NO 92
<211> LENGTH: 290
<212> TYPE: DNA
<213> ORGANISM: Brassica napus

<400> SEQUENCE: 92
tattcttgat ctgcaaaatg attaatttga tcatcaatct taattatatt ctctataaca    60 atctttttt ttattaagct tgctctgat caatctctct ccctcttatt atgttatttt    120
attcatctgg tgatatcaca gaatcaatgg aggaaggtgg gagtagtcac gacgcagaga    180
gtaacaagaa gctagtaagg gaagatagag ataagagga tagagaacac aacaagtcgt    240
caagtaactt tctgtaaacg acgcaatggt cttcttaaga aagcttatga               290

<210> SEQ ID NO 93
<211> LENGTH: 293
<212> TYPE: DNA
<213> ORGANISM: Brassica napus

<400> SEQUENCE: 93
tattcttgat ctgcaaaatg attaatttga tcatcaatct taattatatt ctctataaca    60 atctttttt ttattaagct tgctctgat caatctctct ccctcttatt atgttatttt    120
attcatctgg tgatatcaca gaatcaatgg aggaaggtgg gagtagtcac gacgcagaga    180
```
gtaacaagaa gctagtaaag agggaagata gagataaaga ggatagagaa cacaacaagt      240
cgtcaagtaa ctttctgtaa acgacgcaat ggtcttctta agaaagctta tga            293

<210> SEQ ID NO 94
<211> LENGTH: 293
<212> TYPE: DNA
<213> ORGANISM: Brassica napus

<400> SEQUENCE: 94
tattcttgat ctgcaaaatg attaatttga tcatcaatct taattatatt ctctataaca      60
atcttttttt ttattaagct ttgctctgat caatctctct ccctcttatt atgttatttt     120
attcatctgg tgatatcaca gaatcaatgg aggaaggtgg gagtagtcac gacgcagaga     180
gtaacaagaa gctagtaaag agggaagata gagataaaga ggatagagaa cacaacaagt     240
cgtcaagtaa ctttctgtaa acgacgcaat ggtcttctta agaaagctta tga            293

<210> SEQ ID NO 95
<211> LENGTH: 290
<212> TYPE: DNA
<213> ORGANISM: Brassica napus

<400> SEQUENCE: 95
tattcttgat ctgcaaaatg attaatttga tcatcaatct taattatatt ctctataaca      60
atcttttttt ttattaagct ttgctctgat caatctctct ccctcttatt atgttatttt     120
attcatctgg tgatatcaca gaatcaatgg aggaaggtgg gagtagtcac gacgcagaga     180
gtaacaagaa gctagtgagg gaagatagag ataaagagga tagagaacac aacaagtcgt     240
caagtaactt tctgtaaacg acgcaatggt cttcttaaga aagcttatga                290

<210> SEQ ID NO 96
<211> LENGTH: 293
<212> TYPE: DNA
<213> ORGANISM: Brassica napus

<400> SEQUENCE: 96
tattcttgat ctgcaaaatg attaatttga tcatcaatct taattatatt ctctataaca      60
atcttttttt ttattaagct ttgctctgat caatctctct ccctcttatt atgttatttt     120
attcatctgg tgatatcaca gaatcaatgg aggaaggtgg gagtagtcac gacgcagaga     180
gtaacaagaa gctagtaaag agggaagata gagataaaga ggatagagaa cacaacaagt     240
cgtcaagtaa ctttctgtaa acgacgcaat ggtcttctta agaaagctta tga            293

<210> SEQ ID NO 97
<211> LENGTH: 293
<212> TYPE: DNA
<213> ORGANISM: Brassica napus

<400> SEQUENCE: 97
tattcttgat ctgcaaaatg attaatttga tcatcaatct taattatatt ctctataaca      60
atcttttttt ttattaagct ttgctctgat caatctctct ccctcttatt atgttatttt     120
attcatctgg tgatatcaca gaatcaatgg aggaaggtgg gagtagtcac gacgcagaga     180
gtaacaagaa gctagtaaag agggaagata gagataaaga ggatagagaa cacaacaagt     240
cgtcaagtaa ctttctgtaa acgacgcaat ggtcttctta agaaagctta tga            293

<210> SEQ ID NO 98

<211> LENGTH: 293
<212> TYPE: DNA
<213> ORGANISM: Brassica napus

<400> SEQUENCE: 98

| tattcttgat | ctgcaaaatg | attaatttga | tcatcaatct | taattatatt | ctctataaca | 60 |
| atcttttttt | ttattaagct | ttgctctgat | caatctctct | ccctcttatt | atgttatttt | 120 |
| attcatctgg | tgatatcaca | gaatcaatgg | aggaaggtgg | gagtagtcac | gacgcagaga | 180 |
| gtaacaagaa | gctagtaaag | agggaagata | gagataaaga | ggatagagaa | cacaacaagt | 240 |
| cgtcaagtaa | ctttctgtaa | acgacgcaat | ggtcttctta | agaaagctta | tga | 293 |

<210> SEQ ID NO 99
<211> LENGTH: 293
<212> TYPE: DNA
<213> ORGANISM: Brassica napus

<400> SEQUENCE: 99

| tattcttgat | ctgcaaaatg | attaatttga | tcatcaatct | taattatatt | ctctataaca | 60 |
| atcttttttt | ttattaagct | ttgctctgat | caatctctct | ccctcttatt | atgttatttt | 120 |
| attcatctgg | tgatatcaca | gaatcaatgg | aggaaggtgg | gagtagtcac | gacgcagaga | 180 |
| gtaacaagaa | gctagtaaag | agggaagata | gagataaaga | ggatagagaa | cacaacaagt | 240 |
| cgtcaagtaa | ctttctgtaa | acgacgcaat | ggtcttctta | agaaagctta | tga | 293 |

<210> SEQ ID NO 100
<211> LENGTH: 292
<212> TYPE: DNA
<213> ORGANISM: Brassica napus

<400> SEQUENCE: 100

| tattcttgat | ctgcaaaatg | attaatttga | tcatcaatct | taattatatt | ctctataaca | 60 |
| atcttttttt | ttattaagct | ttgctctgat | caatctctct | ccctcttatt | atgttatttt | 120 |
| attcatctgg | tgatatcaca | gaatcaatgg | aggaaggtgg | gagtagtcac | gacgcagaga | 180 |
| gtaacaagaa | gctagtaaga | gggaagatag | agataaagag | gatagagaac | acaacaagtc | 240 |
| gtcaagtaac | tttctgtaaa | cgacgcaatg | gtcttcttaa | gaaagcttat | ga | 292 |

<210> SEQ ID NO 101
<211> LENGTH: 293
<212> TYPE: DNA
<213> ORGANISM: Brassica napus

<400> SEQUENCE: 101

| tattcttgat | ctgcaaaatg | attaatttga | tcatcaatct | taattatatt | ctctataaca | 60 |
| atcttttttt | ttattaagct | ttgctctgat | caatctctct | ccctcttatt | atgttatttt | 120 |
| attcatctgg | tgatatcaca | gaatcaatgg | aggaaggtgg | gagtagtcac | gacgcagaga | 180 |
| gtaacaagaa | gctagtaaag | agggaagata | gagataaaga | ggatagagaa | cacaacaagt | 240 |
| cgtcaagtaa | ctttctgtaa | acgacgcaat | ggtcttctta | agaaagctta | tga | 293 |

<210> SEQ ID NO 102
<211> LENGTH: 264
<212> TYPE: DNA
<213> ORGANISM: Brassica napus

<400> SEQUENCE: 102

| tattcttgat | ctgcaaaaat | atttaatcat | caagcttacc | taccctcgct | ctctctagat | 60 |

```
caatcatctc cctcctcttt tgttgtttt tattcatttc ttgatattac agaatcaatg    120
gaggaaggtg ggagtagtca cgacgcagag agtaacaaga agctagtgta gagggaagat   180
agagataaag aggatagaga acacgacaag tcgtcaggta actttctgca aacgacgcaa   240
tggtcttctc aagaaagctt atga                                          264
```

<210> SEQ ID NO 103
<211> LENGTH: 264
<212> TYPE: DNA
<213> ORGANISM: Brassica napus

<400> SEQUENCE: 103

```
tattcttgat ctgcaaaaat atttaatcat caagcttacc taccctcgct ctctctagat    60
caatcatctc cctcctcttt tgttgtttt tattcatttc ttgatattac agaatcaatg    120
gaggaaggtg ggagtagtca cgacgcagag agtaacaaga agctagtgta gagggaagat   180
agagataaag aggatagaga acacgacaag tcgtcaggta actttctgca aacgacgcaa   240
tggtcttctc aagaaagctt atga                                          264
```

<210> SEQ ID NO 104
<211> LENGTH: 262
<212> TYPE: DNA
<213> ORGANISM: Brassica napus

<400> SEQUENCE: 104

```
tattcttgat ctgcaaaaat atttaatcat caagcttacc taccctcgct ctctctagat    60
caatcatctc cctcctcttt tgttgtttt tattcatttc ttgatattac agaatcaatg    120
gaggaaggtg ggagtagtca cgacgcagag agtaacaaga agctagtaga gggaagatag   180
agataaagag gatagagaac acgacaagtc gtcaggtaac tttctgcaaa cgacgcaatg   240
gtcttctcaa gaaagcttat ga                                            262
```

<210> SEQ ID NO 105
<211> LENGTH: 264
<212> TYPE: DNA
<213> ORGANISM: Brassica napus

<400> SEQUENCE: 105

```
tattcttgat ctgcaaaaat atttaatcat caagcttacc taccctcgct ctctctagat    60
caatcatctc cctcctcttt tgttgtttt tattcatttc ttgatattac agaatcaatg    120
gaggaaggtg ggagtagtca cgacgcagag agtaacaaga agctagtgaa gagggaagat   180
agagataaag aggatagaga acacgacaag tcgtcaggta actttctgca aacgacgcaa   240
tggtcttctc aagaaagctt atga                                          264
```

<210> SEQ ID NO 106
<211> LENGTH: 264
<212> TYPE: DNA
<213> ORGANISM: Brassica napus

<400> SEQUENCE: 106

```
tattcttgat ctgcaaaaat atttaatcat caagcttacc taccctcgct ctctctagat    60
caatcatctc cctcctcttt tgttgtttt tattcatttc ttgatattac agaatcaatg    120
gaggaaggtg ggagtagtca cgacgcagag agtaacaaga agctagtgaa gagggaagat   180
agagataaag aggatagaga acacgacaag tcgtcaggta actttctgca aacgacgcaa   240
```
tggtcttctc aagaaagctt atga 264

<210> SEQ ID NO 107
<211> LENGTH: 264
<212> TYPE: DNA
<213> ORGANISM: Brassica napus

<400> SEQUENCE: 107
tattcttgat ctgcaaaaat atttaatcat caagcttacc taccctcgct ctctctagat 60
caatcatctc cctcctcttt tgttgtttt tattcatttc ttgatattac agaatcaatg 120
gaggaaggtg ggagtagtca cgacgcagag agtaacaaga agctagtgaa gagggaagat 180
agagataaag aggatagaga acacgacaag tcgtcaggta actttctgca aacgacgcaa 240
tggtcttctc aagaaagctt atga 264

<210> SEQ ID NO 108
<211> LENGTH: 264
<212> TYPE: DNA
<213> ORGANISM: Brassica napus

<400> SEQUENCE: 108
tattcttgat ctgcaaaaat atttaatcat caagcttacc taccctcgct ctctctagat 60
caatcatctc cctcctcttt tgttgtttt tattcatttc ttgatattac agaatcaatg 120
gaggaaggtg ggagtagtca cgacgcagag agtaacaaga agctagtgaa gagggaagat 180
agagataaag aggatagaga acacgacaag tcgtcaggta actttctgca aacgacgcaa 240
tggtcttctc aagaaagctt atga 264

<210> SEQ ID NO 109
<211> LENGTH: 263
<212> TYPE: DNA
<213> ORGANISM: Brassica napus

<400> SEQUENCE: 109
tattcttgat ctgcaaaaat atttaatcat caagcttacc taccctcgct ctctctagat 60
caatcatctc cctcctcttt tgttgtttt tattcatttc ttgatattac agaatcaatg 120
gaggaaggtg ggagtagtca cgacgcagag agtaacaaga agctagtgag agggaagata 180
gagataaaga ggatagagaa cacgacaagt cgtcaggtaa ctttctgcaa acgacgcaat 240
ggtcttctca agaaagctta tga 263

<210> SEQ ID NO 110
<211> LENGTH: 262
<212> TYPE: DNA
<213> ORGANISM: Brassica napus

<400> SEQUENCE: 110
tattcttgat ctgcaaaaat atttaatcat caagcttacc taccctcgct ctctctagat 60
caatcatctc cctcctcttt tgttgtttt tattcatttc ttgatattac agaatcaatg 120
gaggaaggtg ggagtagtca cgacgcagag agtaacaaga agctagtaga gggaagatag 180
agataaagag gatagagaac acgacaagtc gtcaggtaac tttctgcaaa cgacgcaatg 240
gtcttctcaa gaaagcttat ga 262

<210> SEQ ID NO 111
<211> LENGTH: 264
<212> TYPE: DNA
<213> ORGANISM: Brassica napus

<400> SEQUENCE: 111

| | | | | | |
|---|---|---|---|---|---|
| tattcttgat | ctgcaaaaat | atttaatcat | caagcttacc | taccctcgct | ctctctagat | 60 |
| caatcatctc | cctcctcttt | tgttgtttt | tattcatttc | ttgatattac | agaatcaatg | 120 |
| gaggaaggtg | ggagtagtca | cgacgcagag | agtaacaaga | agctagtgaa | gagggaagat | 180 |
| agagataaag | aggatagaga | acacgacaag | tcgtcaggta | actttctgca | aacgacgcaa | 240 |
| tggtcttctc | aagaaagctt | atga | | | | 264 |

<210> SEQ ID NO 112
<211> LENGTH: 264
<212> TYPE: DNA
<213> ORGANISM: Brassica napus

<400> SEQUENCE: 112

| | | | | | |
|---|---|---|---|---|---|
| tattcttgat | ctgcaaaaat | atttaatcat | caagcttact | tagcctcgct | ctctctagat | 60 |
| caatcatctc | cctcctcttt | tgttgtttt | tattcatttc | ttgatattac | agaatcaatg | 120 |
| gaggaaggtg | ggagtagtca | cgacgcagag | agtaacaaga | agctagtgaa | gagggaagat | 180 |
| agagataaag | aggatagaga | acacgacaag | tcgtcaagta | actttctgca | aacgacgcaa | 240 |
| tggtcttctc | aagaaagctt | atga | | | | 264 |

<210> SEQ ID NO 113
<211> LENGTH: 264
<212> TYPE: DNA
<213> ORGANISM: Brassica napus

<400> SEQUENCE: 113

| | | | | | |
|---|---|---|---|---|---|
| tattcttgat | ctgcaaaaat | atttaatcat | caagcttact | tagcctcgct | ctctctagat | 60 |
| caatcatctc | cctcctcttt | tgttgtttt | tattcatttc | ttgatattac | agaatcaatg | 120 |
| gaggaaggtg | ggagtagtca | cgacgcagag | agtaacaaga | agctagtgaa | gagggaagat | 180 |
| agagataaag | aggatagaga | acacgacaag | tcgtcaagta | actttctgca | aacgacgcaa | 240 |
| tggtcttctc | aagaaagctt | atga | | | | 264 |

<210> SEQ ID NO 114
<211> LENGTH: 263
<212> TYPE: DNA
<213> ORGANISM: Brassica napus

<400> SEQUENCE: 114

| | | | | | |
|---|---|---|---|---|---|
| tattcttgat | ctgcaaaaat | atttaatcat | caagcttact | tagcctcgct | ctctctagat | 60 |
| caatcatctc | cctcctcttt | tgttgtttt | tattcatttc | ttgatattac | agaatcaatg | 120 |
| gaggaaggtg | ggagtagtca | cgacgcagag | agtaacaaga | agctagtgag | agggaagata | 180 |
| gagataaaga | ggatagagaa | cacgacaagt | cgtcaagtaa | ctttctgcaa | acgacgcaat | 240 |
| ggtcttctca | agaaagctta | tga | | | | 263 |

<210> SEQ ID NO 115
<211> LENGTH: 264
<212> TYPE: DNA
<213> ORGANISM: Brassica napus

<400> SEQUENCE: 115

| | | | | | |
|---|---|---|---|---|---|
| tattcttgat | ctgcaaaaat | atttaatcat | caagcttact | tagcctcgct | ctctctagat | 60 |
| caatcatctc | cctcctcttt | tgttgtttt | tattcatttc | ttgatattac | agaatcaatg | 120 |

```
gaggaaggtg ggagtagtca cgacgcagag agtaacaaga agctagtgaa gagggaagat      180
agagataaag aggatagaga acacgacaag tcgtcaagta actttctgca aacgacgcaa      240
tggtcttctc aagaaagctt atga                                            264
```

```
<210> SEQ ID NO 116
<211> LENGTH: 264
<212> TYPE: DNA
<213> ORGANISM: Brassica napus

<400> SEQUENCE: 116
tattcttgat ctgcaaaaat atttaatcat caagcttact tagcctcgct ctctctagat      60
caatcatctc cctcctcttt tgttgtttt tattcatttc ttgatattac agaatcaatg       120
gaggaaggtg ggagtagtca cgacgcagag agtaacaaga agctagtgaa gagggaagat      180
agagataaag aggatagaga acacgacaag tcgtcaagta actttctgca aacgacgcaa      240
tggtcttctc aagaaagctt atga                                            264
```

```
<210> SEQ ID NO 117
<211> LENGTH: 264
<212> TYPE: DNA
<213> ORGANISM: Brassica napus

<400> SEQUENCE: 117
tattcttgat ctgcaaaaat atttaatcat caagcttact tagcctcgct ctctctagat      60
caatcatctc cctcctcttt tgttgtttt tattcatttc ttgatattac agaatcaatg       120
gaggaaggtg ggagtagtca cgacgcagag agtaacaaga agctagtgta gagggaagat      180
agagataaag aggatagaga acacgacaag tcgtcaagta actttctgca aacgacgcaa      240
tggtcttctc aagaaagctt atga                                            264
```

```
<210> SEQ ID NO 118
<211> LENGTH: 264
<212> TYPE: DNA
<213> ORGANISM: Brassica napus

<400> SEQUENCE: 118
tattcttgat ctgcaaaaat atttaatcat caagcttact tagcctcgct ctctctagat      60
caatcatctc cctcctcttt tgttgtttt tattcatttc ttgatattac agaatcaatg       120
gaggaaggtg ggagtagtca cgacgcagag agtaacaaga agctagtgta gagggaagat      180
agagataaag aggatagaga acacgacaag tcgtcaagta actttctgca aacgacgcaa      240
tggtcttctc aagaaagctt atga                                            264
```

```
<210> SEQ ID NO 119
<211> LENGTH: 264
<212> TYPE: DNA
<213> ORGANISM: Brassica napus

<400> SEQUENCE: 119
tattcttgat ctgcaaaaat atttaatcat caagcttact tagcctcgct ctctctagat      60
caatcatctc cctcctcttt tgttgtttt tattcatttc ttgatattac agaatcaatg       120
gaggaaggtg ggagtagtca cgacgcagag agtaacaaga agctagtgta gagggaagat      180
agagataaag aggatagaga acacgacaag tcgtcaagta actttctgca aacgacgcaa      240
tggtcttctc aagaaagctt atga                                            264
```

<210> SEQ ID NO 120
<211> LENGTH: 264
<212> TYPE: DNA
<213> ORGANISM: Brassica napus

<400> SEQUENCE: 120
tattcttgat ctgcaaaaat atttaatcat caagcttact tagcctcgct ctctctagat     60
caatcatctc cctcctcttt ttgttgtttt tattcatttc ttgatattac agaatcaatg    120
gaggaaggtg ggagtagtca cgacgcagag agtaacaaga agctagtgta gagggaagat    180
agagataaag aggatagaga acacgacaag tcgtcaagta actttctgca aacgacgcaa    240
tggtcttctc aagaaagctt atga                                           264

<210> SEQ ID NO 121
<211> LENGTH: 264
<212> TYPE: DNA
<213> ORGANISM: Brassica napus

<400> SEQUENCE: 121
tattcttgat ctgcaaaaat atttaatcat caagcttact tagcctcgct ctctctagat     60
caatcatctc cctcctcttt ttgttgtttt tattcatttc ttgatattac agaatcaatg    120
gaggaaggtg ggagtagtca cgacgcagag agtaacaaga agctagtgta gagggaagat    180
agagataaag aggatagaga acacgacaag tcgtcaagta actttctgca aacgacgcaa    240
tggtcttctc aagaaagctt atga                                           264

<210> SEQ ID NO 122
<211> LENGTH: 299
<212> TYPE: DNA
<213> ORGANISM: Brassica napus

<400> SEQUENCE: 122
ctcttgcttt tctcccttga gatcgatctt agaacctaga tagtagctag ctatagtaga     60
tggagtccaa aaagatttta tttgatctct ctcagcgtgt gtgtagtgtt tgactgtgtt    120
tggtttatct ttaagctata ggttgatat aaatggaggg tggtgcgagt gatgaagtag     180
cagagagcag caagaagata gggtagaggg aagatagaga taaagaggat agagaacacc    240
acgaatcgcc aagtcacttt ctgcaaaaga cgcaatggtc tgctcaagaa agcttatga    299

<210> SEQ ID NO 123
<211> LENGTH: 299
<212> TYPE: DNA
<213> ORGANISM: Brassica napus

<400> SEQUENCE: 123
ctcttgcttt tctcccttga gatcgatctt agaacctaga tagtagctag ctatagtaga     60
tggagtccaa aaagatttta tttgatctct ctcagcgtgt gtgtagtgtt tgactgtgtt    120
tggtttatct ttaagctata ggttgatat aaatggaggg tggtgcgagt gatgaagtag     180
cagagagcag caagaagata gggtagaggg aagatagaga taaagaggat agagaacacc    240
acgaatcgcc aagtcacttt ctgcaaaaga cgcaatggtc tgctcaagaa agcttatga    299

<210> SEQ ID NO 124
<211> LENGTH: 299
<212> TYPE: DNA
<213> ORGANISM: Brassica napus

<400> SEQUENCE: 124

```
ctcttgctttt tctcccttga gatcgatctt agaacctaga tagtagctag ctatagtaga    60
tggagtccaa aaagatttta tttgatctct ctcagcgtgt gtgtagtgtt tgactgtgtt   120
tggtttatct ttaagctata ggttgatat  aaatggaggg tggtgcgagt gatgaagtag   180
cagagagcag caagaagata gggtagaggg aagatagaga taaagaggat agagaacacc   240
acgaatcgcc aagtcacttt ctgcaaaaga cgcaatggtc tgctcaagaa agcttatga   299
```

<210> SEQ ID NO 125
<211> LENGTH: 296
<212> TYPE: DNA
<213> ORGANISM: Brassica napus

<400> SEQUENCE: 125

```
ctcttgctttt tctcccttga gatcgatctt agaacctaga tagtagctag ctatagtaga    60
tggagtccaa aaagatttta tttgatctct ctcagcgtgt gtgtagtgtt tgactgtgtt   120
tggtttatct ttaagctata ggttgatat  aaatggaggg tggtgcgagt gatgaagtag   180
cagagagcag caagaagata gagagggaag atagagataa agaggataga gaacaccacg   240
aatcgccaag tcactttctg caaaagacgc aatggtctgc tcaagaaagc ttatga        296
```

<210> SEQ ID NO 126
<211> LENGTH: 299
<212> TYPE: DNA
<213> ORGANISM: Brassica napus

<400> SEQUENCE: 126

```
ctcttgctttt tctcccttga gatcgatctt agaacctaga tagtagctag ctatagtaga    60
tggagtccaa aaagatttta tttgatctct ctcagcgtgt gtgtagtgtt tgactgtgtt   120
tggtttatct ttaagctata ggttgatat  aaatggaggg tggtgcgagt gatgaagtag   180
cagagagcag caagaagata gggtagaggg aagatagaga taaagaggat agagaacacc   240
acgaatcgcc aagtcacttt ctgcaaaaga cgcaatggtc tgctcaagaa agcttatga   299
```

<210> SEQ ID NO 127
<211> LENGTH: 299
<212> TYPE: DNA
<213> ORGANISM: Brassica napus

<400> SEQUENCE: 127

```
ctcttgctttt tctcccttga gatcgatctt agaacctaga tagtagctag ctatagtaga    60
tggagtccaa aaagatttta tttgatctct ctcagcgtgt gtgtagtgtt tgactgtgtt   120
tggtttatct ttaagctata ggttgatat  aaatggaggg tggtgcgagt gatgaagtag   180
cagagagcag caagaagata ggggagaggg aagatagaga taaagaggat agagaacacc   240
acgaatcgcc aagtcacttt ctgcaaaaga cgcaatggtc tgctcaagaa agcttatga   299
```

<210> SEQ ID NO 128
<211> LENGTH: 299
<212> TYPE: DNA
<213> ORGANISM: Brassica napus

<400> SEQUENCE: 128

```
ctcttgctttt tctcccttga gatcgatctt agaacctaga tagtagctag ctatagtaga    60
tggagtccaa aaagatttta tttgatctct ctcagcgtgt gtgtagtgtt tgactgtgtt   120
tggtttatct ttaagctata ggttgatat  aaatggaggg tggtgcgagt gatgaagtag   180
cagagagcag caagaagata ggggagaggg aagatagaga taaagaggat agagaacacc   240
```

```
acgaatcgcc aagtcacttt ctgcaaaaga cgcaatggtc tgctcaagaa agcttatga      299
```

<210> SEQ ID NO 129
<211> LENGTH: 296
<212> TYPE: DNA
<213> ORGANISM: Brassica napus

<400> SEQUENCE: 129

```
ctcttgcttt tctcccttga gatcgatctt agaacctaga tagtagctag ctatagtaga     60
tggagtccaa aaagatttta tttgatctct ctcagcgtgt gtgtagtgtt tgactgtgtt    120
tggtttatct ttaagctata gggttgatat aaatggaggg tggtgcgagt gatgaagtag    180
cagagagcag caagaagata gagagggaag atagagataa agaggataga gaacaccacg    240
aatcgccaag tcactttctg caaaagacgc aatggtctgc tcaagaaagc ttatga        296
```

<210> SEQ ID NO 130
<211> LENGTH: 299
<212> TYPE: DNA
<213> ORGANISM: Brassica napus

<400> SEQUENCE: 130

```
ctcttgcttt tctcccttga gatcgatctt agaacctaga tagtagctag ctatagtaga     60
tggagtccaa aaagatttta tttgatctct ctcagcgtgt gtgtagtgtt tgactgtgtt    120
tggtttatct ttaagctata gggttgatat aaatggaggg tggtgcgagt gatgaagtag    180
cagagagcag caagaagata gggtagaggg aagatagaga taaagaggat agagaacacc    240
acgaatcgcc aagtcacttt ctgcaaaaga cgcaatggtc tgctcaagaa agcttatga    299
```

<210> SEQ ID NO 131
<211> LENGTH: 298
<212> TYPE: DNA
<213> ORGANISM: Brassica napus

<400> SEQUENCE: 131

```
ctcttgcttt tctcccttga gatcgatctt agaacctaga tagtagctag ctatagtaga     60
tggagtccaa aaagatttta tttgatctct ctcagcgtgt gtgtagtgtt tgactgtgtt    120
tggtttatct ttaagctata gggttgatat aaatggaggg tggtgcgagt gatgaagtag    180
cagagagcag caagaagata gggagaggga agatagagat aaagaggata gagaacacca    240
cgaatcgcca agtcactttc tgcaaaagac gcaatggtct gctcaagaaa gcttatga     298
```

<210> SEQ ID NO 132
<211> LENGTH: 306
<212> TYPE: DNA
<213> ORGANISM: Brassica napus

<400> SEQUENCE: 132

```
ctcttgcttt tctcccttga gatcgatctt agaacctaga tagtagctag ctacccttag     60
ctatagtaga tggagtccaa aaatatttta tttgatctct ctcagcttgt gtgtagtgtt    120
tgactgtgtt tggtttatct ttaagctata gggttgatat aaatggaggg tggtgcgagt    180
gatgaggtag cagagagcag caagaagata gagagggaag atagagataa agaggataga    240
gaacaccacg aatcgccaag tcactttctg caaaagacgc aatggtctgc ttaagaaagc    300
ttatga                                                               306
```

<210> SEQ ID NO 133

```
<211> LENGTH: 309
<212> TYPE: DNA
<213> ORGANISM: Brassica napus

<400> SEQUENCE: 133
ctcttgcttt tctcccttga gatcgatctt agaacctaga tagtagctag ctacccttag    60
ctatagtaga tggagtccaa aaatatttta tttgatctct ctcagcttgt gtgtagtgtt   120
tgactgtgtt tggtttatct ttaagctata gggttgatat aaatggaggg tggtgcgagt   180
gatgaggtag cagagagcag caagaagata gggtagaggg aagatagaga taaagaggat   240
agagaacacc acgaatcgcc aagtcacttt ctgcaaaaga cgcaatggtc tgcttaagaa   300
agcttatga                                                          309

<210> SEQ ID NO 134
<211> LENGTH: 309
<212> TYPE: DNA
<213> ORGANISM: Brassica napus

<400> SEQUENCE: 134
ctcttgcttt tctcccttga gatcgatctt agaacctaga tagtagctag ctacccttag    60
ctatagtaga tggagtccaa aaatatttta tttgatctct ctcagcttgt gtgtagtgtt   120
tgactgtgtt tggtttatct ttaagctata gggttgatat aaatggaggg tggtgcgagt   180
gatgaggtag cagagagcag caagaagata gggaagaggg aagatagaga taaagaggat   240
agagaacacc acgaatcgcc aagtcacttt ctgcaaaaga cgcaatggtc tgcttaagaa   300
agcttatga                                                          309

<210> SEQ ID NO 135
<211> LENGTH: 308
<212> TYPE: DNA
<213> ORGANISM: Brassica napus

<400> SEQUENCE: 135 ctcttgctttt tctcccttga gatcgatctt agaacctaga tagtagctag ctacccttag   60
ctatagtaga tggagtccaa aaatatttta tttgatctct ctcagcttgt gtgtagtgtt   120
tgactgtgtt tggtttatct ttaagctata gggttgatat aaatggaggg tggtgcgagt   180
gatgaggtag cagagagcag caagaagata gggagaggga agatagagat aaagaggata   240
gagaacacca cgaatcgcca agtcactttc tgcaaaagac gcaatggtct gcttaagaaa   300
gcttatga                                                           308

<210> SEQ ID NO 136
<211> LENGTH: 308
<212> TYPE: DNA
<213> ORGANISM: Brassica napus

<400> SEQUENCE: 136
ctcttgcttt tctcccttga gatcgatctt agaacctaga tagtagctag ctacccttag    60
ctatagtaga tggagtccaa aaatatttta tttgatctct ctcagcttgt gtgtagtgtt   120
tgactgtgtt tggtttatct ttaagctata gggttgatat aaatggaggg tggtgcgagt   180
gatgaggtag cagagagcag caagaagata gggagaggga agatagagat aaagaggata   240
gagaacacca cgaatcgcca agtcactttc tgcaaaagac gcaatggtct gcttaagaaa   300
gcttatga                                                           308
```

```
<210> SEQ ID NO 137
<211> LENGTH: 308
<212> TYPE: DNA
<213> ORGANISM: Brassica napus

<400> SEQUENCE: 137
ctcttgcttt tctcccttga gatcgatctt agaacctaga tagtagctag ctacccttag      60
ctatagtaga tggagtccaa aaatatttta tttgatctct ctcagcttgt gtgtagtgtt     120
tgactgtgtt tggtttatct ttaagctata gggttgatat aaatggaggg tggtgcgagt     180
gatgaggtag cagagagcag caagaagata gggagaggga agatagagat aaagaggata     240
gagaacacca cgaatcgcca agtcactttc tgcaaaagac gcaatggtct gcttaagaaa     300
gcttatga                                                             308

<210> SEQ ID NO 138
<211> LENGTH: 308
<212> TYPE: DNA
<213> ORGANISM: Brassica napus

<400> SEQUENCE: 138
ctcttgcttt tctcccttga gatcgatctt agaacctaga tagtagctag ctacccttag      60
ctatagtaga tggagtccaa aaatatttta tttgatctct ctcagcttgt gtgtagtgtt     120
tgactgtgtt tggtttatct ttaagctata gggttgatat aaatggaggg tggtgcgagt     180
gatgaggtag cagagagcag caagaagata gggagaggga agatagagat aaagaggata     240
gagaacacca cgaatcgcca agtcactttc tgcaaaagac gcaatggtct gcttaagaaa     300
gcttatga                                                             308

<210> SEQ ID NO 139
<211> LENGTH: 308
<212> TYPE: DNA
<213> ORGANISM: Brassica napus

<400> SEQUENCE: 139
ctcttgcttt tctcccttga gatcgatctt agaacctaga tagtagctag ctacccttag      60
ctatagtaga tggagtccaa aaatatttta tttgatctct ctcagcttgt gtgtagtgtt     120
tgactgtgtt tggtttatct ttaagctata gggttgatat aaatggaggg tggtgcgagt     180
gatgaggtag cagagagcag caagaagata gggagaggga agatagagat aaagaggata     240
gagaacacca cgaatcgcca agtcactttc tgcaaaagac gcaatggtct gcttaagaaa     300
gcttatga                                                             308

<210> SEQ ID NO 140
<211> LENGTH: 308
<212> TYPE: DNA
<213> ORGANISM: Brassica napus

<400> SEQUENCE: 140
ctcttgcttt tctcccttga gatcgatctt agaacctaga tagtagctag ctacccttag      60
ctatagtaga tggagtccaa aaatatttta tttgatctct ctcagcttgt gtgtagtgtt     120
tgactgtgtt tggtttatct ttaagctata gggttgatat aaatggaggg tggtgcgagt     180
gatgaggtag cagagagcag caagaagata gggagaggga agatagagat aaagaggata     240
gagaacacca cgaatcgcca agtcactttc tgcaaaagac gcaatggtct gcttaagaaa     300
gcttatga                                                             308
```

```
<210> SEQ ID NO 141
<211> LENGTH: 307
<212> TYPE: DNA
<213> ORGANISM: Brassica napus

<400> SEQUENCE: 141
ctcttgcttt tctcccttga gatcgatctt agaacctaga tagtagctag ctacccttag      60
ctatagtaga tggagtccaa aaatatttta tttgatctct ctcagcttgt gtgtagtgtt     120
tgactgtgtt tggtttatct ttaagctata gggttgatat aaatggaggg tggtgcgagt     180
gatgaggtag cagagagcag caagaagata ggagagggaa gatagagata aagaggatag     240
agaacaccac gaatcgccaa gtcactttct gcaaaagacg caatggtctg cttaagaaag     300
cttatga                                                               307
```